(12) United States Patent
Smaill et al.

(10) Patent No.: US 9,073,916 B2
(45) Date of Patent: Jul. 7, 2015

(54) PRODRUG FORMS OF KINASE INHIBITORS AND THEIR USE IN THERAPY

(75) Inventors: Jeffrey Bruce Smaill, Auckland (NZ); Adam Vorn Patterson, Auckland (NZ); Michael Patrick Hay, Auckland (NZ); William Alexander Denny, Auckland (NZ); William Robert Wilson, Waiuku (NZ); Guo-Liang Lu, Auckland (NZ); Robert Forbes Anderson, Auckland (NZ); Ho Huat Lee, Auckland (NZ); Amir Ashoorzadeh, Auckland (NZ)

(73) Assignee: AUCKLAND UNISERVICES LIMITED, Auckland (NZ)

( * ) Notice: Subject to any disclaimer, the term of this patent is extended or adjusted under 35 U.S.C. 154(b) by 364 days.

(21) Appl. No.: 13/138,429

(22) PCT Filed: Mar. 11, 2010

(86) PCT No.: PCT/NZ2010/000040
§ 371 (c)(1),
(2), (4) Date: Oct. 21, 2011

(87) PCT Pub. No.: WO2010/104406
PCT Pub. Date: Sep. 16, 2010

(65) Prior Publication Data
US 2012/0077811 A1 Mar. 29, 2012

(30) Foreign Application Priority Data

Mar. 11, 2009 (NZ) .................................... 575490
Sep. 2, 2009 (NZ) .................................... 579458
Nov. 12, 2009 (NZ) .................................... 581170

(51) Int. Cl.
| | |
|---|---|
| A61K 31/5377 | (2006.01) |
| A61K 31/519 | (2006.01) |
| A61K 31/4178 | (2006.01) |
| A61K 31/517 | (2006.01) |
| A61K 31/4709 | (2006.01) |
| C07D 403/12 | (2006.01) |
| C07D 403/14 | (2006.01) |
| C07D 401/12 | (2006.01) |

(Continued)

(52) U.S. Cl.
CPC .......... *C07D 471/04* (2013.01); *A61K 31/4178* (2013.01); *A61K 31/4709* (2013.01); *A61K 31/517* (2013.01); *A61K 31/519* (2013.01); *C07D 239/94* (2013.01); *C07D 403/12* (2013.01); *C07D 403/14* (2013.01); *C07D 405/14* (2013.01)

(58) Field of Classification Search
CPC .. C07D 403/12; C07D 403/14; C07D 401/12; C07D 401/14; C07D 405/14; C07D 239/94; C07D 471/04; C07D 413/14; A61K 31/5377; A61K 31/519; A61K 31/4178; A61K 31/517; A61K 31/4709

USPC ............... 514/234.5, 264.11, 397, 266.22, 514/266.23, 313, 266.4, 266.2, 266.21; 544/119, 279, 284, 293; 546/160; 548/312.1

See application file for complete search history.

(56) References Cited

FOREIGN PATENT DOCUMENTS

| | | |
|---|---|---|
| JP | 2000-502988 | 3/2000 |
| JP | 2009-525956 | 7/2009 |

(Continued)

OTHER PUBLICATIONS

Tercel, M., et al; "Hypoxia-Selective Antitumor Agents. 16. Nitroarylmethyl Quaternary Salts as Bioreductive Prodrugs of the Alkylating Agent Mechlorethamine"; *Journal of Medicinal Chemistry*, vol. 44, No. 21; pp. 3511-3522 (2001).

(Continued)

*Primary Examiner* — James O. Wilson
*Assistant Examiner* — Ebenezer O Sackey
(74) *Attorney, Agent, or Firm* — Kilpatrick Townsend & Stockton LLP

(57) ABSTRACT

The invention provides novel prodrug compounds comprising a kinase inhibitor and a reductively-activated fragmenting aromatic nitroheterocycle or aromatic nitrocarbocycle trigger, where the compound carries a positive charge. In preferred embodiments, the compounds are of Formula I:

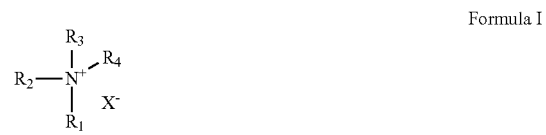

Formula I where: X is any negatively charged counterion; $R_1$ is a group of the formula $-(CH_2)_n Tr$, where Tr is an aromatic nitroheterocycle or aromatic nitrocarbocycle and $-(CH_2)_n Tr$ acts as a reductively-activated fragmenting trigger; and n is an integer from 0 to 6; $R_2$, $R_3$ and $R_4$ may each independently be selected from aliphatic or aromatic groups of a tertiary amine kinase inhibitor $(R_2)(R_3)(R_4)N$, or two of $R_2$, $R_3$, and $R_4$ may form an aliphatic or aromatic heterocyclic amine ring of a kinase inhibitor, or one of $R_2$, $R_3$ and $R_4$ may be absent and two of $R_2$, $R_3$ and $R_4$ form an aromatic heterocyclic amine ring of a kinase inhibitor.

The compounds of the invention are useful in treating proliferative diseases such as cancer.

28 Claims, 25 Drawing Sheets

(51) Int. Cl.
*C07D 405/14* (2006.01)
*C07D 471/04* (2006.01)
*C07D 239/94* (2006.01)

(56) References Cited

FOREIGN PATENT DOCUMENTS

| WO | 97/07101 A1 | 2/1997 |
|---|---|---|
| WO | 97/38983 A1 | 10/1997 |
| WO | 99/06378 A1 | 2/1999 |
| WO | WO 99/09016 A1 | 2/1999 |
| WO | 2004/091625 A1 | 10/2004 |
| WO | WO 2007/054551 A1 | 5/2007 |
| WO | 2007/082434 A1 | 7/2007 |
| WO | WO 2008/151253 A1 | 12/2008 |
| WO | 2010/104406 | 9/2010 |

OTHER PUBLICATIONS

Wissner, A., et al; "Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)"; *Journal of Med. Chem.*, vol. 46, No. 1, pp. 49-63 (2003).

Wisser, et al; *J. Med. Chem.*, vol. 46 No. 1, pp. 49-63 (2003).

Tercel, M., et al; "Nitrobenzyl Mustard Quaternary Salts: A New Class of Hypoxia-Selective Cytotoxins Showing Very High in Vitro Selctivity"; *J. Med. Chem.*, vol. 36, pp. 2578-2579 (1993).

Tercel, M., et al; "Hopoxia-Selective Antitumor Agents. 12. Nitrobenzyl Quaternary Salts as Bioreductive Prodrugs of the Alkylating Agent Mechlorethamine"; *J. Med. Chem.*, vol. 39, pp. 1084-1094 (1996).

Denny, W.A., et al; "Nitrobenzyl Mustard Quaternary Salts: A New Class of Hypoxia-Selective Cytotoxins Capable of Releasing Diffusible Cytotoxins on Bioreduction"; *Int. J. Radiation Oncology Biol. Phys.*, vol. 29, No. 2, pp. 317-321 (1994).

Anderson, R.F., et al; "Pulse Radiolysis Studies on the Fragmentation of Arylmethyl Quaternary Nitrogen Mustards by One-Electron Reduction in Aqueous Solution"; *J. Phys. Chem. A*, vol. 101, pp. 9704-9709 (1997).

Wilson, W.R., et al; "Reduction of Nitroarylmethyl Quaternary Ammonium Prodrugs of Mechlorethamine by Radiation"; *Radiation Research Society*, vol. 149, No. 3, pp. 237-245 (Mar. 1998).

Wilson, W.R., et al; "Radiation-activated prodrugs as hypoxia-selective cytotoxins: model studies with nitroarylmethyl quaternary salts"; *Anti-Cancer Drug Design*, vol. 13, pp. 663-685 (1998).

Kriste, A.G., et al; "Pathways of Reductive Fragmentation of Heterocyclic Nitroarylmethyl Quaternary Ammonium Prodrugs of Mechlorethamine"; *Radiation Research*, vol. 158, No. 6, pp. 753-762 (Dec. 2002).

Tercel, M., et al; "Hypoxia-Selective Antitumor Agents. 16. Nitroarylmethyl Quaternary Salts as Bioreductive Prodrugs of the Alkylating Agent Mechlorethamine"; *J. Med. Chem.*, vol. 44, No. 21, pp. 3511-3522 (2001).

Klutchko et al., "Tyrosine Kinase Inhibitors. 19. 6-Alkynamides of 4-Anilinoquinazolines and 4-Anilinopyrido[3,4-d]pyrimidines as Irreversible Inhibitors of the erbB Family of Tyrosine Kinase Receptors," J. Med. Chem., 2006, vol. 49, pp. 1475-1485.

Mayo Clinic, "Stargardt's disease: Can it be treated?," 2006, printed May 27, 2008, MayoClinic.com, http://www.mayoclinic.com/print/stargardts-disease/AN00846/METHOD=print, 2 pages.

Simone, "Oncology: Introduction," Cecil Textbook of Medicine, 20th Edition, 1996 vol. 1, pp. 1004-1010.

PRODRUG FORMS OF KINASE INHIBITORS AND THEIR USE IN THERAPY

This application is the U.S. national phase of International Application No. PCT/NZ2010/000040 filed 11 Mar. 2010 which designated the U.S. and claims priority to New Zealand Patent Application Nos. 575490 filed 11 Mar. 2009, 579458 filed 2 Sep. 2009 and 581170 filed 12 Nov. 2009, the entire contents of each of which are hereby incorporated by reference.

FIELD OF THE INVENTION

The present invention relates to kinase inhibitors, particularly in prodrug form, compositions and medicaments containing them, and processes for the preparation and use of such inhibitors, compositions and medicaments.

BACKGROUND OF THE INVENTION

Kinases represent a large family of enzymes that catalyse the phosphorylation of proteins, lipids and metabolites and play a central role in the regulation of a wide variety of cellular processes. Abnormal kinase activity has been related to a wide range of disorders, including cancers. This has led to the development of kinase inhibitors as therapeutics, including as anti-cancer agents.

This invention generally relates to compounds having activity as kinase inhibitors, including their prodrug forms, as well as to the application of such compounds in therapy.

SUMMARY OF THE INVENTION

In a first aspect, the invention provides a compound comprising a kinase inhibitor and a reductively-activated fragmenting aromatic nitroheterocycle or aromatic nitrocarbocycle trigger, said compound carrying a positive charge.

In preferred embodiments, the trigger fragments at the one-electron reduction level.

In preferred embodiments, the kinase inhibitor has a quaternisable nitrogen and the trigger is linked directly or indirectly to the nitrogen to form a quaternary nitrogen. A directly linked reductive trigger is presently considered most desirable.

In another aspect, the invention provides a compound comprising a kinase inhibitor and an aromatic nitroheterocycle or aromatic nitrocarbocycle fragmenting trigger which fragments at the one-electron reduction level, said kinase inhibitor containing a quaternisable nitrogen to which said trigger is directly or indirectly linked to provide a quaternary nitrogen.

In preferred embodiments, the compound is such that upon fragmentation of the trigger, the kinase inhibitor is released intact containing the quaternisable nitrogen.

In preferred embodiments, upon release the kinase inhibitor contains a tertiary amine moiety, with the nitrogen of the tertiary amine moiety being the nitrogen to which the trigger was linked.

In certain embodiments, the compound has an E(1) of between −0.6V and −0.2V, such as between −0.5V and −0.3V, such as between −0.35V and −0.45V, such as between −0.4V and −0.45V, against NHE (Normal Hydrogen Electrode).

In certain embodiments, the compound has a fragmentation rate constant, upon 1-electron reduction, of between 1 and 4000 s$^{-1}$, such as between 1 and 3000 s$^{-1}$, such as between 1 and 1500 s$^{-1}$, such as between 2 and 500 s$^{-1}$, such as between 2 and 300 s$^{-1}$, such as between 2 and 60 s$^{-1}$, such as between 20 and 60 s$^{-1}$.

Preferred compounds have an E(1) of between −0.2 V and −0.6 V and a fragmentation rate constant, upon one-electron reduction, of between 1 and 4000 s$^{-1}$, an E(1) of between −0.3 V and −0.5 V and a fragmentation rate constant, upon one-electron reduction, of between 1 and 3000 s$^{-1}$ (more preferably between 1 and 1500 s$^{-1}$), an E(1) of between −0.35 V and −0.45 V and a fragmentation rate constant, upon one-electron reduction, of between 2 and 500 s$^{-1}$, more preferably between 10 and 300 s$^{-1}$, still more preferably between 20 and 60 s$^{-1}$, and an E(1) of between −0.4 V and −0.45 V and a fragmentation rate constant, upon one-electron reduction, of between 20 and 60 s$^{-1}$ (preferably between 40 and 55 s$^{-1}$).

In preferred embodiments, a compound of the invention comprises a kinase inhibitor and a reductively-activated fragmenting trigger, wherein the kinase inhibitor has a quaternisable nitrogen to which said trigger is directly or indirectly linked, and wherein the trigger has the structure of Formula IIId:

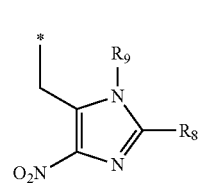

IIId where * is a point of attachment;
$R_8$ is selected from H and C1-C3 alkyl; and
$R_9$ is selected from H and C1-C6 alkyl.

In preferred embodiments, $R_8$ is H. In further preferred embodiments $R_9$ is C1-C3 alkyl, preferably methyl. In particularly preferred embodiments, $R_8$ is H and $R_9$ is methyl.

The kinase inhibitor may be either a reversible kinase inhibitor or an irreversible kinase inhibitor such as an irreversible erbB1, 2, 4 tyrosine kinase inhibitor. Irreversible is preferred.

In certain embodiments, the kinase inhibitor is an irreversible erbB1, 2, 4 tyrosine kinase inhibitor having a basic tertiary amine moiety linked to a cysteine-trapping functionality.

In certain embodiments, the cysteine-trapping functionality is linked to said tertiary amine by a linker moiety (CH2)n where n is an integer from 0 to 6.

In certain embodiments, the cysteine-trapping functionality is a Michael acceptor such as a double- or triple-bond-containing amide Michael acceptor.

Irreversible erbB1, 2, 4 tyrosine kinase inhibitors such as quinazoline, 7-alkoxyquinazoline, 7-alkoxyquinolinecarbonitrile, 4-anilino-[1,7]naphthyridine-3-carbonitrile, 4-anilino-5,7-dihydro-6H-pyrrolo[3',4':4,5]thieno[2,3-d]pyrimidine and 4-anilinopyrido[3,4-d]pyrimidine kinase inhibitors in which the cysteine-trapping functionality is a double or triple bond containing amide Michael acceptor in the 6-position, are particularly suitable.

In still another aspect, the invention provides quaternary nitrogen salts of Formula I:

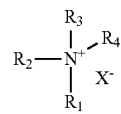

Formula I where:

X is any negatively charged counterion;

$R_1$ is a group of the formula —$(CH_2)_n Tr$, where Tr is an aromatic nitroheterocycle or aromatic nitrocarbocycle and —$(CH_2)_n Tr$ acts as a reductively-activated fragmenting trigger; and n is an integer from 0 to 6;

$R_2$, $R_3$, and $R_4$ may each independently be selected from aliphatic or aromatic groups of a tertiary amine kinase inhibitor $(R_2)(R_3)(R_4)N$, or two of $R_2$, $R_3$, and $R_4$ may form an aliphatic or aromatic heterocyclic amine ring of a kinase inhibitor, or one of $R_2$, $R_3$ and $R_4$ may be absent and two of $R_2$, $R_3$ and $R_4$ form an aromatic heterocyclic amine ring of a kinase inhibitor.

In another aspect, the invention provides quaternary ammonium salts of Formula II:

Formula II

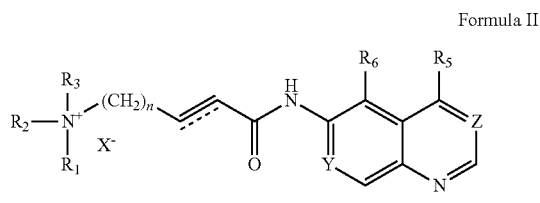

where:

X is any negatively charged counterion;

Y is N or C—$R_7$, where $R_7$ is selected from the group consisting of H, C1-C6 alkyl, C1-C6 alkoxy and groups of Formula VI Formula VI

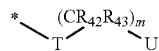 a

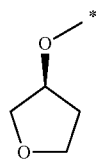 b

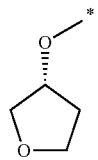 c where * is the point of attachment, and where

T is selected from O, NH, N(C1-C6 alkyl) and a direct link;

m is selected from integers from 0 to 6;

U is selected from $OR_{44}$, $CF_3$, $OCF_3$, CN, $NR_{45}R_{46}$, pyrrolidinyl, piperidinyl, piperazinyl, N1-methylpiperazinyl, morpholinyl, $CON(R_{47})(R_{48})$, $SO_2N(R_{49})(R_{50})$, $N(R_{51})COR_{52}$, $N(R_{53})SO_2R_{54}$, $COR_{55}$, $SOR_{56}$, $SO_2R_{57}$ and $COOR_{58}$; and $R_{42}$, $R_{43}$, $R_{44}$, $R_{45}$, $R_{46}$, $R_{47}$, $R_{48}$ $R_{49}$, $R_{50}$, $R_{51}$, $R_{52}$, $R_{53}$, $R_{54}$, $R_{55}$, $R_{56}$, $R_{57}$, $R_{58}$ are independently selected from H and C1-C6 alkyl;

Z is N or C—CN;

n is an integer from 0 to 6;

$R_1$ is a group of the formula $(CH_2)_n Tr$ where Tr is an aromatic nitroheterocycle or aromatic nitrocarbocycle and —$(CH_2)_n Tr$ acts as a reductively-activated fragmenting trigger, and n is an integer from 0 to 6;

$R_2$ and $R_3$ are independently selected from C1-C6 alkyl, cyclopropyl, cyclobutyl, cyclopentyl, cyclohexyl, $CH_2CH_2OH$, $CH_2CH_2O$(C1-C6 alkyl), or $R_2$ and $R_3$ may together form a non-aromatic carbocyclic ring or non-aromatic heterocyclic ring containing at least one heteroatom;

$R_5$ is selected from anilines, indoles, indolines, amines, aminoindoles and aminoindazoles, each of which may be optionally substituted with one or more substituents selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$, $CONH_2$, CO(C1-C6 $SO_2NH_2$ and $SO_2$(C1-C6 alkyl); and $R_6$ is selected from H, C1-C6 alkyl, C1-C6 alkoxy, NH(C1-C6 alkyl), N(C1-C6 alkyl)$_2$ and groups of Formula V Formula V

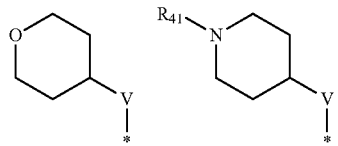

where
* is the point of attachment;

V is selected from $(CH_2)_k$ where k is an integer from 0 to 6, O, NH and N(C1-C6 alkyl); and $R_{41}$ is selected from H and C1-C6 alkyl.

In preferred embodiments, X is selected from halide (fluoride, chloride, bromide, iodide), methanesulfonate, trifluoromethanesulfonate, acetate, trifluoroacetate, tosylate, lactate, citrate and formate.

In certain preferred embodiments, X is halide, preferably bromide or chloride.

In other preferred embodiments, X is formate or trifluoroacetate.

In preferred embodiments, $R_1$ is selected from groups of Formula III.

Formula III

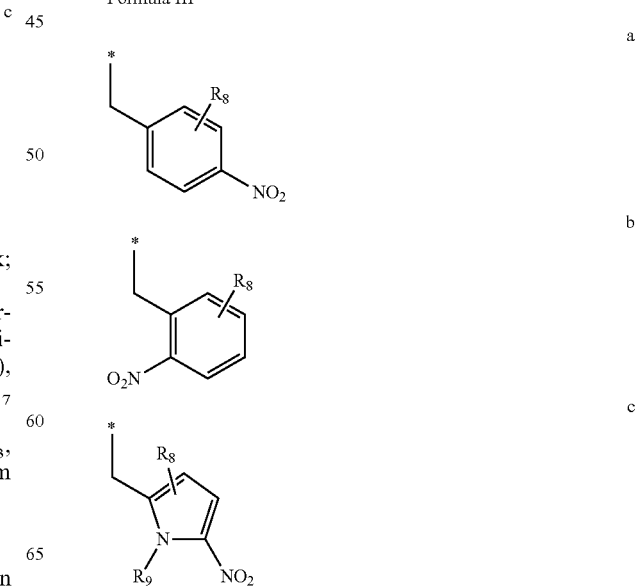

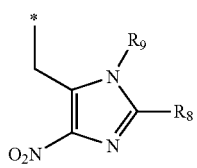
d

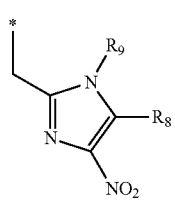
e

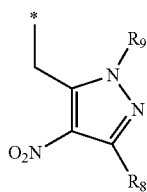
f

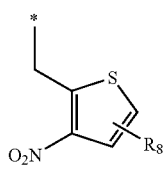
g

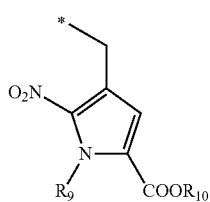
h

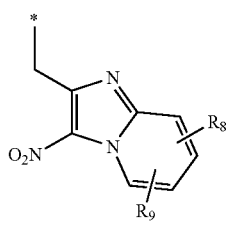
i

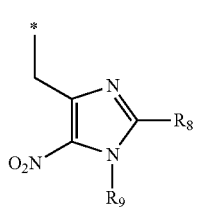
j

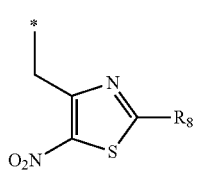
k

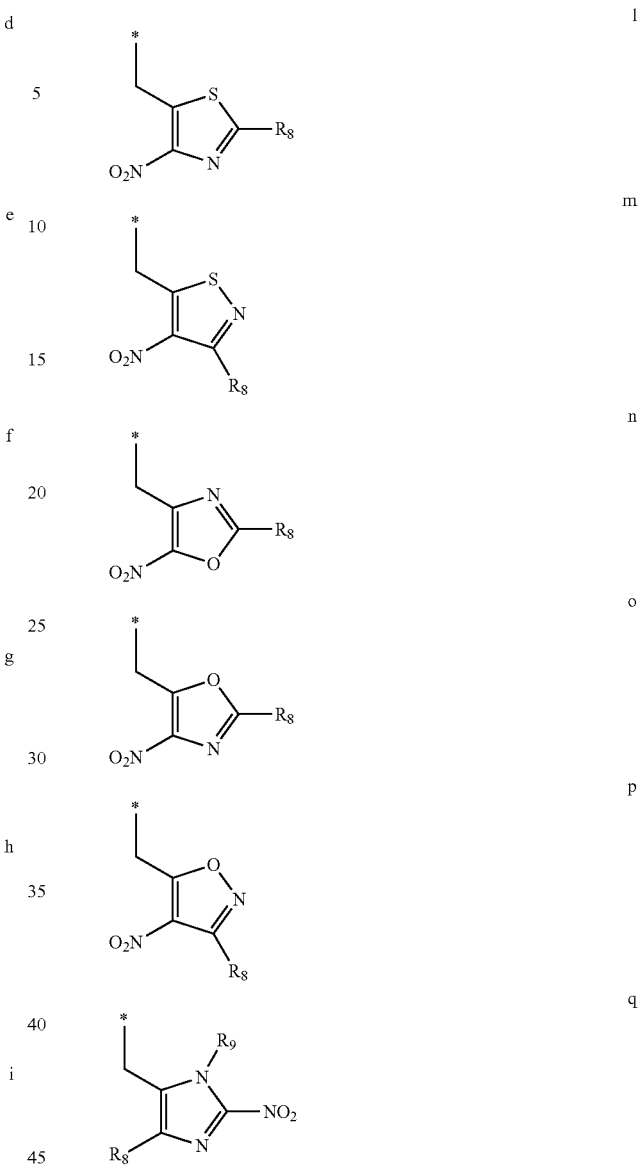

where
* is the point of attachment to the quaternary nitrogen of a compound of Formula II;
$R_8$ is selected from H, C1-C6 alkyl, C1-C6 alkoxy, C2-C6 alkenyl, C2-C6 alkynyl, $CF_3$, $OCF_3$, F, Cl, Br, I, $NO_2$, CN, COOH, COO(C1-C6 alkyl), $CONH_2$, CONH(C1-C6 AA, CON(C1-C6 alkyl)$_2$, CO(C1-C6 alkyl), $SO_2NH_2$, $SO_2NH$(C1-C6 alkyl), $SO_2N$(C1-C6 alkyl)$_2$, $SO_2$(C1-C6 alkyl) and groups of Formula VIa as defined above but where * is the point of attachment to a group of Formula III;
$R_9$ is selected from the group consisting of H, C1-C6 alkyl and groups of Formula VIa as defined above but where * is the point of attachment to a group of Formula III; and
$R_{10}$ is selected from H and C1-C6 alkyl.

In certain preferred embodiments, $R_1$ is selected from groups of Formula IIIc, where $R_8$ is H and $R_9$ is $CH_3$.

In other preferred embodiments, $R_1$ is selected from groups of Formula IIId, where $R_8$ is selected from H, C1-C6 alkyl (such as methyl), C1-C6 alkoxy (such as $OCH_3$), C2-C6 alkynyl (such as ethynyl), CONH$_2$, CONHMe, CF$_3$, OCF$_3$, Br, NO$_2$ and CN, and R$_9$ is selected from CH$_3$, CH$_2$CH$_2$CONH$_2$ and CH$_2$CH$_2$CN.

In other preferred embodiments, R$_1$ is selected from groups of Formula IIId,

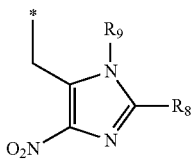

where * is a point of attachment, R$_8$ is selected from H and C1-C3 alkyl, and R$_9$ is selected from H and C1-C6 alkyl.

In preferred embodiments R$_8$ is H. R$_9$ is preferably C1-C3 alkyl, most preferably methyl. In particularly preferred embodiments, R$_8$ is H and R$_9$ is methyl.

In other preferred embodiments, R$_1$ is selected from groups of Formula IIId, where R$_8$ is –1 propynyl and R$_9$ is CH$_3$.

In other preferred embodiments, R$_1$ is selected from groups of Formula IIIq, where R$_8$ is selected from H, C1-C6 alkyl (such as methyl or ethyl) and C1-C6 alkoxy (such as OCH$_3$), and R is CH$_3$.

In certain embodiments, R$_2$ and R$_3$ form a ring selected from pyrrolidinium, piperidinium, piperazinium, N1-methylpiperazinium and morpholinium.

In preferred embodiments, R$_5$ is selected from groups of Formula IV:

Formula IV a

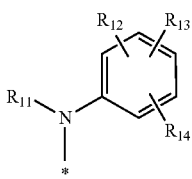

b

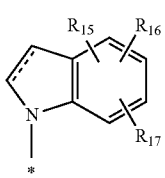

c

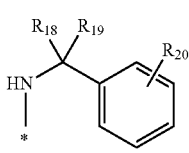

d

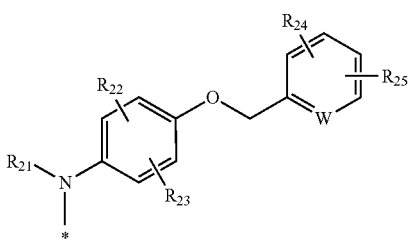

e

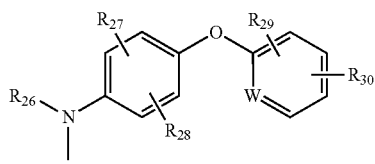

f

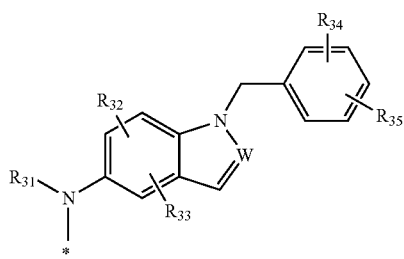

g

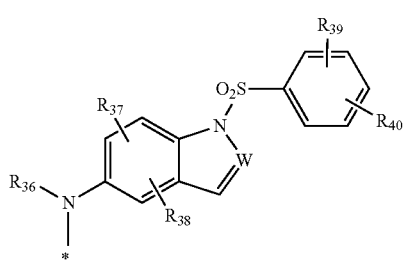

where
* is the point of attachment;
R$_{11}$, R$_{18}$, R$_{19}$, R$_{21}$, R$_{26}$, R$_{31}$ and R$_{36}$, are independently selected from H and C1-C6 alkyl;
R$_{12}$, R$_{13}$, R$_{14}$, R$_{15}$, R$_{16}$, R$_{17}$, R$_{20}$, R$_{22}$, R$_{23}$, R$_{24}$, R$_{25}$, R$_{27}$, R$_{28}$, R$_{29}$, R$_{30}$, R$_{32}$, R$_{33}$, R$_{34}$, R$_{35}$, R$_{37}$, R$_{38}$, R$_{39}$ and R$_{40}$ are independently selected from H, C1-C6 alkyl, C2-C6 alkenyl, C2-C6 alkynyl, C1-C6 alkoxy, F, Cl, Br, I, CN, CH$_2$F, CHF$_2$, CF$_3$, OH, NH$_2$, NO$_2$, NH(C1-C6 alkyl), N(C1-C6 alkyl)$_2$, CONH$_2$, CO(C1-C6 alkyl), SO$_2$NH$_2$ and SO$_2$(C1-C6 alkyl); and
W is N or C—H.

In certain preferred embodiments, Y is N, Z is N or C—CN, R$_1$ is selected from the following:
(a) a group of Formula IIIc, where R$_8$ is H and R$_9$ is CH$_3$;
(b) groups of Formula IIId, where (i) R$_8$ is selected from H, C1-C6 alkyl (such as methyl), C1-C6 alkoxy (such as OCH$_3$), C2-C6 alkynyl (such as ethynyl), CF$_3$, OCF$_3$, Br, NO$_2$ and CN, and R$_9$ is selected from CH$_3$, CH$_2$CH$_2$CONH$_2$ and CH$_2$CH$_2$CN; or (n) R$_8$ is 1-propynyl and R$_9$ is CH$_3$;
(c) groups of Formula IIIf, where R$_8$ is H and R$_9$ is CH$_3$; and
(d) groups of Formula IIIq, where R$_8$ is selected from H, C1-C6 alkyl (such as methyl or ethyl) and C1-C6 alkoxy (such as OCH$_3$), and R$_9$ is CH$_3$;
R$_2$ and R$_3$ are independently selected from C1-C6 alkyl, or together form a ring selected from pyrrolidinium, piperidinium, piperazinium, N1-methylpiperazinium and morpholinium;
R$_5$ is selected from the following:
(a) a group of Formula IVa, where
* is the point of attachment;
R$_{11}$ is H; and
R$_{12}$, R$_{13}$, R$_{14}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
(b) a group of Formula IVd, where
* is the point of attachment;
$R_{21}$ is H; and
$R_{22}$ and $R_{23}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
$R_{24}$ and $R_{25}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
W is N or C—H; and
(c) a group of Formula IVf, where
* is the point of attachment;
$R_{31}$ is H; and
$R_{32}$ and $R_{33}$ are independently selected from H or F;
$R_{34}$ and $R_{35}$ are independently selected from H, C1-C6 alkyl, F, Cl, Br, I, $CH_2F$, $CHF_2$, $CF_3$;
W is N or C—H;
$R_6$ is H;
X is any negatively charged counterion; and
n=1 or 2.

In other preferred embodiments Y is C—H or C—(C1-C6 alkoxy), Z is N or C—CN;
$R_1$ is selected from the following:
(a) a group of Formula IIIc, where $R_8$ is H; and $R_9$ is $CH_3$;
(b) groups of Formula IIId, where
$R_8$ is selected from H, C1-C6 alkyl, C1-C6 alkoxy, C2-C6 alkynyl, $CF_3$, $OCF_3$, Br, $NO_2$ and CN, and $R_9$ is selected from $CH_3$, $CH_2CH_2CONH_2$ and $CH_2CH_2CN$; or $R_8$ is 1-propynyl and $R_9$ is $CH_3$;
(c) groups of Formula IIIf, where $R_8$ is H and $R_9$ is $CH_3$; and
(d) groups of Formula IIIq, where
$R_8$ is selected from H, C1-C6 alkyl (such as methyl or ethyl) and C1-C6 alkoxy (such as $OCH_3$), and $R_9$ is $CH_3$;
$R_2$ and $R_3$ are independently selected from C1-C6 alkyl, or together form a ring selected from pyrrolidinium, piperidinium, piperazinium, N1-methylpiperazinium and morpholinium;
$R_5$ is selected from the following:
(a) a group of Formula IVa, where
* is the point of attachment;
$R_{11}$ is H; and
$R_{12}$, $R_{13}$, $R_{14}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
(b) a group of Formula IVd, where
* is the point of attachment;
$R_{21}$ is H; and
$R_{22}$ and $R_{23}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
$R_{24}$ and $R_{25}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$; and
W is N or C—H; and
(c) a group of Formula IVf, where
* is the point of attachment;
$R_{31}$ is H; and
$R_{32}$ and $R_{33}$ are independently selected from H or F;
$R_{34}$ and $R_{35}$ are independently selected from H, C1-C6 alkyl, F, Cl, Br, I, $CH_2F$, $CHF_2$, $CF_3$; and
W is N or C—H;
$R_6$ is H;
X is any negatively charged counterion; and
n=1 or 2.

In other preferred embodiments Y is C—$R_7$, where $R_7$ is a group of Formula VIb;
Z is N or C—CN;
$R_1$ is selected from the following:
(a) a group of Formula IIIc, where $R_8$ is H; and $R_9$ is $CH_3$;
(b) groups of Formula IIId, where
$R_8$ is selected from H, C1-C6 alkyl, C1-C6 alkoxy, C2-C6 alkynyl, $CF_3$, $OCF_3$, Br, $NO_2$ and CN, and $R_9$ is selected from $CH_3$, $CH_2CH_2CONH_2$ and $CH_2CH_2CN$; or $R_8$ is 1-propynyl; and $R_9$ is $CH_3$;
(c) groups of Formula IIIf, where $R_8$ is H and $R_9$ is $CH_3$; and
(d) groups of Formula IIIq, where $R_8$ is selected from H, C1-C6 alkyl (such as methyl or ethyl) and C1-C6 alkoxy (such as $OCH_3$); and $R_9$ is $CH_3$;
$R_2$ and $R_3$ are independently selected from C1-C6 alkyl, or together form a ring selected from pyrrolidinium, piperidinium, piperazinium, N1-methylpiperazinium and morpholinium;
$R_5$ is selected from the following:
(a) a group of Formula IVa, where
* is the point of attachment to a compound of Formula II;
$R_{11}$ is H; and
$R_{12}$, $R_{13}$, $R_{14}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
(b) a group of Formula IVd, where
* is the point of attachment to a compound of Formula II;
$R_{21}$ is H; and
$R_{22}$ and $R_{23}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$;
$R_{24}$ and $R_{25}$ are independently selected from H, C1-C6 alkyl, C2-C6 alkenyl, C2-C6 alkynyl, C1-C6 alkoxy, F, Cl, Br, I, CN, $CH_2F$, $CHF_2$, $CF_3$, OH, $NH_2$, $NO_2$, NH(C1-C6 alkyl), N(C1-C6 alkyl)$_2$; and W is N or C—H; and
(c) a group of Formula IVf, where
* is the point of attachment to a compound of Formula II;
$R_{31}$ is H; and
$R_{32}$ and $R_{33}$ are independently selected from H or F;
$R_{34}$ and $R_{35}$ are independently selected from H, C1-C6 alkyl, F, Cl, Br, I, $CH_2F$, $CHF_2$, $CF_3$; and W is N or C—H;
$R_6$ is H;
X is any negatively charged counterion; and
n=1 or 2.
Preferred compounds of Formula II include the following:
(2E)-4-{[4-(3-bromoanilino)-6-quinazolinyl]amino}-N,N-dimethyl-N-(4-nitrobenzyl)-4-oxo-2-buten-1-ammonium bromide (17)
(2E)-4-{[4-(3-bromoanilino)-6-quinazolinyl]amino}-N,N-dimethyl-N-(2-nitrobenzyl)-4-oxo-2-buten-1-ammonium bromide (18)
(2E)-4-{[4-(3-bromoanilino)-6-quinazolinyl]amino}-N,N-dimethyl-N-[(1-methyl-5-nitro-1H-pyrrol-2-yl)methyl]-4-oxo-2-buten-1-ammonium bromide (19)

(2E)-4-{[4-(3-bromoanilino)-6-quinazolinyl]amino}-N,N-dimethyl-N-[(1-methyl-4-nitro-1H-imidazol-5-yl)methyl]-4-oxo-2-buten-1-ammonium bromide (20)

(2E)-4-{[4-(3-bromoanilino)-6-quinazolinyl]amino}-N,N-dimethyl-N-[(1-methyl-4-nitro-1H-imidazol-2-yl)methyl]-4-oxo-2-buten-1-ammonium bromide (21)

(2E)-4-{[4-(3-bromoanilino)-6-quinazolinyl]amino}-N,N-dimethyl-N-[(1-methyl-4-nitro-1H-pyrazol-5-yl)methyl]-4-oxo-2-buten-1-ammonium bromide (22)

(2E)-4-{[4-(3-bromoanilino)-6-quinazolinyl]amino}-N,N-dimethyl-N-[(3-nitroimidazo[1,2-a]pyridin-2-yl)methyl]-4-oxo-2-buten-1-ammonium bromide (22A)

1-((2E)-4-{[4-(3-bromoanilino)-6-quinazolinyl]amino}-4-oxo-2-butenyl)-1-[(1-methyl-4-nitro-1H-imidazol-5-yl)methyl]piperidinium bromide (23)

4-((2E)-4-{[4-(3-bromoanilino)-6-quinazolinyl]amino}-4-oxo-2-butenyl)-4-[(1-methyl-4-nitro-1H-imidazol-5-yl)methyl]morpholin-4-ium formate (24)

(2E)-4-{[4-(3-chloro-4-fluoroanilino)-7-methoxy-6-quinazolinyl]amino}-N,N-dimethyl-N-[(1-methyl-4-nitro-1H-imidazol-5-yl)methyl]-4-oxo-2-buten-1-ammonium bromide (25)

(2E)-4-{[4-(3-bromo-4-fluoroanilino)-6-quinazolinyl]amino}-N,N-dimethyl-N-[(1-methyl-4-nitro-1H-imidazol-5-yl)methyl]-4-oxo-2-buten-1-ammonium bromide (27A)

(2E)-4-{[4-(4-fluoro-3-methoxyanilino)pyrido[3,4-d]pyrimidin-6-yl]amino}-N,N-dimethyl-N-[(1-methyl-4-nitro-1H-imidazol-5-yl) methyl]-4-oxo-2-buten-1-ammonium bromide (27B)

(2E)-4-{[4-(3-bromo-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (42)

(2E)-4-{[4-(3-bromo-4-fluoroanilino)pyrido[3,4-d]pyrimidin-6-yl]amino}-N-[(1,2-dimethyl-4-nitro-1H-imidazol-5-yl)methyl]N,N-dimethyl-4-oxo-2-buten-1-ammonium bromide (43)

(2E)-4-{[4-(3-bromo-4-fluoroanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide (44)

(2E)-4-{[4-(3-bromo-4-fluoroanilino)pyrido[3,4-d]pyrimidin-6-yl]amino}-N-[(2-ethynyl-1-methyl-4-nitro-1H-imidazol-5-yl)methyl]-N,N-dimethyl-4-oxo-2-buten-1-ammonium bromide (45)

(2E)-4-{[4-(3-bromo-4-fluoroanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (46)

(2E)-N-{[1-(3-amino-3-oxopropyl)-4-nitro-1H-imidazol-5-yl]methyl}-4-{[4-(3-bromo-4-fluoroanilino)pyrido[3,4-d]pyrimidin-6-yl]amino}-N,N-dimethyl-4-oxo-2-buten-1-ammonium bromide (47)

(2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (48)

(2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium trifluoroacetate (48TF)

(2E)-4-{[4-(3-bromo-4-fluoroanilino)pyrido[3,4-d]pyrimidin-6-yl]amino}-N-{[1-(2-cyanoethyl)-4-nitro-1H-imidazol-5-yl]methyl}-N,N-dimethyl-4-oxo-2-buten-1-ammonium bromide (49)

(2E)-4-({4-[4-fluoro-3-(trifluoromethyl)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (50)

(2E)-N-[(1,2-dimethyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide (51)

(2E)-4-({4-[4-fluoro-3-(trifluoromethyl)anilino]pyrido[3,4-d]pyrimidin-6-yl}amino)-N-[(2-methoxy-1-methyl-4-nitro-1H-imidazol-5-yl)methyl]-N,N-dimethyl-4-oxo-2-buten-1-ammonium bromide (52)

(2E)-N-[(2-ethynyl-1-methyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide (53)

(2E)-4-({4-[4-fluoro-3-(trifluoromethyl)anilino]pyrido[3,4-d]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide (54)

(2E)-N-{[1-(3-amino-3-oxopropyl)-4-nitro-1H-imidazol-5-yl]methyl}-4-({4-[4-fluoro-3-(trifluoromethyl)anilino]pyrido[3,4-d]pyrimidin-6-yl}amino)-N,N-dimethyl-4-oxo-2-buten-1-ammonium bromide (55)

(2E)-N-[(2-cyano-1-methyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide (56)

(2E)-N-{[1-(2-cyanoethyl)-4-nitro-1H-imidazol-5-yl]methyl}-4-({4-[4-fluoro-3-(trifluoromethyl)anilino]pyrido[3,4-d]pyrimidin-6-yl}amino)-N,N-dimethyl-4-oxo-2-buten-1-ammonium bromide (57)

(2E)-4-{[4-(3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (58)

(2E)-N-[(1,2-dimethyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (59)

(2E)-4-{[4-(3-ethynylanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide (60)

(2E)-4-{[4-(3-ethynylanilino)pyrido[3,4-d]pyrimidin-6-yl]amino}-N-[(2-ethynyl-1-methyl-4-nitro-1H-imidazol-5-yl)methyl]-N,N-dimethyl-4-oxo-2-buten-1-ammonium bromide (61)

(2E)-4-{[4-(3-ethynylanilino)pyrido[3,4-d]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide (62)

(2E)-N-{[1-(3-amino-3-oxopropyl)-4-nitro-1H-imidazol-5-yl]methyl}-4-{[4-(3-ethynylanilino)pyrido[3,4-d]pyrimidin-6-yl]amino}-N,N-dimethyl-4-oxo-2-buten-1-ammonium bromide (63)

(2E)-N-[(2-cyano-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (64)

(2E)-N-{[1-(2-cyanoethyl)-4-nitro-1H-imidazol-5-yl]methyl}-4-{[4-(3-ethynylanilino)pyrido[3,4-d]pyrimidin-6-yl]amino}-N,N-dimethyl-4-oxo-2-buten-1-ammonium bromide (65)

(2E)-4-({4-(3-chloro-4-fluoroanilino)-7-[(3S)-tetrahydro-3-furanyloxy]-6-quinazolinyl}amino)-N,N-dimethyl-N-[(1-methyl-4-nitro-1H-imidazol-5-yl)methyl]-4-oxo-2-buten-1-ammonium trifluoroacetate (82)

(2E)-4-({4-[3-chloro-4-(2-pyridinylmethoxy)anilino]-3-cyano-7-ethoxy-6-quinolinyl}amino)-N,N-dimethyl-N-[(1-methyl-4-nitro-1H-imidazol-5-yl)methyl]-4-oxo-2-buten-1-ammonium trifluoroacetate (83)

(2E)-4-{[4-(3-chloro-4-fluoroanilino)-3-cyano-7-ethoxy-6-quinolinyl]amino}-N,N-dimethyl-N-[(1-methyl-4-nitro-1H-imidazol-5-yl)methyl]-4-oxo-2-buten-1-ammonium bromide (84)

2-(4-{[6-(2,6-dichlorophenyl)-8-methyl-7-oxo-7,8-dihydropyrido[2,3-d]pyrimidin-2-yl]amino}phenoxy)-N,N-diethyl-N-[(1-methyl-4-nitro-1H-imidazol-5-yl)methyl]ethanammonium bromide (140)

2-(4-{[6-(2,6-dichlorophenyl)-8-methyl-7-oxo-7,8-dihydropyrido[2,3-d]pyrimidin-2-yl]amino}phenoxy)-N-[(1,2-dimethyl-4-nitro-1H-imidazol-5-yl)methyl]N,N-diethyl-ethanammonium bromide (141)

4-{[6-(2,6-dichlorophenyl)-8-methyl-7-oxo-7,8-dihydropyrido[2,3-d]pyrimidin-2-yl]amino}-1-[(1-methyl-4-nitro-1H-imidazol-5-yl)methyl]pyridinium bromide (142)

1-[2-(4-{[6-(2,6-dichlorophenyl)-8-methyl-7-oxo-7,8-dihydropyrido[2,3-d]pyrimidin-2-yl]amino}phenoxy)ethyl]-1-[(1-methyl-4-nitro-1H-imidazol-5-yl) methyl]piperidinium bromide (143)

N,N-diethyl-2-[({5-[(Z)-(5-fluoro-2-oxo-1,2-dihydro-3H-indol-3-ylidene)methyl]-2,4-dimethyl-1H-pyrrol-3-yl}carbonyl)amino]-N-[(1-methyl-4-nitro-1H-imidazol-5-yl)methyl]ethanammonium trifluoroacetate (144)

N-[(1,2-dimethyl-4-nitro-1H-imidazol-5-yl)methyl]-N,N-diethyl-2-[({5-[(Z)-(5-fluoro-2-oxo-1,2-dihydro-3H-indol-3-ylidene)methyl]2,4-dimethyl-1H-pyrrol-3-yl}carbonyl)amino]ethanammonium bromide (145)

4-({[4-(4-bromo-2-fluoroanilino)-6-methoxy-7-quinazolinyl]oxy}methyl)-1-methyl-1-[(1-methyl-4-nitro-1H-imidazol-5-yl)methyl]piperidinium trifluoroacetate (146)

(2E)-4-{[4-(3-bromo-4-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (172)

(2E)-4-{[4-(3-bromo-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (173)

(2E)-4-{[4-(3-bromo-4-fluoroanilino)pyrido[3,4-d]pyrimidin-6-yl]amino}-N,N-dimethyl-N-[(1-methyl-2-nitro-1H-imidazol-5-yl)methyl]-4-oxo-2-buten-1-ammonium bromide (174)

(2E)-4-{[4-(3-bromo-4-fluoroanilino)pyrido[3,4-d]pyrimidin-6-yl]amino}-N-[(4-ethyl-1-methyl-2-nitro-1H-imidazol-5-yl)methyl]-N,N-dimethyl-4-oxo-2-buten-1-ammonium bromide (175) and (2E)-N-[(2-ethyl-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (176).

The structures of the above compounds are shown in FIGS. 4 to 9, FIG. 17 and FIG. 18.

In certain preferred embodiments of the invention, the reductively-activated fragmenting moiety, (R₁ in the compounds of Formulae I and II), is selected from the group consisting of the following moieties:

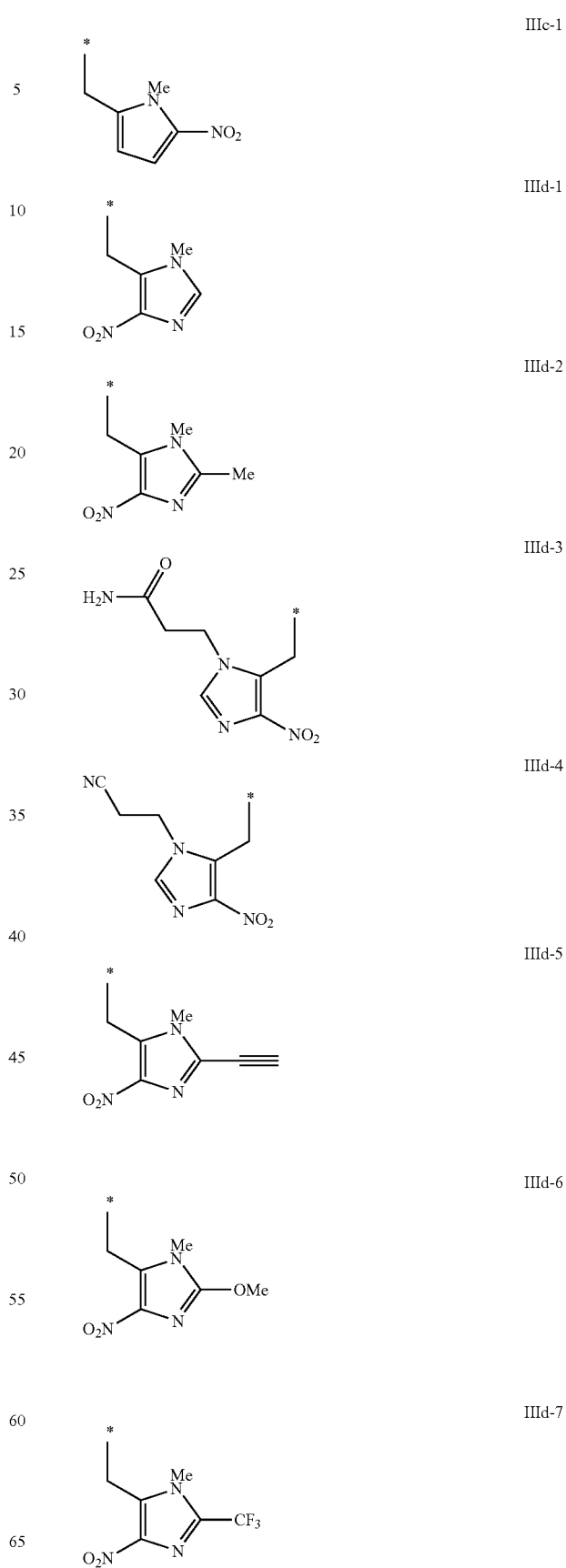

-continued
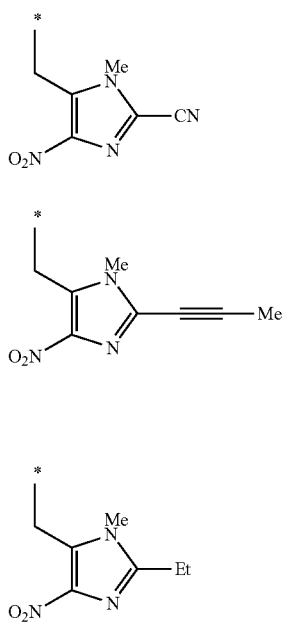
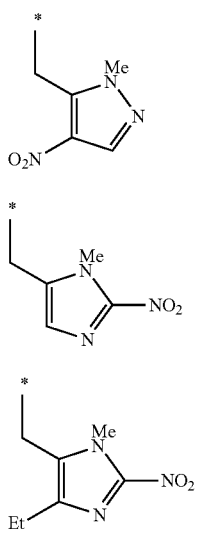
where * is the point of attachment to the quaternary nitrogen.
In certain preferred embodiments of the invention, the kinase inhibitor is selected from radicals derived from the following compounds:
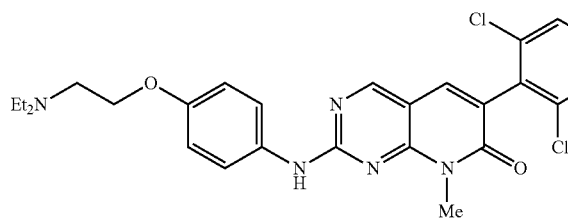
PD 166285
PD 166285 analogue A
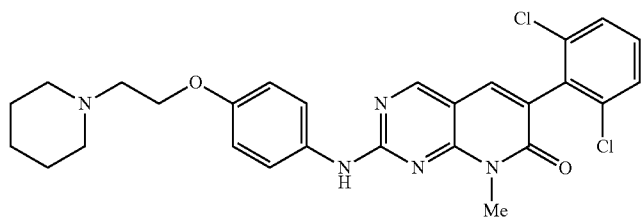
PD 166285 analogue B
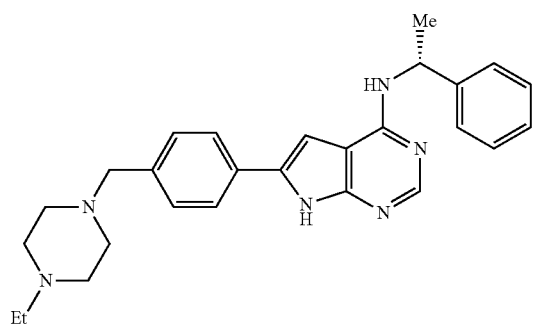
AEE788
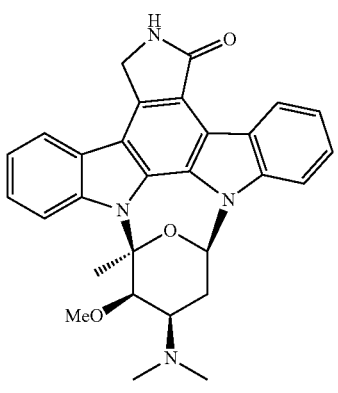
N-methylstaurosporine -continued
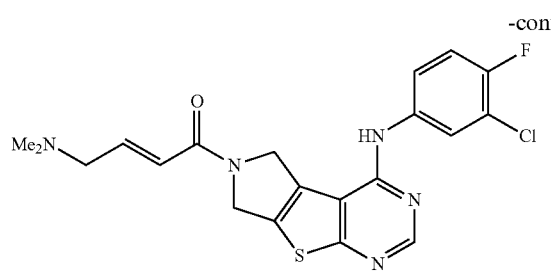
Irreversible
ErbB Inhibitor A
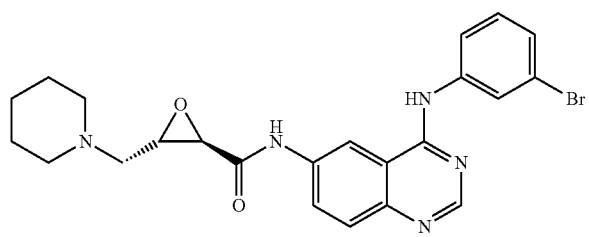
Irreversible
ErbB Inhibitor B
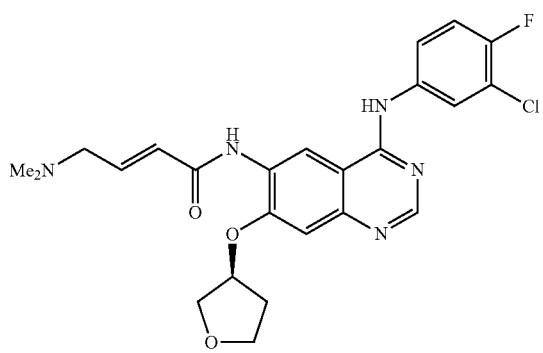
BIBW2992
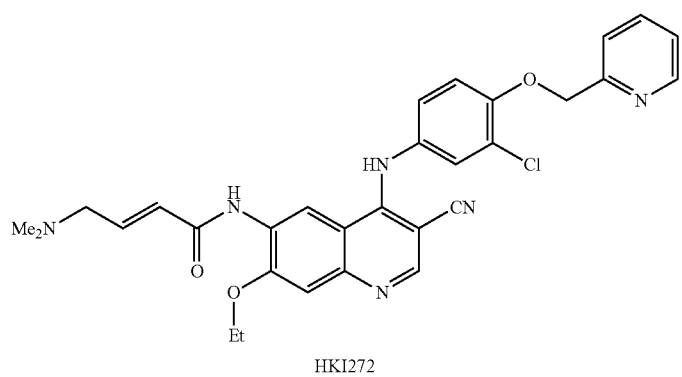
HKI272
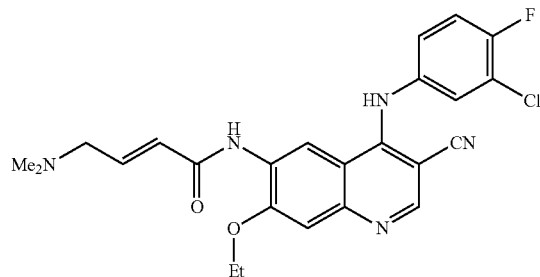
EKB569
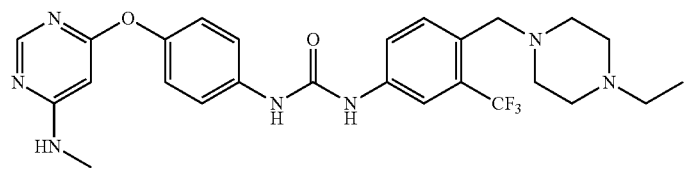
AST-487

19
-continued
CHIR-258
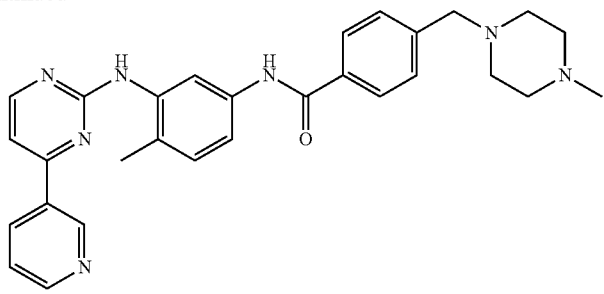
Imatinib
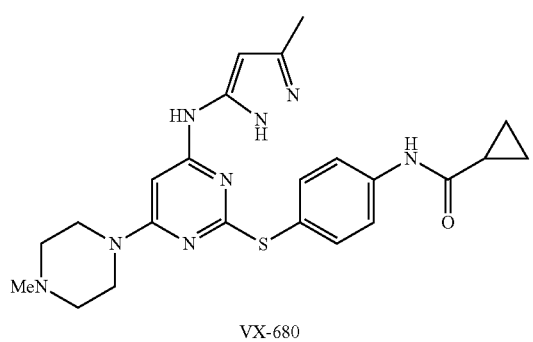
VX-680
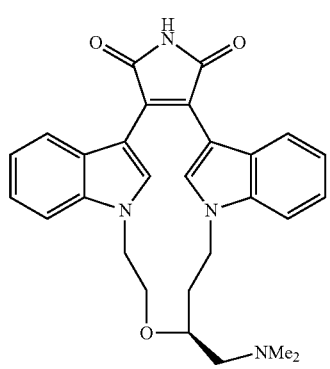
LY-333531
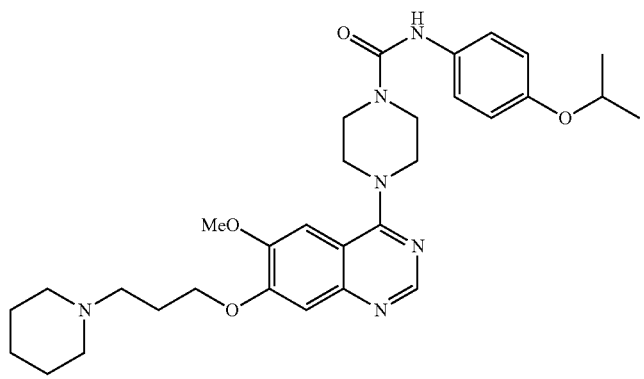
MLN-518
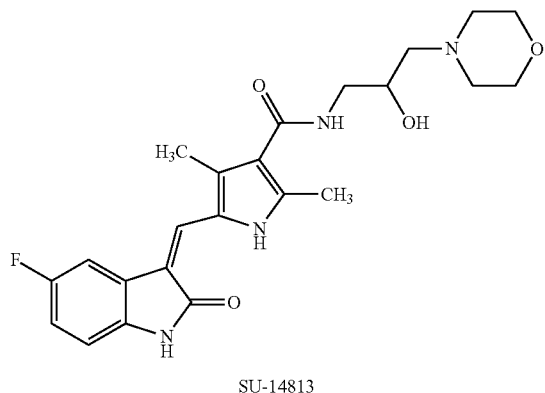
SU-14813
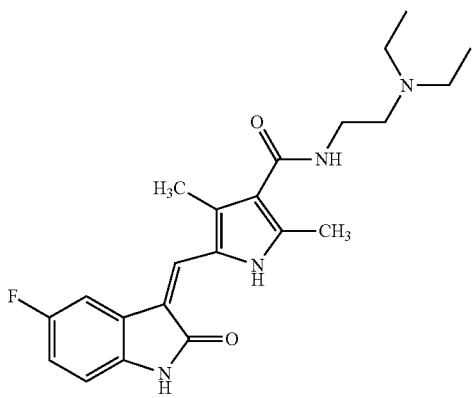
Sunitinib -continued
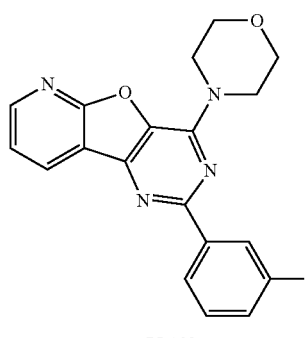
PI-103
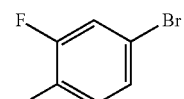
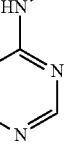
ZD6474
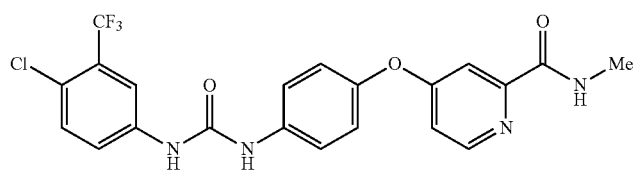
Sorafenib
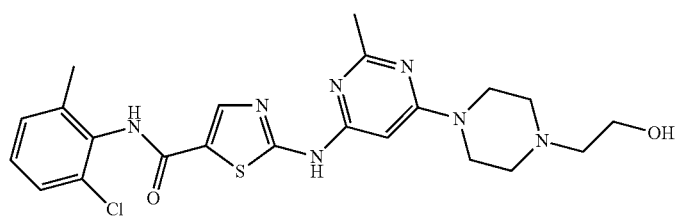
Dasatinib
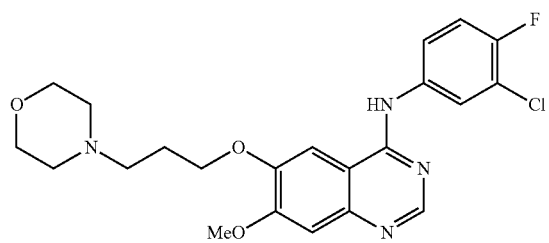
Gefitinib
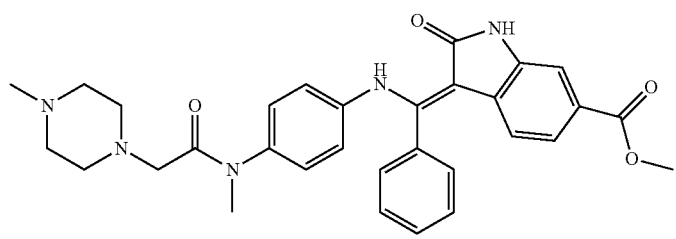
Vargatef
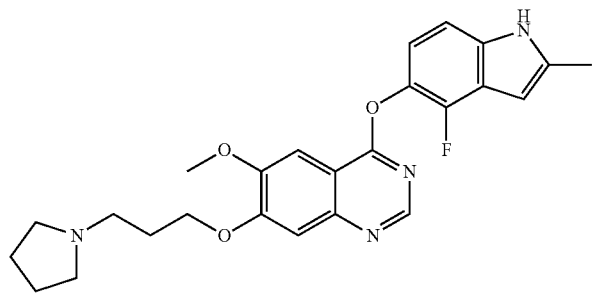
Cediranib -continued
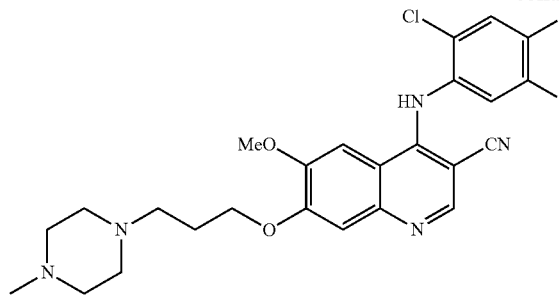
Bosutinib
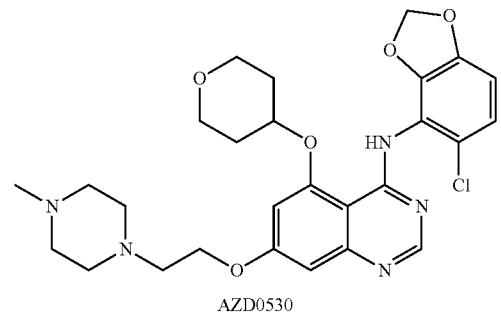
AZD0530
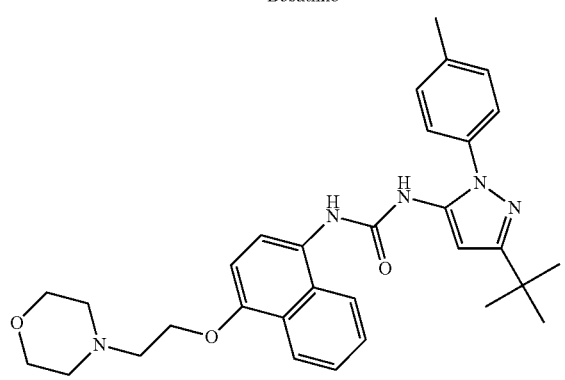
BIRB796
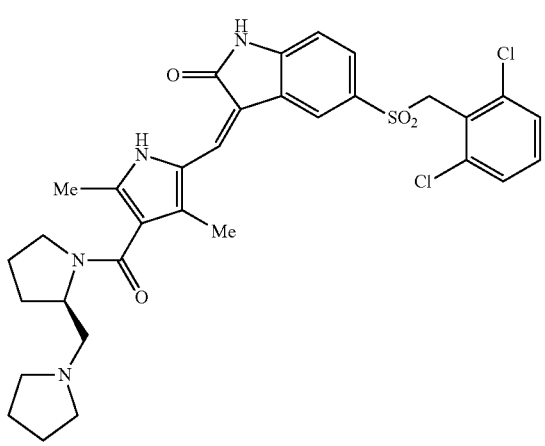
PHA-665752
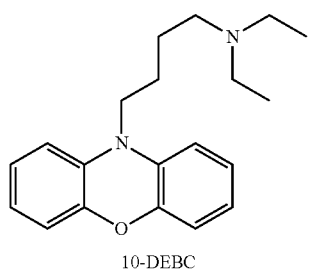
10-DEBC
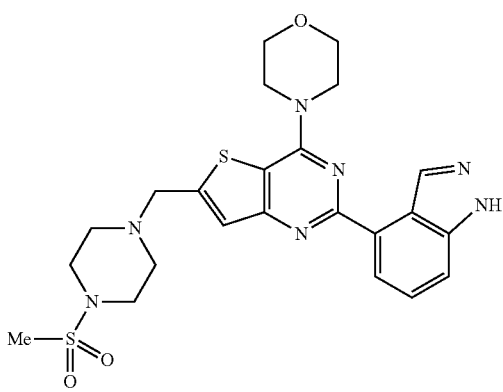
GDC-0941
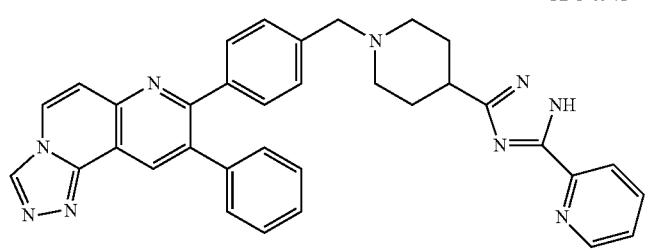
MK-2206 analogue
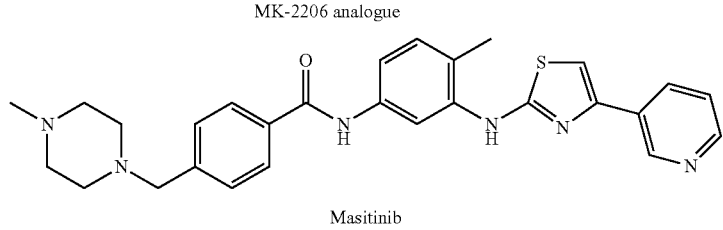
Masitinib -continued
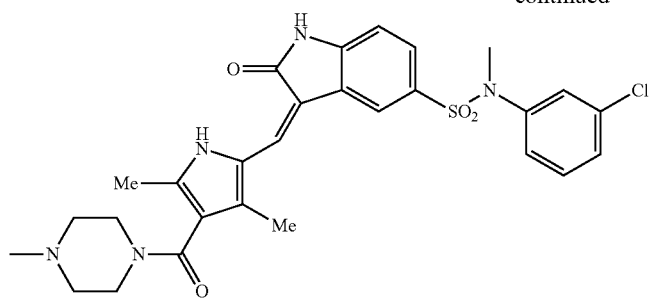
SU11274
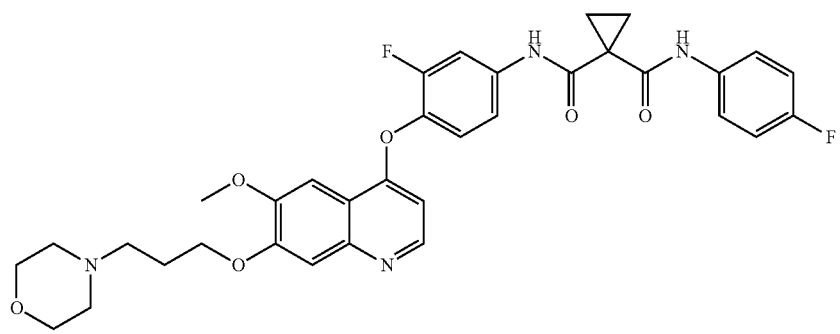
XL880
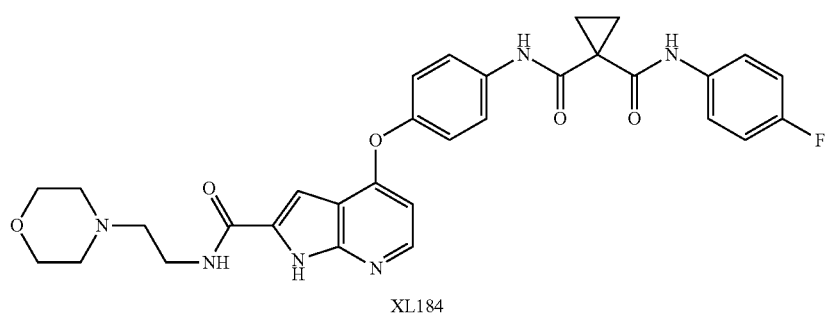
XL184
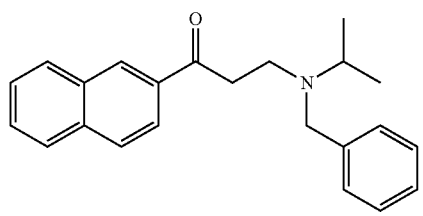
ZM39923
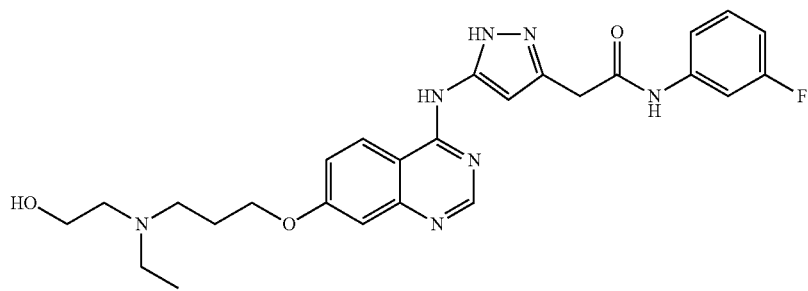
AZD1152

-continued

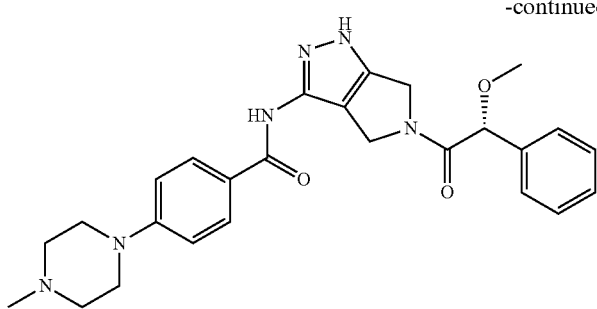
Danusertib

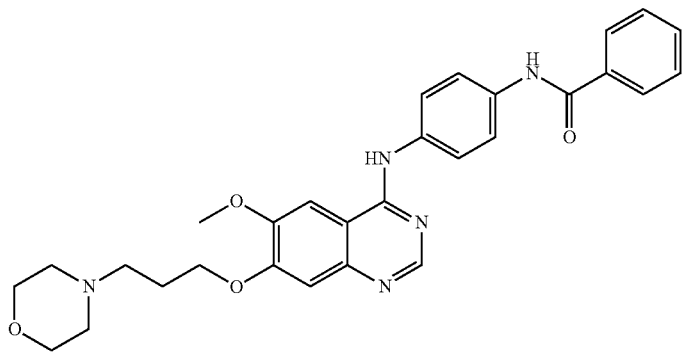
ZM447439

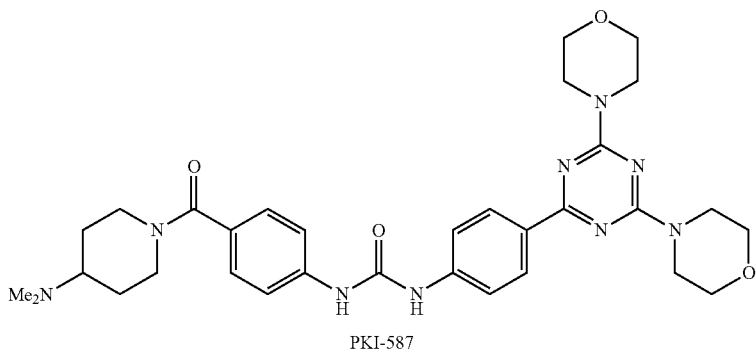 [SMILES: CN(C)C1CCN(C(=O)c2ccc(NC(=O)Nc3ccc(-c4nc(N5CCOCC5)nc(N5CCOCC5)n4)cc3)cc2)CC1]
PKI-587

In a further aspect, the invention provides compounds of the invention as defined above, including compounds of Formula I and II, for use in therapy.

In a further aspect, the invention provides pharmaceutical compositions comprising a compound of the invention as defined above, such as a compound of Formula I or Formula II, in combination with one or more pharmaceutically acceptable excipients or diluents.

The invention also provides pharmaceutical compositions comprising a compound of the invention as defined above, such as a compound of Formula I or Formula II, in combination with one or more pharmaceutically acceptable excipients or diluents, for use in treating proliferative diseases, including cancer, in a mammal, including a human.

In still a further aspect, the invention provides a method of treating a proliferative disease such as cancer in a mammal, including a human, comprising administering to the mammal a therapeutically effective amount of a compound of the invention as defined above, such as a compound of Formula I or Formula II.

In still a further aspect, the invention provides the use of a compound of the invention as defined above, such as a compound of Formula I or Formula II, in the preparation of a medicament for treating a proliferative disease such as cancer.

In still a further aspect, the invention provides the use of a kinase inhibitor in the preparation of a compound of the invention as defined above, such as a compound of Formula I or Formula II, for treating a proliferative disease such as cancer.

In one embodiment, the kinase inhibitor is selected from the kinase inhibitors listed above.

In specific embodiments, the kinase inhibitor is selected from
(2E)-N-[4-(3-bromoanilino)-6-quinazolinyl]-4-(dimethylamino)-2-butenamide (11)
(2E)-N-[4-(3-bromo-4-fluoroanilino)pyrido[3,4-d]pyrimidin-6-yl]-4-(dimethylamino)-2-butenamide (161)
2E)-4-(dimethylamino)-N-{4-[4-fluoro-3-(trifluoromethyl)anilino]pyrido[3,4-d]pyrimidin-6-yl}-2-butenamide (170) and
(2E)-4-(dimethylamino)-N-[4-(3-ethynylanilino)pyrido[3,4-d]pyrimidin-6-yl]-2-butenamide (171).

In yet another aspect, the invention provides a kinase inhibitor, including for use in the preparation of a compound of the invention as defined above, selected from (2E)-N-[4-(3-bromo-4-fluoroanilino)pyrido[3,4-d]pyrimidin-6-yl]-4-(dimethylamino)-2-butenamide (161)
2E)-4-(dimethylamino)-N-{4-[4-fluoro-3-(trifluoromethyl)anilino]pyrido[3,4-d]pyrimidin-6-yl}-2-butenamide (170) and
(2E)-4-(dimethylamino)-N-[4-(3-ethynylanilino)pyrido[3,4-d]pyrimidin-6-yl]-2-butenamide (171).

In still another aspect, the invention provides the use of a reductively-activated fragmenting aromatic nitroheterocycle or aromatic nitrocarbocycle in the preparation of a compound of the invention as defined above, such as a compound of Formula I or Formula II, for treating a proliferative disease such as cancer.

In one embodiment, the nitroheterocycle or nitrocarbocycle is a moiety of Formula IIId as defined above.

DESCRIPTION OF THE INVENTION

Definitions

Figure 1:
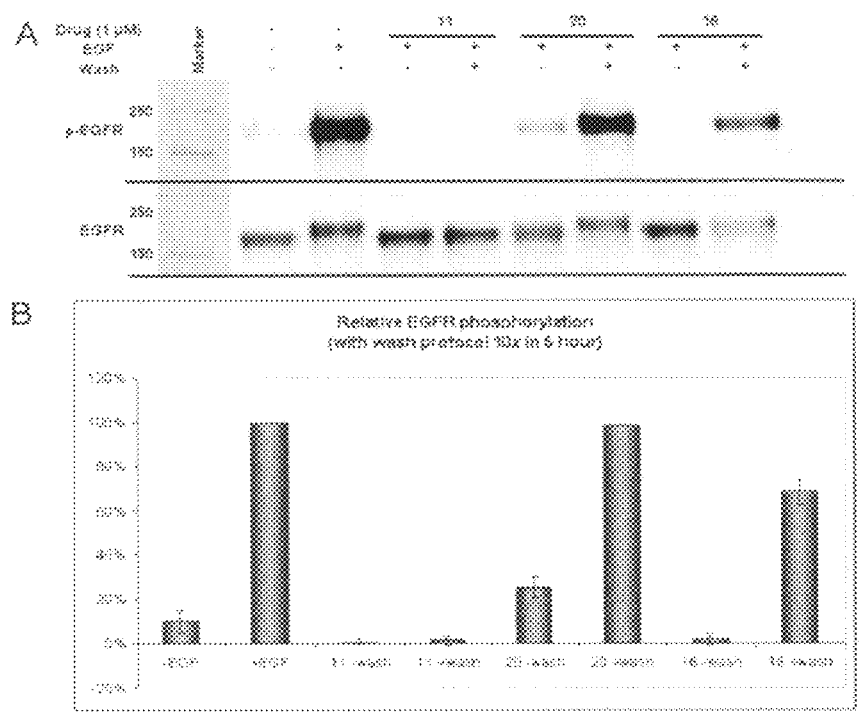
FIG. 1 shows A431 cellular autophosphorylation inhibition for compounds 11, 16 (kinase inhibitors) and 20 (a prodrug compound of the present invention).

As used herein, the terms "alkyl", "alkenyl", "alkenyl" and "alkoxy", unless otherwise specified, include both straight chain and branched chain groups, and unsubstituted and substituted groups. The optional substituents may include, without limitation, halogen, C1-C6 alkoxy, CN, OH, $NH_2$, $NO_2$, NH(C1-C6 alkyl), N(C1-C6 alkyl)$_2$, $CONH_2$, CO(C1-C6 alkyl), $SO_2NH_2$ and $SO_2$(C1-C6 alkyl).

As used herein, the term "quaternisable nitrogen", unless otherwise specified, means a fully substituted nitrogen of sufficient basicity (or nucleophilicity) to react with an electrophilic group such as an α-methyl halide/mesylate/tosylate or triflate to provide a quaternary ammonium salt of the said nitrogen.

As used herein, the term "aromatic nitroheterocycle" means an aromatic heterocyclic moiety substituted at any ring position by one or more nitro ($NO_2$) groups. The aromatic heterocyclic moiety may be a monocyclic or bicyclic ring containing 4 to 12 atoms of which at least one atom is chosen from nitrogen, sulphur or oxygen. The aromatic heterocyclic moiety may be carbon or nitrogen linked. The aromatic heterocyclic moiety may additionally be substituted by one or more additional substituents at any available ring carbon or heteroatom. The substituents may include, but are not limited to the groups as defined for $R_8$ in Formula III.

As used herein, the term "aromatic nitrocarbocycle" means a benzene moiety substituted at any position by one or more nitro ($NO_2$) groups. In addition, two adjacent ring carbon atoms may optionally be linked to form a fused carbocyclic or heterocyclic ring. The benzene moiety (and optional fused ring) may additionally be substituted by one or more additional substituents at any available carbon or heteroatom. The substituents may include, but are not limited to, the groups as defined for $R_8$ in Formula III.

As used herein, the term "cysteine trapping functionality" means an electrophilic group of sufficient reactivity to react covalently with an unpaired cysteine residue of a protein.

DETAILED DESCRIPTION

As defined above, in broad terms the invention relates to compounds which are inhibitors of kinase activity, particularly where such inhibition is for a therapeutic purpose. Kinase inhibition can be useful in treating proliferative disease or disorders, for example. This makes the compounds of the invention useful as anti-cancer agents, particularly as targeted anti-cancer agents.

In one form, the compounds of the invention comprise a kinase inhibitor and an aromatic nitroheterocycle or nitrocarbocycle that fragments when reduced (a reductive trigger), with the compound carrying a positive charge. The positive charge of the compound has important benefits, particularly in the treatment of cancer, as will be described below.

The reducing equivalents required to reduce the trigger may be provided by enzymes, radiation-induced radicals, or chemical reducing agents. Radiation can, for example, be particularly effective in both reducing the trigger and in targeting the release of the kinase inhibitor to regions in which a tumour or tumours exist. However, it is presently preferred that the trigger be reduced by endogenous enzyme(s) present within tumours (especially endogenous one-electron reductases) such that reduction is suppressed in the presence of oxygen. This preferred reduction by one-electron reductases effectively targets the release of the kinase inhibitors to regions of hypoxia within tumours. In this form, the compounds are therefore prodrugs which, upon reduction in a tumour-associated environment (also referred to herein as "reductive activation"), release a kinase inhibitor to produce an anti-cancer effect.

The kinase inhibitor can be any molecule or structure which has activity as a kinase inhibitor once released from the reductive trigger. Usually, the inhibitor will be an intact or substantially intact kinase inhibitor to which the trigger is attached or functionally linked, with the intact kinase inhibitor being released upon reduction.

The kinase inhibitor may be reversible or irreversible. Irreversible inhibitors are however preferred for combination with reductive triggers in the compounds herein. Most preferred are irreversible erbB1, 2, 4 kinase inhibitors, particularly ATP-competitive, irreversible inhibitors of erbB1, 2 and 4 kinases, which inhibit signal transduction pathways that are involved in tumour cell survival, proliferation, metastasis and therapeutic resistance. These inhibitors require a basic tertiary amine moiety. The tertiary amine moiety will be in close proximity to a cysteine-trapping functionality. This can be an epoxide such as with erbB-inhibitor B (Carmi, C et al, *J. Med. Chem.* 2010, ASAP Online, DOI:10:1021/jm901558p). More preferably, the cysteine-trapping functionality is a Michael acceptor. In such embodiments, the Michael acceptor may contain either a double or triple bond. The amine provides base catalysis of the reaction between a cysteine residue at the mouth of the ATP-binding domain of erbB1, 2 and 4 and the Michael acceptor, resulting in irreversible inhibition of the kinase targets. Inhibition of cell signalling through kinase-inactive erbB3 is achieved by such compounds through inhibition of its heterodimerisation partners, so that in effect cell signalling through the entire erbB family (erbB1-4) is inhibited by these compounds.

As referenced above, the reductive trigger of the prodrug is an aromatic nitroheterocycle or nitrocarbocycle that undergoes fragmentation upon reduction. This nitroheterocyclic or nitrocarbocyclic unit is preferably linked to the kinase inhibitor via a quaternisable nitrogen, such as through an exocyclic methylene linker, to form a quaternary nitrogen salt and to thereby create a positive charge. Fragmentation of the trigger under reductive conditions releases the active kinase inhibitor, with the nitrogen to which the trigger was linked remaining part of the released kinase inhibitor.

For activation by endogenous reductases, the requirement that fragmentation of the reductive trigger be effectively suppressed by oxygen is critical. Fragmentation of the trigger occurs at the one-electron reduction level by endogenous one-electron reductases. Suppression of effective fragmentation by oxygen may occur through reoxidation of the one-electron radical by oxygen, or by oxidation by reducing intermediates required for prodrug reduction. The latter would include, for example, scavenging by oxygen of radiation-induced reducing radicals such as the aquated electron, or oxidation of reducing intermediates in the catalytic cycle of reductase enzymes. But whatever the mechanism, an oxygen-suppressive effect is the result.

Such suppression is important for the selective targeting of the prodrugs. Tumour-associated environments will commonly be hypoxic. Without wishing to be bound by theory, restriction of inhibitor release to hypoxic tissue and subsequent back-diffusion of the inhibitor to oxygenated areas of the tumour is believed to be a primary basis for tumour selectivity via endogenous enzymes. This targeting of the release of the kinase inhibitor to tumours is also beneficial in broadening the therapeutic opportunity for such inhibitors, particularly irreversible erbB1, 2, 4 inhibitors with a broad spectrum of kinase-receptor binding targets.

Preferred triggers include those of Formula III:

Formula III

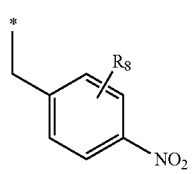

a

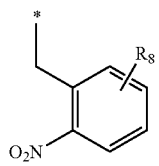

b

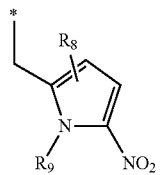

c

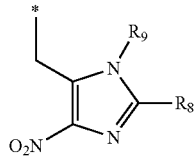

d

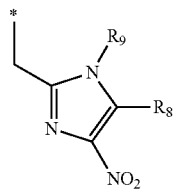

e

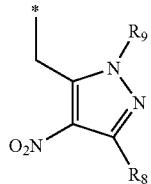

f

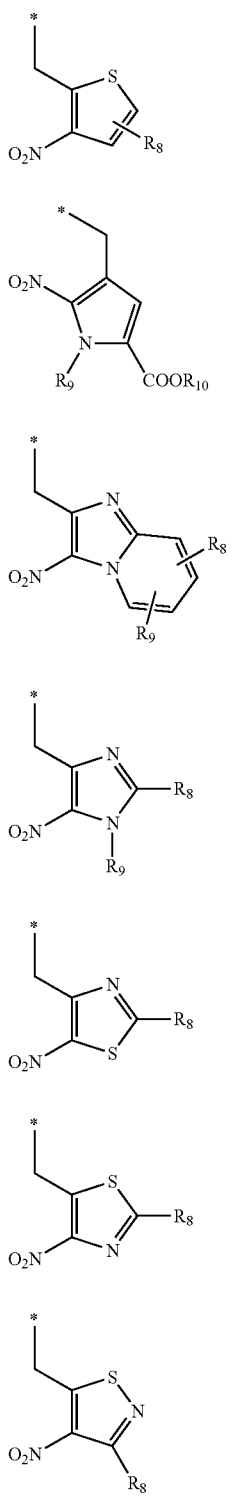

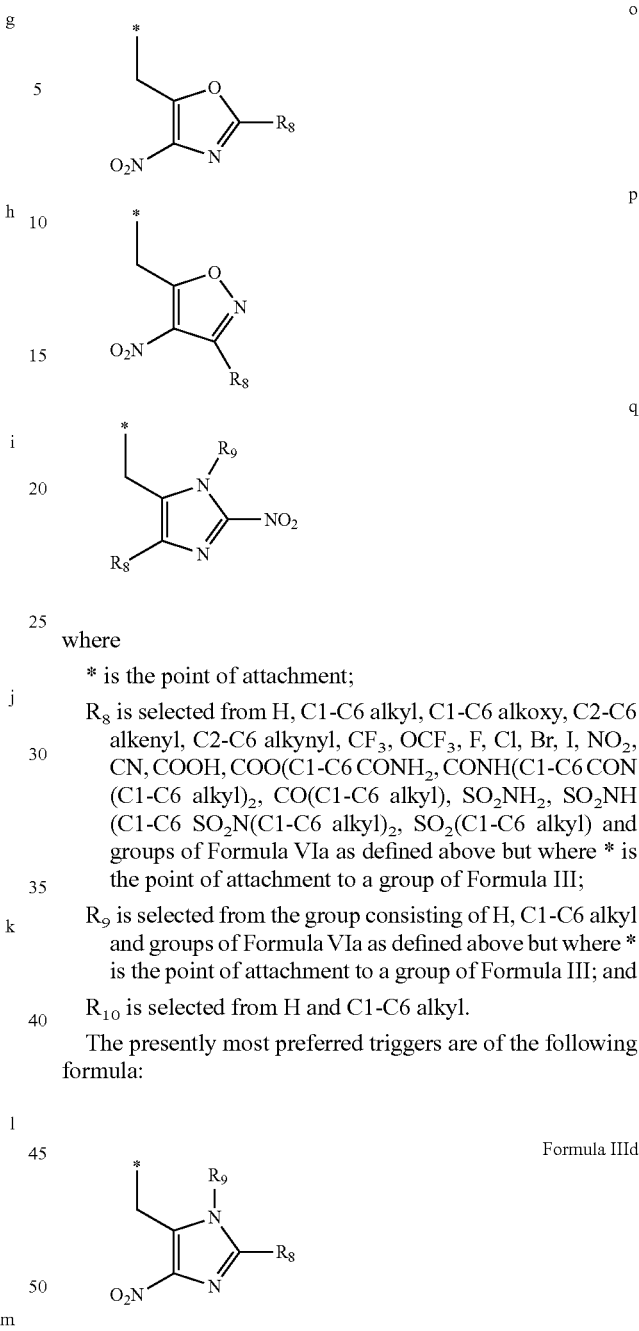

where
* is the point of attachment;

$R_8$ is selected from H, C1-C6 alkyl, C1-C6 alkoxy, C2-C6 alkenyl, C2-C6 alkynyl, $CF_3$, $OCF_3$, F, Cl, Br, I, $NO_2$, CN, COOH, COO(C1-C6 $CONH_2$, CONH(C1-C6 CON (C1-C6 alkyl)$_2$, CO(C1-C6 alkyl), $SO_2NH_2$, $SO_2NH$ (C1-C6 $SO_2N$(C1-C6 alkyl)$_2$, $SO_2$(C1-C6 alkyl) and groups of Formula VIa as defined above but where * is the point of attachment to a group of Formula III;

$R_9$ is selected from the group consisting of H, C1-C6 alkyl and groups of Formula VIa as defined above but where * is the point of attachment to a group of Formula III; and $R_{10}$ is selected from H and C1-C6 alkyl.

The presently most preferred triggers are of the following formula:

Formula IIId where * is a point of attachment, $R_8$ is selected from H and C1-C3 alkyl, and $R_9$ is selected from H and C1-C6 alkyl, preferably C1-C3 alkyl.

A number of these triggers are included in the group consisting of the following moieties:

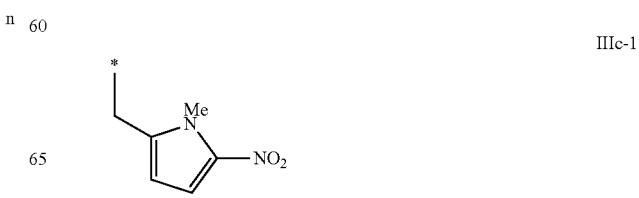

IIIc-1

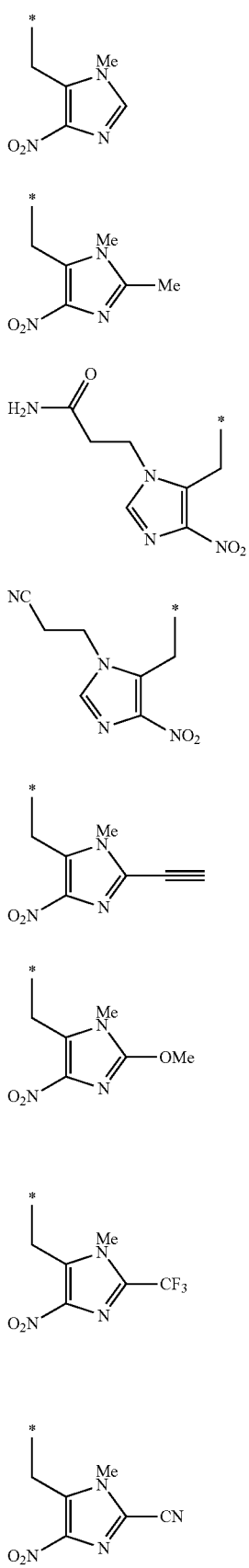
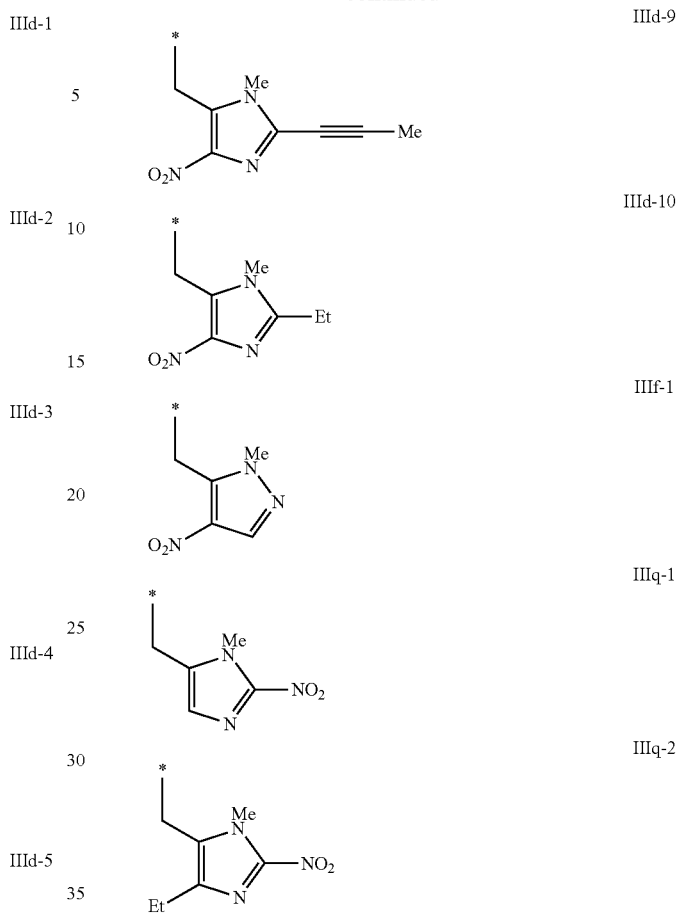

In addition to having a positive charge and a trigger selected as above, it is further preferred that the prodrug have a one-electron reduction potential, (E(1)), of between −0.2 V and −0.6 V against NHE. The E(1) value is of assistance in optimising the compound of the invention for reduction under hypoxic conditions. More preferably, the E(1) value is between −0.3 V and −0.5 V, still more preferably between −0.35 and −0.45 V and most preferably between −04 V and −0.45 V against NHE. The E(1) of a compound can be determined as described in by Meisel and Czapski (J. Phys. Chem., 1975, 79, 1503-1509).

It is also preferred that the prodrugs of the invention meet certain criteria with respect to the rate at which the prodrug fragments under one-electron reduction to release the kinase inhibitor. These rates (expressed as fragmentation rate constants) can be between 1 and 4000 s$^{-1}$, with ranges between 1 and 3000 s$^{-1}$, 1 and 1500 s$^{-1}$, 2 and 500 s$^{-1}$, 2 and 300 s$^{-1}$, 2 and 60 s$^{-1}$ and 20 and 60 s$^{-1}$ being exemplary dependent upon whether a faster or slower fragmentation of the prodrug is viewed as desirable.

The rate constants for fragmentation, kfrag, of the one-electron reduced prodrugs can be measured using pulse radiolysis to observe the formation of the absorption spectrum of the benzyl-type radical [Anderson, R. F. et al, *J. Phys. Chem A*, 101:9704-9769, 1997].

In particularly preferred embodiments, a trigger/kinase inhibitor combination making up the prodrug can be selected to meet certain criteria in combination. For example, the trigger/kinase inhibitor combination can be selected to have an E(1) value of between −0.2 V and −0.6 V and a fragmentation rate constant, upon one-electron reduction, of between 1 and 4000 s$^{-1}$, an E(1) value of between −0.3 V and −0.5 V and a fragmentation rate constant, upon one-electron reduction, of between 1 and 3000 s$^{-1}$ (preferably between 1 and 1500 s$^{-1}$), an E(1) value of between −0.35 V and −0.45 V and a fragmentation rate constant, upon one-electron reduction, of between 2 and 500 s$^{-1}$, 10 and 300 s$^{-1}$ or 20 and 60 s$^{-1}$, and an E(1) value of between −0.4 V and −0.45 V and a fragmentation rate constant, upon one electron reduction, of between 20 and 60 s$^{-1}$ (preferably between 40 and 55 s$^{-1}$).

Overall, the prodrugs of the invention formed by the combination of the fragmenting reductively-activated trigger and a kinase inhibitor have been determined by the applicants to have a number of surprising properties that make them particularly suitable as targeted anti-cancer agents. Foremost amongst these properties is their targeted efficacy. The applicants have determined that, out of the numerous reductive triggers already generally known in the art such as nitrobenzyl carbamates (Hay et al. J Med Chem, 2003, 46, 2456-2466; Sykes et al. J Chem Soc Perk Trans 1, 2000, 10, 1601-1608; Hay et al. J Chem Soc Perk Trans 1, 1999, 2759-2770), nitroarylmethyl carbamates (Hay et al. Tetrahedron, 2000, 56, 645-657; Hay et al. Bioorg Med Chem Lett, 1999, 9, 2237-2242; Davis et al. PCT Int. application WO 2006032921), 5-nitrofuran-2-ylmethylidene ethers (Mahmud et al. Anticancer Drug Des, 1998, 13, 655-662), nitrobenzyl thioethers (Thomson et al. Bioorg Med Chem Lett, 2007, 17, 4320-4322), nitrothienylprop-2-yl ethers (Thomson et al. Mol Cancer Ther, 2006, 5(11), 2886-2894) and 2-aryl-6-methyl-5-nitroquinoline ethers (Couch et al. Tetrahedron, 2008, 64, 2816-2823) it is the triggers defined above and the preferred quaternary salts in particular which first allow safe delivery of the prodrug to the proximate region of the targeted tumour and then efficiently fragment under the prevailing tumour-associated conditions to release the cytotoxic effector to have a therapeutic anti-tumour effect. This contrasts with other reductive triggers which either lack stability, are activated prior to delivery to the tumour region or which inefficiently release the effector with much reduced cytotoxic impact on the tumour. It is this surprising efficacy that underpins the present invention.

This capability of the prodrugs of the invention is particularly surprising where, as is preferred, the reductive trigger is coupled to the kinase inhibitor as a quaternary nitrogen salt. The synthesis and evaluation of a series of nitroarylmethyl quaternary salts as reductive prodrugs of the alkylating agent mechlorethamine was reported in Tercel, M., et al, J. Med. Chem 2001, 44, 3511-3522. The authors reported highly variable toxicity across a series of such prodrug compounds. Even with respect to the most promising compound in terms of tumour-selective cytotoxic activity, it was reported that the activity was accompanied by unpredictable host toxicity. The conclusion was that the nitroarylmethyl quaternary salts were "too unstable with regard to non-specific release of mechlorethamine to be of use as bioreductive agents" (see page 3517).

The preferred selection of prodrugs with defined E(1) and defined fragmentation rate constants also offers advantages, both in terms of assisting with effective one-electron reduction under hypoxia and with the targeting of transient, and shifting, hypoxia within tumours, as will be described below.

Preparation of Quaternary Nitrogen Salt Prodrugs of the Invention

The prodrug compounds of Formula I and Formula II of the present invention comprise an effector moiety linked to a nitroheterocyclic reductive trigger.

The effector moiety can be a reversible or irreversible kinase inhibitor. It may inhibit the kinase by binding in the ATP-binding domain, the kinase substrate-binding domain or in an allosteric binding site. Irreversible inhibitors are preferred, particularly irreversible erbB1, 2, 4 kinase inhibitors.

Examples of other classes of kinase inhibitors include inhibitors of PDGFRα, PDGFRβ, VEGFR1, VEGFR2, VEGFR3, ABL, KIT, AKT1, AKT2, AKT3, p70 S6K, MEK, c-MET, JAK2, JAK3, SRC, LCK, p38 MAPK, CHK1, CHK2, FGFR, DNA-PK, ATM, ATR, AuroraA, AuroraB, P13K family isoforms p110α, β, γ and mTOR.

Specific examples of kinase inhibitors useful in the present invention include AST-487, CHIR-258, Imatinib, VX-680, LY-333531, MLN-518, SU-14813, Sunitinib, PI-103, ZD6474, Sorafenib, Dasatinib, PD 166285, PD 166285 analogue A, PD 166285 analogue B, AEE788, N-methylstaurosporine, BIBW2992, HKI272, EKB569, Gefitinib, Vargatef, Cediranib, Bosutinib, AZD0530, BIRB796, PHA-665752, 10-DEBC, GDC-0941, MK-2206 analogue, Masitinib, SU11274, XL880, XL184, ZM39923, AZD1152, Danusertib, ZM447439 and PKI-587.

The most preferred irreversible erbB1, 2, 4 kinase inhibitors possess an amide Michael acceptor in the 6-position to provide a cysteine-trapping functionality. With these inhibitors, the Michael acceptor may feature either a double or triple bond and be substituted at the beta carbon with a methylene chain of variable length that terminates with a tertiary amine, as shown below.

Formula VII

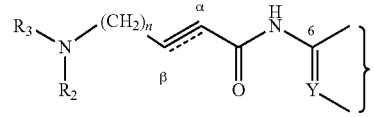

It will be appreciated that the remainder of the effector moiety not shown in Formula VII has a bicyclic aromatic ring structure as defined in Formula II.

In general terms, the preferred prodrug compounds of Formula I and Formula II may be prepared by quaternising an aliphatic tertiary amine or aromatic heterocyclic amine effector moiety with a nitroheterocyclic reductive trigger moiety. Methods of preparing the compounds of Formula I and Formula II are described in more detail below.

Preparation of Irreversible erbB1, 2, 4 Kinase Inhibitors

Effector compounds of the Formula VII as shown above, and where Y and Z are not both N simultaneously and the Michael acceptor contains a double bond, are known and may be prepared according to methods described in the art. For example, such compounds and methods of preparation thereof have been described in Tsou et al. J Med Chem, 2001, 44, 2719-2734, Wissner et al. J Med Chem, 2003, 46, 49-63, Wissner et al. Bioorg Med Chem Lett, 2004, 14, 1411-1416, Tsou et al. J Med Chem, 2005, 48, 1107-1131, Klutchko et al. J Med Chem, 2006, 49, 1475-1485, U.S. Pat. No. 6,251,912 (Wissner et al.), U.S. patent application 2002/0173509 (Himmelsbach et al.), U.S. Pat. No. 7,019,012 (Himmelsbach et al.), U.S. patent application 2005/0250761 (Fakhoury et al.), U.S. Pat. No. 6,288,082 (Wissner et al.), U.S. Pat. No. 6,297,258 (Wissner et al.), U.S. Pat. No. 7,399,865 (Wissner et al.), U.S. Pat. No. 6,355,636 (Wissner et al.), U.S. Pat. No. 6,602,863 (Bridges et al.).

Also by way of example, compounds 11, 12 and 13 shown below can be prepared by the methods disclosed in Tsou et al. J Med Chem 2001; 44:2719-34.

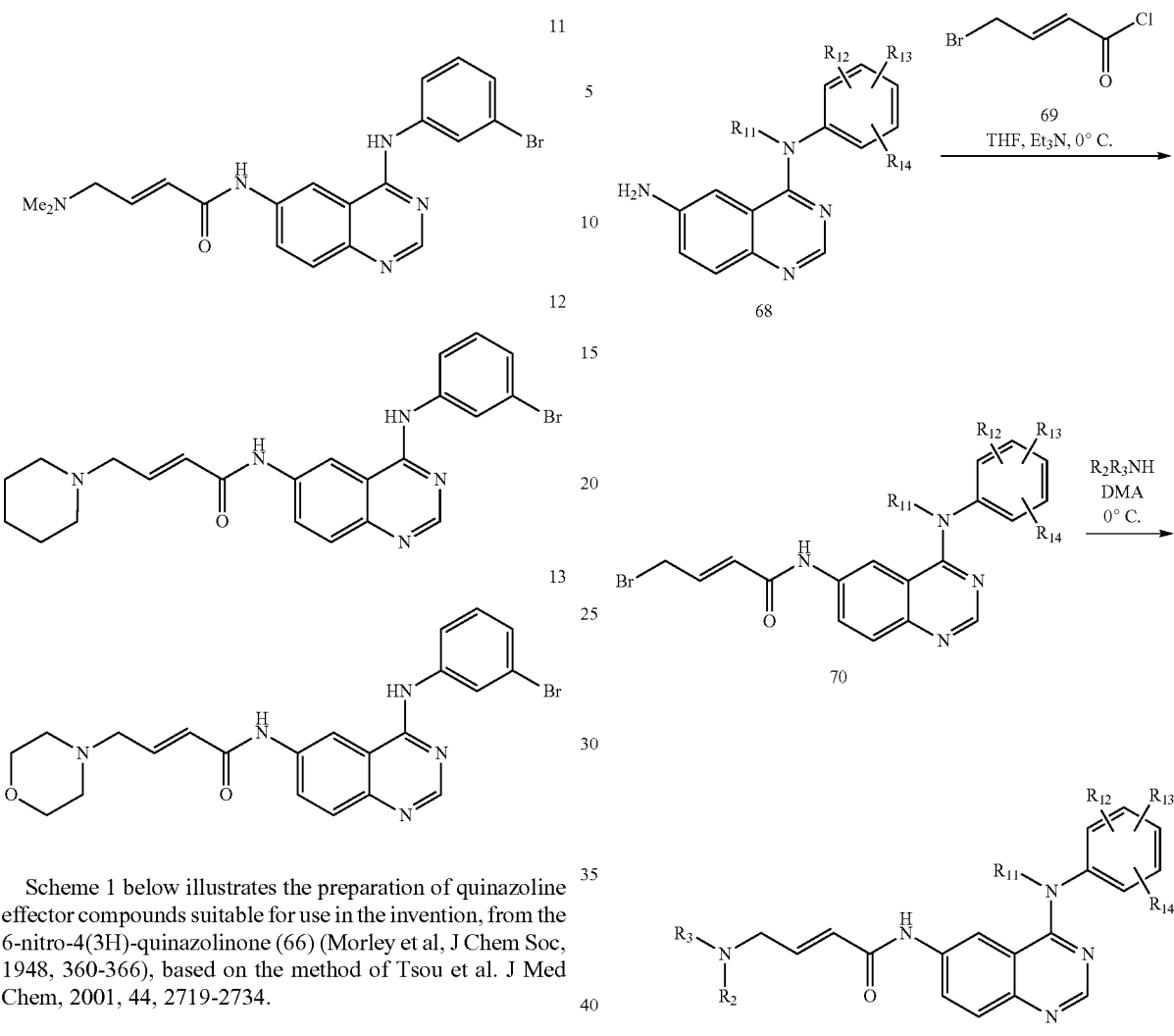

Scheme 1 below illustrates the preparation of quinazoline effector compounds suitable for use in the invention, from the 6-nitro-4(3H)-quinazolinone (66) (Morley et al, J Chem Soc, 1948, 360-366), based on the method of Tsou et al. J Med Chem, 2001, 44, 2719-2734.

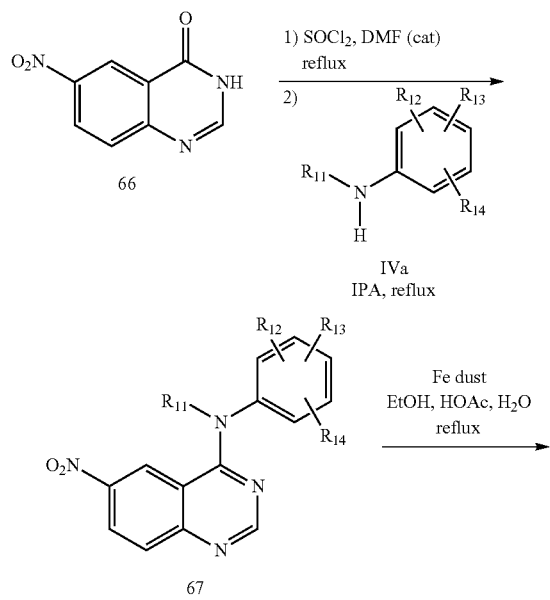

Scheme 2 below illustrates the preparation of 7-alkoxyquinazoline effector compounds suitable for use in the invention, from the 7-fluoro-6-nitro-4(3H)-quinazolinone (72) (Rewcastle et al, J Med Chem, 1996, 39, 918-928) based on the methods of Tsou et al. J Med Chem, 2001, 44, 2719-2734 and Smaill et al. J Med Chem, 2000, 43, 1380-1397.

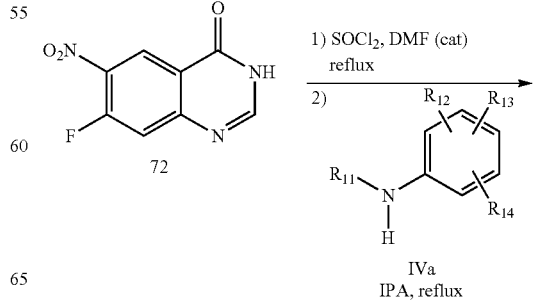

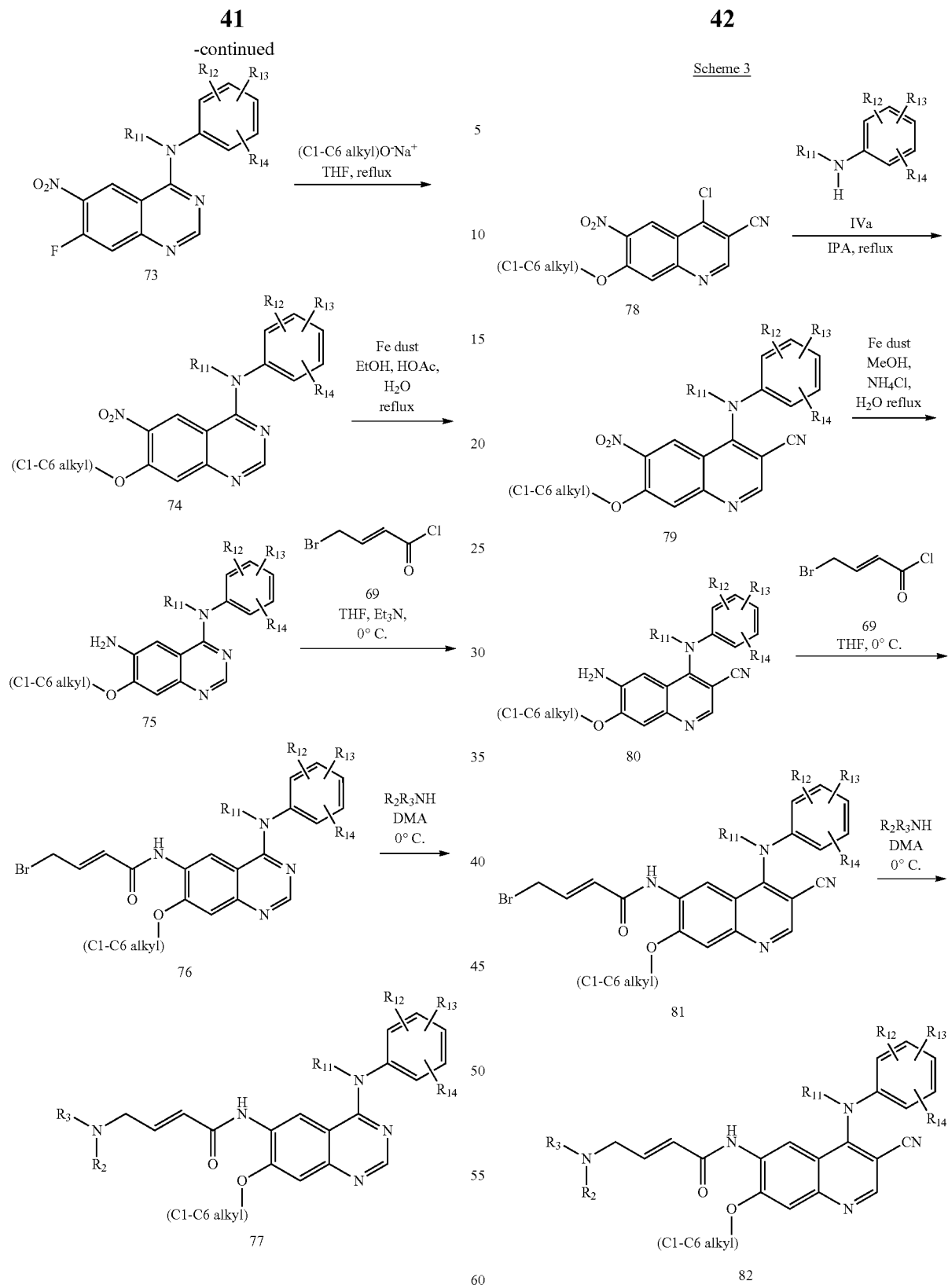

Scheme 3 below illustrates the preparation of 7-alkoxyquinolinecarbonitrile effector compounds suitable for use in the invention, from the 7-alkoxy-4-chloro-6-nitro-3-quinolinecarbonitriles (78) based on the method reported by Wissner et al. J Med Chem, 2003, 46, 49-63.

Scheme 4 below illustrates the preparation of 4-anilino-[1,7]naphthyridine-3-carbonitrile effector compounds suitable for use in the invention, from the 4-chloro-6-fluoro[1,7]naphthyridine-3-carbonitrile (83) based on the method reported by Wissner et al. Bioorg Med Chem Lett, 2004, 14, 1411-1416.

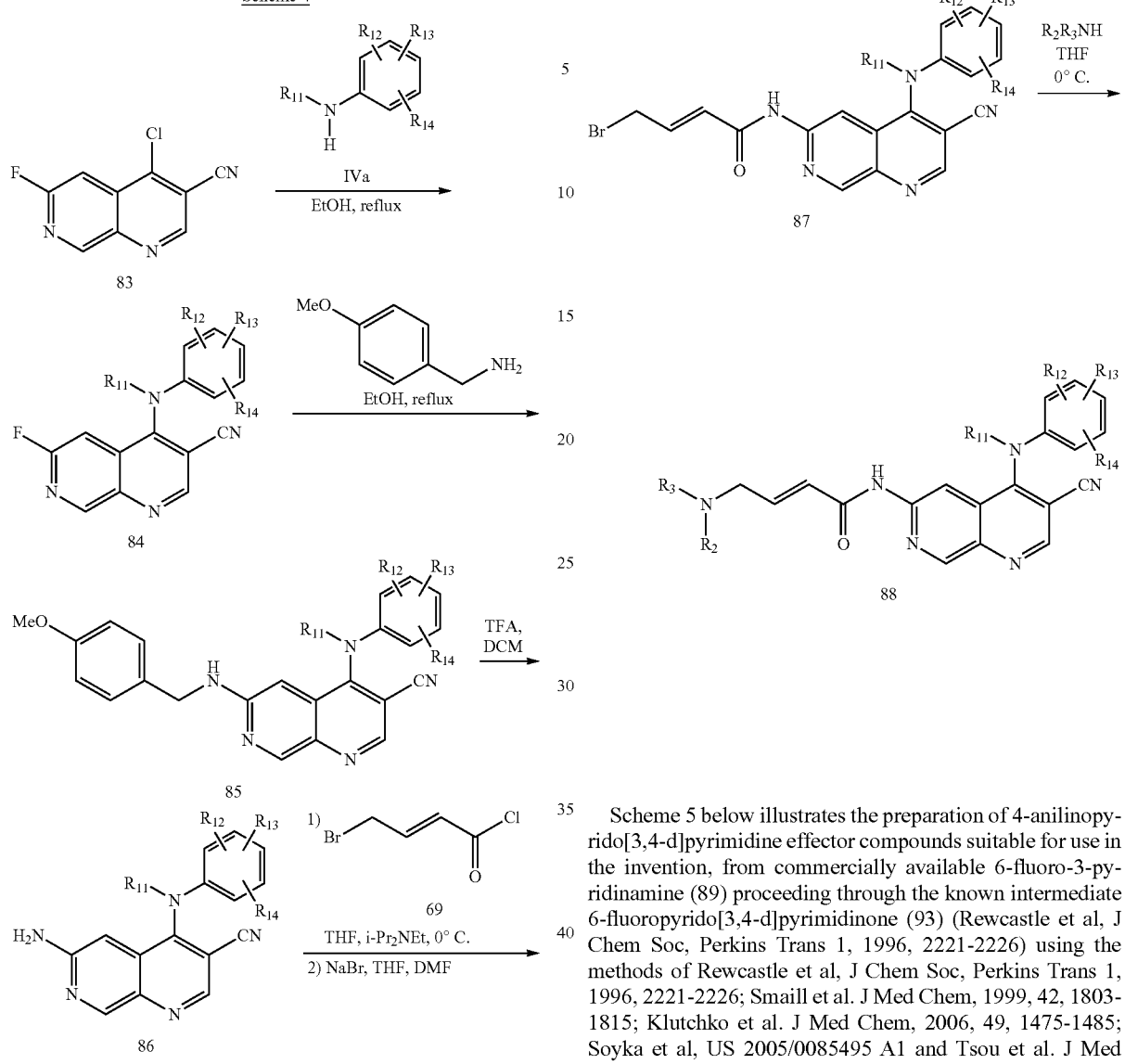

Scheme 5 below illustrates the preparation of 4-anilinopyrido[3,4-d]pyrimidine effector compounds suitable for use in the invention, from commercially available 6-fluoro-3-pyridinamine (89) proceeding through the known intermediate 6-fluoropyrido[3,4-d]pyrimidinone (93) (Rewcastle et al, J Chem Soc, Perkins Trans 1, 1996, 2221-2226) using the methods of Rewcastle et al, J Chem Soc, Perkins Trans 1, 1996, 2221-2226; Smaill et al. J Med Chem, 1999, 42, 1803-1815; Klutchko et al. J Med Chem, 2006, 49, 1475-1485; Soyka et al, US 2005/0085495 A1 and Tsou et al. J Med Chem, 2001, 44, 2719-2734.

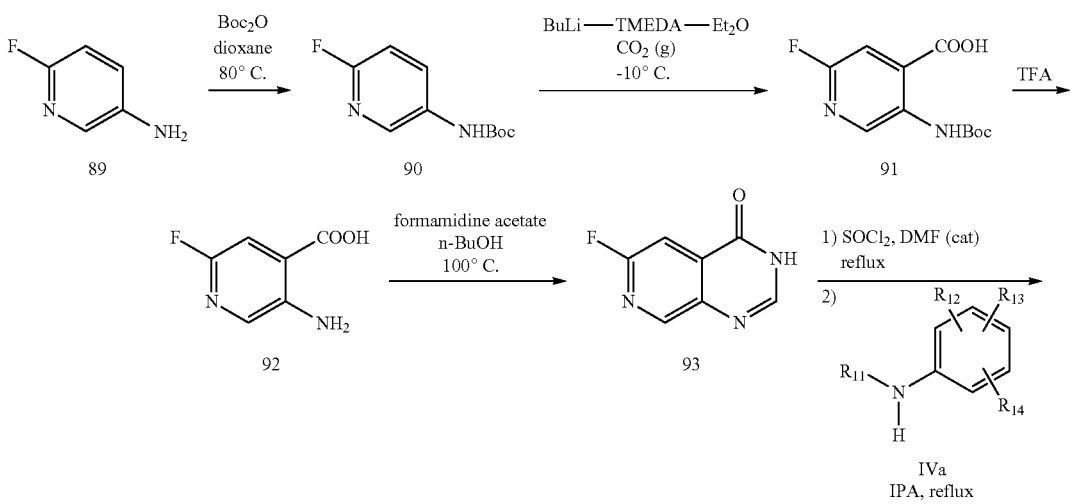

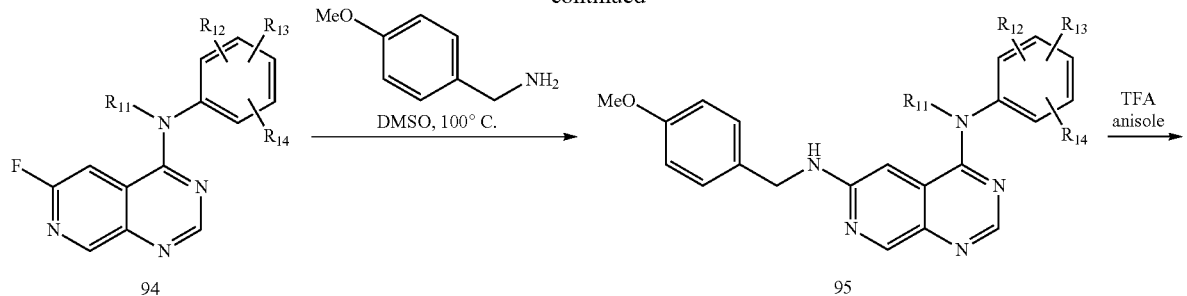

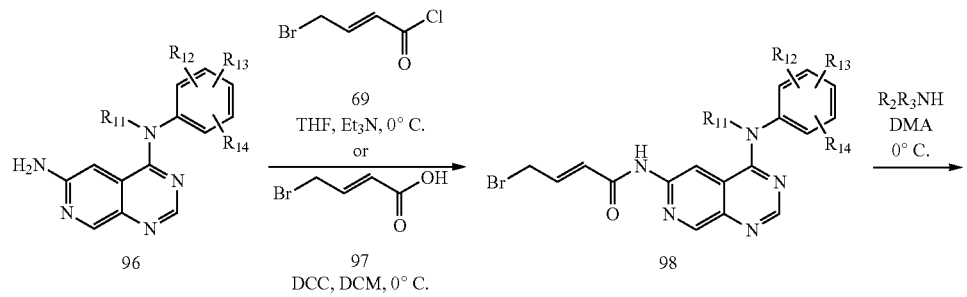

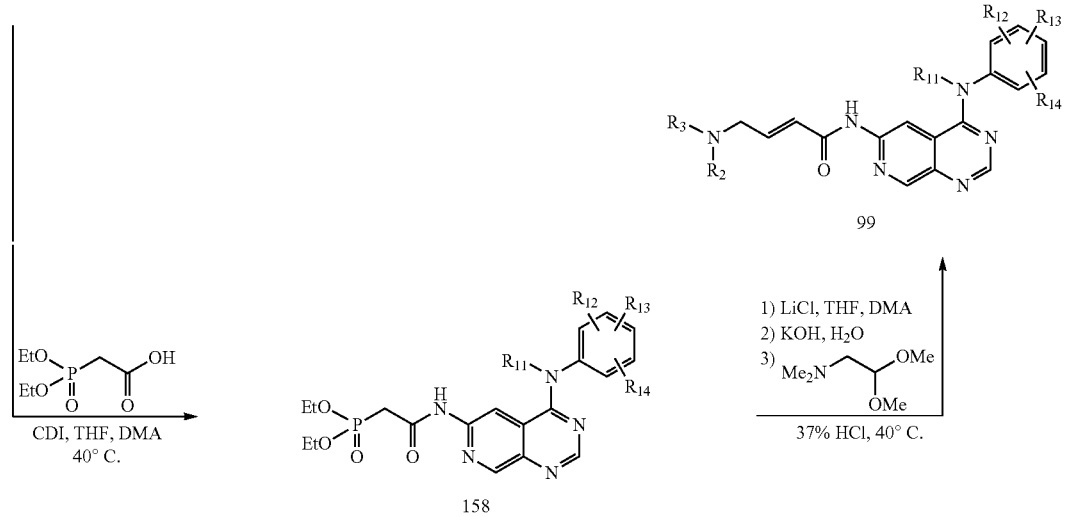

Schemes 1 to 5 above depict examples of synthetic routes where $R_5$ is selected to be of Formula IVa. It will be appreciated that the above routes can equally be applied when $R_5$ is selected from Formulae IVb to IVg as has been demonstrated for the quinolinecarbonitrile effector compounds by Tsou et al. J Med Chem, 2005, 48, 1107-1131.

Scheme 6 below illustrates the preparation of two specific effector compounds suitable for use in the invention. Compounds 14 and 16 may be prepared by reaction of the known 6-amino derivatives 8 (Bridges et al, J Med Chem, 1996, 39, 267-276) and 10 (Rewcastle et al, J Med Chem, 1995, 38, 3482-3487) with either (2E)-4-bromo-2-butenoyl chloride or 4-chlorobutanoyl chloride, followed by reaction of the resultant alkyl halides with aqueous dimethylamine.

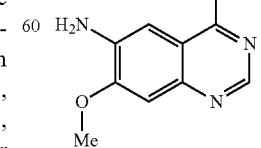

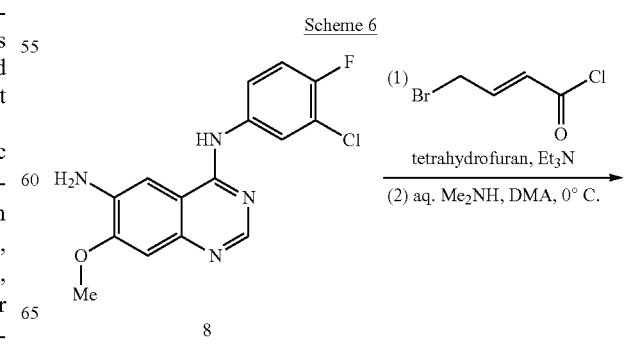

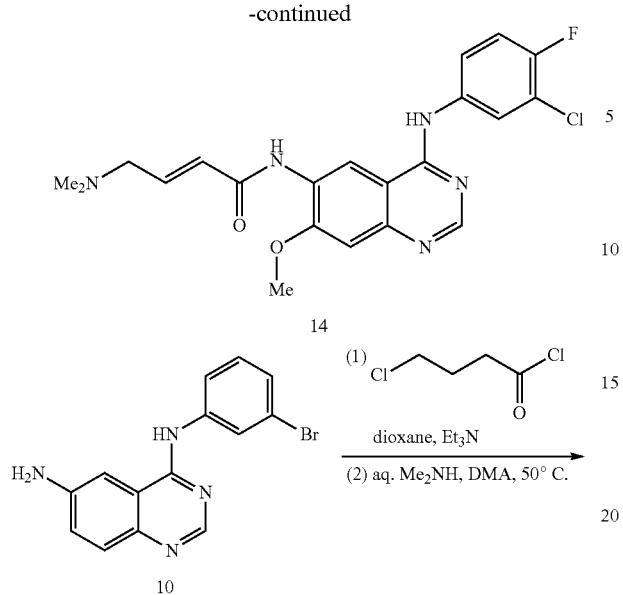
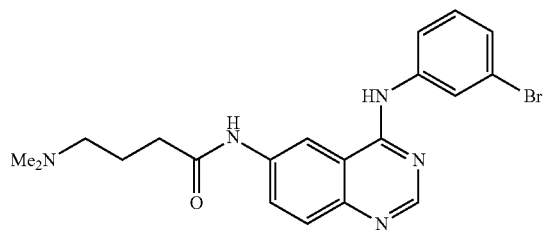
Compounds 161, 170 and 171 can be prepared by Scheme 7 below:
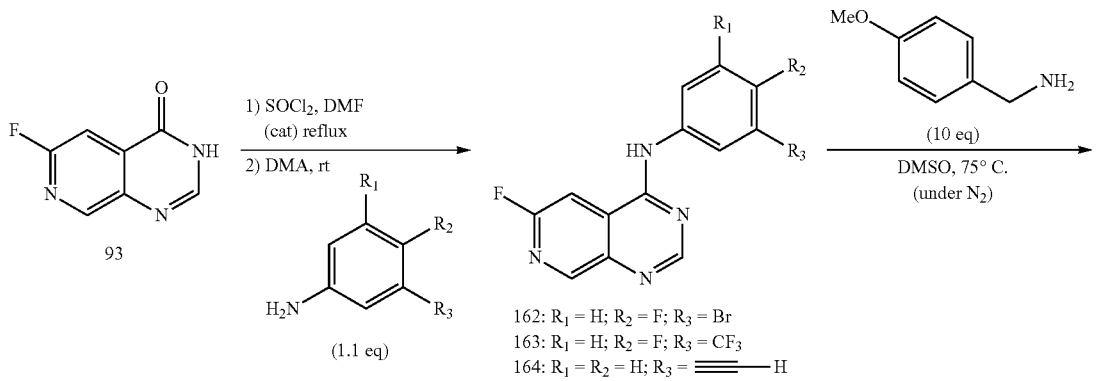
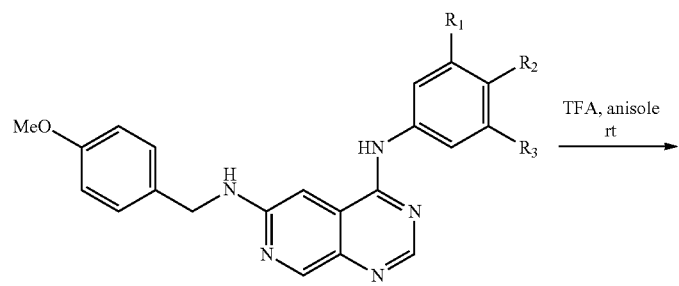

Preparation of Prodrugs

The prodrug compounds of Formula I may, in general terms, be prepared by reacting an aliphatic tertiary amine- or aromatic heterocyclic amine-bearing kinase inhibitor with an appropriate nitroheterocyclic or nitrocarbocylic α-methyl halide/mesylate/tosylate, in a suitable solvent and for a suitable length of time (for example in tetrahydrofuran for about 24 hours), to produce a quaternary nitrogen salt of Formula I.

The prodrug compounds of Formula II may, in general terms, be prepared by reacting an effector compound of the Formula VII as defined above with an appropriate nitroheterocyclic or nitrocarbocylic α-methyl halide/mesylate/tosylate, in a suitable solvent and for a suitable length of time (for example in tetrahydrofuran for about 24 hours), to produce a quaternary ammonium salt of Formula II.

Preferred reductive trigger moieties suitable for use in the prodrugs of the invention are those of Formula III shown below:

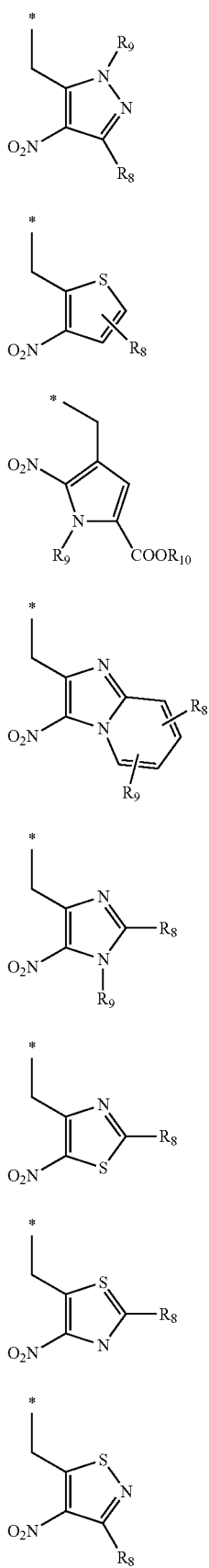
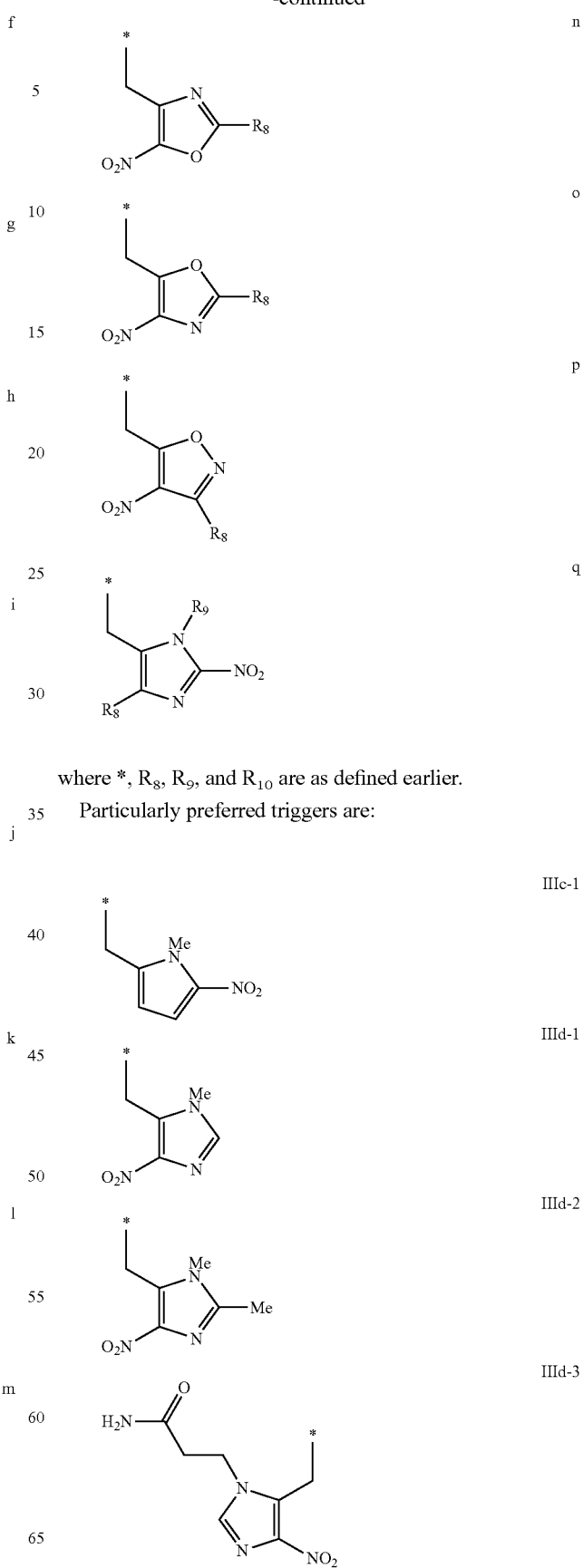
where *, $R_8$, $R_9$, and $R_{10}$ are as defined earlier.
Particularly preferred triggers are:

-continued

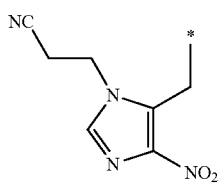
IIId-4

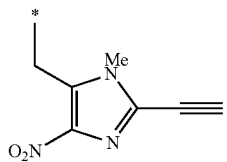
IIId-5

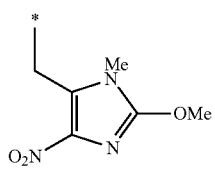
IIId-6

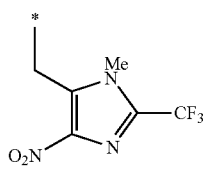
IIId-7

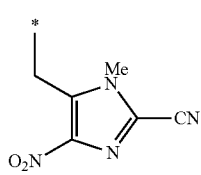
IIId-8

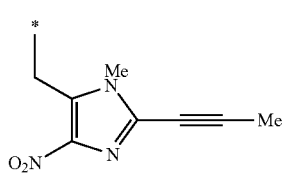
IIId-9

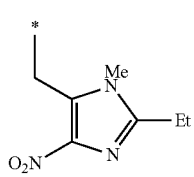
IIId-10

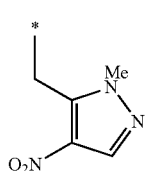
IIIf-1

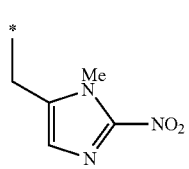
IIIq-1

-continued

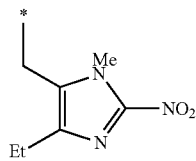
IIIq-2

The α-methyl halides of the above IIIc-1 and IIId-1, are known (bromides; Stribbling et al, PCT International patent publication WO 2008/039087); (chlorides; Tercel et al, J Med Chem, 2001, 44, 3511-3522; Jentzer et al. Eur J Med Chem 1991; 26, 687-697), as are the α-methyl bromides of the above IIIq-1 and IIIq-2 (Everett et al, Bioorg Med Chem Lett, 1999, 9, 1267-1272 and Jiao et al, WO 2008151253 A1, respectively).

Scheme 8 below illustrates three alternate routes to the known α-methyl bromide (105), from commercially available starting materials.

Scheme 8

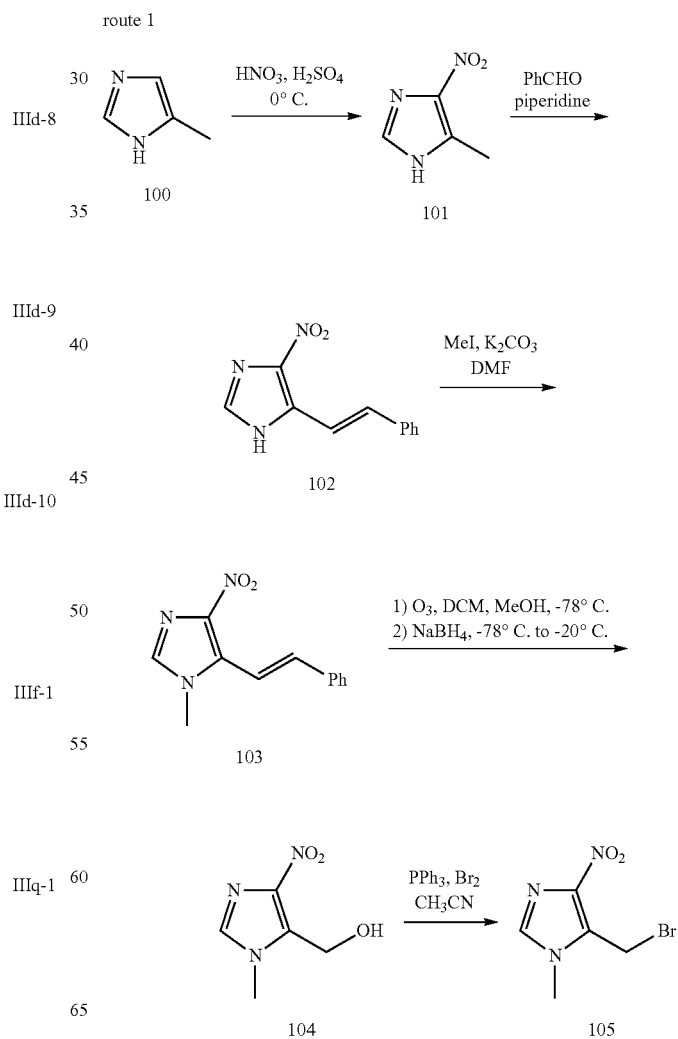

route 2
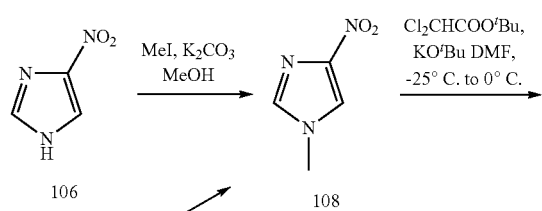
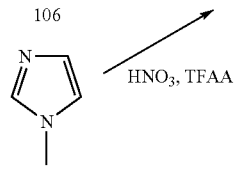
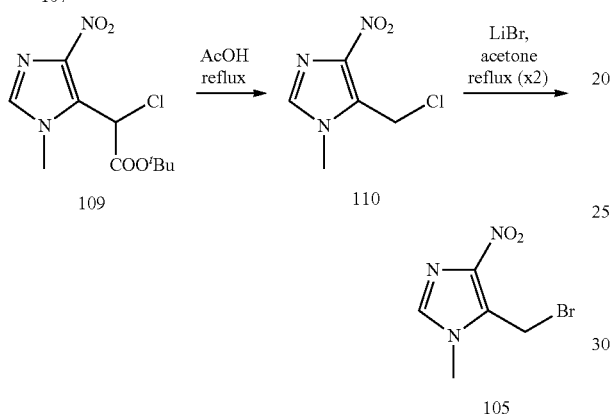
route 3
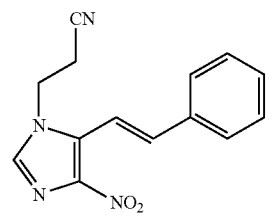
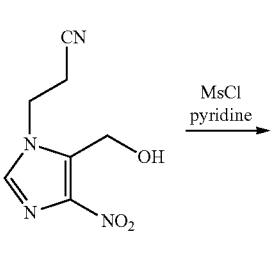
Scheme 9 below illustrates two alternate routes to the novel α-methyl bromides 115 and 116, from commercially available starting materials.
Scheme 9
route 1
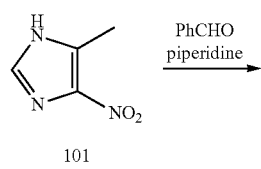
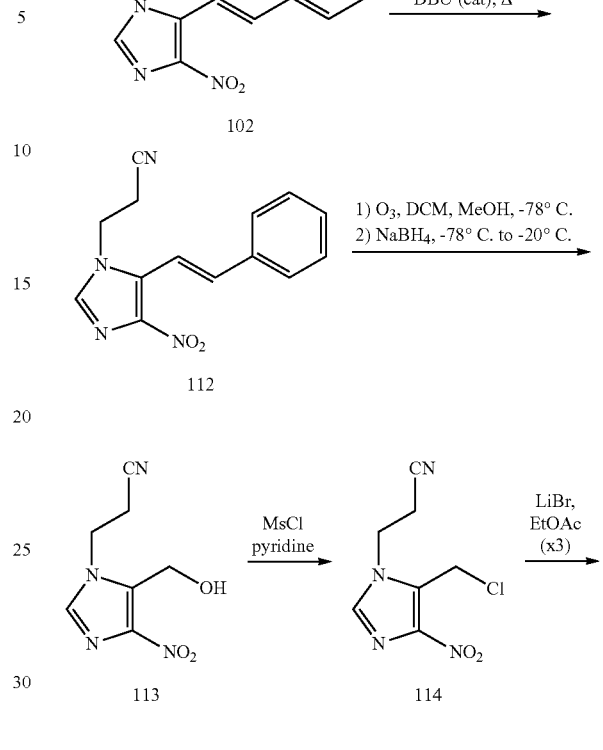
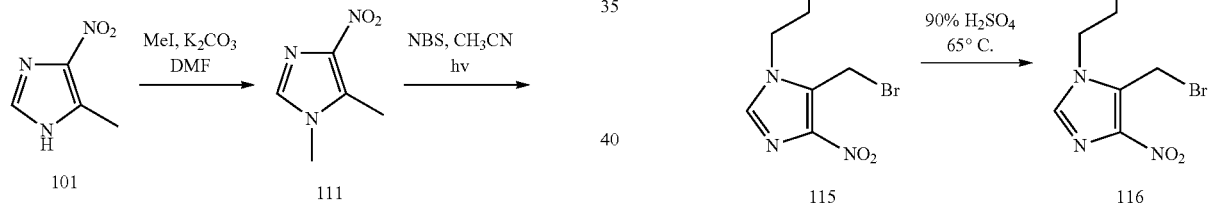
route 2
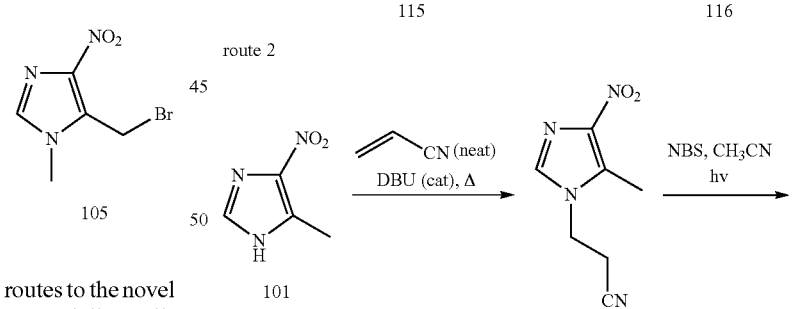
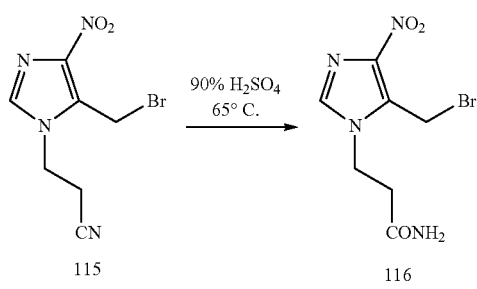

Scheme 10 below illustrates a route to the novel α-methyl bromide 122, from commercially available starting materials.

Scheme 10

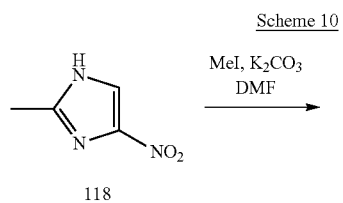

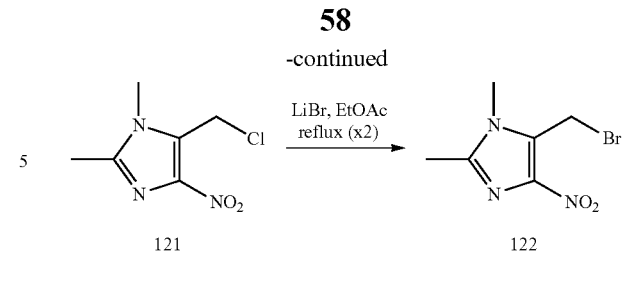

Scheme 11 below illustrates a route to the novel α-methyl bromide 125 from commercially available starting materials and routes to the novel α-methyl bromides 127 and 130 from the 2-bromoimidazole 153 (described below).

Scheme 11

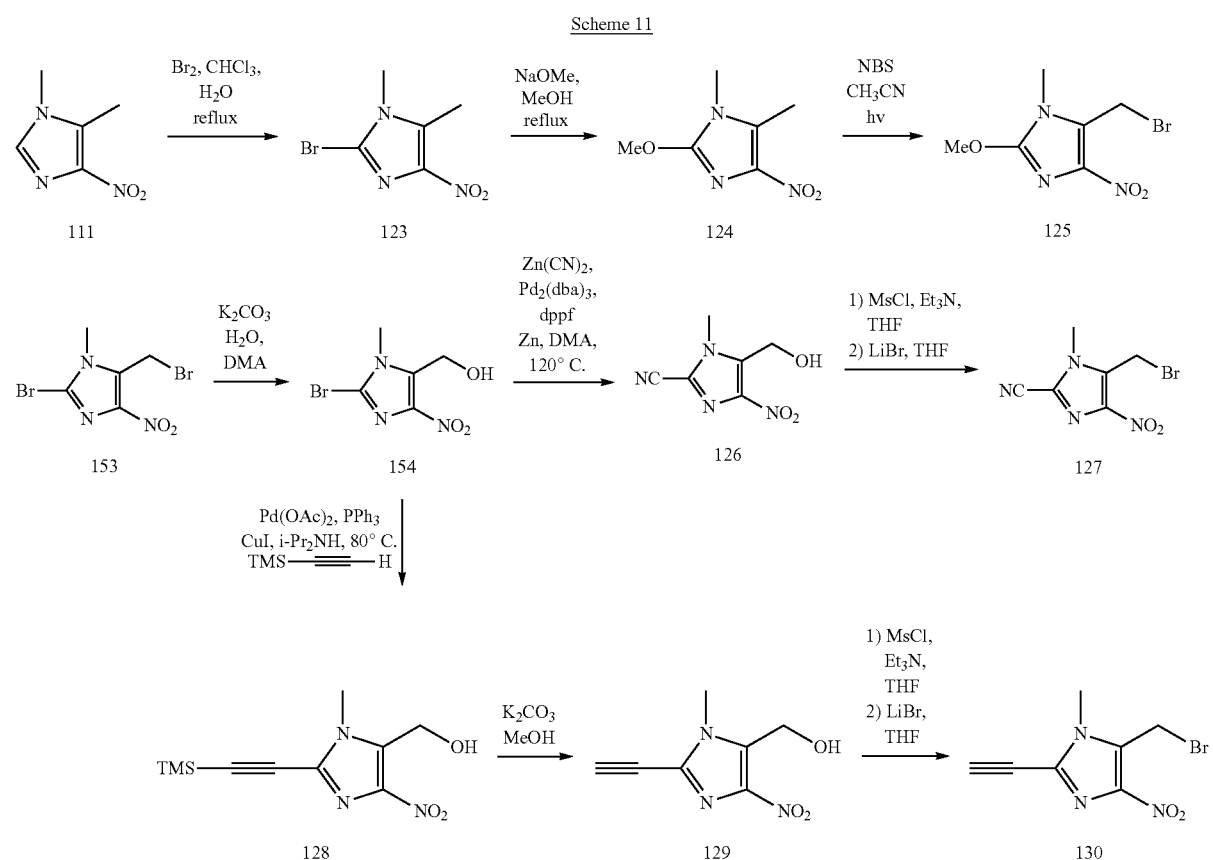

-continued

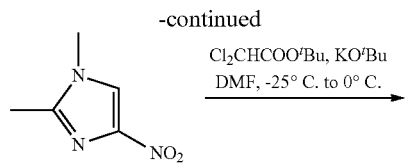

Scheme 12 below illustrates a route to the novel α-methyl bromide 136, from a commercially available starting material or from the 2-bromoimidazole derivatives 123 or 154 (described below).

Scheme 12 route 1

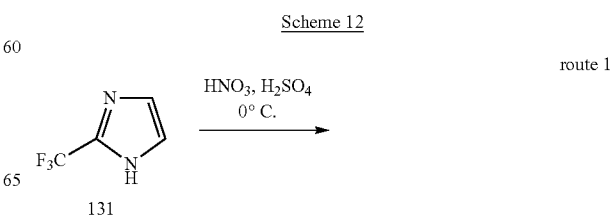

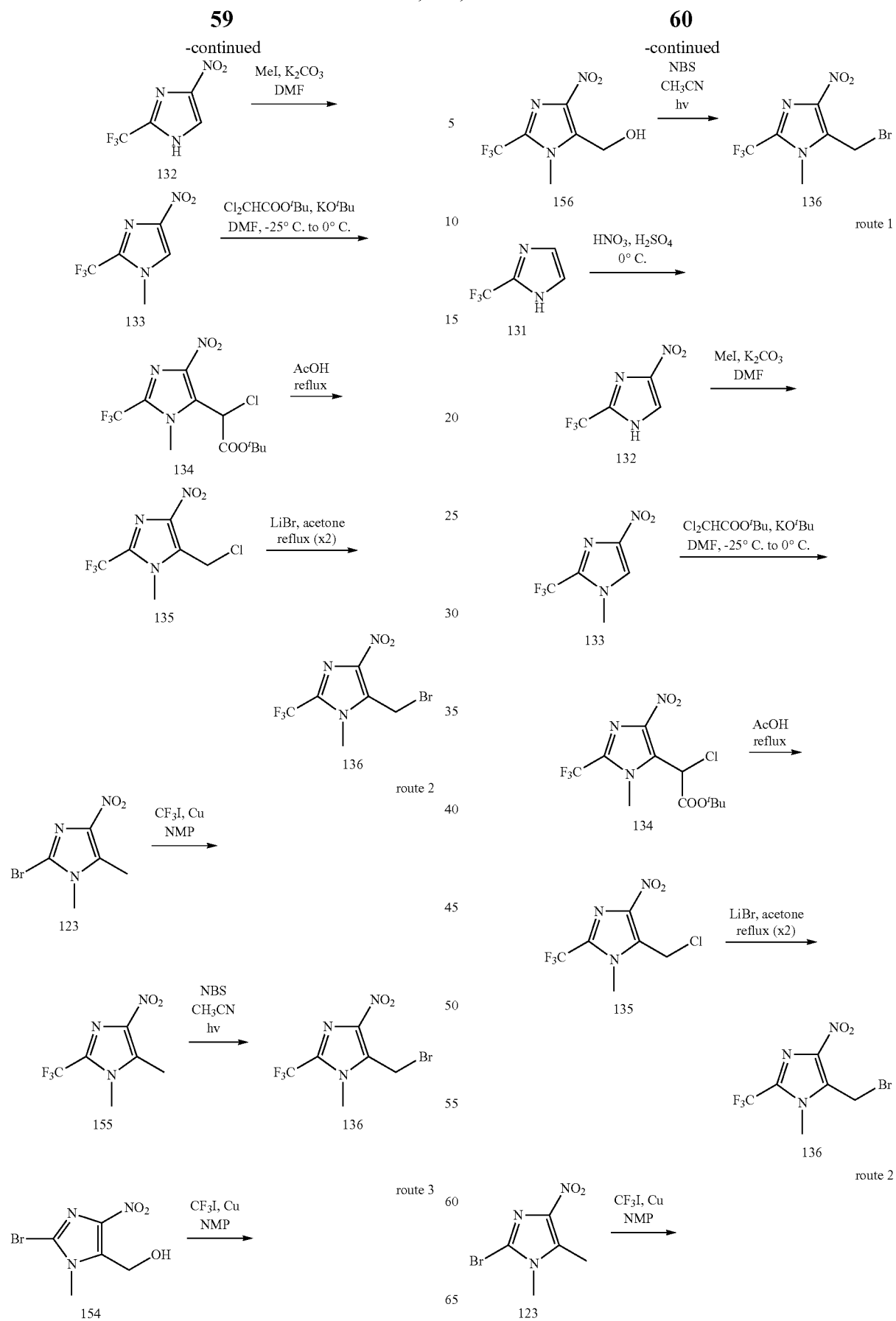

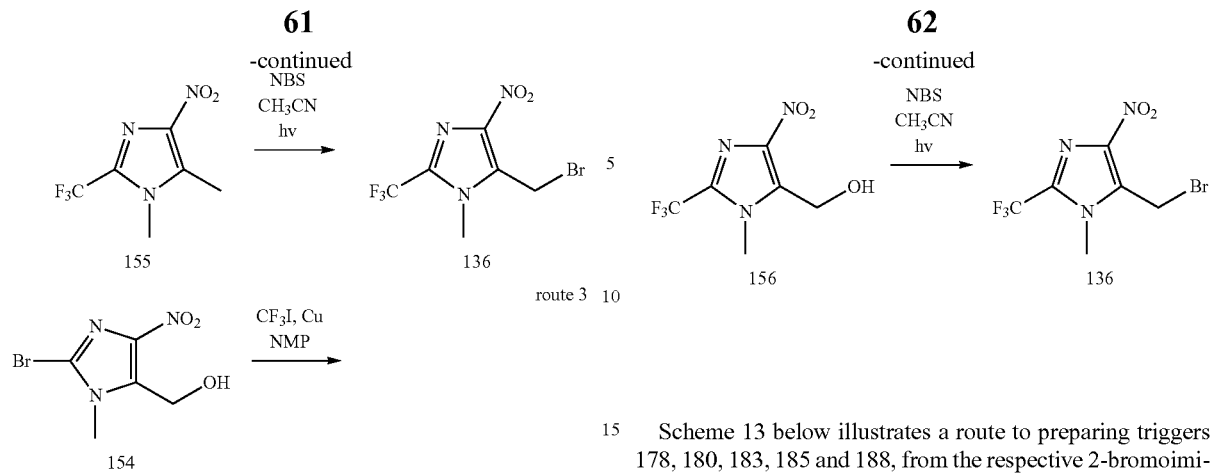
Scheme 13 below illustrates a route to preparing triggers 178, 180, 183, 185 and 188, from the respective 2-bromoimidazole intermediates 123 and 149 (described below).
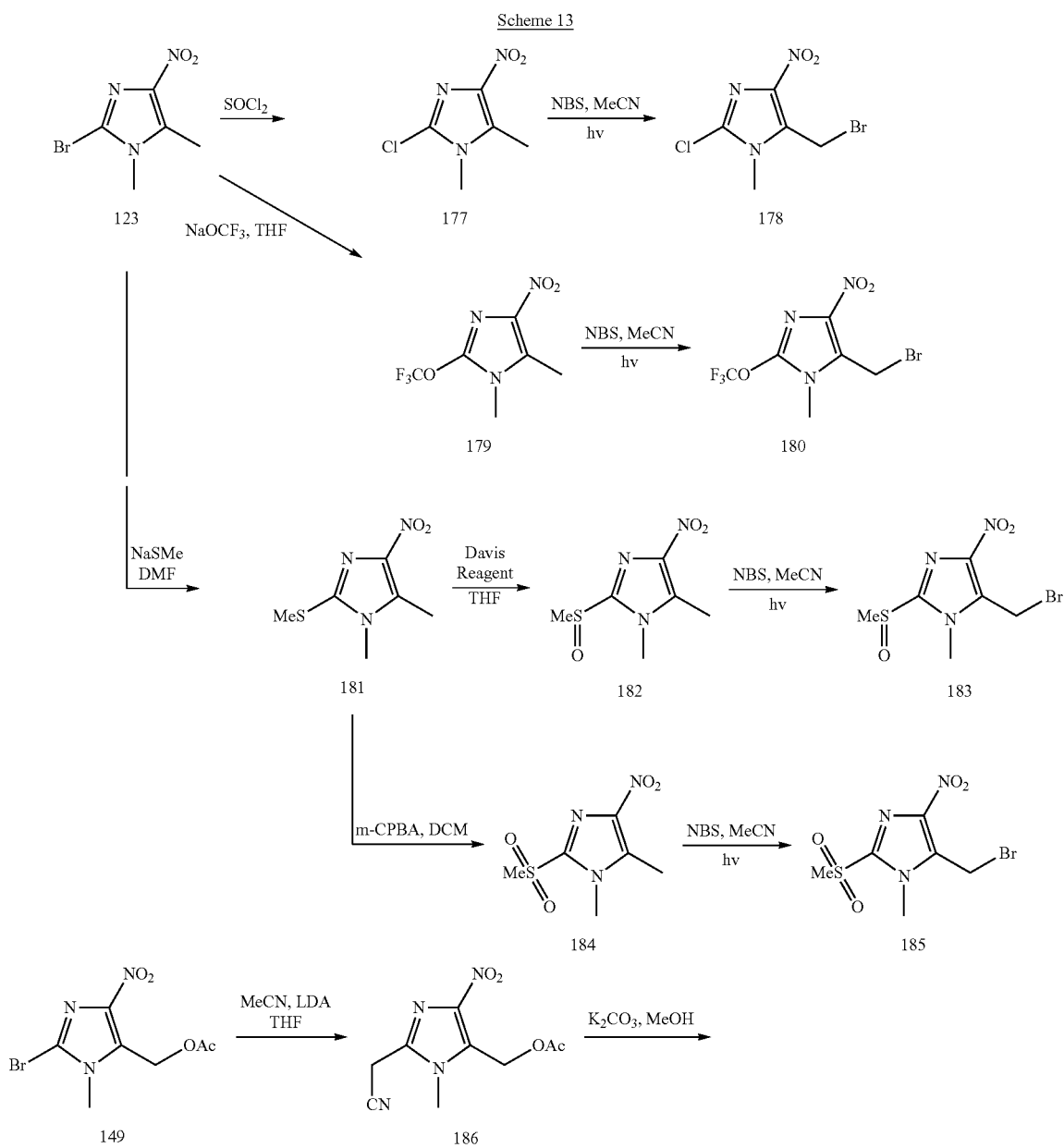

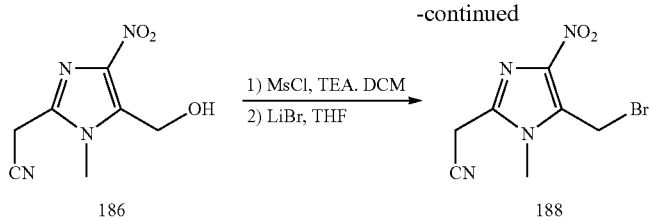

186 → 188

Reagents: 1) MsCl, TEA, DCM; 2) LiBr, THF

Scheme 14 below illustrates a route to quaternary nitrogen salt compounds of Formula I and Formula II by reacting an aliphatic tertiary amine- or aromatic heterocyclic amine-bearing kinase inhibitor with an appropriate nitroheterocyclic α-methyl halide/mesylate/tosylate, in a suitable solvent and for a suitable length of time (for example in tetrahydrofuran for about 24 hours).

Scheme 14

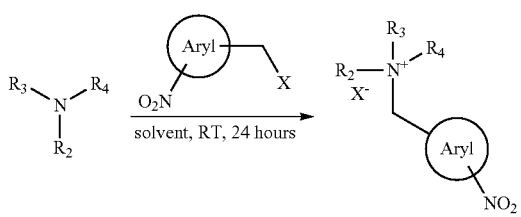

Scheme 15 below illustrates the preparation of a number of prodrug compounds of formula II according to the invention.

Synthesis of the quaternary ammonium salt prodrugs of the current invention was carried as shown in Scheme 15 below. (2E)-N-[4-(3-Bromoanilino)-6-quinazolinyl]-4-(dimethylamino)-2-butenamide (11), (Tsou et al *J Med Chem* 2001; 44:2719-34) was reacted with the appropriate nitroheterocyclic α-methyl halides, typically in tetrahydrofuran for 24 hours, to provide the quaternary ammonium salts (17-22) as a fine precipitate that was collected by filtration and washed with tetrahydrofuran and diethyl ether. Similarly, compounds 12 to 14 and 16 were reacted with 5-(bromomethyl)-1-methyl-4-nitro-1H-imidazole (Stribbling et al, PCT International patent publication WO 2008/039087) to afford the quaternary ammonium salt prodrugs 23 to 25 and 27, respectively. The required nitroheterocyclic α-methyl halides, 2-(bromomethyl)-1-methyl-4-nitro-1H-imidazole and 5-(bromomethyl)-1-methyl-4-nitro-1H-pyrazole were prepared by LiBr mediated bromide exchange of the known chloromethylimidazole (Jentzer et al. *Eur J Med Chem* 1991; 26:687-697) and chloromethylpyrazole (Tercel et al. *J Med Chem* 2001; 44:3511-22) precursors, respectively. Quaternisation of the sterically hindered, slower reacting piperidine and morpholine containing derivatives (12 and 13) was performed in N-methyl-2-pyrrolidinone (NMP) to give compounds 23 and 24 respectively.

Scheme 15

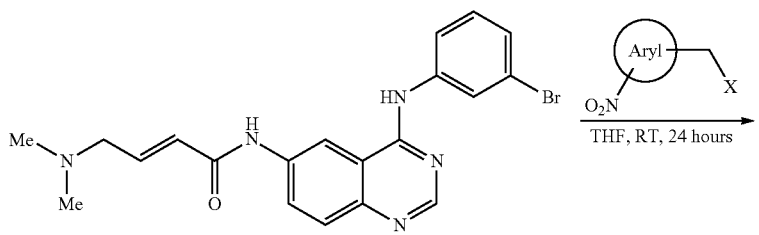

11

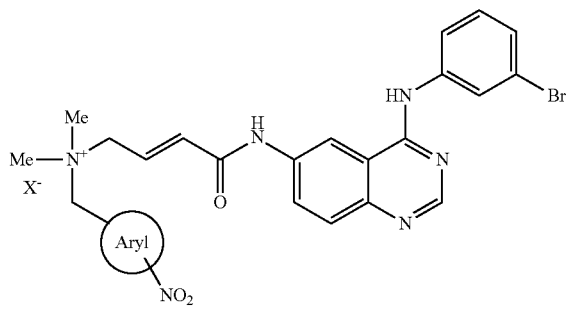

17-22

-continued

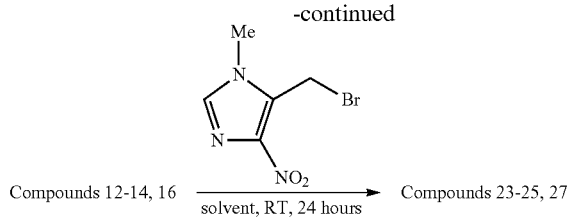

Compounds 12-14, 16 →(solvent, RT, 24 hours) Compounds 23-25, 27

Schemes 16 to 19 below illustrate the preparation of a number of prodrug compounds according to the invention.

Scheme 16

Trigger bromides:

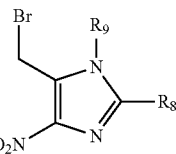

150: $R_8$ = H; $R_9$ = Me
122: $R_8$ = Me; $R_9$ = Me
201: $R_8$ = Et; $R_9$ = Me
125: $R_8$ = OMe; $R_9$ = Me
115: $R_8$ = H; $R_9$ = $CH_2CH_2CN$
116: $R_8$ = H; $R_9$ = $CH_2CH_2CONH_2$
200: $R_8$ = —≡—Me $R_9$ = Me
127: $R_8$ = CN; $R_9$ = Me

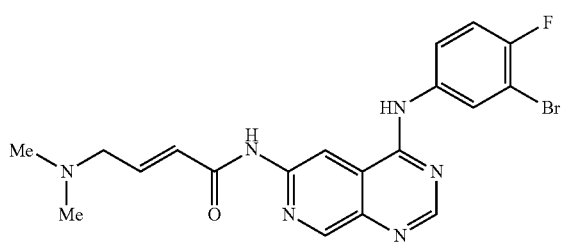

161

NMP, rt

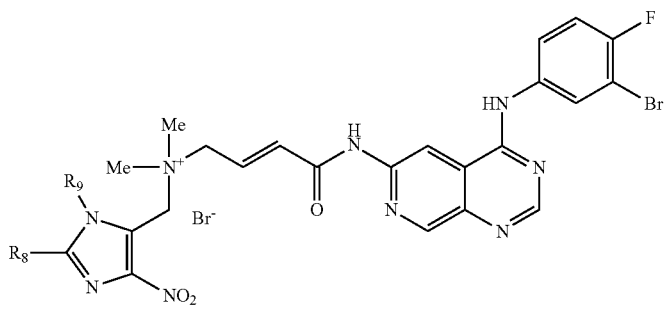

42: $R_8$ = H; $R_9$ = Me
43: $R_8$ = Me; $R_9$ = Me
172: $R_8$ = Et; $R_9$ = Me
44: $R_8$ = OMe; $R_9$ = Me
49: $R_8$ = H; $R_9$ = $CH_2CH_2CN$
47: $R_8$ = H; $R_9$ = $CH_2CH_2CONH_2$
173: $R_8$ = —≡—Me; $R_9$ = Me
48: $R_8$ = CN; $R_9$ = Me

Scheme 17
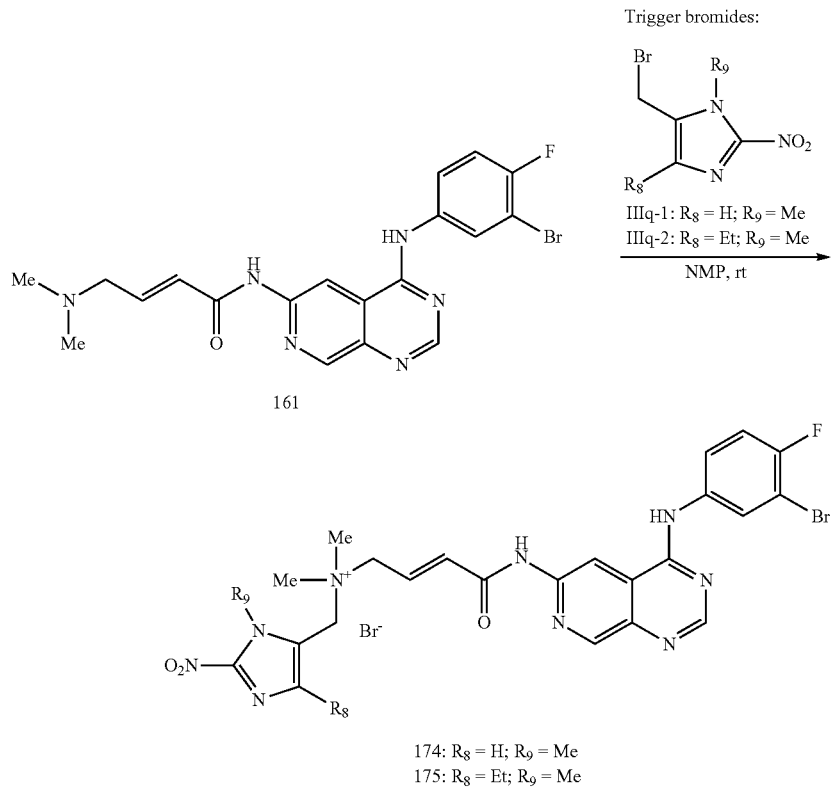
Scheme 18
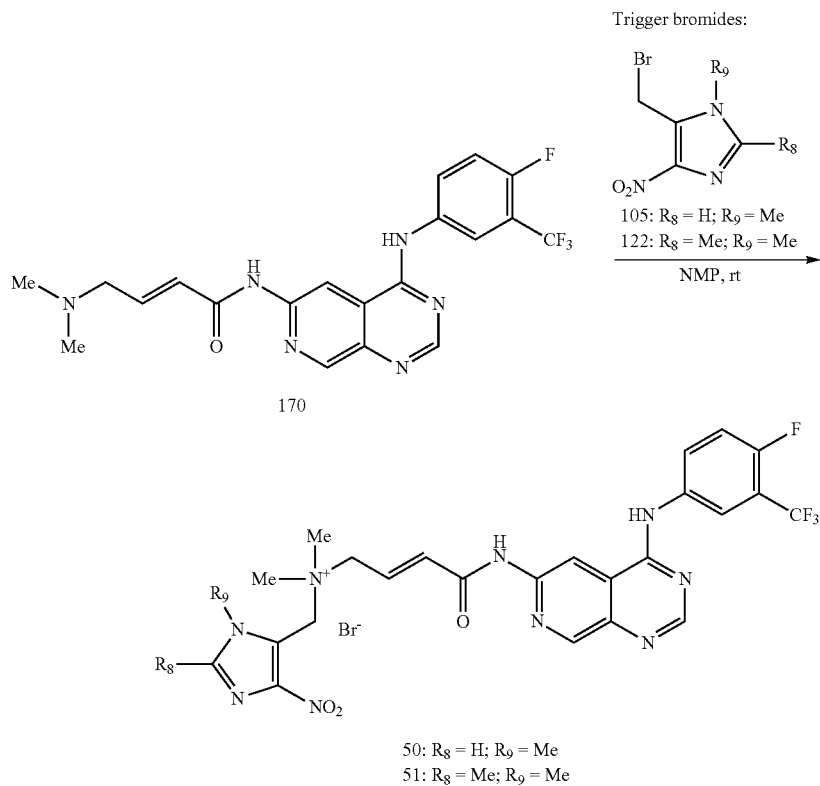

Scheme 19

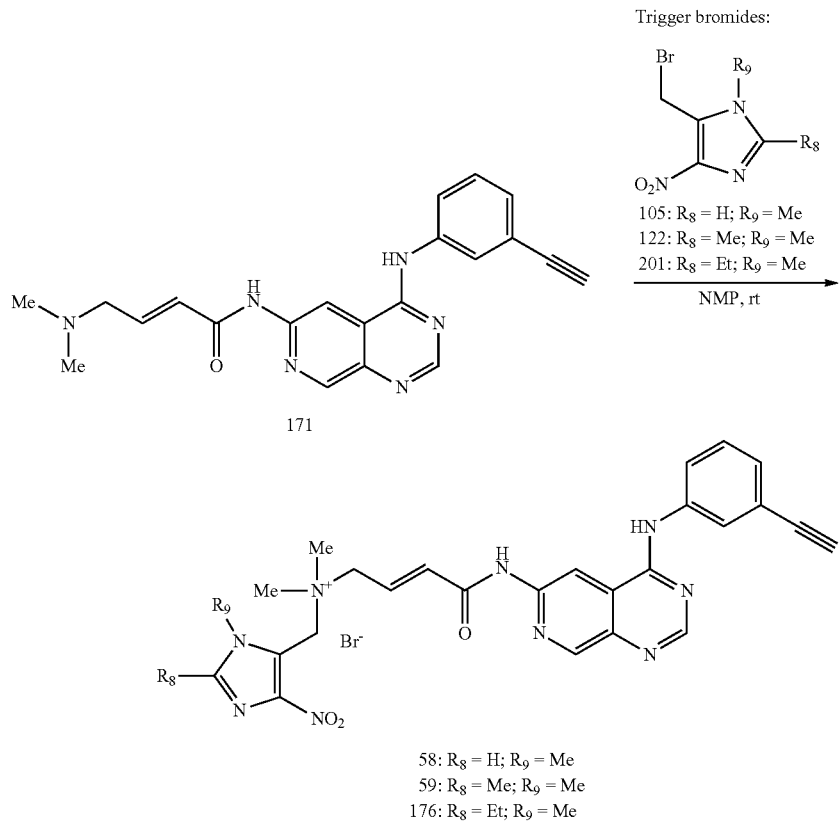

The invention will be better understood by reference to the non-limiting experimental sections A and B below.

EXPERIMENTAL

Section A

A.1. Synthesis

A.1.1 Chemical Synthesis

Combustion analyses were performed by the Microchemical Laboratory, University of Otago, Dunedin, NZ. Melting points were determined using either an Electrothermal Model 9200 and are as read. $^1$H NMR spectra were measured either on a Bruker Avance-400 spectrometer and are referenced to Me$_4$Si. High resolution mass spectra were recorded on a Varian VG-70SE spectrometer at nominal 5000 resolution. Mass spectrometry was performed on a ThermoFinnigan MSQ single quadrupole mass spectrometer. Mass detection was performed with an APCI source, using simultaneous positive and negative ion acquisition. Unless otherwise indicated, compounds were purified by flash column chromatography on Silica gel 60 support (Scharlau, 230-400 mesh ASTM), using the indicated eluants.

A.1.1.1 General Procedure A: The Synthesis of Kinase Inhibitor Effectors.

To a stirred solution of N$^4$-(3-chloro-4-fluorophenyl)-7-methoxy-4,6-quinazolinediamine (8) (4.0 g, 12.5 mmol) in dry tetrahydrofuran (150 mL) under nitrogen was added triethylamine (19 mmol), followed by freshly prepared (2E)-4-bromo-2-butenoyl chloride (15 mmol) in dry tetrahydrofuran (50 mL). The resulting solution was then stirred at room temperature for 2 hours and concentrated under reduced pressure. Trituration from dichloromethane gave crude (2E)-4-bromo-N-[4-(3-chloro-4-fluoroanilino)-7-methoxy-6-quinazolinyl]-2-butenamide (4.6 g) that was used directly.

To a stirred solution of the above crude (2E)-4-bromo-N-[4-(3-chloro-4-fluoroanilino)-7-methoxy-6-quinazolinyl]-2-butenamide (1.0 g, 2.15 mmol) in dimethylacetamide (35 mL) at 0° C. was added excess aqueous dimethylamine solution (40%, 5 mL). After 3 hours the reaction was diluted with brine and extracted with ethyl acetate (3×). The combined organic extracts were washed with brine, dried over anhydrous Na$_2$SO$_4$ and concentrated under reduced pressure. Chromatography on silica gel eluting with dichloromethane/methanol (5:95 to 15:85) then gave (2E)-N-[4-(3-chloro-4-fluoroanilino)-7-methoxy-6-quinazolinyl]-4-(dimethylamino)-2-butenamide (14) (0.74 g, 80%) as a white solid, m.p. (MeOH) 179-181° C. $^1$H NMR [(CD$_3$)$_2$SO] δ 9.78 (s, 1H), 9.64 (s, 1H), 8.93 (s, 1H), 8.53 (s, 1H), 8.13 (dd, J=2.6, 6.9 Hz, 1H), 7.83-7.79 (m, 1H), 7.42 (dd, J=9.1 Hz, J$_{H-F}$=9.1 Hz, 1H), 7.29 (s, 1H), 6.80 (td, J=6.0, 15.4 Hz, 1H), 6.58 (d, J=15.4 Hz, 1H), 4.01 (s, 3H), 3.08 (d, J=6.0 Hz, 2H), 2.19 (s, 6H). Analysis found: C, 56.32; H, 5.14; N, 15.73. C$_{21}$H$_{21}$ClFN$_5$O$_2$.H$_2$O requires: C, 56.32; H, 5.18; N, 15.64.

Reaction of N$^4$-(3-bromophenyl)-4,6-quinazolinediamine (10) (1.76 g, 5.58 mmol) with 4-chlorobutanoyl chloride (0.75 mL, 6.70 mmol) and then aqueous dimethylamine according to the general procedure A, with the exception that the first step was performed in dioxane and the second at 50° C. for 24 hours, gave N-[4-(3-bromoanilino)-6-quinazolinyl]-4-(dimethylamino)butanamide (16) (36%) as a white solid, m.p. (MeOH) 180-182° C. $^1$H NMR [(CD$_3$)$_2$SO] δ 10.23 (s, 1H), 9.87 (s, 1H), 8.72 (d, J=2.0 Hz, 1H), 8.57 (s, 1H), 8.17 (dd, J=1.9, 1.9 Hz, 1H), 7.88-7.84 (m, 2H), 7.77 (d, J=8.9 Hz, 1H), 7.37-7.27 (m, 2H), 2.43 (t, J=7.2 Hz, 2H), 2.29 (t, J=7.2 Hz, 2H), 2.16 (s, 6H), 1.78 (quintet, J=7.2 Hz, 2H). Analysis found: C, 55.46; H, 5.33; N, 15.96. C$_{20}$H$_{22}$BrN$_5$O.¼H$_2$O requires: C, 55.50; H, 5.24; N, 16.18.

A.1.1.2 General Procedure B: LiBr Mediated Halide Exchange (as for Scheme 8, Route 2).

A mixture of 2-(chloromethyl)-1-methyl-4-nitro-1H-imidazole (485 mg, 2.76 mmol) and LiBr (4.80 g, 55.2 mmol) in acetone was heated at reflux for 5 hours before all the solvent was removed under reduced pressure. The residue was partitioned between ethyl acetate and water. The aqueous phase was extracted with ethyl acetate twice. The combined organic phase was washed with brine, dried over Na$_2$SO$_4$ and concentrated in vacuo. The crude product was recrystallised from DCM/hexane to give 2-(bromomethyl)-1-methyl-4-nitro-1H-imidazole (105) (576 mg, 95%) as an off-white solid, m.p. 130-132° C. $^1$H NMR (CDCl$_3$, 400 MHz) δ 7.74 (s, 1H), 4.50 (s, 2H), 3.83 (s, 3H). Analysis found: C, 27.81; H, 3.27; N, 19.05. C$_5$H$_6$BrN$_3$O$_2$.0.04hexane requires: C, 28.16; H, 2.96; N, 18.80. HRMS (FAB+) found: 219.97220, 221.97018 (M+1), calcd. for C$_5$H$_7$$^{79/81}$BrN$_3$O$_2$: 219.97216, 221.97012.

Reaction of 5-(chloromethyl)-1-methyl-4-nitro-1H-pyrazole (80 mg, 0.54 mmol) with LiBr according to general procedure B gave 5-(bromomethyl)-1-methyl-4-nitro-1H-pyrazole (70 mg, 70%) as a white crystalline solid, m.p. 71-73° C. $^1$H NMR (CDCl$_3$, 400 MHz) δ 8.08 (s, 1H), 4.82 (s, 2H), 3.95 (s, 3H). Analysis found: C, 27.76; H, 3.08; N, 18.99. C$_5$H$_6$BrN$_3$O$_2$.0.02hexane requires: C, 27.73; H, 2.86; N, 18.95. HRMS (FAB+) found: 219.97223, 221.97012 (M+1), calcd. for C$_5$H$_7$$^{79/81}$BrN$_3$O$_2$: 219.97216, 221.97012.

A.1.1.3 General Procedure C: Preparation of Quaternary Ammonium Salt Prodrugs.

To a stirred solution of (2E)-N-[4-(3-bromoanilino)-6-quinazolinyl]-4-(dimethylamino)-2-butenamide (11) (150 mg, 0.35 mmol) in dry tetrahydrofuran (15 mL) under nitrogen was added 4-nitrobenzyl bromide (84 mg, 1.1 mol. eq., 0.39 mmol). The resulting solution was then stirred at room temperature for 24 hours to provide a white precipitate which was collected by filtration and washed with dry tetrahydrofuran and diethyl ether to give (2E)-4-{[4-(3-bromoanilino)-6-quinazolinyl]amino}-N,N-dimethyl-N-(4-nitrobenzyl)-4-oxo-2-buten-1-ammonium bromide (17) (101 mg, 45%), m.p. 178-181° C. $^1$H NMR [(CD$_3$)$_2$SO] δ 10.75 (s, 1H), 9.93 (s, 1H), 8.77 (s, 1H), 8.61 (s, 1H), 8.39 (d, J=8.7 Hz, 2H), 8.18 (br s, 1H), 8.04 (d, J=9.0 Hz, 1H), 7.93-7.83 (m, 4H), 7.38-7.29 (m, 2H), 7.04 (td, J=7.3, 15.2 Hz, 1H), 6.68 (d, J=15.2 Hz, 1H), 4.78 (s, 2H), 4.30 (d, J=7.3 Hz, 2H), 3.07 (s, 6H). Analysis found: C, 50.02; H, 4.30; N, 12.75. C$_{27}$H$_{26}$Br$_2$N$_6$O$_3$.¼H$_2$O requires: C, 50.14; H, 4.13; N, 12.99.

Reaction of 11 (200 mg, 0.47 mmol) with 2-nitrobenzyl bromide (111 mg, 0.52 mmol) according to general procedure C gave (2E)-4-{[4-(3-bromoanilino)-6-quinazolinyl] amino}-N,N-dimethyl-N-(2-nitrobenzyl)-4-oxo-2-buten-1-ammonium bromide (18) (221 mg, 73%), m.p. 166-169° C. $^1$H NMR [(CD$_3$)$_2$SO] δ 10.76 (s, 1H), 9.94 (s, 1H), 8.80 (s, 1H), 8.61 (s, 1H), 8.22-8.17 (m, 2H), 8.04 (d, J=9.0 Hz, 1H), 7.95-7.82 (m, 5H), 7.37-7.28 (m, 2H), 7.01 (td, J=7.3, 15.2 Hz, 1H), 6.71 (d, J=15.2 Hz, 1H), 5.01 (s, 2H), 4.38 (d, J=7.3 Hz, 2H), 3.04 (s, 6H). Analysis found: C, 50.66; H, 4.29; N, 12.88. C$_{27}$H$_{26}$Br$_2$N$_6$O$_3$ requires: C, 50.49; H, 4.08; N, 13.08.

Reaction of 11 (200 mg, 0.47 mmol) with 2-(bromomethyl)-1-methyl-5-nitro-1H-pyrrole (123 mg, 0.56 mmol) according to general procedure C gave (2E)-4-{[4-(3-bromoanilino)-6-quinazolinyl]amino}-N,N-dimethyl-N-[(1-methyl-5-nitro-1H-pyrrol-2-yl)methyl]-4-oxo-2-buten-1-ammonium bromide (19) (207 mg, 68%), m.p. 164-168° C. $^1$H NMR [(CD$_3$)$_2$SO] δ 10.74 (s, 1H), 9.93 (s, 1H), 8.77 (s, 1H), 8.61 (s, 1H), 8.18 (br s, 1H), 8.03 (d, J=8.9 Hz, 1H), 7.88-7.82 (m, 2H), 7.37-7.28 (m, 3H), 6.99 (td, J=7.3, 15.2 Hz, 1H), 6.71-6.65 (m, 2H), 4.84 (s, 2H), 4.33 (d, J=7.3 Hz, 2H), 4.01 (s, 3H), 3.08 (s, 6H). Analysis found: C, 48.34; H, 4.68; N, 14.19. C$_{26}$H$_{27}$Br$_2$N$_7$O$_3$.¼THF.½H$_2$O requires: C, 48.23; H, 4.50; N, 14.58.

Reaction of 11 (129 mg, 0.30 mmol) with 5-(bromomethyl)-1-methyl-4-nitro-1H-imidazole (105) (70 mg, 0.32 mmol) according to general procedure C gave (2E)-4-{[4-(3-bromoanilino)-6-quinazolinyl]amino}-N,N-dimethyl-N-[(1-methyl-4-nitro-1H-imidazol-5-yl)methyl]-4-oxo-2-buten-1-ammonium bromide (20) (139 mg, 72%), m.p. 163-167° C. $^1$H NMR [(CD$_3$)$_2$SO] δ 10.75 (s, 1H), 9.96 (s, 1H), 8.81 (s, 1H), 8.61 (s, 1H), 8.17 (br s, 1H), 8.15 (s, 1H), 7.99 (d, J=9.0 Hz, 1H), 7.88-7.83 (m, 2H), 7.38-7.29 (m, 2H), 7.02 (td, J=7.3, 15.2 Hz, 1H), 6.71 (d, J=15.2 Hz, 1H), 5.08 (br s, 2H), 4.48 (d, J=7.3 Hz, 2H), 3.89 (s, 3H), 3.13 (s, 6H). Analysis found: C, 45.23; H, 4.36; N, 16.34. C$_{25}$H$_{26}$Br$_2$N$_8$O$_3$.⅒THF.1¼H$_2$O requires: C, 45.13; H, 4.37; N, 16.57.

A.1.1.4 General Procedure D: Preparation of Quaternary Ammonium Salt Prodrugs in N-methyl-2-pyrrolidinone.

To a stirred solution of (2E)-N-[4-(3-bromoanilino)-6-quinazolinyl]-4-(dimethylamino)-2-butenamide (11) (150 mg, 0.35 mmol) in dry N-methyl-2-pyrrolidinone (NMP) (1 mL) under nitrogen was added 2-(bromomethyl)-1-methyl-4-nitro-1H-imidazole (52 mg, 0.66 mol eq., 0.23 mmol), portionwise over 5 hours. The resulting solution was then stirred at room temperature for 20 hours before diethyl ether was added. The resulting precipitate was filtered and washed thoroughly with dichloromethane. The crude product was purified by fractional precipitation from acetonitrile (containing a trace amount of triethylamine) by the addition of dioxane. The precipitate was separated from the mother liquid by centrifuge, washed with a mixture of THF and DCM (1:1) three times and dried under vacuum to give (2E)-4-{[4-(3-bromoanilino)-6-quinazolinyl]amino}-N,N-dimethyl-N-[(1-methyl-4-nitro-1H-imidazol-2-yl)methyl]-4-oxo-2-buten-1-ammonium bromide (21) (127 mg, 84%), m.p. 184-187° C. $^1$H NMR [(CD$_3$)$_2$SO] δ 10.69 (s, 1H), 9.91 (s, 1H), 8.76 (s, 1H), 8.61 (s, 2H), 8.17 (t, J=1.9 Hz, 1H), 7.99 (d, J=9.0 Hz, 1H), 7.88-7.83 (m, 2H), 7.37-7.29 (m, 2H), 7.00 (td, J=7.3, 15.2 Hz, 1H), 6.64 (d, J=15.2 Hz, 1H), 4.79 (s, 2H), 4.36 (d, J=7.2 Hz, 2H), 3.88 (s, 3H), 3.19 (s, 6H). Analysis found: C, 46.11; H, 4.33; N, 16.78. C$_{25}$H$_{26}$Br$_2$N$_8$O$_3$.½H$_2$O requires: C, 45.82; H, 4.15; N, 17.10. HRMS (FAB+) found: 565.13144, 567.12820 (M-Br), calcd. for C$_{25}$H$_{26}$$^{79/81}$BrN$_8$O$_3$$^+$: 565.13112, 567.12908.

Reaction of 11 (150 mg, 0.35 mmol) with 5-(bromomethyl)-1-methyl-4-nitro-1H-pyrazole (52 mg, 0.23 mmol) for 23 hours according to general procedure D gave (2E)-4-{[4-(3-bromoanilino)-6-quinazolinyl]amino}-N,N-dimethyl-N-[(1-methyl-4-nitro-1H-pyrazol-5-yl)methyl]-4-oxo-2-buten-1-ammonium bromide (22) (94 mg, 62%), imp. 178-182° C. $^1$H NMR [(CD$_3$)$_2$SO] δ 10.71 (s, 1H), 9.93 (s, 1H), 8.79 (s, 1H), 8.61 (s, 1H), 8.56 (s, 1H), 8.17 (br s, 1H), 7.98 (d, J=8.8 Hz, 1H), 7.88-7.83 (m, 2H), 7.37-7.29 (m, 2H), 7.00 (td, J=7.3, 15.2 Hz, 1H), 6.69 (d, J=15.2 Hz, 1H), 5.11 (s, 2H), 4.47 (d, J=7.1 Hz, 2H), 4.11 (s, 3H), 3.15 (s, 6H). Analysis found: C, 45.54; H, 4.50; N, 16.30. C$_{25}$H$_{26}$Br$_2$N$_8$O$_3$.H$_2$O.¼dioxane requires: 45.50; H, 4.41; N, 16.33. HRMS (FAB+) found: 565.13015, 567.13016 (M-Br), calcd. for C$_{25}$H$_{26}$$^{79/81}$BrN$_8$O$_3$$^+$: 565.13112, 567.12908.

Reaction of (E)-N-(4-(3-bromophenylamino)quinazolin-6-yl)-4-(piperidin-1-yl)but-2-enamide (12) (1.0 g, 2.14 mmol) in NMP (4 mL) with 5-(bromomethyl)-1-methyl-4-nitro-1H-imidazole (105) (315 mg, 1.43 mmol) for 3.5 days, according to general procedure D gave 1-((2E)-4-{[4-(3-bromoanilino)-6-quinazolinyl]amino}-4-oxo-2-butenyl)-1-[(1-methyl-4-nitro-1H-imidazol-5-yl)methyl]piperidinium bromide (23) (600 mg, 61%), m.p. 188° C. (dec.). $^1$H NMR [(CD$_3$)$_2$SO] δ 10.73 (s, 1H), 9.94 (s, 1H), 8.82 (s, 1H), 8.61 (s, 1H), 8.17 (t, J=1.8 Hz, 1H), 8.14 (s, 1H), 7.98 (d, J=8.8 Hz, 1H), 7.88-7.83 (m, 2H), 7.37-7.29 (m, 2H), 7.08 (td, J=7.3, 15.1 Hz, 1H), 6.80 (d, J=15.1 Hz, 1H), 5.02 (br s, 2H), 4.62 (br s, 2H), 3.87 (s, 3H), 3.58-3.55 (m, 2H), 2.04-1.99 (m, 2H), 1.78-1.75 (m, 2H), 1.64-1.61 (m, 1H), 1.46-1.36 (m, 1H). Analysis found: C, 48.24; H, 4.58; N, 15.89. C$_{28}$H$_{30}$Br$_2$N$_8$O$_3$·½H$_2$O requires: C, 48.36; H, 4.49; N, 16.11. HRMS (FAB+) found: 605.16226, 607.15997 (M-Br), calcd. for C$_{28}$H$_{30}$$^{79/81}$BrN$_8$O$_3^+$: 605.16242, 607.16038.

Reaction of (E)-N-(4-(3-bromophenylamino)quinazolin-6-yl)-4-morpholinobut-2-enamide (13) (1.0 g, 2.14 mmol) in NMP (4 mL) with 5-(bromomethyl)-1-methyl-4-nitro-1H-imidazole (105) (313 mg, 1.42 mmol) for 3.5 days according to general procedure D, followed by preparative HPLC using MeOH/formic acid/water as mobile phase gave 4-((2E)-4-{[4-(3-bromoanilino)-6-quinazolinyl]amino}-4-oxo-2-butenyl)-4-[(1-methyl-4-nitro-1H-imidazol-5-yl)methyl]morpholin-4-ium formate (24) (110 mg, 12%), m.p. 125-129° C. $^1$H NMR [(CD$_3$)$_2$SO] δ 11.69 (s, 1H), 10.17 (s, 1H), 9.28 (s, 1H), 8.65 (br, 1H), 8.61 (s, 1H), 8.44-8.40 (m, 2H), 8.14 (s, 1H), 8.07 (d, J=8.1 Hz, 1H), 7.34 (t, J=8.1 Hz, 1H), 7.27 (d, J=8.5 Hz, 1H), 7.17-7.10 (m, 2H), 6.82 (d, J=14.6 Hz, 1H), 5.12 (br s, 2H), 4.81 (br s, 2H), 4.16 (t, J=12.0 Hz, 2H), 3.91 (m, 2H), 3.88 (s, 3H), 3.70-3.60 (m, 2H), 3.46 (t, J=12.0 Hz, 2H). FIRMS (FAB+) found: 607.14189, 609.14034 (M-HCOO), calcd. for C$_{27}$H$_{28}$$^{79/81}$BrN$_8$O$_4^+$: 607.14169, 609.13964.

Reaction of (2E)-N-[4-(3-chloro-4-fluoroanilino)-7-methoxy-6-quinazolinyl]-4-(dimethylamino)-2-butenamide (14) (990 mg, 2.30 mmol) in NMP (6 mL) with 5-(bromomethyl)-1-methyl-4-nitro-1H-imidazole (105) (422 mg, 1.92 mmol) for 24 hours, according to general procedure D gave (2E)-4-{[4-(3-chloro-4-fluoroanilino)-7-methoxy-6-quinazolinyl]amino}-N,N-dimethyl-N-[(1-methyl-4-nitro-1H-imidazol-5-yl)methyl]-4-oxo-2-buten-1-ammonium bromide (25) (1076 mg, 86%), m.p. 192° C. (dec.). $^1$H NMR [(CD$_3$)$_2$SO] δ 9.99 (s, 1H), 9.82 (s, 1H), 8.91 (s, 1H), 8.56 (s, 1H), 8.14-8.11 (m, 2H), 7.83-7.78 (m, 1H), 7.42 (t, J=9.1 Hz, 1H), 7.33 (s, 1H), 7.00-6.95 (m, 1H), 6.90-6.86 (d, J=15.3 Hz, 1H), 5.06 (br s, 2H), 4.43 (d, J=6.8 Hz, 2H), 4.03 (s, 3H), 3.88 (s, 3H), 3.12 (s, 6H). Analysis found: C, 47.04; H, 4.32; N, 16.18. C$_{26}$H$_{27}$BrClFN$_8$O$_4$·H$_2$O·¼THF requires: C, 47.28; H, 4.56; N, 16.34. HR-MS (FAB+, $^{35/37}$Cl) found: m/z 569.18207/571.18086 (M-Br), calcd. for C$_{26}$H$_{27}$$^{35/37}$ClFN$_8$O$_4^+$: 569.182782/571.17983.

Reaction of N-(4-(3-bromophenylamino)quinazolin-6-yl)-4-(dimethylamino)butanamide (16) (1.0 g, 2.34 mmol) in NMP (5 mL) with 5-(bromomethyl)-1-methyl-4-nitro-1H-imidazole (105) (342 mg, 1.56 mmol) for 15 hours according to general procedure D gave 4-{([4-(3-bromoanilino)-6-quinazolinyl]amino}-N,N-dimethyl-N-[(1-methyl-4-nitro-1H-imidazol-5-yl)methyl]-4-oxo-1-butanaminium bromide (27) (710 mg, 70%), m.p. 177° C. (dec.). $^1$H NMR [(CD$_3$)$_2$SO] δ 10.39 (s, 1H), 9.99 (s, 1H), 8.69 (d, J=1.6 Hz, 1H), 8.59 (s, 1H), 8.17 (t, J=1.9 Hz, 1H), 8.12 (s, 1H), 7.93-7.84 (m, 2H), 7.80 (d, J=9.0 Hz, 1H), 7.35 (t, J=8.0 Hz, 1H), 7.29 (td, J=1.4, 8.4 Hz, 1H), 5.02 (br s, 2H), 3.86 (s, 3H), 3.62-3.58 (m, 2H), 3.10 (s, 6H), 2.55 (t, J=7.0 Hz, 2H), 2.20-2.12 (m, 2H). Analysis found: C, 45.69; H, 4.95; N, 15.57. C$_{25}$H$_{28}$Br$_2$N$_8$O$_3$·H$_2$O·½dioxane requires: C, 45.65; H, 4.82; N, 15.77. HRMS (FAB+) found: 567.14724, 569.14564 (M-Br), calcd. for C$_{25}$H$_{28}$$^{79/81}$BrN$_8$O$_3^+$: 567.14677, 569.14473.

A.1.1.5 Preparation of Trigger Bromide 200

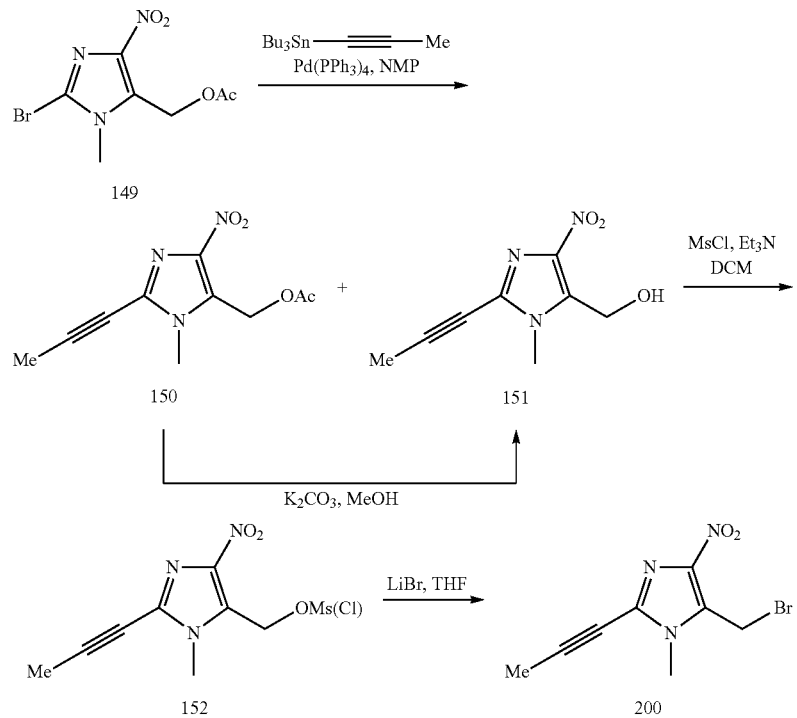

A mixture of bromide 149 (500 mg, 1.80 mmol) (Scheme 20), tributyl(1-propynyl)tin (1.64 mL, 5.39 mmol) and tetrakis(triphenylphosphine)palladium (416 mg, 0.36 mmol) in NMP (15 mL) was heated at 80° C. overnight (14 hours) before undergoing a standard aqueous-ethyl acetate workup. The crude product obtained was further purified by flash column chromatography eluting with MeCN/DCM (gradient from 1:20 to 1:5) to give compound 150 (147 mg, 34%) as white solid, $^1$H NMR (CDCl$_3$, 400 MHz) δ 5.47 (s, 2H), 3.77 (s, 3H), 2.14 (s, 3H), 2.10 (s, 3H). LR-MS (+): m/e 238.5 (M+1); followed by compound 151 (105 mg, 30%) also as white solid, $^1$H NMR (CDCl$_3$, 400 MHz) δ 4.96 (d, J=7.0 Hz, 2H), 3.79 (s, 3H), 2.60 (t, J=7.0 Hz, 1H), 2.14 (s, 3H). LR-MS (+): m/e 196.5 (M+1). Compound 151 was obtained quantitatively by treating compound 150 with K$_2$CO$_3$ in MeOH.

Bromide 149 can be obtained from intermediate compound 123 (Scheme 11) by reaction with N-bromosuccinimide (NBS) in acetonitrile to give the bromomethylene derivative 153, followed by sodium acetate mediated bromide displacement in dimethylformamide (DMF) (Scheme 20).

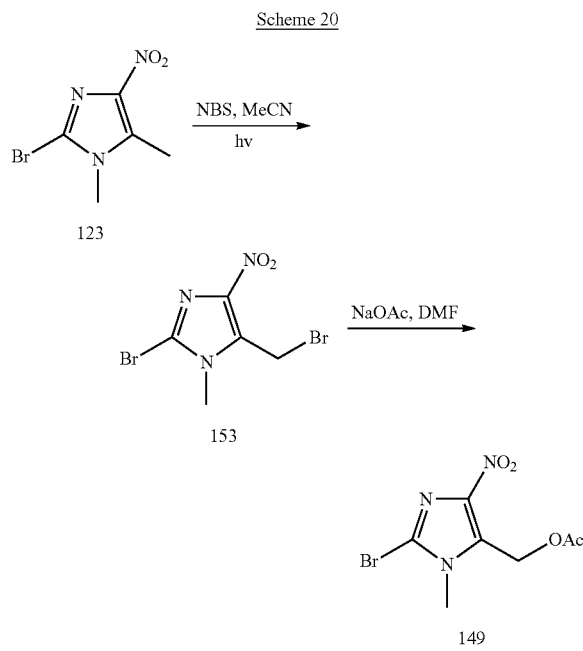

To a solution of compound 151 (110 mg, 0.56 mmol) in DCM (10 mL) at 0° C. was added triethylamine (0.118 mL, 0.84 mmol) followed by MsCl (0.052 mL, 0.68 mmol) dropwise. After 30 minutes at 0° C. and 30 minutes at room temperature, the mixture was washed twice with saturated aqueous ammonium chloride and brine, before being dried over anhydrous sodium sulphate and filtered through celite. Concentration under reduced pressure gave compound(s) 152 (145 mg, ~94%) as an off-white solid, which was found by $^1$H NMR to be a mixture of mesylate and chloride (3.6:1) and was used without further purification. $^1$H NMR (CDCl$_3$, 400 MHz) for the mesylate: δ 5.62 (s, 2H), 3.81 (s, 3H), 3.13 (s, 3H), 2.15 (s, 31-1); for the chloride: δ 5.02 (s, 2H), 3.79 (s, 3H), 2.14 (s, 3H). LR-MS (+): 274.5 (M+1 of the mesylate); 214.4/216.4 (3:1, M+1 of the chloride).

Mixture 152 (145 mg, ~0.53 mmol) was treated with LiBr (922 mg, 10.61 mmol) in refluxing THF (10 mL) for 30 minutes. The THF was then removed in vacuo and the resulting residue was distributed between water and ethyl acetate. The organic phase was washed with water and brine, dried over anhydrous sodium sulphate and filtered through celite, before being concentrated in vacuo. The crude product thus obtained was purified by flash column chromatography eluting with ethyl acetate/hexane (1:1) to give 5-(bromomethyl)-1-methyl-4-nitro-2-(1-propynyl)-1H-imidazole (200) (95 mg, 69%) as white solid. $^1$H NMR (CDCl$_3$, 400 MHz) δ 4.86 (s, 2H), 3.76 (s, 3H), 2.14 (s, 3H). LR-MS (+): m/e 258.5/260.5 (1:1, M+1).

A.1.1.6 Preparation of α-methyl bromide 127 (Scheme 11)

To a solution of bromide 153 (Scheme 14) (1.40 g, 4.68 mmol) in DMA (14 mL) containing several drops of water, was added K$_2$CO$_3$ (647 mg, 4.68 mmol). The resulting solution was stirred over night before a standard EtOAc workup, followed by silica gel column chromatography eluting with MeCN/DCM (5:95-15:85), gave alcohol 154 (330 mg, 30%) as an off-white solid. $^1$H NMR ($^6$d-DMSO, 400 MHz) δ 5.56 (t, J=5.8 Hz, 1H), 4.86 (d, J=5.8 Hz, 2H), 3.70 (s, 3H). LR-MS (+): m/e 236.5/238.5 (1:1, M+1).

A mixture of alcohol 154 (300 mg, 1.27 mmol), Zn(CN) (90 mg, 0.76 mmol), Zinc powder (10 mg, 0.15 mmol), Pd$_2$(dba)$_3$ (23 mg, 0.025 mmol) and dppf (28 mg, 0.051 mmol) in DMA (3 mL) was stirred under nitrogen at 120° C. for 3.5 hours. A standard aqueous NH$_4$Cl/EtOAc workup followed by silica gel column chromatography eluting with EtOAc/hexanes (1:1 to 2:1) then gave the cyanoimidazole 126 (180 mg) as an off-white solid, which was found by $^1$H NMR to contain a small amount of unreacted starting material 154 and was used directly in the next step. $^1$H NMR (CDCl$_3$, 400 MHz) δ 5.09 (d, J=6.7 Hz, 2H), 4.00 (s, 3H), 2.49 (t, J=6.7 Hz, 1H).

To the solution of cyanoimidazole 126 (173 mg, ca. 0.93 mmol) in THF (10 mL) at 0° C. was added MsCl (0.088 mL, 1.14 mmol), followed by DIPEA (0.182 mL, 1.04 mmol) dropwise. After stirring for 1 hour, the reaction mixture was subjected to a standard aqueous NH$_4$Cl/EtOAc workup to give a yellow oil (237 mg; mixture of mesylate and α-methyl chloride by $^1$H NMR) that was used directly. To a solution of this oil (235 mg, ca. 0.90 mmol) in THF (10 mL) was added LiBr (1.57 g, 18.06 mmol). After 0.5 hr heating at reflux the solvent was removed in vacuo and the residue was subjected to a standard aqueous NH$_{14}$Cl/EtOAc workup. The crude product was further purified by silica gel column chromatography eluting with EtOAc/hexanes (1:4 to 1:2) to give α-methyl bromide 127 (65 mg, 21% over three steps) as a pink oil. $^1$H NMR (CDCl$_3$, 400 MHz) δ 4.86 (s, 2H), 3.95 (s, 3H). LR-MS (+): m/e 277.6/279.6 (1:1, M+1+MeOH).

A.1.1.7 Preparation of α-methyl bromide Trigger 201

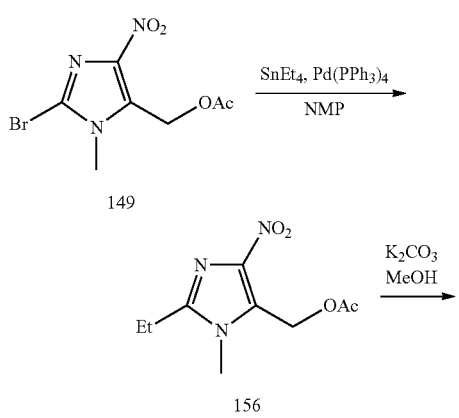

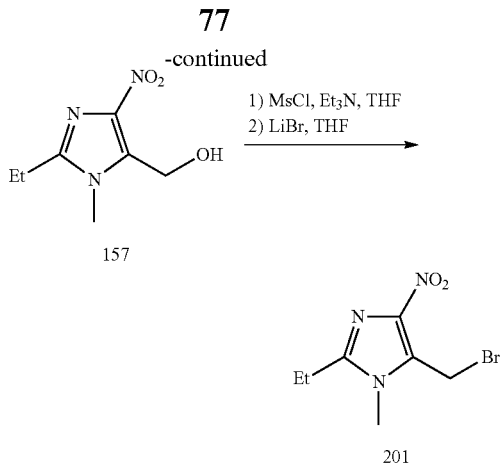

A mixture of bromoimidazole 149 (1.90 g, 6.83 mmol) (Scheme 14), tetraethyltin (5.42 mL, 27.34 mmol) and tetrakis(triphenylphosphine)palladium (790 mg, 0.68 mmol) in NMP (20 mL) was heated at 110-120° C. for 5 hours before undergoing a standard aqueous ethyl acetate workup. The crude product obtained was purified by flash column chromatography eluting with MeCN/DCM (1:5) before being precipitated from DCM by the addition of hexane, to give ethylimidazole 156 (1.04 g, 67%) as a white solid, m.p. 71-73° C. $^1$H NMR (CDCl$_3$, 400 MHz) δ 5.48 (s, 2H), 3.64 (s, 3H), 2.76 (q, J=7.43 Hz, 2H), 2.10 (s, 3H), 1.37 (t, J=7.43 Hz, 3H). Analysis found: C, 48.11; H, 5.90; N, 18.23%. C$_9$H$_{13}$N$_3$O$_4$.0.04hexane requires: C, 48.11; H, 5.92; N, 18.22%. LR-MS (+): m/e 228.5 (M+1).

To the solution of ethylimidazole 156 (1.25 g, 5.50 mmol) in MeOH (10 mL) was added dry K$_2$CO$_3$ (1.52 g, 11.0 mmol). After stirring for 20 minutes the solvent was removed at reduced pressure and the residue was dissolved in DCM, filtered through a layer of silica gel and washed with ethyl acetate. The filtrate was concentrated to give white crystals, which were collected by filtration and washed with a mixture of ethyl acetate/hexane (1:1) to give alcohol 157 (949 mg, 93%) as white crystalline solid, m.p. 153-155° C. $^1$H NMR (CDCl$_3$, 400 MHz) δ 4.96 (d, J=6.80 Hz, 2H), 3.67 (s, 3H), 2.79 (t, J=6.80 Hz, 1H), 2.74 (q, J=7.50 Hz, 2H), 1.36 (t, J=7.50 Hz, 3H). Analysis found: C, 45.71; H, 6.07; N, 22.87%. C$_7$H$_{11}$N$_3$O$_3$ requires: C, 45.40; H, 5.99; N, 22.68%. LR-MS (+): m/e 186.5 (M+1).

To the solution of alcohol 157 (685 mg, 3.70 mmol) in DCM (30 mL) at 0° C. was added triethylamine (0.773 mL, 5.55 mmol), followed by MsCl (0.344 mL, 4.44 mmol) dropwise. After stirring for 45 minutes, the mixture was washed twice with saturated aqueous ammonium chloride and once with brine before being dried over anhydrous sodium sulphate and filtered through celite. Concentration of the filtrate in vacuo gave a white solid (971 mg) which was found by $^1$H NMR to be a mixture of mesylate and α-methyl chloride (3:1) and used directly in the next step. A solution of this solid (968 mg) in THF (50 mL) was treated LiBr (6.39 g, 86.85 mmol) at reflux for 0.5 hour. The solvent was then removed under reduced pressure and the resulting residue was distributed between water and ethyl acetate. The organic phase was washed with water twice and brine once before being dried over anhydrous sodium sulphate and filtered through celite. The solvent was removed in wax) to give α-methyl bromide IIId-10 (851 mg, 93%) as white solid, m.p. 91-93° C. $^1$H NMR (CDCl$_3$, 400 MHz) δ 4.88 (s, 2H), 3.65 (s, 3H), 2.76 (q, J=7.60 Hz, 2H), 1.37 (t, J=7.60 Hz, 3H). Analysis found: C, 34.41; H, 4.07; N, 16.96%. C$_7$H$_{10}$BrN$_3$O$_2$.0.04EtOAc requires: C, 34.18; H, 4.13; N, 16.70%. LR-MS (+): m/e 248.4/250.4 (1:1, M+1).

A.1.1.8 Preparation of Prodrugs of Other Kinase Inhibitors

To a solution of (2E)-N-{4-(3-chloro-4-fluoroanilino)-7-[(3S)-tetrahydro-3-furanyloxy]-6-quinazolinyl}-4-(dimethylamino)-2-butenamide (BIBW2992; Himmelsbach et al, U.S. Ser. No. 07/019,012 B2) (1500 mg, 3.09 mmol) in NMP (4 mL) was added 5-(bromomethyl)-1-methyl-4-nitro-1H-imidazole (105) (747 mg, 3.40 mmol) according to general procedure C, to give (2E)-4-({4-(3-chloro-4-fluoroanilino)-7-[(3S)-tetrahydro-3-furanyloxy]-6-quinazolinyl}amino)-N,N-dimethyl-N-[(1-methyl-4-nitro-1H-imidazol-5-yl)methyl]-4-oxo-2-buten-1-ammonium bromide (1210 mg, 56%), which was further purified by preparative HPLC eluting with CH$_3$CN/H$_2$O/TFA to give (2E)-4-({4-(3-chloro-4-fluoroanilino)-7-[(3S)-tetrahydro-3-furanyloxy]-6-quinazolinyl}amino)-N,N-dimethyl-N-[(1-methyl-4-nitro-1H-imidazol-5-yl)methyl]-4-oxo-2-buten-1-ammonium trifluoroacetate (82) (730 mg, 32%), m.p. 149-152° C. (dec.). $^1$H NMR [(CD$_3$)$_2$SO] δ 10.80 (s, 1H), 9.93 (s, 1H), 9.07 (s, 1H), 8.78 (s, 1H), 8.14 (s, 1H), 8.03-8.01 (dd, J=6.8, 2.5 Hz, 1H), 7.73-7.69 (m, 1H), 7.50 (t, J=9.1 Hz, 1H), 7.38 (s, 1H), 7.04-6.96 (m, 1H), 6.88 (d, J=15.2 Hz, 1H), 5.32-5.31 (m, 1H), 5.05 (br, 2H), 4.42 (d, J=6.9 Hz, 2H), 4.02-3.91 (m, 3H), 3.87 (s, 3H), 3.82-3.77 (m, 1H), 3.12 (s, 6H), 2.43-2.34 (m, 1H), 2.18-2.08 (m, 1H). Analysis found: C, 44.42; H, 3.88; N, 12.21%. C$_{31}$H$_{31}$ClF$_4$N$_8$O$_7$.1.2CF$_3$COOH.1.5H$_2$O requires: C, 44.43; H, 3.93; N, 12.41%.

To a solution of (2E)-N-{4-[3-chloro-4-(2-pyridinylmethoxy)anilino]-3-cyano-7-ethoxy-6-quinolinyl}-4-(dimethylamino)-2-butenamide (HKI272; Tsou et al. J Med Chem, 2005, 48, 1107-1131) (700 mg, 1.26 mmol) in NMP (4 mL) was added 5-(bromomethyl)-1-methyl-4-nitro-1H-imidazole (105) (304 mg, 1.38 mmol) according to general procedure C, except MeCN/EtOAc (1:3) was used instead of MeCN, to give (2E)-4-({4-[3-chloro-4-(2-pyridinylmethoxy)anilino]-3-cyano-7-ethoxy-6-quinolinyl}amino)-N,N-dimethyl-N-[(1-methyl-4-nitro-1H-imidazol-5-yl)methyl]-4-oxo-2-buten-1-ammonium bromide (703 mg, 72%), which was further purified by preparative HPLC eluting with CH$_3$CN/H$_2$O/TFA to give (2E)-4-({4-[3-chloro-4-(2-pyridinylmethoxy)anilino]3-cyano-7-ethoxy-6-quinolinyl}amino)-N,N-dimethyl-N-[(1-methyl-4-nitro-1H-imidazol-5-yl)methyl]-4-oxo-2-buten-1-ammonium trifluoroacetate (83) (410 mg, 40%), m.p. 147-149° C. (dec.). $^1$H NMR [(CD$_3$)$_2$SO] δ 9.93 (br, 1H), 9.84 (s, 1H), 8.97 (s, 1H), 8.62-8.59 (m, 1H), 8.14 (s, 1H), 7.90-7.86 (dt, J=7.7, 1.8 Hz, 1H), 7.59 (d, J=7.8 Hz, 1H) 7.44 (s, 2H), 7.40-7.36 (m, 1H), 7.29-7.22 (m, 2H), 6.99-6.84 (m, 2H), 5.30 (s, 2H), 5.04 (br, 2H), 4.40 (d, J=6.7 Hz, 2H), 4.36-4.31 (q, J=7.0 Hz, 2H), 3.86 (s, 3H), 3.11 (s, 6H), 1.47 (t, J=7.0 Hz, 3H). Analysis found: C, 49.42; H, 4.57; N, 13.90%. C$_{37}$H$_{35}$ClF$_3$N$_9$O$_7$.0.5CF$_3$COOH.3H$_2$O requires: C, 49.54; H, 4.54; N, 13.68%.

To a solution of N-(4-bromo-2-fluorophenyl)-6-methoxy-7-[(1-methyl-4-piperidinyl)methoxy]-4-quinazolinamine (ZD6474; Hennequin et al, J Med Chem, 2002, 45, 1300-1312) (250 mg, 0.53 mmol) in NMP (1 mL) was added 5-(bromomethyl)-1-methyl-4-nitro-1H-imidazole (105) (139 mg, 0.63 mmol) according to general procedure C, except the reaction was stirred for 48 hours and EtOAc was used instead of MeCN in the work-up to give 4-({[4-(4-bromo-2-fluoroanilino)-6-methoxy-7-quinazolinyl]oxy}methyl)-1-methyl-1-[(1-methyl-4-nitro-1H-imidazol-5-yl)methyl]piperidinium bromide (392 mg), which was further purified by preparative HPLC eluting with CH$_3$CN/

H$_2$O/TFA to give 4-({[4-(4-bromo-2-fluoroanilino)-6-methoxy-7-quinazolinyl]oxy}methyl)-1-methyl-1-[(1-methyl-4-nitro-1H-imidazol-5-yl)methyl]piperidinium trifluoroacetate (146) (246 mg, 64%) as a mixture of trans/cis isomers in a ratio of ~2:5 by $^1$H NMR, hereafter named as A for the minor isomer and B for the major isomer, m.p. 185-188° C. (dec.). $^1$H NMR [(CD$_3$)$_2$SO] δ 10.42 (br, 1H), 8.60 (s, 1H), 8.114 & 8.110 (s×2, A & B isomers, 1H), 7.74-7.71 (m, 1H), 7.56-7.53 (m, 1H), 7.34 & 7.27 (s×2, A & B isomers, 1H), 5.07 (br, 2H), 4.29 & 4.14 (d×2, A & B isomers, J=6.6 Hz, 2H), 3.99 & 3.97 (s×2, A & B isomers, 3H), 3.88 (s, 3H), 3.75-3.60 (m, 4H), 3.15 & 3.01 (s×2, A & B isomers, 3H), 2.33-1.82 (m, 5H).

To a stirred solution of 6-(2,6-dichlorophenyl)-2-{4-[2-(diethylamino)ethoxy]anilino}-8-methylpyrido[2,3-d]pyrimidin-7(8H)-one (PD166285; Klutchko et al, J Med Chem, 1998, 41(17), 3276-3292) (200 mg, 0.39 mmol) in dry NMP (2 mL) was added 5-(bromomethyl)-1-methyl-4-nitro-1H-imidazole (105) (103 mg, 0.47 mmol). The resulting solution was then stirred at room temperature for 72 h before Et$_2$O was added. The resulting precipitate was filtered and washed with Et$_2$O and CH$_2$Cl$_2$. The crude product was purified by precipitation from CH$_3$CN/Et$_2$O. The precipitate was filtered and washed with CH$_2$Cl$_2$ and dried under vacuum to give 2-(4-{[6-(2,6-dichlorophenyl)-8-methyl-7-oxo-7,8-dihydropyrido[2,3-d]pyrimidin-2-yl]amino}phenoxy)-N,N-diethyl-N-[(1-methyl-4-nitro-1H-imidazol-5-yl)methyl]ethanammonium bromide (140) (170 mg, 59%) as a pale yellow powder, m.p. 142-145° C. $^1$H NMR [(CD$_3$)$_2$SO] δ 10.12 (s, 1H), 8.82 (s, 1H), 8.13 (s, 1H), 7.88 (s, 1H), 7.78 (d, J=8.9 Hz, 2H), 7.59 (dd, J=8.1, 0.7 Hz, 2H), 7.46 (dd, J=8.8, 7.4 Hz, 1H), 7.05 (d, J=9.1 Hz, 2H), 5.15 (s, 2H), 4.48 (t, J=4.4 Hz, 2H), 3.89 (s, 3H), 3.86 (t, J=4.5 Hz, 2H), 3.65 (s, 3H), 3.58 (q, J=6.8 Hz, 4H), 1.31 (t, J=7.0 Hz, 6H). Analysis found: C, 47.13; H, 4.26; N, 13.76. C$_{31}$H$_{33}$BrCl$_2$N$_8$O$_4$.CH$_2$Cl$_2$ requires: C, 47.02; H, 4.32; N, 13.71.

To a stirred solution of 6-(2,6-dichlorophenyl)-2-{4-[2-(diethylamino)ethoxy]anilino}-8-methylpyrido[2,3-d]pyrimidin-7(8H)-one (PD166285; Klutchko et al, J Med Chem, 1998, 41(17), 3276-3292) (200 mg, 0.39 mmol) in dry NMP (1.5 mL) was added 5-(bromomethyl)-1,2-dimethyl-4-nitro-1H-imidazole (122) (110 mg, 0.47 mmol). The resulting solution was then stirred at room temperature for 120 h before Et$_2$O was added. The resulting precipitate was filtered and washed with Et$_2$O and CH$_2$Cl$_2$ and dried under vacuum to give 2-(4-{[6-(2,6-dichlorophenyl)-8-methyl-7-oxo-7,8-dihydropyrido[2,3-d]pyrimidin-2-yl]amino}phenoxy)-N-[(1,2-dimethyl-4-nitro-1H-imidazol-5-yl)methyl]-N,N-diethylethanammonium bromide (141) (210 mg, 72%) as a pale yellow powder, m.p. 163-166° C. $^1$H NMR [(CD$_3$)$_2$SO] δ 10.13 (s, 1H), 8.82 (s, 1H), 7.89 (s, 1H), 7.78 (d, J=8.8 Hz, 2H), 7.59 (dd, J=8.0, 0.6 Hz, 2H), 7.45 (dd, J=8.8, 7.4 Hz, 1H), 7.05 (d, J=9.1 Hz, 2H), 5.15 (s, 2H), 4.47 (t, J=4.4 Hz, 2H), 3.85 (t, J=4.2 Hz, 2H), 3.75 (s, 3H), 3.65 (s, 3H), 3.58 (q, J=7.2 Hz, 4H), 2.44 (s, 3H), 1.31 (t, J=7.0 Hz, 6H). Analysis found: C, 51.74; H, 4.79; N, 14.86. C$_{32}$H$_{35}$BrCl$_2$N$_8$O$_4$ requires: C, 51.49; H, 4.73; N, 15.01.

To a stirred solution of 6-(2,6-dichlorophenyl)-8-methyl-2-(4-pyridinylamino)pyrido[2,3-d]pyrimidin-7(8H)-one (PD166285 analogue A; Klutchko et al, J Med Chem, 1998, 41(17), 3276-3292) (200 mg, 0.50 mmol) in dry NMP (3 mL)/THF (200 mL) was added 5-(bromomethyl)-1-methyl-4-nitro-1H-imidazole (105) (133 mg, 0.60 mmol). The resulting solution was then stirred at room temperature for 25 days before THF was removed. The resulting solution was partitioned between EtOAc/water. The aqueous portion was subjected to freeze drying and the resulting gum was triturated with Et$_2$O/EtOAc/CH$_2$Cl$_2$ to give 4-{[6-(2,6-dichlorophenyl)-8-methyl-7-oxo-7,8-dihydropyrido[2,3-d]pyrimidin-2-yl]amino}-1-[(1-methyl-4-nitro-1H-imidazol-5-yl)methyl]pyridinium bromide (142) (200 mg, 65%) as a pale yellow powder, m.p. 252° C. (dec.). $^1$H NMR [(CD$_3$)$_2$SO] δ 11.83 (bs, 1H), 9.08 (s, 1H), 8.68 (d, J=7.0 Hz, 2H), 8.21 (bs, 2H), 8.09 (s, 1H), 8.05 (s, 1H), 7.61 (dd, J=8.1, 0.6 Hz, 2H), 7.5 (dd, J=8.9, 7.4 Hz, 1H), 6.00 (s, 2H), 3.84 (s, 3H), 3.73 (s, 3H). Analysis found: C, 44.33; H, 3.42; N, 17.00. C$_{24}$H$_{19}$BrCl$_2$N$_8$O$_3$.2H$_2$O requires: C, 44.06; H, 3.54; N, 17.13.

To a stirred solution of 6-(2,6-dichlorophenyl)-8-methyl-2-{4-[2-(1-piperidinyl)ethoxy]anilino}pyrido[2,3-d]pyrimidin-7(8H)-one (PD 166285 analogue B; Klutchko et al, J Med Chem, 1998, 41(17), 3276-3292) (230 mg, 0.44 mmol) in dry NMP (5 mL) was added 5-(bromomethyl)-1-methyl-4-nitro-1H-imidazole (122) (116 mg, 0.53 mmol). The resulting solution was then stirred at room temperature for 12 days before Et$_2$O was added. The resulting precipitate was filtered and washed with EtOAc and CH$_2$Cl$_2$. The crude product was purified by precipitation from NMP/EtOAc (×2). The precipitate was filtered and dried under vacuum to give 1-[2-(4-{[6-(2,6-dichlorophenyl)-8-methyl-7-oxo-7,8-dihydropyrido[2,3-d]pyrimidin-2-yl]amino}phenoxy)ethyl]-1-[(1-methyl-4-nitro-1H-imidazol-5-yl)methyl]piperidinium bromide (143) (100 mg, 31%) as a pale yellow powder, m.p. 176-178° C. $^1$H NMR [(CD$_3$)$_2$SO] δ 10.14 (s, 1H), 8.82 (s, 1H), 8.14 (s, 1H), 7.89 (s, 1H), 7.80 (d, J=8.9 Hz, 2H), 7.59 (dd, J=8.1, 0.7 Hz, 2H), 7.46 (dd, J=8.8, 7.4 Hz, 1H), 7.10 (d, J=9.1 Hz, 2H), 5.22 (bs, 2H), 4.61 (t, J=4.4 Hz, 2H), 4.17 (bs, 2H), 3.86 (s, 3H), 3.72-3.64 (m, 2H), 3.65 (s, 3H), 2.10-1.95 (m, 4H), 1.74 (bd, J=14.3 Hz, 2H), 1.60 (bd, J=14.3 Hz, 1H), 1.46-1.31 (m, 1H), 2 protons not observed. Analysis found: C, 48.33; H, 4.64; N, 13.32. C$_{32}$H$_{33}$BrCl$_2$N$_8$O$_4$.3H$_2$O.¼EtOAc requires: C, 48.31; H, 5.04; N, 13.66.

To a solution of N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide (sunitinib; Sun et al, J Med Chem, 2003, 46(7), 1116-1119) (199 mg, 0.50 mmol) in NMP (1 mL) was added 5-(bromomethyl)-1-methyl-4-nitro-1H-imidazole (105) (100 mg, 0.45 mmol) according to general procedure B to give N,N-diethyl-2-[({5-[(Z)-(5-fluoro-2-oxo-1,2-dihydro-3H-indol-3-ylidene)methyl]2,4-dimethyl-1H-pyrrol-3-yl}carbonyl)amino]N-[(1-methyl-4-nitro-1H-imidazol-5-yl)methyl]ethanammonium bromide, which was further purified by preparative HPLC to give N,N-diethyl-2-[({5-[(Z)-(5-fluoro-2-oxo-1,2-dihydro-3H-indol-3-ylidene)methyl]-2,4-dimethyl-1H-pyrrol-3-yl}carbonyl)amino]-N-[(1-methyl-4-nitro-1H-imidazol-5-yl)methyl]ethanammonium trifluoroacetate (144) (190 mg, 64%), m.p. 162-165° C. (dec.). $^1$H NMR [(CD$_3$)$_2$SO] δ 13.74 (s, 1H), 10.89 (s, 1H), 8.13 (s, 1H), 7.80-7.75 (m, 2H), 7.73 (s, 1H), 6.96-6.91 (m, 1H), 6.87-6.84 (m, 1H), 5.03 (s, 2H), 3.90 (s, 3H), 3.61-3.48 (m, 8H), 2.45 (s, 3H), 2.42 (s, 3H), 1.34 (t, J=7.1 Hz, 6H). $^{19}$F NMR [(CD$_3$)$_2$SO, 376.5 MHz] δ −73.97 (s, 3.31 F), −122.71 (m, 1 F). Analysis found: C, 50.50; H, 4.89; N, 13.88. C$_{29}$H$_{33}$F$_4$N$_7$O$_6$.0.31(F$_3$CCOOH).H$_2$O requires: C, 50.46; H, 5.05; N, 13.91.

To a solution of N-[2-(diethylamino)ethyl]-5-[(Z)-(5-fluoro-2-oxo-1,2-dihydro-3H-indol-3-ylidene)methyl]-2,4-dimethyl-1H-pyrrole-3-carboxamide (sunitinib; Sun et al, J Med Chem, 2003, 46(7), 1116-1119) (199 mg, 0.50 mmol) in NMP (1 mL) was added 5-(bromomethyl)-1,2-dimethyl-4-nitro-1H-imidazole (122) (106 mg, 0.45 mmol) according to general procedure C, except EtOAc was used instead of MeCN, to give N-[(1,2-dimethyl-4-nitro-1H-imidazol-5-yl)methyl]-N,N-diethyl-2-[({5-[(Z)-(5-fluoro-2-oxo-1,2-dihydro-3H-indol-3-ylidene) methyl]-2,4-dimethyl-1H-pyrrol-3- yl}carbonyl)amino]ethanammonium bromide (145) (268 mg, 93%), m.p. 244-248° C. (dec). $^1$H NMR [(CD$_3$)$_2$SO] δ 13.74 (s, 1H), 10.89 (s, 1H), 7.79-7.75 (m, 2H), 7.73 (s, 1H), 5.04 (br, 2H), 3.77 (s, 3H), 3.58-3.46 (m, 8H), 2.46 (s, 3H), 2.45 (s, 3H), 2.42 (s, 3H), 1.34 (t, J=7.1 Hz, 6H). Analysis found: C, 52.59; H, 5.64; N, 14.98. C$_{28}$H$_{35}$BrFN$_7$O$_4$.0.5H$_2$O requires: C, 52.42; H, 5.66; N, 15.28.

A.2. Efficacy of the Prodrugs

The irreversible erbB1, 2, 4 inhibitors (11-14) and a comparative reversible inhibitor (16), where the Michael acceptor double bond has been saturated, were compared to a series of their quaternary ammonium salt prodrugs (17-23, 27) bearing a range of fragmenting reductive triggers. A range of assays to assess the degree of deactivation of the prodrugs, their activation in cells under hypoxia, their fragmentation upon one-electron reduction and their efficacy in A431 tumour xenografts were employed.

Experimental: Methods and Materials

A.2.1 Cellular erbB1 Inhibition: Oxic and Hypoxic Conditions Experimental

Human A431 epidermoid carcinoma cells were seeded at 400,000 cells/well in a 6 well plate in alpha minimal essential media (αMEM) containing 10% fetal bovine serum, 10 mM D-Glucose and 0.2 mM 2'-deoxycytidine. A431 cells were allowed to attach for 90 minutes under oxic or anoxic conditions, then exposed to test compounds at a concentration of 1 uM for a further 4 hours under oxic or anoxic conditions. The cells were then washed free of test compounds three times using serum free media and then returned to the incubator under oxic conditions overnight. The cells were then stimulated with 100 ng/mL EGF for 15 minutes before the medium was aspirated and the cells were washed with ice-cold PBS. Cells were lysed in modified RIPA buffer (50 mM Tris-HCl, pH 7.4, 1% NP-40, 0.25% Na-deoxycholate, 150 mM NaCl, 1 mM EDTA, 1 mM Na$_3$VO$_4$, 1 mM NaF and 1× protease inhibitor cocktail (Sigma) and incubated on ice for 5-10 min. The BCA assay was employed to determine protein concentrations of samples. Phosphorylation of EGFR relative to actin loading was determined by western blot using appropriate antibodies. 1 ug of total protein was loaded per well into a 15 well NuPAGE 4-12% gel (Invitrogen). After electrophoresis the proteins are transferred to a 0.45 μm nitrocellulose membrane (Biorad) and blocked for 1 hour with 2% BSA (ICPBio) in TBS-Tween 0.1%. Antibodies are diluted as indicated in TBS-Tween 0.1%.

| α-Phosphotyrosine (Upstate) | 1:500 | O/N 4☐ C. |
| Goat-anti-Rabbit-IgG-HRP conjugated (Santa Cruz) | 1:5000 | 2 hrs RT |
| α-Actin (Chemicon) | 1:10,000 | O/N 4☐ C. |
| Goat-anti-mouse-IgG-HRP conjugated (Santa Cruz) | 1:5000 | 2 hrs RT |

Proteins are detected using Supersignal West Pico Chemiluminescent Substrate (Pierce/Thermo Scientific). After detection of the phosphorylated protein the blot is stripped for 30 minutes with Restore Western Blot Stripping Buffer (Pierce/Thermo Scientific), washed, reblocked and incubated with the antibody against actin.

A.2.2 Cellular Growth Inhibition Experimental

Human A431, BT474, SKBR3, SKOV3, SW620, H1975 and HT29 carcinoma cells in log phase exponential growth in alpha minimal essential media (αMEM) containing 5% fetal bovine serum (FBS), were harvested by trypsinisation (1× trypsin/EDTA, Gibco Brl), counted, and seeded into 96 well plates (Nunc) at cell densities ranging from 800-1500 cells/well. Half of the cell samples were seeded into plates that were pre-equilibrated and held in an anoxic environment (90% N$_2$, 5% H$_2$, 5% CO$_2$, 37° Q Anaerobic chamber, Coy Laboratory Products). After 3 hours attachment under either aerobic (21% O$_2$) or anoxic (<10 ppm O$_2$) conditions, cells were exposed to a range of prodrug or effector concentrations over appropriate dilution ranges for 4 hours. At the end of this period the anoxic plates were recovered from the anaerobic camber and held under normoxia in a standard CO$_2$ incubator (37° C.) for 20 hours. All plates were washed free of compound and cells were allowed to proliferate for a further 4 days in αMEM containing 5% FBS+antibiotics. Cells were fixed in trichloroacteic acid (30 min), washed and stained with sulforhodamine B (SRB, 60 min) prior to washing in acidified water. SRB was solubilised and absorption read at 450 nm to calculate cell densities. Inhibition of proliferation was calculated relative to untreated control wells.

A.2.3 Oxic and Hypoxic Cellular Metabolism Experimental

A431 and SKOV3 cells were grown in a 175 flask and seeded at 40K, a density which gave an 80-90% confluent cell layer after 7 days growth. Cells were washed with PBS, harvested with 0.05% trypsin/EDTA, centrifuged at 1000 rpm for 5 mins at room temperature and re-suspended in a 1 mL of cell culture medium (α-MEM containing 10% FCS, 10 mM D-Glucose and 0.2 mM 2'-deoxycytidine). Cell numbers were determined with the Coulter counter and the appropriate number of cells was transferred to a new tube. 5×10$^5$ cells per well were plated into wells of a 24-well plate in a total volume of 350 μL/well (i.e. 14.3×10$^5$ cells/mL). Cells were incubated at 37° C. for two hours to attach to the wells and for anoxic samples to equilibrate. 50 μL of cell culture media (to 350 uL/well) containing 80 μM compound 20 was added to each well to give a final compound 20 concentration of 10 μM in each well in duplicate for each of the 2 cell lines. The cells were incubated for 1, 2 or 3 hours at 37° C. At the appropriate time the 24 well plate was removed from the incubator/anoxic chamber and placed on ice. The contents of each well was transferred to the microcentrifuge tube kept on ice. 800 μL of acetonitrile (spiked with D6 internal standards of compounds 11 and 20, each 0.5 uM) was added to each of the drug treated wells to allow efficient extraction from the cell monolayer. Then the entire contents (1200 uL=400+800 uL) was vortex mixed and transferred to −80° C. for storage until they were run on the LC-MS/MS system. A similar procedure was followed for the control samples. The control samples were used to construct the calibration curve by spiking compound 20 and compound 11 separately. On the day of the analysis, samples from −80° C. freezer were thawed on ice, vortex mixed and centrifuged at 13000 rpm for 5 min to sediment the cell debris. 35 uL of supernatant was carefully transferred to HPLC inserts and mixed with 85 uL of formate buffer (45 mM, pH 4.5). 25 uL of the reconstituted samples were injected into the LC-MS/MS system.

A.2.4 Plasma and Tumour Pharmacokinetics Experimental

Compound 20 was administered at a dose of 133 μmol/kg to 24 female NIH-III mice bearing A431 tumour xenografts, as a solution in pH 4.0 lactate buffer via intraperitoneal injection. Blood samples were collected at T=0.25, 1, 3, 5, 24, 36, 48 and 72 hours by terminal bleed (n=3 per cohort) under isoflurane anaesthesia. A431 tumour samples were collected at T=0.25, 1, 3, 5, 24, 36, 48 and 72 hours (n=3 per cohort) and immediately frozen in liquid nitrogen and stored at −80° C. before sample preparation for drug analysis. A small piece (~100 mg) of tissue was placed in biopulveriser well (previously cooled in liquid nitrogen) and reduced to fine powder with a 2-3 strong blows to the stainless steel pestle. The frozen powder was collected in pre-weighed microcentrifuge tube (kept on dry ice). Four volumes of ice cold acetonitrile (contain 0.5 uM each of D6 internal standards of compound 20 and compound 11) was added to extract the drug from the pulverised tissue. The microcentrifuge tubes were spun at 13,000 rpm for 10 min to precipitate the cell debris and proteins. To 10 μl of plasma (collected in EDTA) was added 40 μl of ice cold acetonitrile (0.5 uM D6 internal standards of compound 20 and compound 11). The resulting solution was mixed and then centrifuged at 13,000 rpm for 5 min. The supernatant (40 ul) was transferred to the HPLC inserts and mixed with 80 ul of 45 mM formate buffer pH 4.5 and then concentrations of compound 20, compound 11 and compound 11 in samples from mice dosed with compound 20 were determined on an Agilent 6410 LC-MS/MS equipped with diode array absorbance detector (DAD) in line with a mass detector. The analysis was performed by configuring the multimode ion source detector in electrospray negative mode, drying gas flow 5.5 L/min, nebuliser pressure 55 psi, drying gas temperature 350° C., vaporiser temperature 225° C., capillary voltage 2500 V, charging voltage 2000 V, DAD detection was 322 nm, 8 nm bandwidth. Quantitation was based on MRM transition at m/z of 564>314 (prodrug), and m/z of 425>314 (effector) and 570>314 (D6 internal standard of prodrug), 431>314 (D6 internal standard of effector). The analytes were eluted using a gradient of 0.01% formic acid in acetonitrile (80%)-water (20%) mixture and 0.01% formic acid in water (100%) on Zorbax SB 018, rapid resolution HT 3.0×50 mm, 1.8 micron (Agilent) HPLC column with a flow rate of 0.6 ml/min.

A.2.5 In Vivo Efficacy Experimental

A431 Xenografts:

Specific pathogen-free homozygous female CD-1 nude mice (Charles River Laboratories, Wilmington, Mass.) were inoculated subcutaneously with a single cell suspension of A431 cells (5×10$^6$ cells/100 pt; right flank). When A431 tumour xenografts were established (typically 6-10 days) mice were randomized to treatment groups. All compounds were prepared in lactate buffer (pH4). Mice were dosed by intraperitoneal injection (0.01-0.03 ml/g) using the stated schedules and dose levels. Tumour size and body weights were measured at regular intervals. Tumour volume was calculated as π (length×width$^2$)/6. The time for tumours to increase in volume 4-fold relative to pre-treatment volume (RTV$^4$) was determined, and the % Tumour Growth Inhibition (% TGI) was calculated as the median percentage increase in RTV$^4$ for treated versus control. Differences in RTV$^4$ were tested for statistical difference by Mann Whitney U test using SigmaStat v3.5.

SKOV3 Xenografts:

Specific pathogen-free homozygous female NIH-III nude mice (Charles River Laboratories, Wilmington, Mass.) were inoculated subcutaneously with a single cell suspension of SKOV3 cells (1×10$^7$ cells/100 μL; right flank). When SKOV3 tumour xenografts were established (typically 50-65 days) mice were randomized to treatment groups. All compounds were prepared in lactate buffer (pH4). Mice were dosed by intraperitoneal injection (0.01-0.03 ml/g) using the stated schedules and dose levels. Tumour size and body weights were measured at regular intervals. Tumour volume was calculated as π (length×width$^2$)/6. The time for tumours to increase in volume 4-fold relative to pre-treatment volume (RTV$^4$) was determined, and the % Tumour Growth Inhibition (% TGI) was calculated as the median percentage increase in RTV$^4$ for treated versus control. Differences in RTV$^4$ were tested for statistical difference by Mann Whitney U test using SigmaStat v3.5.

A.2.6 Radiolytic Reduction Experimental

The relative activities of example prodrugs in solution to release effectors, upon the introduction of reducing equivalents, were determined by the use of a $^{60}$Co γ-ray irradiator. Prodrugs were dissolved in Millipore water (containing added 50 mM sodium formate buffered at pH 7 by 5 mM sodium phosphate) at a concentration of 50 μM or below. Solutions, contained in air-tight glassware continuously saturated with N$_2$O gas for 30 mins prior to radiolysis at a dose rate of 7.5 Gy min$^{-1}$, previously determined using Fricke dosimetry (Fricke and Hart, "Chemical Dosimetry" in *Radiation Dosimetry* Vol. 2, Attrix, F. H.; Roesch, W. C.; Tochilin, E. (Eds.), Academic Press, New York, 1966, pp 167-239.) Under the radiation conditions employed above, a concentration of 0.66 μM in 1-electron reducing equivalents (the CO$_2$.$^-$ radical) are produced per Gy (Mulazzani et al, J. Phys. Chem., 90, 5347-5352, 1980) and the prodrugs, (P), are reduced by electron transfer.

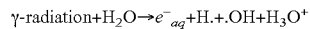

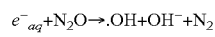

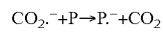

The loss of each prodrug and formation of its effector were monitored by HPLC-mass spectrophotometry (MS) in duplicate irradiated samples. The percentage loss in the concentration of the prodrugs and formation of the effectors at the 0.95 reducing equivalents level was determined. In addition, the detection of the methyl-nitroaromatic from each prodrug was recorded. Prodrugs exhibiting >50% loss in concentration at the 0.95 reducing equivalents level, indicate 1-electron stoichiometry.

Pulse radiolysis was used to monitor the 1-electron reduction and stability of the compounds in real time. A linear accelerator delivering short pulses of high energy electrons (2-3 Gy in 200 ns of 4 MeV) equipped with a fast spectophotometric detection system was used. (Anderson et al, J. Phys. Chem. A, 101, 9704-9709, 1997). Prodrugs were dissolved in N$_2$O-saturated solutions containing formate ions, as above, which, following pulse radiolysis, resulted in the rapid formation of the radical anions of the compounds within a few microseconds. The rate of fragmentation was determined by analysing kinetic transients at wavelengths corresponding to the formation of the benzyl-type radical of the trigger moiety. (Bays et al, J. Am. Chem. Soc., 105, 320-324, 1983; Anderson et al, J. Phys. Chem. A, 101, 9704-9709, 1997).

Results and Discussion

A.2.7 Enzyme Inhibitory Activities

The compounds of Table 1 were tested for their ability to inhibit erbB1, erbB1$^{T790M}$, erbB2 and erbB4 in an isolated enzyme assay. This assay utilises synthetic FRET-capable peptide substrates. Phosphorylation of these substrates protects them from cleavage by a development reagent, leaving their FRET-capabilities intact. The data is presented as a concentration of drug required to inhibit the phosphorylation of the peptide substrate by 50% (IC$_{50}$). As has been pointed out by others (Tsou et al, J Med Chem, 2001, 44, 2719-2734) considerable variations exist when comparing compounds between particular isolated enzyme assays, due to differences in the nature of the enzyme, substrate and overall assay conditions. As a further consideration, for compounds capable of irreversible inhibition of an enzyme, the IC$_{50}$ reflects both reversible and irreversible binding to the enzyme. For compounds capable of rapid and complete alkylation of the enzyme, the $IC_{50}$ values derive from essentially titrating the enzyme activity in a stoichiometric manner (i.e. infinite inhibition) and are therefore considered only as 'apparent' $IC_{50}$s. Assays of this nature have been used commonly (Tsou et al. J Med Chem, 2001, 44, 2719-2734; Wissner et al. J Med Chem, 2003, 46, 49-63; Wissner et al. Bioorg Med Chem Lett, 2004, 14, 1411-1416; Tsou et al. J Med Chem, 2005, 48, 1107-1131; Klutchko et al. J Med Chem, 2006, 49, 1475-1485) to rank compounds within one set of assay conditions as described herein.

Under these assay conditions the known irreversible erbB1/2 inhibitor 11 was confirmed to be a potent inhibitor of erbB1, 2 and 4 ($IC_{50}$ 0.22 nM, 8 nM and 2.7 nM respectively), consistent with an ability to alkylate the cysteine residue at the mouth of the ATP-binding domain of each of these enzymes and confer pan-erbB potency to the otherwise erbB1-selective 4-anilinoquinazoline scaffold. In this assay 11 is more potent than previously reported (Tsou et al. J Med Chem, 2001, 44, 2719-2734) in a solid-phase ELISA-based assay (erbB1 $IC_{50}$=11 nM, erbB2 $IC_{50}$=301 nM), but is directly comparable to the recently reported erbB1 $IC_{50}$ (0.22 nM) performed using the identical Z'-LYTE assay (Michalczyk et al, Bioorg Med Chem, 16, 2008, 3482-3488). Compound 11 further shows good potency ($IC_{50}$ 10.3 nM) against the T790M mutant form of erbB1 known to be sensitive to irreversible erbB inhibitors. This mutant possesses a bulky gatekeeper residue that is considered to both block binding of the clinical reversible 4-anilinoquinazolines gefitinib and erlotinib, and restore ATP-binding affinity, leading to ~50% of patient relapse in gefitinib and erlotinib sensitive non-small cell lung cancer. By way of contrast compound 16 is the direct reversible analogue of compound 11 and it is indeed erbB1-selective, showing a 10 to 42-fold loss of potency against erbB2, erbB4 and erbB1$^{T790M}$, consistent with an inability to alkylate these enzymes and improve inhibitory potency. Most importantly within this assay, the quaternary ammonium salt prodrugs (17-22) of compound 11 were shown to be potent inhibitors of isolated erbB1 (IC50s 0.20-0.56 nM) but were also at least 14 to 44-fold less effective at inhibiting isolated erbB2, erbB4 and erbB1$^{T790M}$. A trend consistent with quaternisation of the tertiary amine of compound 11 resulting in compounds that are reversible inhibitors of the erbB family (see also cell-based drug wash-out data later), as the known erbB1-selective nature of the 4-anilinoquinazoline scaffold and the loss of potency against isolated erbB1$^{T790M}$, is apparent for the prodrugs (17-22).

TABLE 1

Isolated enzyme inhibition ($IC_{50}$) of the erbB family.

| Compound | Isolated Enzyme Inhibition $IC_{50}$ (nM)$^a$ | | | |
| --- | --- | --- | --- | --- |
| | erbB1 | erbB1$^{T790M}$ | erbB2 | erbB4 |
| 11 | 0.22 | 10.3 | 7.7 | 2.7 |
| 16 | 0.41 | 140 | 74 | 113 |
| 17 | 0.56 | ND$^b$ | 110 | ND |
| 18 | 0.20 | ND | 123 | ND |
| 19 | 0.40 | 451 | 113 | 61 |
| 20 | 0.47 | 594 | 112 | 85 |
| 21 | 0.53 | 531 | 128 | 76 |
| 22 | 0.46 | ND | 135 | ND |
| 27 | 0.64 | 798 | 191 | 174 |

Footnotes for Table 1
$^a$Invitrogen Z'-LYTE kinase assay performed in duplicate as a commercial service by Invitrogen SelectScreen Kinase Profiling using 10 µM ATP.
$^b$ND = not determined.

The compounds of Table 2 were tested for their ability to inhibit the autophosphorylation of erbB1 in EGF-stimulated A431 cells by Western immunoblotting measurement of phospho-erbB1 status. Compounds 11-13 were shown to be potent inhibitors of cellular erbB1 ($IC_{50}$s of 9, 45, and 16 nM respectively), as was compound 16 ($IC_{50}$ 18 nM), the direct reversible analogue of compound 11. In contrast the quaternary ammonium salt derivatives (19-23, 27) ranged from 27- to 201-fold less effective at inhibiting erbB1 autophosphorylation in intact A431 cells, relative to their respective effector molecules. This loss of cellular erbB1 inhibitory potency for the prodrugs, in concert with retained isolated enzyme erbB1 inhibitory potency, as described above, is attributed primarily to cellular exclusion of the positively charged quaternary ammonium salt prodrugs.

TABLE 2

Inhibition ($IC_{50}$) of erbB1 autophosphorylation in intact A431 cells.

| Compound | Cellular Enzyme Inhibition $IC_{50}$ (µM)$^a$ | |
| --- | --- | --- |
| | erbB1 | Deact.$^b$ |
| 11 | 0.009 | |
| 12 | 0.045 | |
| 13 | 0.016 | |
| 16 | 0.018 | |
| 19 | 0.962 | 105 |
| 20 | 0.555 | 61 |
| 21 | 1.19 | 130 |
| 22 | 1.39 | 151 |
| 23 | 1.20 | 27 |
| 27 | 3.60 | 201 |

Footnotes for Table 2
$^a$Concentration required to inhibit the EGF-stimulated autophosphorylation of erbB1 in intact A431 cells by 50%, as determined by Western blotting with an antiphosphotyrosine antibody. Values are the average of two determinations, (STDEV <20%).
$^b$Fold reduction in cellular erbB1 inhibition relative to the parent kinase inhibitor.

A.2.8 Cellular erbB1 Inhibition: Irreversibility Wash-Out Assay

The quaternary ammonium salt prodrug 20 was assessed alongside the known irreversible erbB1/2 inhibitor 11 (effector for prodrug 20) and compound 16 for their ability to irreversibly inhibit erbB1 autophosphorylation in intact A431 cells. The cells were either continuously exposed to drug (1 µM) for one hour then stimulated with EGF and whole cell lysates measured for phospho-erbB1 levels by Western blot, or exposed to drug (1 µM) for one hour and then washed free of unbound drug prior to EGF stimulation and phospho-erbB1 Western blotting (FIG. 1A/B). As previously described for compound 11, (Tsou et al, J Med Chem, 2001, 44, 2719-2734) erbB1 autophosphorylation was completely inhibited in A431 cells irrespective of whether the cells were washed free of unbound drug prior to EGF stimulation, strongly supporting the interpretation that irreversible inhibition of erbB1 had occurred. In contrast, compound 16 has been shown to be a potent inhibitor of cellular autophosphorylation ($IC_{50}$=18 nM, Table 2) but is incapable of enzyme alkylation as it is not substituted in the 6-position with a Michael acceptor. Accordingly, compound 16 shows complete inhibition of erbB1 autophosphorylation in cells that were not washed free of drug, while cells washed free of drug are restored in their ability to autophosphorylate erbB1, indicating compound 16 is a potent, reversible inhibitor of erbB1. A similar trend was observed for prodrug 20, while autophosphorylation was not completely inhibited in the non-washed cells using a drug exposure of 1 µM (consistent with the cellular $IC_{50}$ for erbB1 autophosphorylation for this compound (555 nM, Table 2)), cells washed free of drug had their ability to autophosphorylate erbB1 fully restored, consistent with prodrug 20 being a reversible inhibitor of erbB1.

FIG. 1 shows A431 cellular autophosphorylation inhibition for compounds 11, 16 and 20. Cells were given a 1 hour exposure to 1 μM of test compound and either directly stimulated with EGF, lysed and western blotted for EGFR (erbB1) and phospho-EGFR (phospho-erbB1), or washed extensively with drug free media to remove test compounds, prior to EGF stimulation, cell lysis and western blotting. A Western blots. B Quantification of western immunoblots normalised for protein loading using total cellular EGFR protein.

A.2.9 Cell Growth Inhibitory Activity

The compounds of Table 3 were tested for their ability to inhibit the proliferation of three human carcinoma cell lines, selected to provide a comparison with literature precedent: (Tsou et al, J Med Chem, 2001, 44, 2719-2734) A431 (epidermoid), which overexpresses erbB1; SKBR3 (breast), which overexpresses erbB2 and to a lesser extent, erbB1; and SW620 (colon), which serves as a control line not expressing erbB1 or erbB2 to any significant extent. The cells were exposed to test compounds for either 24 hours under oxic conditions or for 4 hours under anoxia followed by 20 hours under oxic conditions. They were then washed free of drug and incubated for a further 4 days, before being stained for cell survival with sulforhodamine B.

the erb1/2 driven cell lines. Compounds 11-14 and 16 did not show any significant change in potency when the cells received 4 hours of anoxia.

Relative to their respective kinase inhibitors (11, 12, 16), the quaternary ammonium salt prodrugs (17-23, 27) were 12- to 277-fold less effective at inhibiting the growth of A431 cells; 19- to 332-fold less effective at inhibiting the growth of SKBR3 cells; and 18- to 123-fold less effective at inhibiting the growth of SW620 cells. Several prodrugs (19, 20, 22 and 23) of Table 4 were significantly more potent at inhibiting the growth of A431 and SKBR3 cells (but not SW620 cells), after the cells received 4 hours of anoxia. The hypoxic cytotoxicity ratios (HCR) ranged from 10.4 to 26.8 in A431 cells and 6.7 to 18.1 in SKBR3 cells, consistent with hypoxia-selective reduction of the nitroheterocyclic reductive trigger, followed by trigger fragmentation to release an irreversible erbB1, 2, 4 inhibitor.

A.2.10 Radiolytic Reduction

Electron-affinic prodrugs can be selectively reduced by 1-electron processes in the hypoxic regions of solid tumours, in contrast to under normoxic conditions in normal tissues, to form or release a cytotoxic effector (Brown and Wilson, Nature Rev. Cancer, 2004, 4, 437-447). The prodrug should contain a trigger moiety possessing a 1-electron reduction potential, E(1), of between $-0.6V$ to $-0.2$ V and preferably between $-0.5$ V to $-0.3V$ vs. NHE. The E(1) values of many

TABLE 3

Inhibition ($IC_{50}$) of cellular proliferation in A431, SKBR3 and SW620 cells.

| | Cellular Growth Inhibition $IC_{50}$ (μM)[a] | | | | | | | | | | | |
|---|---|---|---|---|---|---|---|---|---|---|---|---|
| | A431 | | | | SKBR3 | | | | SW620 | | | |
| Compound | Oxic[b] | Deact.[c] | Anoxic[d] | HCR[e] | Oxic[b] | Deact.[c] | Anoxic[d] | HCR[e] | Oxic[b] | Deact.[c] | Anoxic[d] | HCR[e] |
| 11 | 0.040 | | 0.040 | 1.0 | 0.081 | | 0.141 | 0.6 | 3.43 | | 2.89 | 1.2 |
| 12 | 0.010 | | 0.023 | 0.4 | 0.044 | | 0.028 | 1.6 | 3.81 | | 4.01 | 1.0 |
| 13 | 0.430 | | 0.784 | 0.5 | 1.04 | | 0.664 | 1.6 | 27.4 | | 29.0 | 1.5 |
| 14 | 0.015 | | 0.009 | 1.7 | 0.028 | | 0.027 | 1.1 | 2.02 | | 2.46 | 0.8 |
| 16 | 1.26 | | 1.30 | 1.0 | 3.19 | | 5.51 | 0.6 | 18.6 | | 19.6 | 0.9 |
| 17 | 0.462 | 12 | 0.444 | 1.0 | 1.52 | 19 | 1.84 | 0.8 | 112.5 | 33 | 111.5 | 1.0 |
| 18 | 2.34 | 59 | 0.401 | 5.8 | 3.75 | 44 | 1.29 | 2.8 | 92.2 | 27 | 79.8 | 1.2 |
| 19 | 2.64 | 66 | 0.201 | 13.1 | 6.33 | 78 | 0.483 | 13.1 | 156.4 | 46 | 28.0 | 5.6 |
| 20 | 2.09 | 53 | 0.078 | 26.8 | 3.93 | 49 | 0.217 | 18.1 | 63.3 | 18 | 20.2 | 3.1 |
| 21 | 11.0 | 277 | 13.7 | 1.3 | 26.9 | 332 | 30.0 | 0.9 | 422.6 | 123 | 365.1 | 1.2 |
| 22 | 5.86 | 147 | 0.564 | 10.4 | 11.0 | 136 | 1.64 | 6.7 | 281.3 | 82 | 123.1 | 2.3 |
| 23 | 0.670 | 65 | 0.025 | 26.9 | 2.47 | 56 | 0.068 | 36.1 | 100.8 | 27 | 13.8 | 7.3 |
| 27 | 255.3 | 203 | 76.1 | 3.4 | 506.8 | 159 | 74.3 | 7.6 | 684.3 | 37 | 584.7 | 1.2 |

Footnotes for Table 3

[a]Dose-response curves were determined at 5 concentrations. Cells received a 24 hour exposure to test compounds before being continuously washed with drug-free media. The $IC_{50}$ (μM) values are the concentrations required to inhibit cell growth by 50%, as determined from the dose-response curves. Values are the average of between three and nine independent determinations (% CV < 20 in all cases).
[b]Experiment performed entirely under oxic conditions.
[c]Fold reduction in oxic cellular growth inhibition relative to the parent kinase inhibitor.
[d]The first 4 hours of the 24 hour drug exposure was performed under anoxic conditions.
[e]Hypoxic Cytotoxicity Ratio = fold increase in cellular growth inhibition for cells receiving 4 hours of anoxia relative to cells that received only oxic conditions.

Irreversible erbB1/2 inhibitor 11 more potently inhibited proliferation of A431 ($IC_{50}$=0.040 μM) and SKBR3 ($IC_{50}$=0.081 μM) cells, than it did SW620 ($IC_{50}$=3.43 μM) cells. This trend and the $IC_{50}$ values for this compound and the other reported compounds (12 and 13) are consistent with previously reported results (given differences in drug exposure and incubation times) (Tsou et al, J Med Chem, 2001, 44, 2719-2734). The inhibitor 14, bearing a 7-methoxyquinazoline scaffold, showed activity comparable to compound 11, most potently inhibiting the growth of cells expressing erbB family members. In contrast, the reversible inhibitor 16 was 32 to 39-fold less active than its irreversible counterpart 11 in compounds can be obtained from the literature, (for example, Wardman, P. J. Phys. Chem. Ref. Data, 1989, 18, 1637-1755) or determined by a number of methods. The pulse radiolysis method, for example, measures the equilibrium constant between the radical anions of the prodrugs, formed upon their 1-electron reduction, and reference standards such as viologen and quinone compounds, from which data the E(1) values of the compounds can be calculated. (Meisel and Czapski. J. Phys. Chem., 1975, 79, 1503-1509.) The E(1) values of prodrugs 17-22, 140-145 were measured by the pulse radiolysis method and determined to range between $-0.493V$ and $-0.388V$ (Table 4). All are considered to possess appropriate E(1) values to enable enzymatic formation of their radical anions in a biological context.

Prodrugs possessing appropriate E(1) values can be tested for their ability to release effector moieties by a number of methods, following the radiolysis of the prodrugs in solution. For example, mass spectrometry (MS) and/or high performance liquid chromatography (HPLC) before and after radiolysis identifies the starting compound and the products formed as a result of the radiolysis. Several 1-electron reductants can be produced upon the radiolysis of solutions containing different solutes. For example the $CO_2^{.-}$ radical, formed in γ-irradiated solutions containing formate ions, possesses a low E(1) of −1.90 V (Schwarz et al, Inorg. Chem., 1985, 24, 433-439) and undergoes facile electron transfer to compounds of higher E(1). Under the radiation conditions employed, a concentration of 0.66 μM in 1-electron reducing equivalents (the $CO_2^{.-}$ radical) are produced per Gy (J kg$^{-1}$) of absorbed radiation dose. (Mulazzani et al, J. Phys. Chem., 1980, 90, 5347-5352.) By comparing the loss in prodrug concentration with the concentration of reducing equivalents produced upon the radiolysis of the solution, it is possible to determine whether one or multi-electron reduction is required for complete loss of each prodrug. Typically, evidence for 1-electron removal of a prodrug is sought after 0.95 reducing equivalents are transferred to the prodrug, to minimise multi-electron reduction of the same prodrug molecule. In the case of 1-electron removing a prodrug, this often indicates fragmentation of its radical anion. This conclusion is further supported by combined HPLC-MS identification of the released cytotoxic effector and the products arising from the transient benzyl-type radical (e.g. the methyl nitroaromatic compound (MNA) formed by H-atom abstraction). This has been shown to occur in the case of certain related arylmethyl quaternary nitrogen mustards. (Anderson et al. J. Phys. Chem., 1997, 101, 9704-9709; Wilson et al. Radiat. Res., 1998, 149, 237-245.) The data obtained for prodrugs 19 and 20 are consistent with their consumption at the 1-electron reduction level (>50% loss of prodrug at the 0.95 reducing equivalents level) with the released effector (compound 11) detected by HPLC-MS, Table 4. Similarly, steady state radiolysis followed by HPLC-MS confirmed that prodrugs 140, 143 and 144 released their respective effector compounds following 1-electron reduction. In contrast, data obtained for prodrug 21 is consistent with consumption requiring two-electron reduction. Release of the effector (compound 11) was not observed following 1-electron reduction. Prodrugs 17, 18, 22 and 142 did not release their respective effector compounds following 1-electron reduction and were only consumed following multi-electron reduction.

It is desirable that the reductive prodrugs are selected to have controlled fragmentation rate constants upon 1-electron reduction of the trigger moiety. Whilst fast fragmentation to release high concentrations of the cytotoxic effectors in the hypoxic regions of tumour cells is desirable, this is not so for normal tissue cells under normoxia. The rate constant of the back oxidation of the 1-electron reduced nitroarene-based prodrugs by oxygen, $kO_2$, which effectively inhibits the release of the effector, is given by the expression:

$$\log kO_2/M^{-1} s^{-1} = (4.6 \pm 0.1) - (5.0 \pm 0.2) \times E(1)C/C^{.-}$$

where E(1)C/C$^{.-}$ is the 1-electron reduction potential of the prodrug (Wardman et al, Biochem. Soc. Symp., 1995, 61, 171-194; Anderson et al, Org. Biomol. Chem. 2005, 3, 2167-2174).

The rate constants for fragmentation, kfrag, of the 1-electron reduced prodrugs can be measured using pulse radiolysis to observe the time-resolved formation of the absorption spectrum of the benzyl-type radical produced upon fragmentation of the radical anion. (Anderson et al, J. Phys. Chem. A, 1997, 101, 9704-9709.) The kfrag values of prodrugs 19, 20, 140, 141 and 143-145 were measured by pulse radiolysis and are presented in Table 4. Of the prodrugs described in Table 3, prodrugs 19 and 20 possess fragmentation rates upon 1-electron reduction under hypoxia in the most desirable range, consistent with them showing the greatest hypoxic cytotoxicity ratios (HCRs) in vitro in A431 and SKBR3 cell-based anti-proliferative assays (Table 3).

TABLE 4

Radiolytic reduction of selected prodrugs by the $CO_2^{.-}$ radical.

| Prodrug | E (1)/V[a] | % Loss of prodrug[b] | % Release of effector | Effector release/Prodrug loss | Detection of MNA[c] | kfrag.[d]/s$^{-1}$ |
|---|---|---|---|---|---|---|
| 17 | −0.408 | 33 | | | No | |
| 18 | −0.388 | 33 | | | No | |
| 19 | −0.493 | 63 | 46 | 0.73 | No | 90 ± 10 |
| 20 | −0.427 | 55 | 55 | 1.00 | Yes | 130 ± 10 |
| 21 | −0.468 | 33 | 10 | 0.30 | No | |
| 22 | −0.449 | 35 | 17 | 0.49 | No | |
| 23 | −0.427 | | | | | 420 ± 60 |
| 140 | −0.429 | 92 | | | Yes | 310 ± 20 |
| 141 | −0.456 | 83 | | | Yes | 1100 ± 100 |
| 142 | −0.471 | 8 | | | No | |
| 143 | −0.465 | 69 | | | Yes | 170 ± 20 |
| 144 | −0.449 | 68 | | | Yes | 470 ± 20 |
| 145 | −0.456 | 87 | | | Yes | 1050 ± 40 |

Footnotes for Table 4
[a]Determined against methylviologen, E (1)MV$^{2+}$/MV$^{+.}$ = −447 ± 7 mV.
[b]Measurements made by HPLC-MS at 0.95 reducing equivalents; >50% indicates fragmentation upon 1-electron reduction.
[c]Detection of methyl nitroaromatic (MNA) by HPLC-MS.
[d]Pulse radiolysis data for the formation of the benzyl-type radicals absorbing in the 360-390 nm region.

A.2.11 In Vivo Screening of Compounds 19, 20 and 21 in A431 Xenografts

Figure 2:
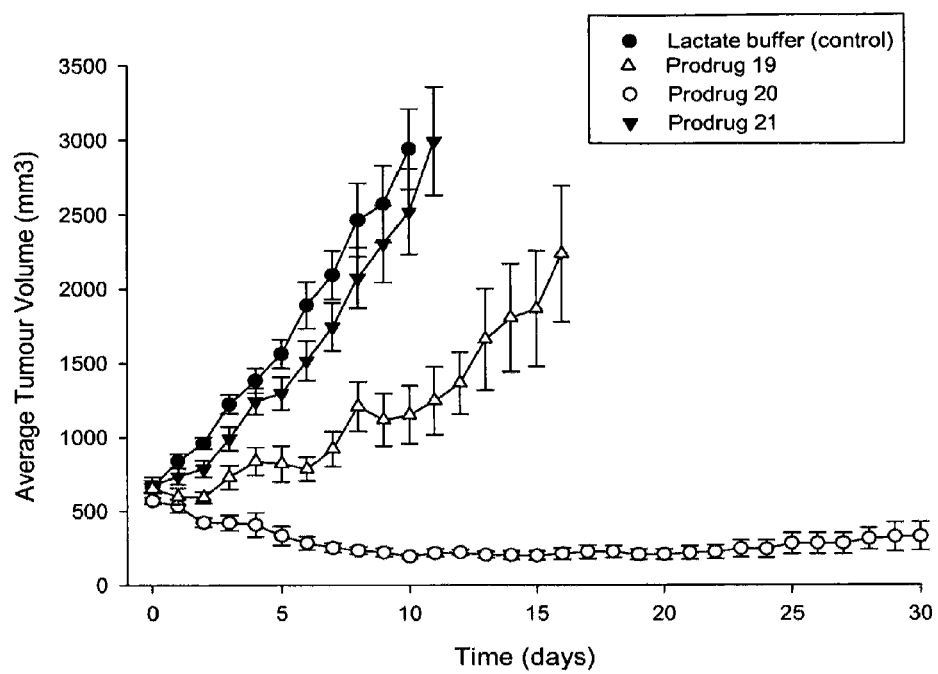
FIG. 2 shows efficacy of compounds 19, 20 and 21 (prodrug compounds of the present invention) against A431 xenografts.

Prodrugs 19, 20 and 21 were compared for efficacy in A431 xenografts at their respective maximum tolerated doses on a q4dx3 schedule, following IP dosing in lactate buffer (FIG. 2).

FIG. 2 shows efficacy of compounds 19, 20 and 21 against A431 xenografts.

Prodrug 20 (q4dx3 MTD=133 μmol/kg/dose) demonstrated considerable efficacy in A431 xenografts (calculated Tumour Growth Inhibition, TGI>>210%), while prodrug 19 (q4dx3 MTD=75 μmol/kg/dose) was only weakly active (TGI=120%) and prodrug 21 (q4dx3 MTD=75 μmol/kg/dose) was inactive (TGI=10%). Each prodrug is based on the same effector (compound 11), differing only in the nature of the reductive trigger employed. The rank order of activity for the prodrugs (20>19>21) is consistent with the rate constant of fragmentation of the triggers following one-electron reduction by pulse radiolysis (20>19>21) and the HCR observed for the prodrugs in A431 cells in vitro (20>19>21), supporting the hypothesis that hypoxia-selective activation of the prodrug and release of the effector in the hypoxic compartment of A431 xenografts, followed by back-diffusion of the effector to oxic cells in the tumour is the mechanism of action of prodrugs 19 and 20.

A.2.12 Solubility and Stability of Compound 20

The quaternary ammonium salt prodrug 20 has been studied for solubility and chemical stability in a range solutes by HPLC. It has been determined to have a solubility of 1112 μM in α-MEM cell culture medium while also possessing good stability (half life=58 hours). No release of effector 11 was observed by HPLC after 24 h in α-MEM at 37° C. In addition prodrug 20 is essentially stable in DMSO and lactate buffer (pH=4) (half life>96 hours).

A.2.13 Murine Toxicity and Pharmacokinetics of Compounds 11 and 20

Table 5 describes the maximum tolerated dose (MTD) and plasma pharmacokinetics of irreversible erbB1/2 inhibitor 11 and prodrug 20 after intraperitoneal injection of each compound as a solution in lactate buffer (pH 4). Both compounds demonstrated diarrhea and body weight loss, suggesting gastrointestinal toxicity as dose limiting. Humane cull was performed if body weight loss was >15% of starting weight. MID value was defined as less than 1 in 7 deaths by all drug related causes. Prodrug 20 was determined to be 1.8-fold better tolerated than compound 11 when delivered as a single dose or on a q4dx3 schedule. Both compounds were well tolerated on multi-dose schedules at a fraction of their respective single-dose MTD's (see next section) with body weight loss as the only observable toxicity. The plasma pharmacokinetics of each compound was measured after a single intraperitoneal dose at 42% of the single dose MID. Prodrug 20 exhibited an area under the curve (AUC) 23-fold higher than that of compound 11, while the amount of compound 11 found in plasma after dosing with prodrug 20 was minimal (effector AUC is one percent of prodrug AUC), indicating prodrug 20 is stable to non-specific release in vivo.

TABLE 5

In vivo toxicity and pharmacokinetics of compounds 11 and 20

| | In Vivo (Murine, IP)[a] | | | | |
|---|---|---|---|---|---|
| | | | | Pharmacokinetics[d] | |
| | Single dose MTD[b] | Q4dx3 MTD[c] | Dose | $AUC_{0-250\,min}$ (µM·hr) | |
| Compound | (µmol/kg) | (µmol/kg) | (µmol/kg) | Parent | Effector |
| 11 | 100 | 75 | 42 | 12 | |
| 20 | 178 | 133 | 75 | 279 | 2.7 |

Footnotes for Table 5
[a]Test compounds were dosed as solutions in lactate buffer at pH 4.0 via intraperitoneal injection.
[b]Performed in female non-tumour bearing CD-1 nude mice; n = 3 mice per cohort..
[c]Performed in female A431 tumour bearing CD-1 nude mice; n = 7 mice per cohort. Mice were dose on a q4dx3 schedule (e.g. Mon, Thurs, Tues).
[d]Predicted AUC from modelled plasma concentration/time curves. The plasma concentrations of test compound were determined by LC-MS at 5, 15 min, 1, 2, and 4 hr at 42% of the single dose MTD. See experimental section for methods.

A.2.14 Comparison of Efficacy of Compounds 11 and 20

Figure 3A:
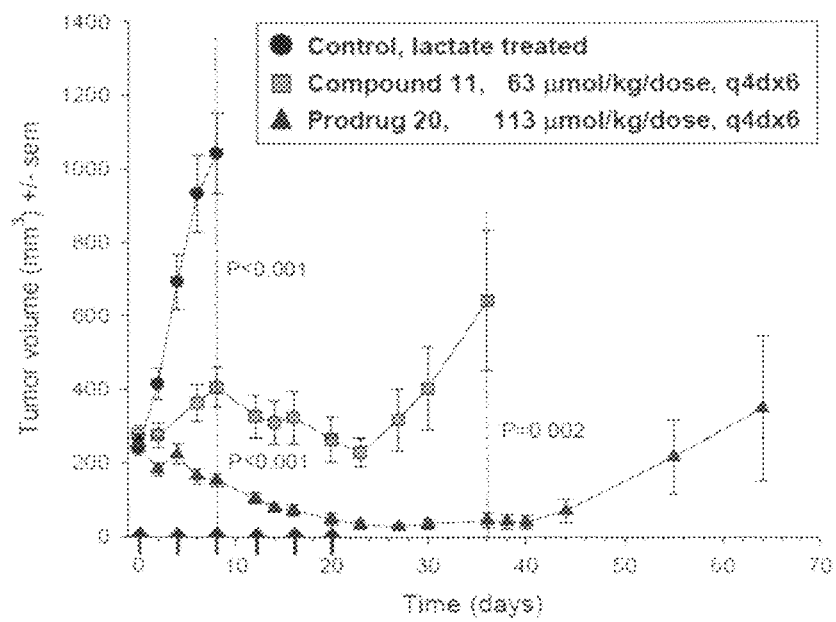
FIG. 3A shows efficacy of compounds 11 and 20 against A431 xenografts.

Prodrug 20 was compared directly to effector 11 for efficacy in A431 xenografts at an equitoxic dose (63% of single dose MTD) on a more protracted q4dx6 schedule following IP dosing in lactate buffer. Prodrug 20 showed superior efficacy to effector 11 by growth delay, that was determined to be statistically significant (FIG. 3A). The dose and schedule employed for each agent was determined to be equitoxic as judged by average body weight loss (FIG. 3B), with 2/12 deaths observed for mice treated with effector 11 and 0/12 deaths observed for mice treated with prodrug 20.

FIG. 3A shows efficacy of compounds 11 and 20 against A431 xenografts.

Figure 3B:
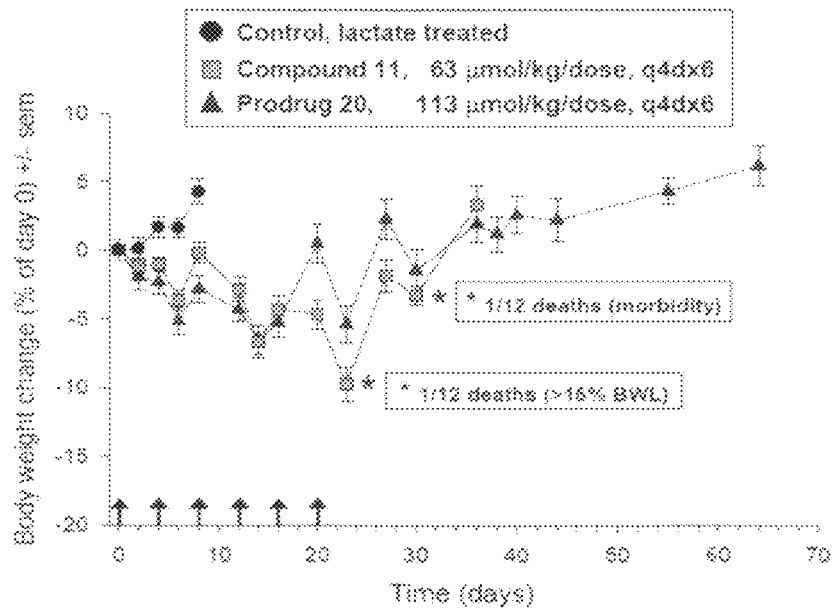
FIG. 3B shows average body weight change of A431-bearing mice treated with compounds 11 and 20.
Figure 4:
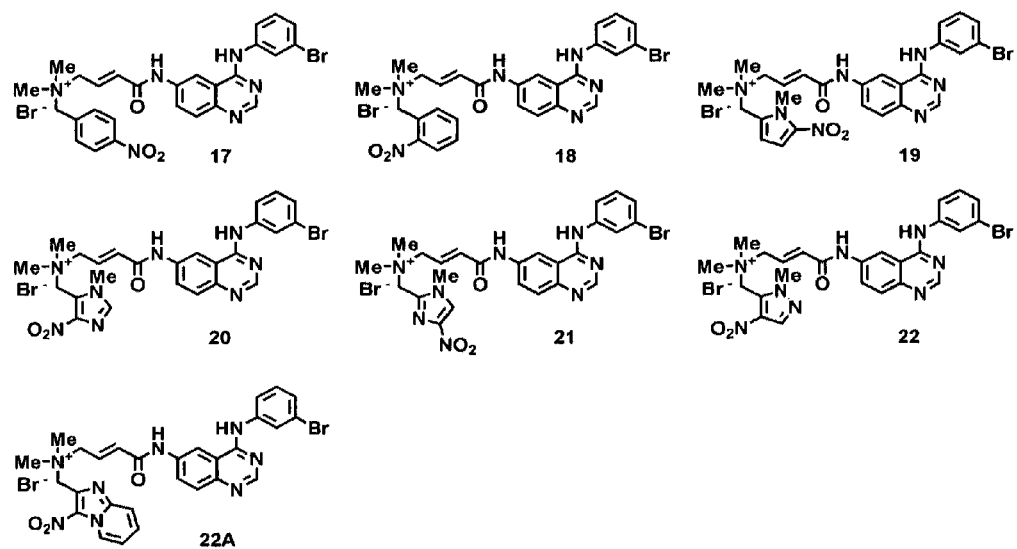
FIGS. 4 to 9, 17 and 18 show the structures of certain compounds of the invention.
Figure 5:
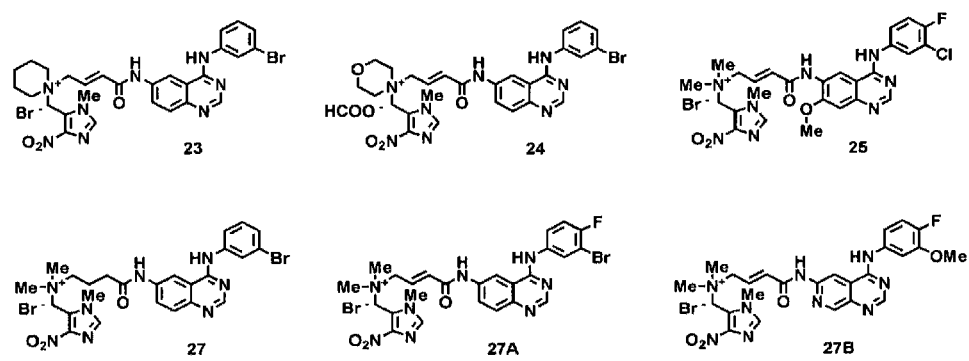
Figure 6:
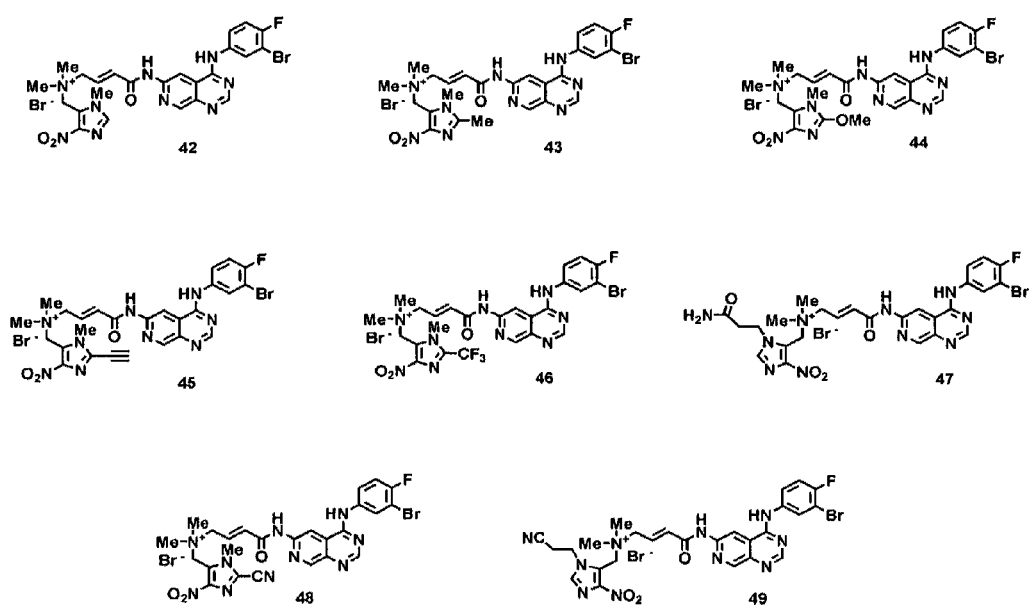
Figure 7:
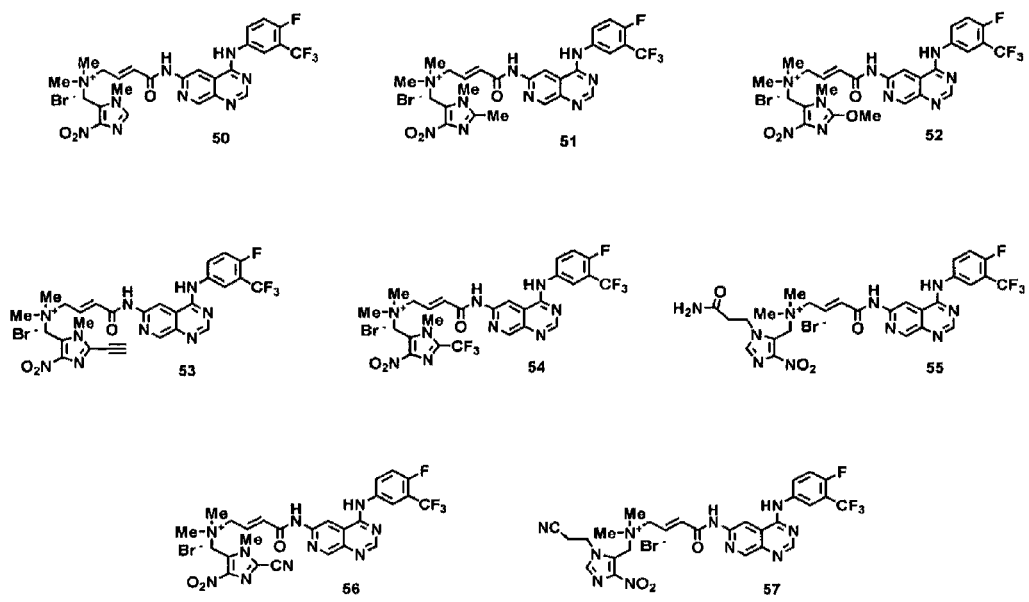
Figure 8:
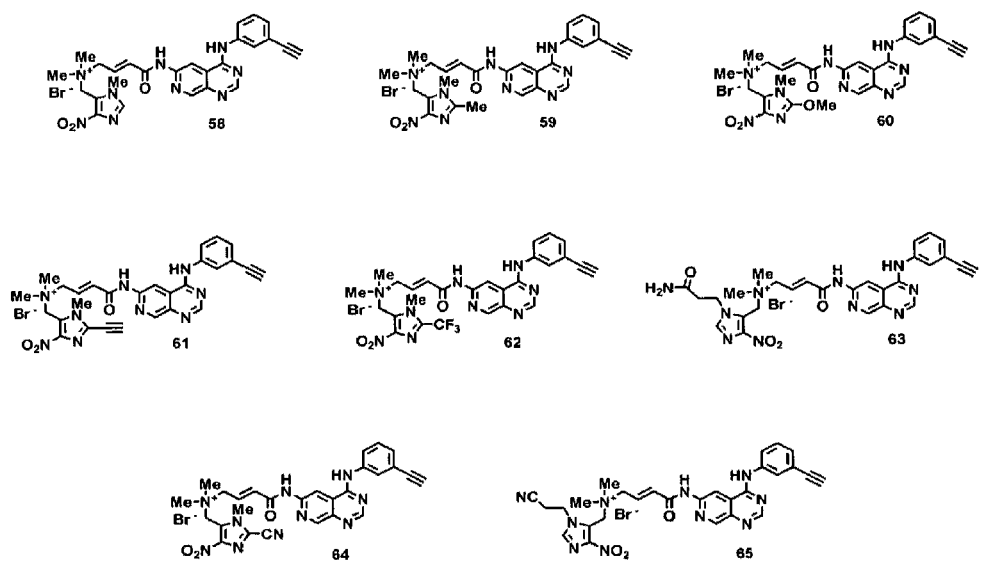
Figure 9:
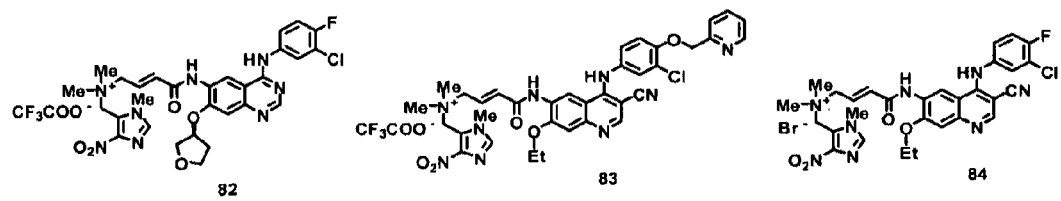

FIG. 3B shows average body weight change of A431-bearing mice treated with compounds 11 and 20.

A.2.15 Cellular erbB1 Inhibition: Oxic and Hypoxic Conditions

Figure 10:
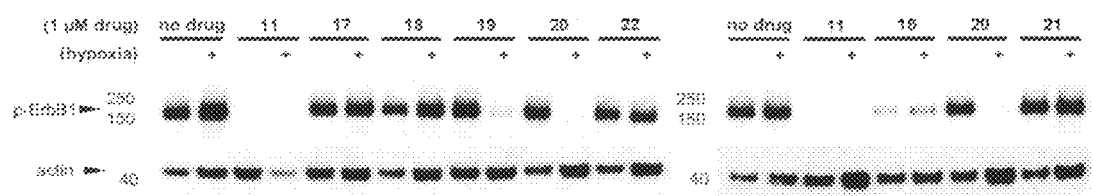
FIG. 10 shows A431 cellular autophosphorylation inhibition for compounds 11 and 16-22 (compounds 11 and 16 are kinase inhibitors; compounds 17-22 are prodrug compounds of the present invention).

FIG. 10 shows A431 cellular autophosphorylation inhibition for compounds 11 and 16-22. Cells were given a 4 hour exposure to 1 µM of test compound under oxic or hypoxic conditions, before being washed extensively with drug free media to remove test compounds, serum starved overnight and then stimulated with EGF, lysed and western blotted for phospho-EGFR (phospho-erbB1) or actin as a protein loading control.

Compounds 19 and 20 demonstrated hypoxia-selective inhibition of p-erbB1. Compounds 17, 18, 21 and 22 showed no apparent hypoxia-selective inhibition of p-erbB1.

Figure 11:
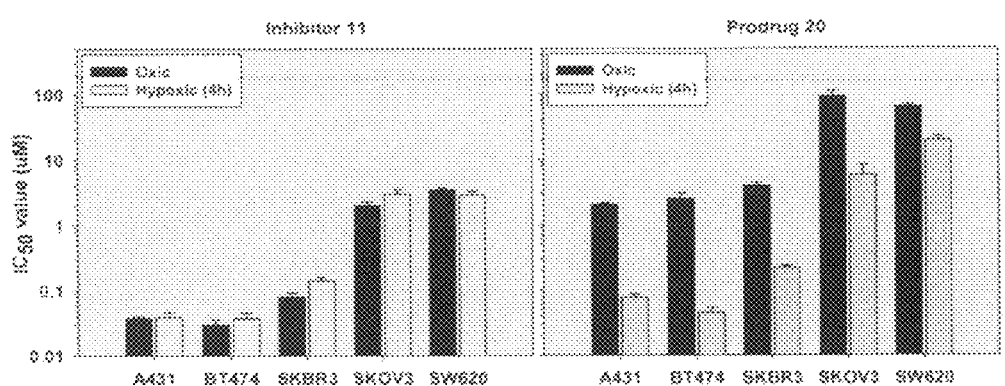
FIG. 11 shows inhibition ($IC_{50}$) of cellular proliferation of compounds 11 and 20 under oxic and hypoxic conditions in A431, BT474, SKBR3, SKOV3 and SW620 cells.

A.2.16 Cell Growth Inhibitory Activity of Compounds 11 and 20 in a Cell Line Panel FIG. 11 shows inhibition ($IC_{50}$) of cellular proliferation of compounds 11 and 20 under oxic and hypoxic conditions in A431, BT474, SKBR3, SKOV3 and SW620 cells.

Compound 20 demonstrates hypoxia-selective anti-proliferative activity across a cell line panel and that selectivity is greatest in cell lines known to over-express members of the erbB-family (A431, BT474, SKBR3, SKOV3). In contrast the irreversible erbB1/2 inhibitor 11 does not demonstrate hypoxia-selective anti-proliferative activity across the cell line panel.

A.2.17 Cellular Metabolism of Compound 20: Oxic and Hypoxic Conditions

Figure 12:
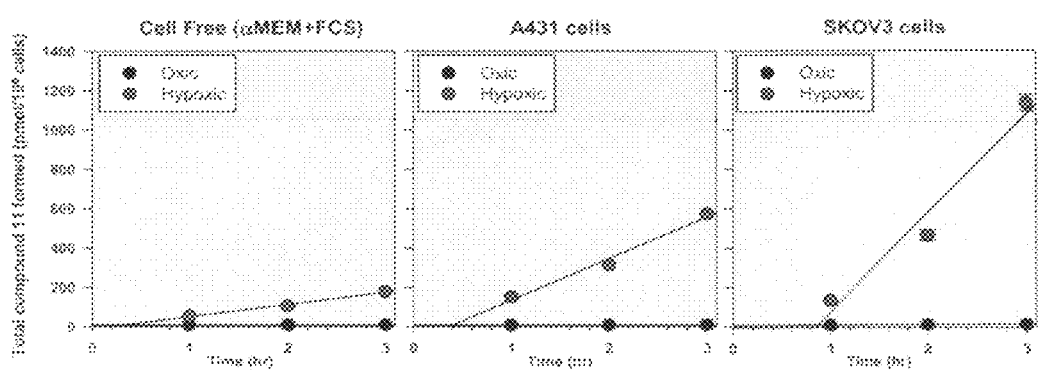
FIG. 12 shows the time dependant release of inhibitor 11 as detected by LCMS when A431 and SKOV3 cells are treated with 10 uM of prodrug 20 under oxic and hypoxic conditions, relative to the cell free control.

FIG. 12 shows the time dependant release of inhibitor 11 as detected by LCMS when A431 and SKOV3 cells are treated with 10 uM of prodrug 20 under oxic and hypoxic conditions, relative to the cell free control.

A431 and SKOV3 cells have been demonstrated to metabolise prodrug 20 selectively under hypoxic conditions to produce the irreversible erbB1/2 inhibitor 11 at a rate of 200 and 500 pmol/hour/million cells, respectively. Some hypoxia-selective reduction of prodrug 20 occurs in cell free media containing 5% fetal calf serum to release inhibitor 11 at a rate of 62 pmol/hour.

Figure 13:
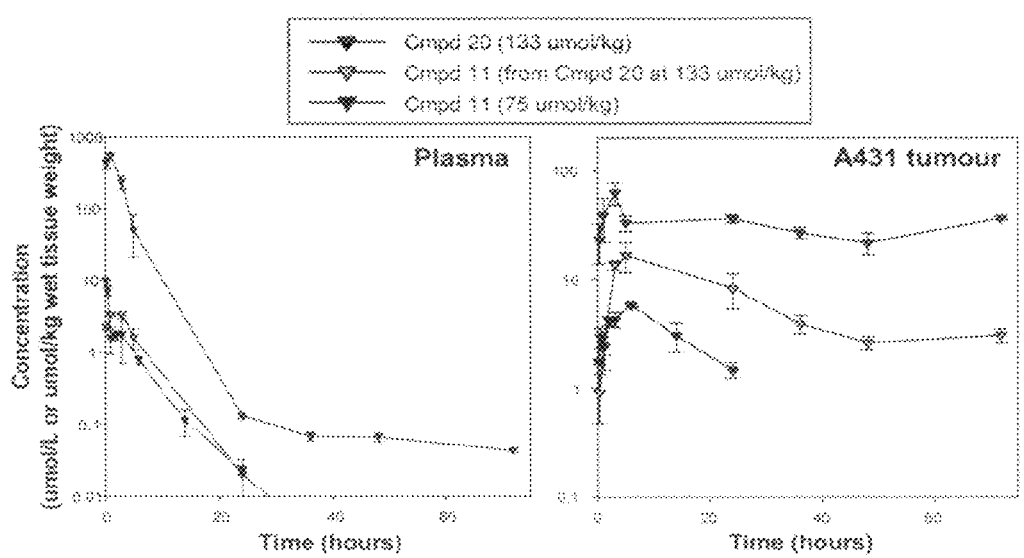
FIG. 13 shows the concentration of compound 20 and compound 11 (coming from dosing compound 20 and when dosed directly) as a function of time, in plasma and A431 tumour, when female A431-tumour bearing NIHIII mice are administered a single dose (ip) of each test compound at the q4dx3 MTD (133 and 75 umol/kg, respectively).

A.2.18 Plasma and A431 Tumour Pharmacokinetics of Compounds 11 and 20 at their Respective q4dx3 MTDs FIG. 13 shows the concentration of compound 20 and compound 11 (coming from dosing compound 20 and when dosed directly) as a function of time, in plasma and A431 tumour, when female A431-tumour bearing NIHIII mice are administered a single dose (ip) of each test compound at the q4dx3 MTD (133 and 75 umol/kg, respectively).

Table 6 shows the calculated Area Under the Curve (AUC) from 0-72 hours, in plasma and A431 tumour of compound 20 and compound 11 (coming from dosing compound 20) when female A431-tumour bearing NIHIII mice are administered a single dose (ip) of compound 20 at the q4dx3 MTD (133 umol/kg).

TABLE 6

| | $AUC_{0-72\,hr}$ (µM·hr) | |
|---|---|---|
| Tissue | Compound 20 | Compound 11 coming from 20 |
| Plasma | 2016 | 30 |
| A431 Tumour | 2245 | 464 |

Plasma and A431 tumour pharmacokinetics of prodrug 20 and inhibitor 11 were measured in female NIHIII mice by LC/MS/MS detection (with D6 internal standards) following administration at their respective MTDs (133 and 75 umol/kg; ip). Prodrug 20 gave a plasma $AUC_{0-72h}$ of 2016 umol-h/L, some ~110-fold greater than achieved for administration of inhibitor 11 (18 umol-h/L). The latter gave a tumour $AUC_{0-inf}$ of 100 umol-h/kg with a half-life (t½) of 9 h. In contrast the prodrug 20 gave a tumour $AUC_{0-72h}$ of 2245 umol-h/kg with a stable tumour tissue concentration of ~30 umol/kg out to 72 h, such that a t½ could not be determined. Consistent with this long prodrug residency, inhibitor 11 released from prodrug 20 had a t½ in tumour tissue of >72 h, providing an $AUC_{0-72h}$ of 464 umol-h/kg. Thus the AUC of inhibitor 11 in A431 tumours was at least 4.6-fold higher after administration of prodrug 20 than following administration of inhibitor 11 itself at equivalent toxicity.

Figure 14:
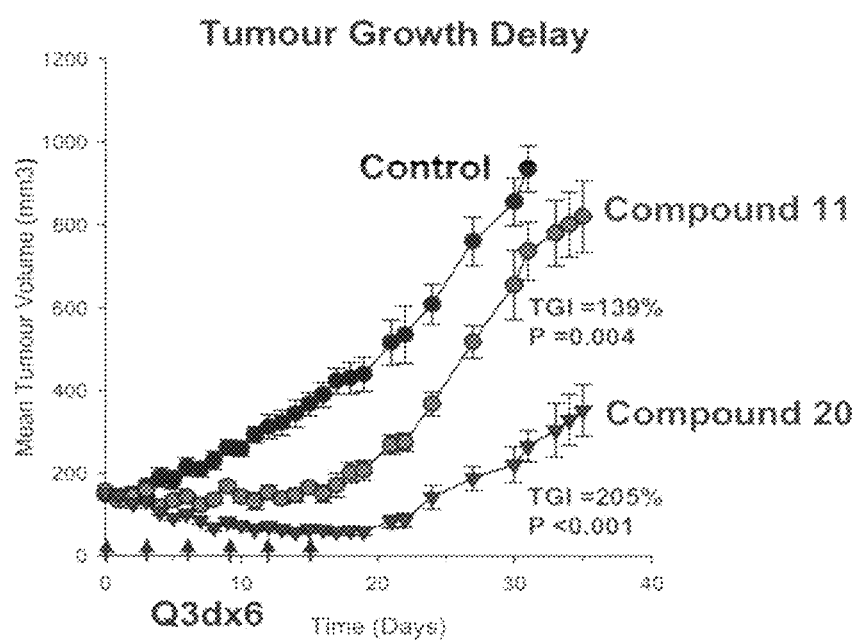
FIG. 14 shows efficacy of compounds 11 and 20 against SKOV3 xenografts.

FIG. 14 shows efficacy of compounds 11 and 20 against SKOV3 xenografts.

Figure 15:
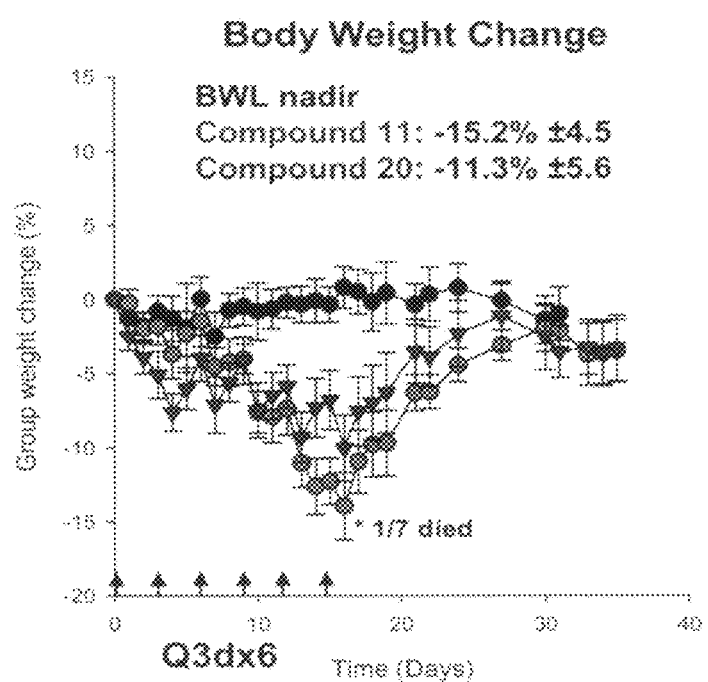
FIG. 15 shows average body weight change of SKOV3-bearing mice treated with compounds 11 and 20.

FIG. 15 shows average body weight change of SKOV3-bearing mice treated with compounds 11 and 20.

Prodrug 20 was compared directly to effector 11 for efficacy in SKOV3 xenografts at an equitoxic dose (133 and 56 umol/kg/dose, respectively) on a q3dx6 schedule following IP dosing in lactate buffer. Prodrug 20 showed superior efficacy to effector 11 by growth delay, that was determined to be statistically significant (FIG. 14). The dose and schedule employed for each agent was determined to be equitoxic as judged by average body weight loss (FIG. 15), with 1/7 deaths observed for mice treated with effector 11 and 0/7 deaths observed for mice treated with prodrug 20.

Figure 16:
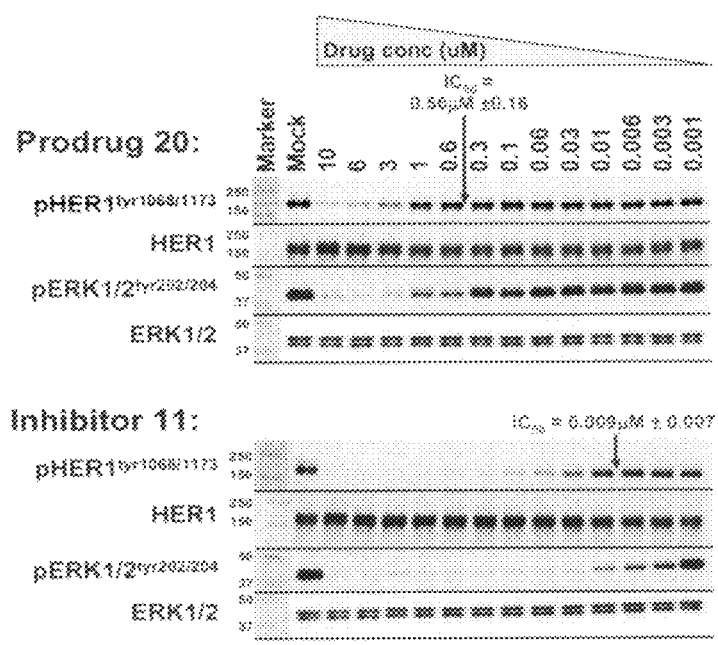
FIG. 16 shows dose-dependent inhibition of cellular HER1 (erbB1, EGFR) and Erk1/2 phosphorylation by prodrug 20 and effector 11 in A431 cells in vitro.
Figure 17:
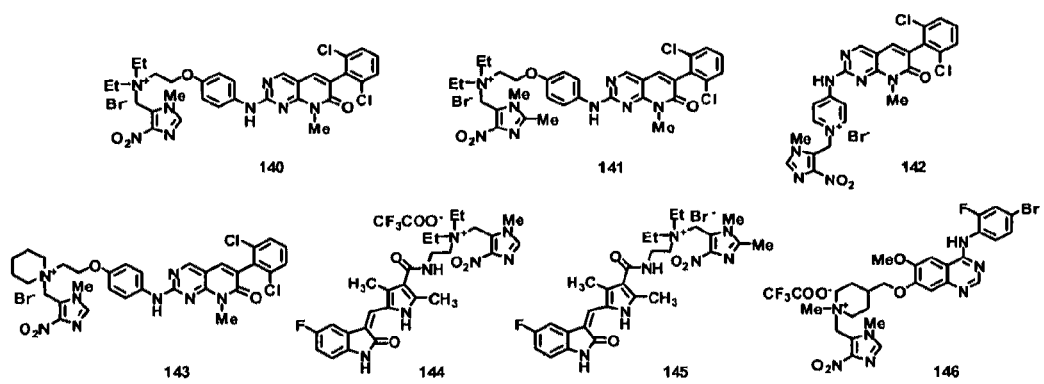
Figure 18:
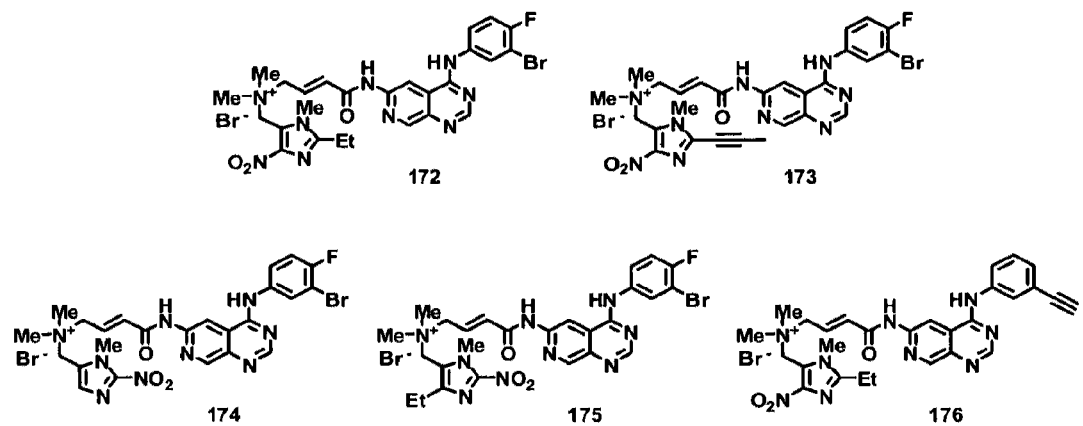

FIG. 16 shows dose-dependent inhibition of cellular HER1 (erbB1, EGFR) and Erk1/2 phosphorylation by prodrug 20 and effector 11 in A431 cells in vitro.

Prodrug 20 and effector 11 were tested for their ability to inhibit phosphorylation of HER1 (erbB1) and Erk1/2 in EGF-stimulated A431 cells by Western immunoblotting measurement of phospho-HER1 and phosphor-Erk1/2 status. Compound 11 was shown to be a potent inhibitor of cellular HER1 and Erk1/2. In contrast the quaternary ammonium salt derivative 20 was approximately 60-fold less effective at inhibiting HER1 and Erk1/2.

A.2.19 Inhibitory Activity of Compounds 82 and 140-144 in a Cell Line Panel

Table 7 shows the inhibitory effect of prodrugs 82, 140, 141, 142, 143 and 144 on cell proliferation in A431, H1975 and HT29 cells.

erocyclic reductive trigger, followed by trigger fragmentation to release a kinase inhibitor. The nature of the kinase inhibitor released influences the spectrum of cell line sensitivity. For example, prodrug 82 displays greatest antiproliferative activity and hypoxic selectivity against A431 cells, and prodrug 144 displays greatest antiproliferative activity and hypoxic selectivity against HT29 cells A.2.20 Summary The collected data indicates quaternary ammonium salt prodrugs of irreversible erbB1, 2, 4 inhibitors, bearing a tertiary amine adjacent to a Michael acceptor, are less active in cell-based target modulation and anti-proliferative assays performed under oxic conditions. Prodrugs employing a fragmenting reductive trigger appropriately selected to fragment with a desirable rate constant upon one-electron reduction to release the tertiary amine-bearing irreversible erbB1, 2, 4 inhibitor are selectively more potent in cell-based anti-proliferative assays performed under anoxic conditions, can be delivered to mice in quantitatively larger drug exposure levels and therefore can possess an improved therapeutic index relative to their parent irreversible erbB1, 2, 4 inhibitor in tumour xenograft experiments.

Section B

B.1. Synthesis

B.1.1 Chemical Synthesis

Combustion analyses were performed by the Microchemical Laboratory, University of Otago, Dunedin, NZ. Melting points were determined using either an Electrothermal Model 9200 and are as read. $^1$H NMR spectra were measured either on a Bruker Avance-400 spectrometer and are referenced to $Me_4Si$. High resolution mass spectra were recorded on a Varian VG-70SE spectrometer at nominal 5000 resolution. Mass spectrometry was performed on a ThermoFinnigan

TABLE 7

Inhibition ($IC_{50}$) of cellular proliferation in A431, H1975 and HT29 cells

| | Cellular Growth Inhibition $IC_{50}$ (μM)[a] | | | | | | | | |
|---|---|---|---|---|---|---|---|---|---|
| | A431 | | | H1975 | | | HT29 | | |
| Compound | Oxic[b] | Anoxic[c] | HCR[d] | Oxic[b] | Anoxic[c] | HCR[d] | Oxic[b] | Anoxic[c] | HCR[d] |
| 82 | 3.6 | 0.059 | 62 | 64.5 | 2.3 | 28 | >100 | >30 | — |
| 140 | 7.9 | 0.51 | 15 | 4.70 | 0.43 | 13 | 4.6 | 0.31 | 15 |
| 141 | 12.3 | 0.44 | 30 | 6.1 | 0.37 | 18 | 5.6 | 0.32 | 18 |
| 142 | 555 | >100 | <6 | 216 | >100 | <3 | 154 | 119 | 1 |
| 143 | 42.8 | 1.0 | 43 | 17.9 | 2.0 | 9 | 7.8 | 1.5 | 5 |
| 144 | 146 | 24.1 | 7 | 203 | 57.2 | 3 | 298 | 10.7 | 31 |

Footnotes for Table 7.

[a] compound dose-response curves were determined at 5 concentrations. Cells received a 24 hour exposure to test compounds before being washed (x3) with drug-free media. The IC50 (umol/L) values are the concentrations required to inhibit cell growth by 50% relative to untreated controls. Values are the average of 2-5 independent determinations (% CV < 20 in all cases).

[b] Experiment performed entirely under oxic conditions.

[c] The initial 4 hours of the 24 hour drug exposure was performed under anoxic conditions.

[d] Hypoxic Cytotoxicity Ratio = fold change in intra-experimental IC50 for cells receiving 4 hours of anoxia relative to cells that received only oxic conditions.

The prodrugs (82, 140, 141, 143 and 144) of Table 7 were significantly more potent at inhibiting the growth of all three cell lines after the cells received 4 hours of anoxia. The hypoxic cytotoxicity ratios (HCR) ranged from 7 to 62 in A431 cells, 3 to 28 in H1975 cells and 5 to 31 in HT29 cells, consistent with hypoxia-selective reduction of the nitrohet- MSQ single quadrupole mass spectrometer. Mass detection was performed with an APCI source, using simultaneous positive and negative ion acquisition. Unless otherwise indicated, compounds were purified by flash column chromatography on Silica gel 60 support (Scharlau, 230-400 mesh ASTM), using the indicated eluants.

B.1.1.1 The Synthesis of 4-anilinopyrido[3,4-d]pyrimidine kinase Inhibitors (Scheme 7)

B.1.1.1.1 (2E)-N-[4-(3-bromo-4-fluoroanilino)pyrido[3,4-d]pyrimidin-6-yl]-4-(dimethylamino)-2-butenamide (161)

A heterogeneous mixture of 6-fluoropyrido[3,4-d]pyrimidin-4(3H)-one (93) (4.0 g, 24.2 mmol), thionyl chloride (100 mL) and a catalytic amount of DMF (3 drops) was stirred under reflux for 1 h. The resulting solution was evaporated under reduced pressure at 45° C. (bath temperature) to give a light brown solid. To this solid was added a mixture of 3-bromo-4-fluoroaniline (5.1 g, 26.8 mmol) and dry DMA (25 mL). The reaction mixture was stirred at room temperature for 40 min, then a 5% solution of sodium bicarbonate (250 mL) was added and the mixture was stirred at room temperature for 15 min. The precipitated solid was collected by filtration and washed successively with water and hexane several times, before being dried under vacuum over silica gel to give N-(3-bromo-4-fluorophenyl)-6-fluoropyrido[3,4-d]pyrimidin-4-amine (162) (8.13 g, 99%), mp 275-277° C. (literature mp 269-270° C.; Smaill et al. J Med Chem, 1999, 42, 1803-1815); $^1$H NMR δ [(CD$_3$)$_2$SO] 10.12 (s, 1H), 8.97 (s, 1H), 8.74 (s, 1H), 8.32 (dd, J=6.4, 2.6 Hz, 1H), 8.23 (poorly resolved d, J=0.8 Hz, 1H), 7.93-7.87 (m, 1H), 7.46 (t, J=8.8 Hz, 1H). Anal. Calcd for C$_{13}$H$_7$BrF$_2$N$_4$: C, 46.32; H, 2.09; N, 16.62%. Found C, 46.54; H, 3.33; N, 16.42%.

A mixture of compound 162 (13.9 g, 41.3 mmol) and 4-methoxybenzylamine (54.3 mL, 413 mmol) in dry DMSO (100 mL) was stirred under a nitrogen atmosphere at 75° C. (bath temperature) for 95 h. The solution was then cooled and petroleum ether (500 mL) was added. After 15 min stirring at room temperature the layers were allowed to separate and the petroleum ether layer was decanted. This procedure was repeated a further two times and then water (500 mL) was added to the resultant DMSO layer and the mixture was stirred at room temperature for 1 h to precipitate a yellow/orange solid that was collected by filtration and washed with water (5×100 mL), before being dried under vacuum and then washed with petroleum ether (2×100 mL). The yellowish orange solid was then stirred with warm acetone (1 L) for ca. 3 h before water (1 L) was added to precipitate the required product. The solid was collected by filtration, washed with acetone/water (1:1, 5×80 mL) and dried in vacuo over silica-gel, to give pure N$^4$-(3-bromo-4-fluorophenyl)-N$^6$-(4-methoxybenzyl)pyrido[3,4-d]pyrimidine-4,6-diamine (165) (14.8 g, 79%) as a yellow/orange solid, mp 181-184° C.; $^1$H NMR δ [(CD$_3$)$_2$SO] 9.69 (s, 1H), 8.75 (s, 1H), 8.37 (s, 1H), 8.26 (dd, J=6.4, 2.6 Hz, 1H), 7.91-7.83 (m, 1H), 7.42 (t, J=8.8 Hz, 1H), 7.33 (br d, J=8.6 Hz, 2H), 7.27 (t, J=6.3 Hz, 1H), 7.16 (s, 1H), 6.91-6.85 (m, 2H), 4.49 (d, J=6.3 Hz, 2H), 3.71 (s, 3H). Anal. Calcd for C$_{21}$H$_{17}$BrFN$_5$O: C, 55.52; H, 3.77; N, 15.42%. Found C, 55.75; H, 3.88; N, 15.44%.

To a stirred homogeneous solution of compound 165 (15.9 g, 34.9 mmol) in trifluoroacetic acid (80 mL) was added anisole (7.58 mL, 69.8 mmol). The mixture was then stirred at room temperature for 20 h. Most of the trifluoroacetic acid was evaporated under reduced pressure at 35° C. (bath temperature). The resultant red-brown oil was stirred with petroleum ether (400 mL) at room temperature for ca. 10 min. The petroleum ether layer was then decanted and the process was repeated with more petroleum ether (2×300 mL). The residue was then stirred with 5M NH$_3$ at 0° C. for 5 min, then at room temperature for another 45 min. The solid thus obtained was collected by filtration and washed with water (3×60 mL) before being dried in vacuo. The solid was then stirred with warm acetone (500 mL) for 30 min. Water (800 mL) was added and the suspension was stirred at room temperature for 1 h. The solid was again collected by filtration and washed successively with water (6×70 mL) and then petroleum ether/ethyl acetate (3:1, 4×100 mL) before being dried under reduced pressure, to give N$^4$-(3-bromo-4-fluorophenyl)pyrido[3,4-d]pyrimidine-4,6-diamine (159) (11.5 g, 99%), mp 269-271° C. (literature mp 268-270° C.). $^1$H NMR identical with that reported (Smaill et al. J Med Chem, 1999, 42, 1803-1815).

To a stirred homogeneous solution of (E)-methyl 4-bromobut-2-enoate (53.7 g, 300 mmol) in THF (100 mL) at 0° C. (bath temperature) under a nitrogen atmosphere, was added a solution of lithium hydroxide monohydrate (16.4 g, 390 mmol) in water (80 mL) dropwise (over 35 min). After addition the mixture was stirred at 0° C. for 3 h. Cold water (300 mL) and petroleum ether (400 mL) were added and the mixture was stirred at 0° C. for 10 min. The organic layer was separated and discarded. Ethyl acetate/petroleum ether (1:10, 300 mL) was then added and the mixture was again stirred at 0° C. for 10 min before the organic layer was separated and discarded. The aqueous solution was acidified with conc. sulfuric acid at 0° C. to pH<1. The product was extracted into dichloromethane (400 mL; 200 mL) and the combined organic extracts were dried (MgSO$_4$) and evaporated under reduced pressure at 35° C. (bath temperature) to give a yellow oil. The oil was stirred with petroleum ether (2×500 mL) at 50° C. (bath temperature). The combined petroleum ether extracts were concentrated under reduced pressure at 20-25° C. (bath) to induce precipitation of the product. The suspension was then stood at 5° C. overnight before the solid was collected by filtration, washed with cold petroleum ether and dried to give (E)-4-bromobut-2-enoic acid (9) (19.9 g, 40%).

Method A: Amide Coupling Using the Add Chloride.

Oxalyl chloride (508 mg, 4.00 mmol) was added to a solution of acid 159 (496 mg, 3.00 mmol) in dry dichloromethane (6 mL) and the mixture was stirred at room temperature for 40 min. The solution was then evaporated under reduced pressure at room temperature to give an oil which was dissolved in dry THF (5 mL) and added to a stirred mixture of compound 8a (668 mg, 2.00 mmol), triethylamine (0.84 mL, 6.00 mmol), and ITT (15 mL) at 0° C. After 1 h another batch of acid chloride preformed from oxalyl chloride (508 mg, 4.00 mmol) and acid 9 (496 mg, 3.00 mmol) was added and stirred further at 0° C. for another 30 min. A mixture of 40% NHMe$_2$ (15.2 mL, 12.0 mmol) and DMA (10 mL) was added and the reaction mixture was stirred at 0° C. to room temperature for 19 h. Volatiles were evaporated under reduced pressure at 25° C. to give a brown oil which was stirred with 1% sodium carbonate solution (100 mL) at 0° C. for 30 min. The solid thus formed was collected by filtration, washed with water several times, and dried. Column chromatography of this material on silica gel eluting with dichloromethane to dichloromethane/MeOH (15:1) gave (2E)-N-[4-(3-bromo-4-fluoroanilino)pyrido[3,4-d]pyrimidin-6-yl]-4-(dimethylamino)-2-butenamide (161) (400 mg, 45%) as a yellow/orange solid, mp 163-166° C.; $^1$H NMR δ [(CD$_3$)$_2$SO] 10.96 (s, 1H), 10.33 (s, 1H), 9.02 (br s, 1H), 8.99 (br s, 1H), 8.63 (s, 1H), 8.24 (dd, J=6.4, 2.6 Hz, 1H), 7.92-7.84 (m, 1H), 7.44 (t, J=8.8 Hz, 1H), 6.87 (dt, J=15.5, 6.0 Hz, 1H), 6.52 (br d, J=15.5 Hz, 1H), 3.09 (dd, J=6.0, 1.2 Hz, 2H), 2.19 (s, 6H). Anal. Calcd for C$_{19}$H$_{18}$BrFN$_6$O.MeOH: C, 50.33; H, 4.65; N, 17.61%. Found C, 50.38; H, 4.31; N, 17.86%.

Method B: Amide Coupling Using DCC.

To a stirred solution of DCC (7.23 g, 35.1 mmol) in dry THF (10 mL), at 0° C. under a nitrogen atmosphere, was added a solution of acid 9 (5.79 g, 35.1 mmol) in dry THF (25 mL). After the reaction mixture was stirred for 45 min a suspension of aniline 159 (2.34 g, 7.01 mmol) in dry DMA (18 mL) was added. Di-iso-propylethylamine (DIPEA) (6.11 mL, 35.1 mmol) was then added and the final reaction mixture was stirred at 0° C. for 45 min before 40% aqueous dimethylamine (10.6 mL, 84.0 mmol) was added. After another 20 min ice-water (100 mL) was added, followed by cold 2% aqueous sodium carbonate (400 mL). The product was extracted into ethyl acetate (600 mL) which was washed successively with water (300 mL), cold 2% aqueous sodium carbonate (300 mL) and water (300 mL). The ethyl acetate solution was dried ($Na_2SO_4$) and evaporated under reduced pressure to give a solid which was purified by column chromatography on silica gel eluting with DCM/MeOH (gradient from 100:0 to 15:1) to give, (2E)-N-[4-(3-bromo-4-fluoroanilino)pyrido[3,4-d]pyrimidin-6-yl]-4-(dimethylamino)-2-butenamide (161) (2.4 g, 77%).

Method C: Amide Coupling Followed by Homer Wadsworth Emmons Coupling

To a stirred mixture of CDI (8.44 g, 52.0 mmol) and dry THF (32 mL), at room temperature under a nitrogen atmosphere, was added a solution of 2-(diethoxyphosphoryl)acetic acid (10.2 g, 52.0 mmol) in THF (28 mL). After addition the reaction mixture was stirred further at 40° C. (bath) for 20 min (whence evolution of gases ceased). A solution of compound 159 (13.4 g, 40.0 mmol) in a mixture of dry THF (45 mL) and DMA (50 mL) was added and the reaction was stirred further at 40° C. The reaction was monitored by TLC (ethyl acetate) and found to be only ca. 70% complete after 1.5 hours. Thus, another batch of reagent was prepared by adding CDI (4.22 g, 26.0 mmol) in dry THF (16 mL) to 2-(diethoxyphosphoryl)acetic acid (5.10 g, 26.0 mmol) in dry THF (7 mL). This additional reagent was added to the reaction mixture before it was stirred further for 2 h at 40° C. and then poured into water (1,000 mL) and stirred with petroleum ether (1,500 mL) at room temperature for 16 h. The petroleum ether layer was then decanted. More petroleum ether (800 mL) was added and the mixture was stirred for 15 min. The solid was collected by filtration, washed with water (5×200 mL) and dried to give diethyl 2-(4-(3-bromo-4-fluorophenylamino)pyrido[3,4-d]pyrimidin-6-ylamino)-2-oxoethylphosphonate (160) (20.1 g, 98%), m.p. 214-217° C. $^1$H NMR δ ($CDCl_3$) 9.45 (s, 1H), 9.03 (s, 1H), 8.73 (s, 1H), 8.55 (s, 1H), 8.13 (dd, J=6.0, 2.6 Hz, 1H), 7.77 (s, 1H), 7.70-7.63 (m, 1H), 7.18 (dd, J=8.7, 8.2 Hz, 1H), 4.31-4.18 (m, 4H), 3.15 (d, J=21.0 Hz, 2H), 1.39 (t, J=7.1 Hz, 6H). Anal. Calcd for $C_{19}H_{20}BrFN_5O_4P.0.2H_2O$: C, 44.24; H, 3.99; N, 13.58%. Found C, 44.00; H, 4.09; N, 13.42%.

To a stirred mixture of 2,2-diethoxy-N,N-dimethylethanamine (15.7 g, 97.5 mmol) and water (16.4 mL) at room temperature under a nitrogen atmosphere was added aq. 37% HCl (16.4 mL, 195 mmol). After addition the mixture was stirred at 40° C. (bath) for 25 hours. It was then cooled to 0° C. (bath) to give Solution A. KOH (14.0 g, 250 mmol) was dissolved in water (75 mL) at room temperature under a nitrogen atmosphere. It was then cooled to 0° C. (bath) to give Solution B. To a stirred heterogeneous mixture of compound 160 (19.97 g, 39.0 mmol) at room temperature under a nitrogen atmosphere was added a minimum amount of DMA (60 mL) to give a homogeneous solution. LiCl (1.65 g, 39.0 mmol) was then added and the resulting mixture was stirred at 0° C. (bath) for 15 min. The cold Solution B was then added and the reaction was stirred at 0° C. for 2 min. Cold Solution A was then added and the final reaction mixture was stirred further at 0° C. under a nitrogen atmosphere. The reaction was monitored by TLC (DCM/MeOH=10:1). After 30 min more KOH (s) (5.0 g, 89 mmol) was added and the reaction was stirred further at 0° C. for 1.5 hours. It was then poured into water (1,000 mL). Petroleum ether (1,000 mL) was added and the mixture was stirred at room temperature for 20 min. The petroleum ether layer was decanted before more petroleum ether (600 mL) was added and the mixture was again stirred for 15 min. The solid was collected by filtration, washed with water (5×200 mL) and dried under reduced pressure over silica gel/KOH to give (2E)-N-[4-(3-bromo-4-fluoroanilino)pyrido[3,4-d]pyrimidin-6-yl]-4-(dimethylamino)-2-butenamide (161) (16.9 g, 97%).

B.1.1.1.2 (2E)-4-(dimethylamino)-N-{4-[4-fluoro-3-(trifluoromethyl)anilino]pyrido[3,4-d]pyrimidin-6-yl}-2-butenamide (170)

A suspension of 6-fluoropyrido[3,4-d]pyrimidin-4(3H)-one (93) (4.90 g, 29.68 mmol) in $SOCl_2$ (250 mL), $CH_2Cl_2$ (50 mL) and DMF (8 drops) was heated under reflux for 3 h. The solvents were then removed by vacuum distillation and the residue was evaporated to dryness. The resulting crude 4-chloro-6-fluoropyrido[3,4-d]pyrimidine was dissolved in $CH_2Cl_2$ (50 mL) and $^i$PrOH (120 mL), to which 4-fluoro-3-(trifluoromethyl)aniline (5.85 g, 32.66 mmol) was added before the solution was heated under reflux at 84° C. for 30 min using an air condenser. During reflux the $CH_2Cl_2$ was evaporated and the crude product precipitated from the remaining $^i$PrOH as a pale yellow solid. The mixture was cooled to the room temperature, poured into an ice-cold beaker of 5% aqueous $Na_2CO_3$ and stirred for 15 min at 0° C. The solid was collected by filtration, washed several times with water and then hexane before being dried in a vacuum oven (45° C.) overnight to give 6-fluoro-N-(4-fluoro-3-(trifluoromethyl)phenyl)pyrido[3,4-d]pyrimidin-4-amine (163) (9.68 g, 100%) as a yellow solid, m.p. 247-249° C. $^1$H NMR [$(CD_3)_2SO$] δ 10.25 (s, 1H), 8.99 (s, 1H), 8.75 (s, 1H), 8.34 (dd, J=6.5, 2.7 Hz, 1H), 8.26-8.30 (m, 1H), 8.24 (s, 1H), 7.60 (t, J=9.7 Hz, 1H). Anal. Calcd for $C_{14}H_7F_5N_4$: C, 51.54; H, 2.16; N, 17.17%. found: C, 51.37; H, 2.30; N, 16.93%.

A stirred solution of compound 163 (14.30 g, 43.87 mmol) in DMSO (90 mL) was treated with slow addition of 4-methoxybenzylamine (57.3 mL, 482.52 mmol) under nitrogen at 70° C. The resultant mixture was stirred at 70 to 75° C. for 48 h, then cooled to room temperature and poured into a beaker of ice-water (1 L) with stirring. The resulted solid was collected by filtration, washed with water and dried in a vacuum oven (45° C.) for 2 h. The crude product was triturated with $CH_2Cl_2$ to provide $N^4$-(4-fluoro-3-(trifluoromethyl)phenyl)-$N^6$-(4-methoxybenzyl)pyrido[3,4-d]pyrimidine-4,6-diamine (166) (14.40 g, 74%) as a yellow solid, m.p. 202-204° C. $^1$H NMR [$(CD_3)_2SO$] δ 9.83 (s, 1H), 8.77 (s, 1H), 8.38 (s, 1H), 8.27-8.30 (m, 1H), 8.21-8.24 (m, 1H), 7.55 (t, J=9.7 Hz, 1H), 7.28-7.34 (m, 3H), 7.17 (s, 1H), 6.86-6.90 (m, 2H), 4.50 (d, J=6.3 Hz, 2H), 3.71 (s, 3H). Anal. Calcd for $C_{22}H_{17}F_4N_5O$: C, 59.59; H, 3.86; N, 15.79%. found: C, 59.31; H, 4.07; N, 15.46%.

A stirred solution of compound 166 (1.0 g, 2.26 mmol) in TFA (20 mL) was treated with anisole (490 μL, 4.51 mmol) at room temperature. The mixture was stirred overnight, then diluted with ethyl acetate and the solvents were removed under reduced pressure. The residue was triturated with hexane and then treated with aqueous ammonia (5N, 100 mL) with stirring for 30 min. The resulting solid was collected by filtration, washed with water and dried under vacuum to give $N^4$-(4-fluoro-3-(trifluoromethyl)phenyl)pyrido[3,4-d]pyrimidine-4,6-diamine (168) (720 mg, 99%) as a yellow solid, m.p. 252-255° C. $^1$H NMR [$(CD_3)_2SO$] δ 9.90 (s, 1H), 8.72 (s, 1H), 8.38 (s, 1H), 8.34 (dd, J=6.5, 2.6 Hz, 1H), 8.24-8.28 (m, 1H), 7.54 (t, J=9.7 Hz, 1H), 7.14 (s, 1H), 6.30 (s, 2H). Anal. Calcd for $C_{14}H_9F_4N_5 \cdot 0.55EtOAc$: C, 52.35; H, 3.63; N, 18.84%. found: C, 51.96; H, 3.70; N, 18.46%.

A stirred solution of DCC (633 mg, 3.07 mmol) in THF (2 mL) under nitrogen was treated with a solution of acid 9 (506 mg, 3.07 mmol) in anhydrous THF (2 mL) at 0° C. The mixture was stirred for 2 h, then treated with compound 168 (200 mg, 0.62 mmol) in DMA (2 mL) followed by di-iso-propylethylamine (DIPEA) (535 µL, 3.07 mmol), before being stirred for a further 3 h at 0° C. The resulting crude (E)-4-bromo-N-(4-(4-fluoro-3-(trifluoromethyl)phenylamino)pyrido[3,4-d]pyrimidin-6-yl)but-2-enamide thus formed was treated in situ with 40% aqueous dimethylamine (942 µL, 18.60 mmol) at 0° C. with stirring for 1 h. The mixture was then diluted with ethyl acetate (300 mL), then poured into a beaker of ice-water (600 mL), stirred for 10 min and then extracted with EtOAc. The combined organic extracts were washed with 2% cold aqueous $Na_2CO_3$, water and brine before being dried ($Na_2SO_4$) and concentrated under reduced pressure. The residue was purified by column chromatography on silica gel eluting with EtOAc/MeOH (9:1). Recrystallization from $CH_2Cl_2$/diisopropyl ether then gave (2E)-4-(dimethylamino)-N-{4-[4-fluoro-3-(trifluoromethyl)anilino]pyrido[3,4-d]pyrimidin-6-yl}-2-butenamide (170) (175 mg, 65%) as a pale yellow solid, 170-172° C. $^1$H NMR [$(CD)_2SO$] δ 10.93 (s, 1H), 10.42 (s, 1H), 9.04 (s, 1H), 9.01 (s, 1H), 8.64 (s, 1H), 8.24-8.28 (m, 2H), 7.56 (t, J=9.6 Hz, 1H), 6.88 (dt, J=15.4, 6.0 Hz, 1H), 6.53 (d, J=15.4 Hz, 1H), 3.10 (dd, J=6.0, 1.1 Hz, 2H), 2.19 (s, 6H). Anal. Calcd for $C_{20}H_{18}F_4N_6O \cdot 0.4CH_2Cl_2$: C, 52.32; H, 4.05; N, 17.94%. found: C, 51.99; H, 4.28; N, 18.07%.

B.1.1.1.3 (2E)-4-(dimethylamino)-N-[4-(3-ethynylanilino)pyrido[3,4-d]pyrimidin-6-yl]-2-butenamide (171)

A suspension of 6-fluoropyrido[3,4-d]pyrimidin-4(3H)-one (93) (6.64 g, 40.2 mmol), thionyl chloride (150 mL) and a catalytic amount of DMF (5 drops) was stirred under reflux for 30 min to give a homogeneous mixture which was evaporated under reduced pressure at 45° C. (bath temperature) to give a light brown solid. To this solid was added a mixture of 3-ethynylaniline (6.56 g, 44.2 mmol) and dry DMA (40 mL). The reaction mixture was then stirred at room temperature for 40 min before a 5% solution of sodium bicarbonate (500 mL) was added and the resultant mixture was stirred at room temperature for 15 min. The solid was collected by filtration and washed several times with water and then hexane, respectively. The solid was then dried under vacuum over silica gel to give N-(3-ethynylphenyl)-6-fluoropyrido[3,4-d]pyrimidin-4-amine (164) (10.5 g, 99%), mp 225-227° C.; $^1$H NMR δ [$(CD_3)_2SO$] 10.06 (s, 1H), 8.96 (s, 1H), 8.74 (s, 1H), 8.28 (poorly resolved d, J=0.6 Hz, 1H), 8.10 (t, J=1.7 Hz, 1H), 7.95-7.90 (m, 1H), 7.46 (t, J=7.9 Hz, 1H), 7.32-7.27 (m, 1H), 4.22 (s, 1H). Anal. Calcd for $C_{15}H_9BrFN_4$: C, 68.18; H, 3.43; N, 21.20%. Found C, 67.80; H, 3.50; N, 20.81%.

A mixture of compound 164 (8.90 g, 33.7 mmol) and 4-methoxybenzylamine (44.2 mL, 337 mmol) in dry DMSO (80 mL) was stirred under nitrogen at 70° C. (bath temperature) for 158 h. The resultant solution was cooled briefly and then stirred with petroleum ether (2×400 mL) at room temperature for 15 min before the petroleum ether layer was decanted. Water (400 mL) was added to the DMSO layer and the mixture was stirred at room temperature for 3 h. The solid thus precipitated was collected by filtration and washed with water (5×100 mL), before being suctioned dry and then washed with petroleum ether (2×100 mL) and suctioned dry again. The resultant brownish orange solid was dissolved in warm acetone (400 mL) and water (500 mL) was added. The mixture was then stirred at room temperature for 1 h and the resultant solid was collected by filtration, washed with acetone/water (1:1, 5×80 mL) and dried in vacuo over silica-gel, to give $N^4$-(3-ethynylphenyl)-$N^6$-(4-methoxybenzyl)pyrido[3,4-d]pyrimidine-4,6-diamine (167) (10.3 g, 80%) as a yellow/orange solid, mp 200-203° C.; $^1$H NMR δ [$(CD_3)_2SO$] 9.63 (s, 1H), 8.75 (s, 1H), 8.38 (s, 1H), 8.03 (br s, 1H), 7.94-7.88 (m, 1H), 7.41 (t, J=7.9 Hz, 1H), 7.34 (br d, J=8.6 Hz, 2H), 7.28-7.21 (m, 2H), 7.19 (s, 1H), 6.92-6.85 (m, 2H), 4.50 (d, J=6.3 Hz, 2H), 4.19 (s, 1H), 3.71 (s, 3H). Anal. Calcd for $C_{23}H_{19}N_5O$: C, 72.42; H, 5.02; N, 18.36%. Found C, 72.28; H, 5.05; N, 18.22%.

To a stirred homogeneous solution of compound 167 (12.3 g, 32.3 mmol) in dry DCM (325 mL) was added trifluoroacetic acid (24.5 mL, 323 mmol), followed by anisole (7.11 mL, 64.6 mmol). The resultant mixture was stirred at room temperature for 70 h and then poured into petroleum ether (1 L) and stirred at room temperature for ca. 30 min. The petroleum ether layer was decanted and discarded. This process was repeated with more petroleum ether (800 mL). The residue left behind was dissolved in acetone/water (1:1, 200 mL) and stirred with 5M $NH_3$ (500 mL) at room temperature for 1 h. The solid was collected by filtration and washed successively with acetone/water (1:4, 5×100 mL) and then petroleum ether/ethyl acetate (3:1, 5×100 mL) before being dried in vacuo to give $N^4$-(3-ethynylphenyl)pyrido[3,4-d]pyrimidine-4,6-diamine (169) (8.56 g, 98%), mp 220-225° C. (decomp); $^1$H NMR δ [$(CD_3)_2SO$] 9.69 (s, 1H), 8.70 (s, 1H), 8.38 (s, 1H), 8.08 (t, J=1.7 Hz, 1H), 7.95-7.89 (m, 1H), 7.40 (t, J=7.9 Hz, 1H), 7.34 (br d, J=7.7 Hz, 1H), 7.16 (s, 1H), 6.25 (s, 2H), 4.17 (s, 1H). Anal. Calcd for $C_{15}H_{11}N_5 \cdot 2H_2O \cdot 0.2CH_3COCH_3$: C, 60.65; H, 5.29; N, 22.67%. Found C, 60.54; H, 5.01; N, 22.56%.

To a solution of DCC (7.23 g, 35.1 mmol) in dry THF (25 ml) at 0° C. under nitrogen, was added solid acid 9 (5.79 g, 35.1 mmol). The reaction mixture was stirred at 0° C. for 35 min before solid aniline 169 (1.83 g, 7.01 mmol) was added, followed by dry DMA (20 mL) and di-iso-propylethylamine (DIPEA) (6.11 ml, 35.1 mmol). The final reaction mixture was stirred at 0° C. for 45 min before being cooled to −15 to −20° C. (bath). 40% Aqueous dimethylamine (10.6 mL, 84.0 mmol) was then added and after 25 min the reaction mixture was poured into cold 2% aqueous sodium carbonate (200 mL) and the product was extracted into ethyl acetate (600 mL), which was washed successively with water (300 mL), cold 2% aqueous sodium carbonate (300 mL) and water (300 mL). The ethyl acetate solution was dried ($Na_2SO_4$) and evaporated under reduced pressure to give a solid which was purified by column chromatography on silica gel eluting with DCM/MeOH (gradient from 100:0 to 15:1), to give (2E)-4-(dimethylamino)-N-[4-(3-ethynylanilino)pyrido[3,4-d]pyrimidin-6-yl]-2-butenamide (171) (1.33 g, 51%) as a yellow/orange solid, mp 163-166° C. $^1$H NMR δ [$(CD_3)_2SO$] 10.89 (s, 1H), 10.25 (s, 1H), 9.02 (s, 1H), 9.00 (s, 1H), 8.63 (s, 1H), 8.02 (br s, 1H), 7.94-7.87 (m, 1H), 7.42 (t, J=7.9 Hz, 1H), 7.26 (br d, J=7.7 Hz, 1H), 6.88 (dt, J=15.4, 6.0 Hz, 1H), 6.52 (br d; J=15.4 Hz, 1H), 4.19 (s, 1H), 3.09 (dd, J=6.0, 1.2 Hz, 2H), 2.19 (s, 6H). Anal. Calcd for $C_{21}H_{20}N_6O \cdot 0.2H_2O$: C, 67.08; H, 5.47; N, 22.35%. Found C, 66.88; H, 5.47; N, 22.22%.

B.1.1.2 The Synthesis of the Reductive Trigger α-Methyl Bromides

B.1.1.2.1 5-(bromomethyl)-1-methyl-4-nitro-1H-imidazole (105) (Scheme 8, Route 3)

To a suspension of compound 101 (20.0 g, 157.36 mmol) (prepared according to the method of Chauviére et al, J. Med.

Chem. 2003, 46, 427-440) and K$_2$CO$_3$ (32.62 g, 236.04 mmol) in DMF (200 mL) at 0° C. was added methyl iodide (14.70 mL, 236.04 mmol) dropwise. The resulting mixture was allowed to warm to room temperature and then stirred for 2 hours before the excess methyl iodide was evaporated at room temperature. The precipitate was removed by filtration and the DMF filtrate was concentrated under reduced pressure at 45-50° C. The residue obtained was extracted thoroughly with MeCN/DCM (1:9) and the combined extracts were filtered through a short column of silica gel. After solvents were removed the crude was recrystallised from MeCN and toluene to give compound 111 as an off-white crystalline solid (15.74 g, 71%), m.p. 161-163° C. $^1$H NMR (CDCl$_3$) δ 7.33 (s, 1H), 3.65 (s, 3H), 2.63 (s, 3H). Identical to that previously reported (Hosmane et al, J. Org. Chem., 1985, 50(26), 5892-5).

A solution of compound 111 (4.00 g, 28.34 mmol) and NBS (5.30 g, 29.78 mmol) in MeCN (200 mL) was irradiated at reflux for 2 hours with a 1000 W tungsten halide lamp. Approximately half of the solvent was removed in vacuo before water (100 mL) was added. Further concentration under reduced pressure afforded a white precipitate, which was collected by filtration, washed with water and dried under vacuum to give 5-(bromomethyl)-1-methyl-4-nitro-1H-imidazole (105) (4.69 g, 75%) as a white solid. $^1$H NMR (CDCl$_3$) δ 7.44 (s, 1H), 4.89 (s, 2H), 3.78 (s, 3H). Identical to that previously reported (Stribbling et al, PCT International patent publication WO 2008/039087).

B.1.1.2.2 5-(bromomethyl)-1,2-dimethyl-4-nitro-1H-imidazole (122) (Scheme 10)

To a suspension of compound 118 (50.0 g, 393.39 mmol) and K$_2$CO$_3$ (81.55 g, 590.08 mmol) in DMF (300 mL) at 0° C. was added methyl iodide (36.74 mL, 590.08 mmol) dropwise. The resulting mixture was allowed to warm to room temperature and then stirred for 2 hours before the excess methyl iodide was evaporated at room temperature. The precipitate was removed by filtration and the DMF filtrate was concentrated under reduced pressure at 45-50° C. The residue obtained was extracted thoroughly with MeCN/DCM (1:9) and filtered through a short column of silica gel. After solvents were removed the crude was recrystallised from MeCN (containing a small amount of MeOH) and toluene to give compound 119 (52.22 g, 94.0%) as a white crystalline solid. $^1$H NMR (CDCl$_3$) δ 7.66 (s, 1H), 3.67 (s, 3H), 2.43 (s, 3H). LR-MS (APCI +ve): m/e 142.5 (M+1). Identical to that previously reported (Rav-Acha and Cohen, J. Org. Chem. 1981, 46(23), 4717-4720).

A solution of compound 119 (33.0 g, 233.83 mmol) and t-butyl dichloroacetate (64.90 g, 350.74 mmol) (prepared from dichloroacetyl chloride, t-butanol and triethyl amine in DCM) in DMF (400 mL) was added dropwise to a suspension of potassium t-butoxide (91.83 g, 818.40 mmol) in DMF (400 mL) at −35 to −25° C. (dry-ice/MeCN bath). The resulting mixture was stirred at −25° C. for an additional 20 minutes before being poured into 0.5N HCl (approximately 1000 mL). A standard ethyl acetate/aqueous workup and column chromatography on silica gel eluting with ethyl acetate/hexane (3:2) then gave crude compound 120 as a dark solid (23.83 g, 35%), which was used without further purification. LR-MS (APCI +ve) m/e 290.5/292.5 (3:1, M+1).

Compound 120 as prepared above (23.83 g, 82.25 mmol) was treated with refluxing acetic acid (120 mL) for 45 minutes before being concentrated to dryness under reduced pressure. A standard NaHCO$_3$/DCM workup of the residue followed by column chromatography on silica gel eluting with ethyl acetate then gave compound 121 (10.00 g, 64%) as white solid. $^1$H NMR (CDCl$_3$) δ 5.03 (s, 2H), 3.67 (s, 3H), 2.46 (s, 3H). LR-MS (APCI +ve): m/e 190.4/192.4 (3:1, M+1).

A suspension of compound 121 (10.00 g, 52.74 mmol) and LiBr (4.80 g, 55.20 mmol) in ethyl acetate (500 mL) was heated at reflux for 4 hours before being subjected to a standard ethyl acetate/aqueous workup. The solid thus obtained was treated once again with LiBr/ethyl acetate as above. The crude product was then precipitated from DCM/i-Pr$_2$O by the addition of hexane, to give 5-(bromomethyl)-1,2-dimethyl-4-nitro-1H-imidazole (122) (11.46 g, 93%) as an off-white solid. $^1$H NMR (CDCl$_3$) δ 4.88 (s, 2H), 3.64 (s, 3H), 2.46 (s, 3H). Anal. Calcd for C$_5$H$_6$BrN$_3$O$_2$.4% hexane: C, 28.16; H, 2.96; N, 18.80%. Found: C, 27.81; H, 3.27; N, 19.05%. LR-MS (APCI +ve): m/e 234.4/236.4 (1:1, M+1).

1.1.2.3 5-(bromomethyl)-2-methoxy-1-methyl-4-nitro-1H-imidazole (125) (Scheme 11)

To a suspension of compound 111 (12.65 g, 90.00 mmol) in chloroform (100 mL), was added bromine (5.53 mL, 108.00 mmol), slowly. The resulting mixture was then stirred for 2 hours before water (130 mL) was added. The chloroform was then removed by distillation and the resulting precipitate was collected by filtration, washed with water and dried under vacuum to give compound 123 (15.50 g, 79%) as a white solid, m.p. 180-181° C., identical to the reported value (Pyman and Timmis, J. Chem. Soc., Trans., 1923, 123, 494-503). $^1$H NMR (CDCl$_3$) δ 3.63 (s, 3H), 2.69 (s, 3H). Anal. Calcd for C$_5$H$_6$BrN$_3$O$_2$: C, 27.29; H, 2.75; N, 19.10%. Found: C, 27.56; H, 2.83; N, 19.10%. LR-MS (APCI +ve): m/e 220.3/222.3 (1:1, M+1).

A solution of compound 123 (1.00 g, 4.54 mmol) in refluxing MeOH (40 mL) was treated with excess NaOMe (1.72 g, 31.78 mmol) for 3 hours. The solvent was then removed under reduced pressure and the resulting residue was suspended in MeOH/DCM (1:9) and filtered through a short column of silica gel. Solvent was then removed in vacuo to give compound 124 (442 mg, 57%) as an off-white solid, m.p. 103-105° C. $^1$H NMR (CDCl$_3$) δ 4.11 (s, 3H), 3.40 (s, 3H), 2.59 (s, 3H). Anal. Calcd for C$_6$H$_9$N$_3$O$_3$: C, 42.10; H, 5.30; N, 24.55%. Found: C, 42.20; H, 5.37; N, 24.61%. LR-MS (APCI +ve): m/e 172.5 (M+1).

A solution of compound 124 (750 mg, 4.38 mmol) and NBS (858 mg, 4.82 mmol) in MeCN (30 mL) was irradiated at reflux for 10 minutes with a 1000 W tungsten halide lamp. The solvent was then removed in vacuo and the residue was subjected to column chromatography on silica gel eluting with ethyl acetate/hexane (gradient from 1:2 to 2:1), to give 5-(bromomethyl)-2-methoxy-1-methyl-4-nitro-1H-imidazole (125) (200 mg, 18%) as a white solid. $^1$H NMR (CDCl$_3$) δ 4.85 (s, 2H), 4.14 (s, 3H), 3.51 (s, 3H). LR-MS (APCI +ve): m/e 250.4/252.4 (1:1, M+1).

B.1.1.2.4 3-[5-(bromomethyl)-4-nitro-1H-imidazol-1-yl]propanenitrile (115) (Scheme 9, Route 2)

A mixture of compound 101 (1.00 g, 7.87 mmol), acrylonitrile (1.56 mL, 23.60 mmol) and MTBD (48 mg, 0.31 mmol) in MeCN (10 mL) was heated at reflux overnight (16 hours). The mixture was then filtered to remove some precipitate and to the filtrate was added toluene (10 mL). The resulting solution was then partially concentrated under reduced pressure to remove the acetonitrile and afford a white precipitate, which was collected by filtration to give compound 117 (1.26 g, 89%) as an off-white solid. $^1$H NMR (d$^6$-DMSO) δ 7.84 (s, 1H), 4.37 (t, J=6.6 Hz, 2H), 3.08 (t, J=6.6 Hz, 2H), 2.61 (s, 3H). LR-MS (APCI +ve): m/e 181.4 (M+1).

A solution of compound 117 (540 mg, 3.00 mmol) and NBS (560 mg, 3.15 mmol) in MeCN (20 mL) was irradiated at reflux for 1 hour with a 1000 W tungsten halide lamp. Approximately half of the solvent was removed in vacuo before water (10 mL) was added. Further concentration under reduced pressure afforded a white precipitate, which was collected by filtration, washed with water and dried under vacuum to give 3-[5-(bromomethyl)-4-nitro-1H-imidazol-1-yl]propanenitrile (115) (689 mg, 89%) as an off-white solid. $^1$H NMR (d$^6$-DMSO) δ 8.04 (s, 1H), 5.08 (s, 2H), 4.48 (t, J=6.8 Hz, 2H), 3.17 (t, J=6.8 Hz, 2H). LR-MS (APCI +ve): m/e 259.4/261.4 (1:1, M+1).

B.1.1.2.6 3-[5-(bromomethyl)-4-nitro-1H-imidazol-1-yl]propanamide (116) (Scheme 9, Route 2)

3-[5-(Bromomethyl)-4-nitro-1H-imidazol-1-yl]propanenitrile (115) (680 mg, 2.62 mmol) was treated with 90% sulphuric acid (5 mL) at 65-70° C. for 1 hour, before being poured onto ice. After a standard ethyl acetate/NaHCO$_3$ workup, the crude product obtained was precipitated from THF by the addition of i-Pr$_2$O to give 3-[5-(bromomethyl)-4-nitro-1H-imidazol-1-yl]propanamide (116) (420 mg, 58%) as an off-white solid, m.p. 139-141° C. $^1$H NMR (d$^6$-DMSO) δ 7.90 (s, 1H), 7.44 (br, 1H), 7.00 (br, 1H), 5.06 (s, 2H), 4.32 (t, J=6.8 Hz, 2H), 2.70 (t, J=6.8 Hz, 2H). LR-MS (APCI +ve): m/e 277.5/279.5 (1:1, M+1).

B.1.1.3 The Synthesis of the Quaternary Ammonium Salt Reductive Prodrugs (Schemes 16 to 19)

Method D: Preparation of Quaternary Ammonium Salt Prodrugs in NMP Followed by Et$_2$O Precipitation.

To a solution of the dimethylamine effector in N-methyl-2-pyrrolidinone (NMP) was added the α-methyl bromide trigger (0.7-1.0 eq.), portionwise under nitrogen. The resulting mixture was then stirred for 12 hours to several days, before diethyl ether was added. The precipitate thus formed was collected by filtration and washed with DCM thoroughly. The crude product was then further purified by fractional precipitation from a mixture of acetonitrile and dioxane containing a few drops of triethylamine (performed one to three times as necessary). The precipitated product was collected by centrifugation followed by decantation of the mother liquor. The product was then washed with THF/DCM (1:1) and then hexane, before being dried under vacuum to give the prodrug as a white or off-white solid.

Method E: Preparation of Quaternary Ammonium Salt Prodrugs in NMP Followed by MeCN Precipitation.

To a solution of the dimethylamine effector in NMP was added the α-methyl bromide trigger (1.0-1.2 eq.). The resulting mixture was stirred overnight (~15 hours). MeCN was then added to the reaction mixture dropwise with continued stirring until a precipitate started to form. The resulting mixture was then stirred for a further 2 hours before the precipitate was collected by filtration or by centrifugation, washed with MeCN, ethyl acetate and hexane. Drying under vacuum then gave the prodrug as a white or off-white solid. If necessary, the product was further purified by recrystallisation from NMP and MeCN.

B.1.1.3.1 (2E)-4-{[4-(3-bromo-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (42)

Reaction of the compound 161 (500 mg, 1.12 mmol) in NMP (3 mL) with α-methyl bromide 105 (225 mg, 1.02 mmol) for 16 hours according to Method C gave (2E)-4-{[4-(3-bromo-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (42) (658 mg, 97%), m.p. 166-170° C. $^1$H NMR [(CD$_3$)$_2$SO] δ 11.31 (s, 1H), 10.35 (s, 1H), 9.07 (s, 1H), 9.00 (s, 1H), 8.66 (s, 1H), 8.25-8.23 (dd, J=6.4, 2.6 Hz, 1H), 8.14 (s, 1H), 7.90-7.86 (m, 1H), 7.44 (t, J=8.8 Hz, 1H), 7.06-6.99 (m, 1H), 6.80 (d, J=15.3 Hz, 1H), 5.06 (br s, 2H), 4.45 (d, J=7.2 Hz, 2H), 3.88 (s, 3H), 3.13 (s, 6H). Anal. Calcd for C$_{24}$H$_{24}$Br$_2$FN$_9$O$_3$.1.2H$_2$O: C, 41.96; H, 3.87; N, 18.35%. Found: C, 42.05; H, 3.77; N, 18.14%.

Reaction of the compound 161 (2.0 g, 4.49 mmol) in NMP (5 mL) with α-methyl bromide 105 (1186 mg, 5.39 mmol) according to Method D gave (2E)-4-([4-(3-bromo-4-fluoroanilino)pyrido[3,4-d]pyrimidin-6-yl]amino)-N,N-dimethyl-N-[(1-methyl-4-nitro-1H-imidazol-5-yl)methyl]-4-oxo-2-buten-1-ammonium bromide (42) (2.11 g, 70%). $^1$H NMR identical to above.

B.1.1.3.2 (2E)-4-{[4-(3-bromo-4-fluoroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide (43)

Reaction of the compound 161 (700 mg, 1.57 mmol) in NMP (3 mL) with α-methyl bromide IIa-2 (442 mg, 1.87 mmol) according to Method D gave (2E)-4-{[4-(3-bromo-4-fluoroanilino)pyrido[3,4-d]pyrimidin-6-yl]amino}-N-[(1,2-dimethyl-4-nitro-1H-imidazol-5-yl) methyl]-N,N-dimethyl-4-oxo-2-buten-1-ammonium bromide (43) (750 mg, 70%), m.p. 181-184° C. $^1$H NMR [(CD$_3$)$_2$SO] δ 11.30 (s, 1H), 10.36 (s, 1H), 9.07 (s, 1H), 9.00 (s, 1H), 8.66 (s, 1H), 8.25-8.23 (dd, J=6.4, 2.6 Hz, 1H), 7.90-7.86 (m, 1H), 7.44 (t, J=8.8 Hz, 1H), 7.07-6.99 (m, 1H), 6.80 (d, J=15.3 Hz, 1H), 5.07 (br s, 2H), 4.44 (d, J=7.0 Hz, 2H), 3.76 (s, 3H), 3.11 (s, 6H), 2.44 (s, 3H). Anal. Calcd for C$_{25}$H$_{26}$Br$_2$FN$_9$O$_3$.0.1hexane.1.2H$_2$O: C, 43.33; H, 4.23; N, 17.76%. Found: C, 43.21; H, 4.46; N, 17.77%.

B.1.1.3.3 (2E)-4-{[4-(3-bromo-4-fluoroanilino)pyrido[3,4-d]pyrimidin-6-yl]amino}-N-[(2-ethyl-1-methyl-4-nitro-1H-imidazol-5-yl) methyl]-N,N-dimethyl-4-oxo-2-buten-1-ammonium bromide (172)

Reaction of the compound 161 (700 mg, 1.57 mmol) in NMP (3 mL) with α-methyl bromide 201 (468 mg, 1.89 mmol) according to Method D gave (2E)-4-{[4-(3-bromo-4-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide (172) (930 mg, 85%), m.p. 173-176° C. $^1$H NMR [(CD$_3$)$_2$SO] δ 11.30 (s, 1H), 10.35 (s, 1H), 9.06 (s, 1H), 9.00 (s, 1H), 8.65 (s, 1H), 8.25-8.23 (dd, J=6.4, 2.6 Hz, 1H), 7.90-7.86 (m, 1H), 7.43 (t, J=8.8 Hz, 1H), 7.06-6.99 (m, 1H), 6.80 (d, J=15.3 Hz, 1H), 5.07 (br s, 2H), 4.44 (d, J=7.2 Hz, 2H), 3.76 (s, 3H), 3.11 (s, 6H), 2.79 (q, J=7.4 Hz, 2H), 1.29 (t, J=7.4 Hz, 3H). Anal. Calcd for C$_{26}$H$_{28}$Br$_2$FN$_9$O$_3$.0.05hexane.2H$_2$O: C, 43.05; H, 4.49; N, 17.18%. Found: C, 43.17; H, 4.75; N, 17.36%.

B.1.1.3.4 (2E)-4-{[4-(3-bromo-4-fluoroanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide (44)

Reaction of the compound 161 (481 mg, 1.08 mmol) in NMP (3 mL) with α-methyl bromide 125 (270 mg, 1.08 mmol) for 15 hours according to Method C gave (2E)-4-{[4-(3-bromo-4-fluoroanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide (44) (530 mg, 71%), m.p. 245° C. (dec.). $^1$H NMR [(CD$_3$)$_2$SO] δ 11.29 (s, 1H), 10.35 (s, 1H), 9.06 (s, 1H), 9.00 (s, 1H), 8.65 (s, 1H), 8.25-8.22 (m, 1H), 7.90-7.86 (m, 1H), 7.43 (t, J=8.8 Hz, 1H), 7.06-6.99 (m, 1H), 6.79 (d, J=15.3 Hz, 1H), 5.07 (br, 2H), 4.42 (d, J=7.2 Hz, 2H), 4.09 (s, 3H), 3.57 (s, 3H), 3.12 (s, 6H). Anal. Calcd for C$_{25}$H$_{26}$Br$_2$FN$_9$O$_4$.0.2hexane.1.5H$_2$O: C, 42.55; H, 4.33; N, 17.04%. Found: C, 42.47; H, 4.14; N, 16.89%.

B.1.1.3.5 (2E)-4-{[4-(3-bromo-4-fluoroanilino)pyrido[3,4-d]pyrimidin-6-yl]amino}-N-{[1-(2-cyanoethyl)-4-nitro-1H-imidazol-5-yl]methyl}-N,N-dimethyl-4-oxo-2-buten-1-ammonium bromide (49)

Reaction of the compound 161 (700 mg, 1.57 mmol) in NMP (2 mL) with α-methyl bromide 115 (411 mg, 1.59 mmol) for 15 hours according to Method C gave (2E)-4-{[4-(3-bromo-4-fluoroanilino)pyrido[3,4-d]pyrimidin-6-yl]amino}-N-{[1-(2-cyanoethyl)-4-nitro-1H-imidazol-5-yl]methyl}-N,N-dimethyl-4-oxo-2-buten-1-ammonium bromide (49) (897 mg, 81%), m.p. 132° C. (dec.). $^1$H NMR [(CD$_3$)$_2$SO] δ 11.31 (s, 1H), 10.35 (s, 1H), 9.07 (s, 1H), 9.00 (s, 1H), 8.66 (s, 1H), 8.32 (s, 1H), 8.25-8.22 (dd, J=6.4, 2.8 Hz, 1H), 7.90-7.86 (m, 1H), 7.44 (t, J=8.8 Hz, 1H), 7.04-6.97 (m, 1H), 6.79 (d, J=15.2 Hz, 1H), 5.08 (br, 2H), 4.61 (t, J=6.8 Hz, 2H), 4.43 (d, J=6.8 Hz, 2H), 3.20 (t, J=6.8 Hz, 2H), 3.11 (s, 6H). Anal. Calcd for C$_{26}$H$_{25}$Br$_2$FN$_{10}$O$_3$.0.8THF.H$_2$O: C, 44.96; H, 4.32; N, 17.96%. Found: C, 44.80; H, 4.48; N, 17.84%.

B.1.1.3.6 (2E)-N-{[1-(3-amino-3-oxopropyl)-4-nitro-1H-imidazol-5-yl]methyl}-4-{[4-(3-bromo-4-fluoroanilino)pyrido[3,4-d]pyrimidin-6-yl]amino}-N,N-dimethyl-4-oxo-2-buten-1-ammonium bromide (47)

Reaction of the compound 161 (400 mg, 0.90 mmol) in NMP (2 mL) with α-methyl bromide 116 (249 mg, 0.90 mmol) for 15 hours according to Method C gave (2E)-N-{[1-(3-amino-3-oxopropyl)-4-nitro-1H-imidazol-5-yl]methyl}-4-{[4-(3-bromo-4-fluoroanilino) pyrido[3,4-d]pyrimidin-6-yl]amino}-N,N-dimethyl-4-oxo-2-buten-1-ammonium bromide (47) (306 mg, 47%), m.p. 168° C. (dec.). $^1$H NMR [(CD$_3$)$_2$SO] δ 11.31 (s, 1H), 10.36 (s, 1H), 9.07 (s, 1H), 9.00 (s, 1H), 8.66 (s, 1H), 8.25-8.23 (m, 2H), 7.90-7.86 (m, 1H), 7.46-7.42 (m, 2H), 7.05-6.98 (m, 2H), 6.80 (d, J=15.3 Hz, 1H), 5.12 (br s, 2H), 4.47-4.41 (m, 4H), 3.12 (s, 6H), 2.76 (t, J=6.2 Hz, 2H). Anal. Calcd for C$_{26}$H$_{27}$Br$_2$FN$_{10}$O$_4$.0.3THF.1.5H$_2$O: C, 42.37; H, 4.24; N, 18.17%. Found: C, 42.40; H, 4.20; N, 18.17%.

B.1.1.3.7 (2E)-4-{[4-(3-bromo-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (173)

Reaction of compound 161 (100 mg, 0.22 mmol) in NMP (0.5 mL) with α-methyl bromide 200 (64 mg, 0.25 mmol) according to Method E gave (2E)-4-{[4-(3-bromo-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide (173) (94 mg, 60%), m.p. 185-188° C. (dec.). $^1$H NMR [(CD$_3$)$_2$SO] δ 11.30 (s, 1H), 10.35 (s, 1H), 9.07 (s, 1H), 9.00 (s, 1H), 8.66 (s, 1H), 8.25-8.22 (dd, J=6.4, 2.6 Hz, 1H), 7.90-7.86 (m, 1H), 7.44 (t, J=8.8 Hz, 1H), 7.05-6.98 (m, 1H), 6.79 (d, J=15.3 Hz, 1H), 5.05 (br, 2H), 4.43 (d, J=6.9 Hz, 2H), 3.86 (s, 3H), 3.13 (s, 6H), 2.22 (s, 3H). Analysis found: C, 44.59; H, 3.92; N, 16.97%. C$_{27}$H$_{26}$Br$_2$FN$_9$O$_3$.1.5H$_2$O requires: C, 44.40; H, 4.00; N, 17.26%.

B.1.1.3.8 (2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (48)

Reaction of compound 161 (100 mg, 0.22 mmol) in NMP (0.5 mL) with α-methyl bromide 127 (63 mg, 0.26 mmol) according to Method E gave (2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium bromide (48) (132 mg, 85%), which was further purified by preparative HPLC eluting with CH$_3$CN/H$_2$O/TFA to give (2E)-4-{[4-(3-bromo-4-fluoroanilino)pyrido[3,4-d]pyrimidin-6-yl]amino}-N-[(2-cyano-1-methyl-4-nitro-1H-imidazol-5-yl)methyl]-N,N-dimethyl-4-oxo-2-buten-1-ammonium trifluoroacetate (48TF) (112 mg, 69%), m.p. 151-154° C. (dec). $^1$H NMR [(CD$_3$)$_2$SO] δ 11.32 (s, 1H), 10.39 (s, 1H), 9.06 (s, 1H), 9.01 (s, 1H), 8.66 (s, 1H), 8.22 (s, 1H), 7.86 (s, 1H), 7.44 (t, J=8.8 Hz, 1H), 7.07-7.00 (m, 1H), 6.79 (d, J=15.2 Hz, 1H), 5.15 (br, 2H), 4.44 (d, J=7.2 Hz, 2H), 4.06 (s, 3H), 3.15 (s, 6H).

B1.1.3.9 (2E)-4-{[4-(3-bromo-4-fluoroanilino)pyrido[3,4-d]pyrimidin-6-yl]amino}-N,N-dimethyl-N-[(1-methyl-2-nitro-1H-imidazol-5-yl)methyl]-4-oxo-2-buten-1-ammonium bromide (174)

Reaction of compound 161 (100 mg, 0.22 mmol) in NMP (0.5 mL) with 5-(bromomethyl)-1-methyl-2-nitro-1H-imidazole (IIIq-1) (54 mg, 0.25 mmol) (Everett et al, Bioorg Med Chem Lett, 1999, 9, 1267-1272) according to Method E gave (2E)-4-{[4-(3-bromo-4-fluoroanilino)pyrido[3,4-d]pyrimidin-6-yl]amino}-N,N-dimethyl-N-[(1-methyl-2-nitro-1H-imidazol-5-yl)methyl]-4-oxo-2-buten-1-ammonium bromide (174) (131 mg, 88%), m.p. 197° C. (dec.). $^1$H NMR [(CD$_3$)$_2$SO] δ 11.29 (s, 1H), 10.36 (s, 1H), 9.07 (s, 1H), 8.99 (s, 1H), 8.66 (s, 1H), 8.24-8.22 (dd, J=6.4, 2.6 Hz, 1H), 7.89-7.85 (m, 1H), 7.56 (s, 1H), 7.44 (t, J=8.8 Hz, 1H), 7.03-6.96 (m, 1H), 6.77 (d, J=15.2 Hz, 1H), 4.87 (s, 2H), 4.29 (d, J=7.2 Hz, 2H), 4.02 (s, 3H), 3.09 (s, 6H). Analysis found: C, 41.72; H, 3.82; N, 18.18%. C$_{24}$H$_{24}$Br$_2$FN$_9$O$_3$.1.5H$_2$O requires: C, 41.64; H, 3.93; N, 18.21%.

B1.1.3.10 (2E)-4-{[4-(3-bromo-4-fluoroanilino)pyrido[3,4-d]pyrimidin-6-yl]amino}-N-[(4-ethyl-1-methyl-2-nitro-1H-imidazol-5-yl)methyl]-N,N-dimethyl-4-oxo-2-buten-1-ammonium bromide (175)

Reaction of compound 161 (200 mg, 0.45 mmol) in NMP (1 mL) with 5-(bromomethyl)-4-ethyl-1-methyl-2-nitro-1H-imidazole (IIIq-2) (123 mg, 0.49 mmol) (Jiao et al, WO 2008151253 A1) according to Method E gave (2E)-4-{[4-(3-bromo-4-fluoroanilino)pyrido[3,4-d]pyrimidin-6-yl]amino}-N-[(4-ethyl-1-methyl-2-nitro-1H-imidazol-5-yl)methyl]-N,N-dimethyl-4-oxo-2-buten-1-ammonium bromide (175) (198 mg, 84%), m.p. 181-184° C. (dec.). $^1$H NMR [(CD$_3$)$_2$SO] δ 11.29 (s, 1H), 10.36 (s, 1H), 9.07 (s, 1H), 9.00 (s, 1H), 8.66 (s, 1H), 8.24-8.22 (dd, J=6.4, 2.6 Hz, 1H), 7.89-7.85 (m, 1H), 7.44 (t, J=8.8 Hz, 1H), 7.03-6.96 (m, 1H), 6.76 (d, J=15.2 Hz, 1H), 4.86 (s, 2H), 4.33 (d, J=7.2 Hz, 2H), 3.99 (s, 3H), 3.06 (s, 6H), 2.75-2.70 (q, J=6.6 Hz, 2H), 1.23 (t, J=6.6 Hz, 3H). Analysis found: C, 43.25; H, 4.21; N, 17.37%. $C_{26}H_{28}Br_2FN_9O_3 \cdot 1.6H_2O$ requires: C, 43.24; H, 4.36; N, 17.46%.

B.1.1.3.11 (2E)-4-({4-[4-fluoro-3-(trifluoromethyl) anilino]pyrido[3,4-d]pyrimidin-6-yl}amino)-N,N-dimethyl-N-[(1-methyl-4-nitro-1H-imidazol-5-yl) methyl]-4-oxo-2-buten-1-ammonium bromide (50)

Reaction of the compound 170 (700 mg, 1.61 mmol) in NMP (3 mL) with α-methyl bromide 105 (425 mg, 1.93 mmol) according to Method D gave (2E)-4-({4-[4-fluoro-3-(trifluoromethyl)anilino]pyrido[3,4-d]pyrimidin-6-yl}amino)-N,N-dimethyl-N-[(1-methyl-4-nitro-1H-imidazol-5-yl)methyl]-4-oxo-2-buten-1-ammonium bromide (50) (895 mg, 85%), m.p. 176-180° C. $^1$H NMR [$(CD_3)_2$SO] δ 11.32 (s, 1H), 10.48 (s, 1H), 9.08 (s, 1H), 9.02 (s, 1H), 8.67 (s, 1H), 8.28-8.23 (m, 2H), 8.14 (s, 1H), 7.58 (t, J=9.7 Hz, 1H), 7.06-6.99 (m, 1H), 6.81 (d, J=15.3 Hz, 1H), 5.06 (br s, 2H), 4.45 (d, J=7.3 Hz, 2H), 3.88 (s, 3H), 3.13 (s, 6H). Anal. Calcd for $C_{25}H_{24}BrF_4N_9O_3 \cdot 0.5(EtOAc) \cdot H_2O$: C, 45.26; H, 4.22; N, 17.59%. Found: C, 45.22; H, 4.43; N, 17.57%.

B.1.1.3.12 (2E)-N-[(1,2-dimethyl-4-nitro-1H-imidazol-5-yl)methyl]-4-({4-[4-fluoro-3-(trifluoromethyl) anilino]pyrido[3,4-d]pyrimidin-6-yl}amino)-N,N-dimethyl-4-oxo-2-buten-1-ammonium bromide (51)

Reaction of the compound 170 (700 mg, 1.61 mmol) in NMP (3 mL) with α-methyl bromide 122 (453 mg, 1.93 mmol) according to Method D gave (2E)-N-[(1,2-dimethyl-4-nitro-1H-imidazol-5-yl)methyl]-4-({4-[4-fluoro-3-(trifluoromethyl)anilino]pyrido[3,4-d]pyrimidin-6-yl}amino)-N,N-dimethyl-4-oxo-2-buten-1-ammonium bromide (51) (909 mg, 84%), m.p. 174° C. (dec.). $^1$H NMR [$(CD_3)_2$SO] δ 11.32 (s, 1H), 10.47 (s, 1H), 9.08 (s, 1H), 9.02 (s, 1H), 8.67 (s, 1H), 8.27-8.23 (m, 2H), 7.57 (t, J=9.7 Hz, 1H), 7.07-6.99 (m, 1H), 6.80 (d, J=15.3 Hz, 1H), 5.05 (br s, 2H), 4.43 (d, J=6.9 Hz, 2H), 3.75 (s, 3H), 3.11 (s, 6H), 2.44 (s, 3H). Anal. Calcd for $C_{26}H_{26}BrF_4N_9O_3 \cdot 1.5H_2O$: C, 44.90; H, 4.20; N, 18.13%. Found: C, 44.95; H, 4.42; N, 17.98%.

B.1.1.3.13 (2E)-4-{[4-(3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (58)

Reaction of the compound 171 (580 mg, 1.56 mmol) in NMP (3 mL) with α-methyl bromide 105 (411 mg, 1.86 mmol) according to Method D gave (2E)-4-{[4-(3-ethynylanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide (58) (730 mg, 79%), m.p. 179-182° C. $^1$H NMR [$(CD_3)_2$SO] δ 11.29 (s, 1H), 10.30 (s, 1H), 9.06 (s, 1H), 9.02 (s, 1H), 8.66 (s, 1H), 8.14 (s, 1H), 8.02 (t, J=1.6 Hz, 1H), 7.90-7.88 (dd, J=8.3, 1.1 Hz, 1H), 7.43 (t, J=8.0 Hz, 1H), 7.27 (d, J=7.4 Hz, 1H), 7.07-6.99 (m, 1H), 6.80 (d, J=15.3 Hz, 1H), 5.06 (br s, 2H), 4.45 (d, J=7.2 Hz, 2H), 4.20 (s, 1H), 3.88 (s, 3H), 3.13 (s, 6H). Anal. Calcd for $C_{26}H_{26}BrN_9O_3 \cdot 1.3H_2O$: C, 50.71; H, 4.68; N, 20.47%. Found: C, 50.63; H, 4.82; N, 20.26%.

B.1.1.3.14 (2E)-N-[(1,2-dimethyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (59)

Reaction of the compound 171 (580 mg, 1.56 mmol) in NMP (3 mL) with α-methyl bromide 122 (437 mg, 1.87 mmol) according to Method D gave (2E)-N-[(1,2-dimethyl-4-nitro-1H-imidazol-5-yl)methyl]-4-{[4-(3-ethynylanilino) pyrido[3,4-d]pyrimidin-6-yl]amino}-N,N-dimethyl-4-oxo-2-buten-1-ammonium bromide (59) (705 mg, 75%), m.p. 177-181° C. $^1$H NMR [$(CD_3)_2$SO] δ 11.28 (s, 1H), 10.31 (s, 1H), 9.06 (s, 1H), 9.02 (s, 1H), 8.66 (s, 1H), 8.02 (s, 1H), 7.89 (d, J=8.2 Hz, 1H), 7.43 (t, J=8.0 Hz, 1H), 7.27 (d, J=7.6 Hz, 1H), 7.07-6.99 (m, 1H), 6.80 (d, J=15.3 Hz, 1H), 5.06 (br s, 2H), 4.43 (d, J=7.0 Hz, 2H), 4.20 (s, 1H), 3.75 (s, 3H), 3.11 (s, 6H), 2.44 (s, 3H). Anal. Calcd for $C_{27}H_{28}BrN_9O_3 \cdot 1.3H_2O$: C, 51.48; H, 4.90; N, 20.01%. Found: C, 51.54; H, 4.92; N, 19.88%.

B.1.1.3.15 (2E)-N-[(2-ethyl-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (176)

Reaction of the compound 171 (475 mg, 1.28 mmol) in NMP (3 mL) with α-methyl bromide 201 (375 mg, 1.52 mmol) according to Method D gave (2E)-N-[(2-ethyl-1-methyl-4-nitro-1H-imidazol-5-yl)methyl]-4-{[4-(3-ethynylanilino)pyrido[3,4-d]pyrimidin-6-yl]amino}-N,N-dimethyl-4-oxo-2-buten-1-ammonium bromide (176) (595 mg, 75%), m.p. 173-177° C. $^1$H NMR [$(CD_3)_2$SO] δ 11.29 (s, 1H), 10.30 (s, 1H), 9.06 (s, 1H), 9.02 (s, 1H), 8.66 (s, 1H), 8.02 (t, J=1.7 Hz, 1H), 7.90-7.88 (m, 1H), 7.43 (t, J=8.0 Hz, 1H), 7.27 (d, J=7.7 Hz, 1H), 7.07-6.99 (m, 1H), 6.81 (d, J=15.2 Hz, 1H), 5.06 (br s, 2H), 4.43 (d, J=6.8 Hz, 2H), 4.20 (s, 1H), 3.76 (s, 3H), 3.11 (s, 6H), 2.79 (q, J=7.4 Hz, 2H), 1.29 (t, J=7.4 Hz, 3H). Anal. Calcd for $C_{28}H_{30}BrN_9O_3 \cdot 1.2H_2O$: C, 52.37; H, 5.09; N, 19.63%. Found: C, 52.31; H, 4.93; N, 19.76%.

B.2. Efficacy of the Prodrugs

The irreversible erbB1, 2, 4 inhibitors (161, 170, 171) were compared with their quaternary ammonium salt prodrugs (42, 50, 58) bearing the fragmenting reductive trigger IIId-1 (compound 105). A range of assays to assess the degree of deactivation of the prodrugs, their activation in cells under hypoxia, their fragmentation upon one-electron reduction and their efficacy in various tumour xenografts were employed.
Experimental: Methods and Materials
B.2.1 Cellular erbB1 Inhibition Experimental Human A431 epidermoid carcinoma cells and SKOV3 ovarian carcinoma cells, growing in alpha minimal essential media (α-MEM) containing 5% fetal bovine serum, were exposed to a range of concentrations of test compounds for 1 hour prior to preparation of total cell lysates. Cells were lysed in 300 μl modified RIPA buffer (50 mM Tris-HCl, pH 7.4, 1% NP-40, 0.25% Na-deoxycholate, 150 mM NaCl, 1 mM EDTA, 1 mM $Na_3VO_4$, 1 mM NaF and 1× protease inhibitor cocktail (Sigma, 100×)) and incubate on ice for 30 min. The BCA assay was employed to determine protein concentrations of samples. A BSA calibration curve was made using an Albumin standard (Pierce) ranging from 15.625-1000 μg/ml. Standard and samples are diluted in 0.1M NaOH. Store protein samples in −20° C. freezer afterwards for Western blot analysis. Expression of erbB1 and erbB2 and their degree of phosphorylation was determined by western blot using appropriate antibodies. For detection of erbB1/2 load 5 μg of total protein/well and 5 μl Kaleidoscope protein standard (Biorad) on a 15 well 7.5% PAGE gel. Run the samples at 100V until blue front reached the bottom of the gel. After electrophoresis the proteins are transferred to a 0.45 μm nitrocellulose membrane (Biorad) and blocked for 1 hour with 2% BSA in TBS-Tween 0.1%. Antibodies are diluted as indicated in TBS-Tween 0.1%. Proteins are detected using Supersignal West Pico Chemiluminescent Substrate (Pierce/Thermo Scientific). After detection of the phosphorylated protein the blot is stripped for 10 minutes with Restore Western Blot Stripping Buffer (Pierce/Thermo Scientific), washed and incubated with the antibody against the total protein. Densitometry of the blots is performed with the ImageJ software. Values are plotted using SigmaPlot 10. Equivalent protein loading was determined by BCA assay (as described) and confirmed by total erbB1/2 signal intensity, with band intensity calculated by densitometry (ImageJ) from which IC50 values were determined.

B.2.2 Cellular Growth Inhibition Experimental

Human A431, H1975 and SKOV3 carcinoma cells in log phase exponential growth in alpha minimal essential media (αMEM) containing 5% fetal bovine serum (FBS), were harvested by trypsinisation (1× trypsin/EDTA, Gibco Brl), counted, and seeded into 96 well plates (Nunc) at cell densities ranging from 800-1500 cells/well. Half of the cell samples were seeded into plates that were pre-equilibrated and held in an anoxic environment (90% $N_2$, 5% $H_2$, 5% $CO_2$, 37° C.; Anaerobic chamber, Coy Laboratory Products). After 3 hours attachment under either aerobic (21% $O_2$) or anoxic (<10 ppm $O_2$) conditions, cells were exposed to a range of prodrug or effector concentrations over appropriate dilution ranges for 4 hours. At the end of this period the anoxic plates were recovered from the anaerobic camber and held under normoxia in a standard $CO_2$ incubator (37° C.) for 20 hours. All plates were washed free of compound and cells were allowed to proliferate for a further 4 days in αMEM containing 5% FBS+antibiotics. Cells were fixed in trichloroacteic acid (30 min), washed and stained with sulforhodamine B (SRB, 60 min) prior to washing in acidified water. SRB was solubilised and absorption read at 450 nm to calculate cell densities. Inhibition of proliferation was calculated relative to untreated control wells.

B.2.3 In Vivo Efficacy Experimental

Specific pathogen-free homozygous female NIH-III nude mice (Charles River Laboratories, Wilmington, Mass.) were inoculated subcutaneously with a single cell suspension of H1975 cells (5×10$^6$ cells/100 µL; right flank). When H1975 tumour xenografts were established (typically 8-12 days) mice were randomized to treatment groups. All compounds were prepared in lactate buffer (pH4). Mice were dosed by intraperitoneal injection (0.01-0.03 ml/g) using the stated schedules and dose levels. For growth delay experiments mice were randomized to treatment and tumor volume [$\pi$(length×width$^2$)/6] and body weight were measured daily following treatment. The median time for tumors to increase in volume 4-fold relative to pre-treatment volume ($RTV^4$) was determined, and the Tumor Growth Inhibition (TGI) was calculated as the percentage increase in $RTV^4$ for treated over control. Differences in $RTV^4$ were tested for statistical difference by Mann Whitney U test using SigmaStat v3.5.

B.2.4 SKOV3 Xenografts Experimental

Specific pathogen-free homozygous female NIH-III nude mice (Charles River Laboratories, Wilmington, Mass.) were inoculated subcutaneously with a single cell suspension of SKOV3 cells (1×10$^7$ cells/100 µL; right flank). When SKOV3 tumour xenografts were established (typically 50-65 days) mice were randomized to treatment groups. Compounds 42 and 161 were prepared in lactate buffer (pH4). Mice were dosed by intraperitoneal injection (0.01-0.03 ml/g) using the stated schedules and dose levels. Tumour size and body weights were measured at regular intervals. Tumour volume was calculated as $\pi$ (length×width$^2$)/6. The time for tumours to increase in volume 4-fold relative to pre-treatment volume ($RTV^4$) was determined, and the % Tumour Growth Inhibition (% TGI) was calculated as the median percentage increase in $RTV^4$ for treated versus control. Differences in $RTV^4$ were tested for statistical difference by Mann Whitney U test using SigmaStat v3.5.

B.2.5 Plasma and Tissue Pharmacokinetics Experimental

Compound 42 was dosed at a nominal low dose of 20 µmol/kg to nine female NIH-III mice bearing H1975 tumour xenografts, as a solution in DMSO/5% dextrose (20:80) via intravenous injection. Blood samples were collected at T=2, 6 and 24 hours by terminal bleed (n=3 per cohort) under isoflurane anaesthesia. H1975 tumour, skin, and liver samples were collected at T=2, 6 and 24 hours (n=3 per cohort), immediately frozen in liquid nitrogen and stored at −80° C. before sample preparation for drug analysis. A small piece (~100 mg) of each respective tissue was placed in a biopulveriser well (previously cooled in liquid nitrogen) and reduced to a fine powder with a strong blow to the steel pestle. The frozen powders were then collected in pre-weighed microcentrifuge tubes (kept on dry ice). Four volumes of ice cold acetonitrile (containing 0.5 µM D6-161 as an internal standard) was added to each sample to extract the drug from the tissue powder. The microcentrifuge tubes were then spun at 13,000 rpm for 10 min to precipitate the cell debris and proteins. To 10 µL of plasma (collected in EDTA) was added 40 µL of ice cold acetonitrile (containing 0.5 µM D6-161 as an internal standard). The resulting solution was mixed and then centrifuged at 13,000 rpm for 5 min. The supernatant (40 µL) was then transferred to an HPLC insert and mixed with 80 µL of 45 mM formate buffer (pH 4.5) and then concentrations of compound 42 and compound 161 in samples from mice dosed with compound 42 were determined on an Agilent 6410 LC-MS/MS equipped with diode array absorbance detector (DAD) in line with a mass detector. The analysis was performed by configuring the multimode ion source detector in electrospray positive mode, drying gas flow 5 L/min, nebuliser pressure 60 psi, drying gas temperature 275° C., vaporiser temperature 150° C., capillary voltage 2000 V, charging voltage 2000 V, DAD detection was 322 nm, 8 nm bandwidth. Quantitation was based on MRM transition at m/z of 584>400 (prodrug 42), and m/z of 445>400 (compound 161) and 451>400 (D6-161 internal standard). The analytes were eluted using a gradient of 100% acetonitrile and 0.01% formic acid-water on Zorbax SB C-18, rapid resolution HT 3.0×50 mm, 1.8 micron (Agilent) HPLC column with a flow rate of 0.6 ml/min.

Compound 42 and compound 161 were dosed at 75% of their respective q3dx4 MTDs (100 µmol/kg and 31.6 µmol/kg respectively) to thirty female NIH-III mice bearing A431 tumour xenografts, as a solution in lactate buffer via intraperitoneal injection. Blood samples were collected at T=2, 6, 24, 48 and 72 hours by terminal bleed (n=3 per cohort) under isoflurane anaesthesia. A431 tumour samples were collected at T=2, 6, 24, 48 and 72 hours (n=3 per cohort), immediately frozen in liquid nitrogen and stored at −80° C. before sample preparation for drug analysis as described above.

B.2.6 Radiolytic Reduction Experimental

Pulse radiolysis was used to monitor the one-electron reduction and stability of prodrug 42 in real time. A linear accelerator delivering short pulses of high energy electrons (2-3 Gy in 200 ns of 4 MeV) equipped with a fast spectophotometric detection system was used. (Anderson et al, J. Phys. Chem. A, 101, 9704-9709, 1997.) Test compound was dissolved in a NO-saturated solution containing formate ions, as above, which, following pulse radiolysis, resulted in the rapid formation of the radical anion of the compound within a few microseconds. The rate of fragmentation was determined by analysing kinetic transients at wavelengths corresponding to the formation of the benzyl-type radical of the trigger moiety. (Bays et al, J. Am. Chem. Soc., 105, 320-324, 1983; Anderson et al., J. Phys. Chem. A, 101, 9704-9709, 1997.)

Results and Discussion

B.2.7 Cellular Enzyme Inhibitory Activities

The compounds 161, 170 and 171 and their respective prodrugs 42, 50 and 58 were tested for their ability to inhibit the autophosphorylation of erbB1 in EGF-stimulated A431 cells by Western immunoblotting measurement of phospho-erbB1 status (Table 8). The compound 161 and its prodrug 42 were similarly tested for their ability to inhibit basal levels of phospho-erbB2 in SKOV3 cells. Compounds 161, 170 and 171 were shown to be potent inhibitors of cellular erbB1 ($IC_{50}$s of 5, 8 and 8 nM, respectively). In contrast the quaternary ammonium salt derivatives prodrugs 42, 50 and 58 were 82-fold, 121-fold and 64-fold less effective at inhibiting erbB1 autophosphorylation in intact A431 cells respectively. Compound 161 was also shown to be a potent inhibitor of cellular erbB2 ($IC_{50}$ of 6 nM) in SKOV3 cells, while in contrast the quaternary ammonium salt prodrug 42 was 35-fold less effective in this regard. This loss of cellular erbB1/2 inhibitory potency for the prodrugs is attributed primarily to cellular exclusion of the prodrugs due to the presence of a positively charged quaternary ammonium salt.

TABLE 8

Inhibition ($IC_{50}$) of erbB1 and erbB2 autophosphorylation in intact A431 and SKOV3 cells, respectively.

| | Cellular Enzyme Inhibition $IC_{50}$ (μM)[a] | | | |
|---|---|---|---|---|
| Compound | erbB1 | Deact.[b] | erbB2 | Deact.[b] |
| 161 | 0.005 | | 0.006 | |
| 170 | 0.008 | | | |
| 171 | 0.008 | | | |
| 42 | 0.411 | 82 | 0.212 | 35 |
| 50 | 0.969 | 121 | | |
| 58 | 0.513 | 64 | | |

Footnotes for Table 8
[a]Concentration required to inhibit the EGF-stimulated autophosphorylation of erbB1 in intact A431 cells or the basal levels of phospho-erbB2 in SKOV3 cells by 50%, as determined by Western blotting with an antiphosphotyrosine antibody.
[b]Fold reduction in cellular erbB1/2 inhibition relative to the parent kinase inhibitor.

B.2.8 Cellular erbB1 Inhibition: Irreversibility Wash-Out Assay

Figure 19:
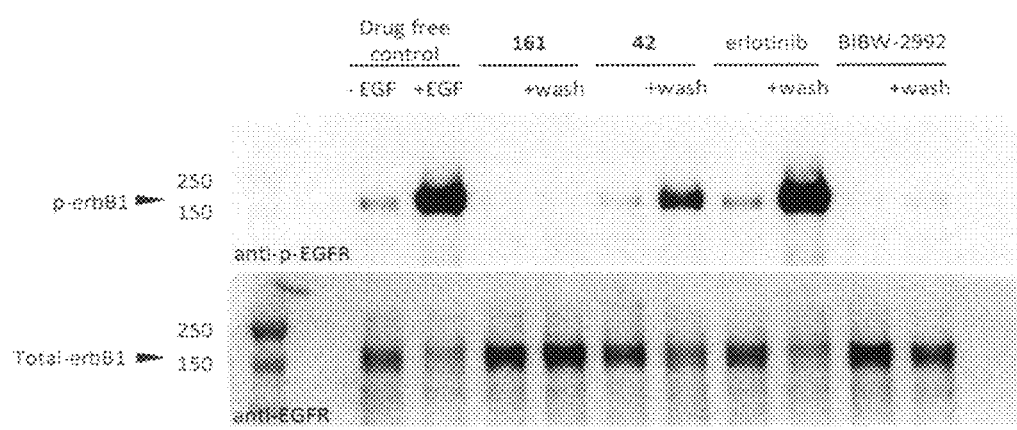
FIG. 19 shows A431 cellular erbB1 autophosphorylation inhibition for compounds 161 and 42 of the invention relative to the known reversible and irreversible erbB1 inhibitors, erlotinib and BIBW-2992 respectively.

The erbB1, 2, 4 inhibitor 161 and its quaternary ammonium salt prodrug 42 were assessed alongside the irreversible erbB1/2 inhibitor BIBW-2992 (Minkovsky and Berezov. Current Opinion in Investigational Drugs, 2008, 9(12), 1336-1346) and the reversible erbB1 inhibitor erlotinib (Sanborn and Davies, Expert Review of Clinical Pharmacology, 2009, 2(1), 15-36) for their ability to irreversibly inhibit erbB1 autophosphorylation in intact A431 cells. The cells were either continuously exposed to drug (1 μM) for one hour then stimulated with recombinant epidermal growth factor (EGF; Invitrogen, NZ) or exposed to drug (1 μM) for one hour and then washed free of unbound drug (15 times) prior to EGF stimulation. Whole cell lysates were prepared and detection of phospho-erbB1 was visualised by Western blotting with anti-phoshotyrosine polyclonal antibody (Upstate Biotech, #06-427) (FIG. 19). As has been previously described for a number of irreversible erbB1 inhibitors (Fry et al, PNAS, 1998, 95(20), 12022-12027; Smaill et al. J Med Chem, 1999, 42, 1803-1815; Smaill et al. J Med Chem, 2001, 44, 429-440; Tsou et al. J Med Chem, 2001, 44, 2719-2734; Wissner et al. J Med Chem, 2003, 46, 49-63; Tsou et al. J Med Chem, 2005, 48, 1107-1131; Klutchko et al. J Med Chem, 2006, 49, 1475-1485), BIBW-2992 completely inhibited erbB1 autophosphorylation in A431 cells irrespective of whether the cells were washed free of unbound drug prior to EGF stimulation, an observation also shown for the inhibitor 161 strongly supporting the interpretation that irreversible inhibition of erbB1 had occurred. In contrast erlotinib, a known reversible inhibitor of cellular erbB1 autophosphorylation, is incapable of enzyme alkylation as it is not substituted in the 6-position with a Michael acceptor. Accordingly, erlotinib showed significant inhibition of erbB1 autophosphorylation in cells that were not washed free of drug, but cells washed free of drug are fully restored in their ability to autophosphorylate erbB1 in response to EGF stimulation. A similar trend was observed for prodrug 42 where cells washed free of drug had their ability to autophosphorylate erbB1 fully restored, consistent with prodrug 42 being a reversible inhibitor of erbB1.

FIG. 19 shows A431 cellular erbB1 autophosphorylation inhibition for compounds 161 and 42 relative to the reversible and irreversible erbB1 inhibitors, erlotinib and BIBW-2992 respectively. Cells were given a 1 hour exposure to 1 μM of test compound and either directly stimulated with EGF, lysed and western blotted for EGFR (erbB1) and EGF-stimulated phosphotyrosine (i.e. phospho-erbB1), or washed extensively with drug free media to remove test compounds, prior to EGF stimulation, cell lysis and western blotting.

B.2.9 Cell Growth Inhibitory Activity

The compounds of Table 9 were tested for their ability to inhibit the proliferation of three human carcinoma cell lines, selected to provide a comparison with literature precedent: A431 (epidermoid), which overexpresses erbB1; H1975 (non-small-cell lung), which overexpresses erbB1$^{L858R,}$ $_{T790M}$ a double mutant form of erbB1 that is known to confer resistance to the approved reversible erbB1 inhibitor erlotinib and SKOV3 (ovarian), which overexpresses erbB2. The cells were exposed to test compounds for either 24 hours under oxic conditions or for 4 hours under anoxia followed by 20 hours under oxic conditions. They were then washed free of drug and incubated for a further 4 days, before being stained for cell survival with sulforhodamine B.

TABLE 9

Inhibition ($IC_{50}$) of cellular proliferation in A431, H1975 and SKOV3 cells.

| | Cellular Growth Inhibition $IC_{50}$ (μM)[a] | | | | | | | | | | | |
|---|---|---|---|---|---|---|---|---|---|---|---|---|
| | A431 | | | | H1975 | | | | SKOV3 | | | |
| Compound | Oxic[b] | Deact.[c] | Anoxic[d] | HCR[e] | Oxic[b] | Deact.[c] | Anoxic[d] | HCR[e] | Oxic[b] | Deact.[c] | Anoxic[d] | HCR[e] |
| 161 | 0.030 | | 0.028 | 1.6 | 1.26 | | 1.40 | 0.9 | 0.84 | | 1.31 | 0.8 |
| 170 | 0.24 | | 0.25 | 1.5 | 1.70 | | 1.38 | 1.2 | 0.99 | | 1.80 | 0.7 |
| 171 | 0.027 | | 0.017 | 1.7 | 1.15 | | 1.12 | 1.1 | 0.55 | | 0.74 | 0.8 |
| 42 | 1.69 | 56 | 0.075 | 60.0 | 37.2 | 30 | 4.22 | 10.8 | 35.5 | 42 | 2.85 | 20.3 |

TABLE 9-continued

Inhibition (IC$_{50}$) of cellular proliferation in A431, H1975 and SKOV3 cells.

| | Cellular Growth Inhibition IC$_{50}$ (µM)[a] | | | | | | | | | | | |
|---|---|---|---|---|---|---|---|---|---|---|---|---|
| | A431 | | | | H1975 | | | | SKOV3 | | | |
| Compound | Oxic[b] | Deact.[c] | Anoxic[d] | HCR[e] | Oxic[b] | Deact.[c] | Anoxic[d] | HCR[e] | Oxic[b] | Deact.[c] | Anoxic[d] | HCR[e] |
| 50 | 15.3 | 64 | 0.25 | 65.8 | 119.6 | 70 | 3.78 | 43.5 | 124.7 | 126 | 4.78 | 28.7 |
| 58 | 2.00 | 74 | 0.035 | 77.9 | 98.9 | 86 | 3.81 | 77.7 | 73.1 | 133 | 2.51 | 38.5 |

Footnotes for Table 9
[a]Dose-response curves were determined at 5 concentrations. Cells received a 24 hour exposure to test compounds before being washed (x3) with drug-free media. The IC$_{50}$ (µM) values are the concentrations required to inhibit cell growth by 50% relative to untreated controls. Values are the average of between two and twelve independent determinations (% CV < 20 in all cases).
[b]Experiment performed entirely under oxic conditions.
[c]Fold reduction in oxic cellular growth inhibition relative to the parent kinase inhibitor.
[d]The first 4 hours of the 24 hour drug exposure was performed under anoxic conditions.
[e]Hypoxic Cytotoxicity Ratio = fold increase in cellular growth inhibition for cells receiving 4 hours of anoxia relative to cells that received only oxic conditions.

Irreversible erbB1, 2, 4 inhibitors 161, 170 and 171 more potently inhibited proliferation of A431 cells (IC$_{50}$s=0.027 to 0.24 µM) than H1975 (IC$_{50}$s=1.15 to 1.70 µM) and SKOV3 (IC$_{50}$s=0.55 to 0.99 µM) cells and did not show any significant change in potency when the cells received 4 hours of anoxia.

Relative to their respective kinase inhibitors (161, 170 and 171), the quaternary ammonium salt prodrugs (42, 50 and 58) were 56- to 74-fold less effective at inhibiting the growth of A431 cells; 30- to 86-fold less effective at inhibiting the growth of H1975 cells; and 42- to 133-fold less effective at inhibiting the growth of SKOV3 cells. In addition all of the prodrugs (42, 50 and 58) of Table 9 were significantly more potent at inhibiting the growth of all three cell lines after the cells received 4 hours of anoxia. The hypoxic cytotoxicity ratios (HCR) ranged from 60.0 to 77.9 in A431 cells, 10.8 to 77.7 in H1975 cells and 20.3 to 38.5 in SKOV3 cells, consistent with hypoxia-selective reduction of the nitroheterocyclic reductive trigger, followed by trigger fragmentation to release an irreversible erbB1, 2, 4 inhibitor.

B.2.10 Radiolytic Reduction

Electron-affinic prodrugs can be selectively reduced by one-electron processes in the hypoxic regions of solid tumours in contrast to under normoxic conditions in normal tissues. (Brown and Wilson, Nature Rev. Cancer, 2004, 4, 437-447.) The prodrug should have a one-electron reduction potential, E(1), of between −0.6V to −0.2 V and preferably between −0.5 V to −0.3V vs. NHE. The E(1) values of many compounds can be obtained from the literature, (for example, Wardman, P. J. Phys. Chem. Ref. Data, 1989, 18, 1637-1755) or determined by a number of methods. The pulse radiolysis method, for example, measures the equilibrium constant between the radical anions of the prodrugs, formed upon their one-electron reduction, and reference standards such as viologen and quinone compounds, from which data the E(1) values of the compounds can be calculated. (Meisel and Czapski. J. Phys. Chem., 1975, 79, 1503-1509.) The E(1) value of prodrug 42 was measured by the pulse radiolysis method and determined to be −0.425±0.008 V, which is considered to be an appropriate E(1) value to enable enzymatic formation of the prodrug radical anion in a biological setting.

It is desirable that the reductive prodrugs are selected to have controlled fragmentation rate constants upon one-electron reduction of the trigger moiety. Whilst fast fragmentation to release high concentrations of the cytotoxic effectors in the hypoxic regions of tumour cells is desirable, this is not so for normal tissue cells under normoxia. The rate constant of the back oxidation of the one-electron reduced nitroarene-based prodrugs by oxygen, kO$_2$, is given by the expression:

$$\log kO_2/M^{-1} s^{-1} = (4.6 \pm 0.1) - (5.0 \pm 0.2) \times E(1)C/C.^-$$

(Wardman et al, Biochem. Soc. Symp., 1995, 61, 171-194; Anderson et al, Org. Biomol. Chem. 2005, 3, 2167-2174).

The rate constants for fragmentation, kfrag, of the one-electron reduced prodrugs can be measured using pulse radiolysis to observe the formation of the absorption spectrum of the benzyl-type radical produced by trigger fragmentation. (Anderson et al, J. Phys. Chem. A, 1997, 101, 9704-9709.) The kfrag value of prodrug 42 was measured by pulse radiolysis and determined to be 50±10 s$^{-1}$, considered to be a fragmentation rate upon one-electron reduction under hypoxia in the desirable range consistent with prodrug 42 displaying hypoxic cytotoxicity ratios (HCRs) in vitro in A431, H1975 and SKOV3 cell-based anti-proliferative assays (Table 8).

B.2.11 Solubility and Stability of Prodrugs 42, 50 and 58

The quaternary ammonium salt prodrugs 42, 50 and 58 have been studied for solubility and chemical stability in a range of solutes by HPLC (Table 10). All displayed excellent solubility and stability in water. Prodrug 58 was notably more soluble in α-MEM and PBS than prodrugs 42 and 50, which nevertheless possess acceptable solubility in these solutes. All of the prodrugs also displayed acceptable stability in α-MEM and PBS, each having a half life >24 hours.

TABLE 10

Solubility and stability of prodrugs 42, 50 and 58 in α-MEM, PBS and water.

| | α-MEM + FCS (5%) | | PBS | | Water | |
|---|---|---|---|---|---|---|
| Compound | Solubility (µM) | Stability[a] | Solubility (µM) | Stability[a] | Solubility (µM) | Stability[a] |
| 42 | 175 | 61 | 129 | 77 | >1165 | 98 |
| 50 | 131 | 64 | 72 | 88 | >1300 | 99 |
| 58 | >1180 | 61 | >1285 | 78 | >1275 | 98 |

Footnotes for Table 10
[a]Percentage parent remaining in solution by HPLC after 24 h at 37° C. in the indicated solute.

B.2.12 In Vivo Efficacy of Compounds 42, 50 and 58 in H1975 Xenografts

Figure 20:
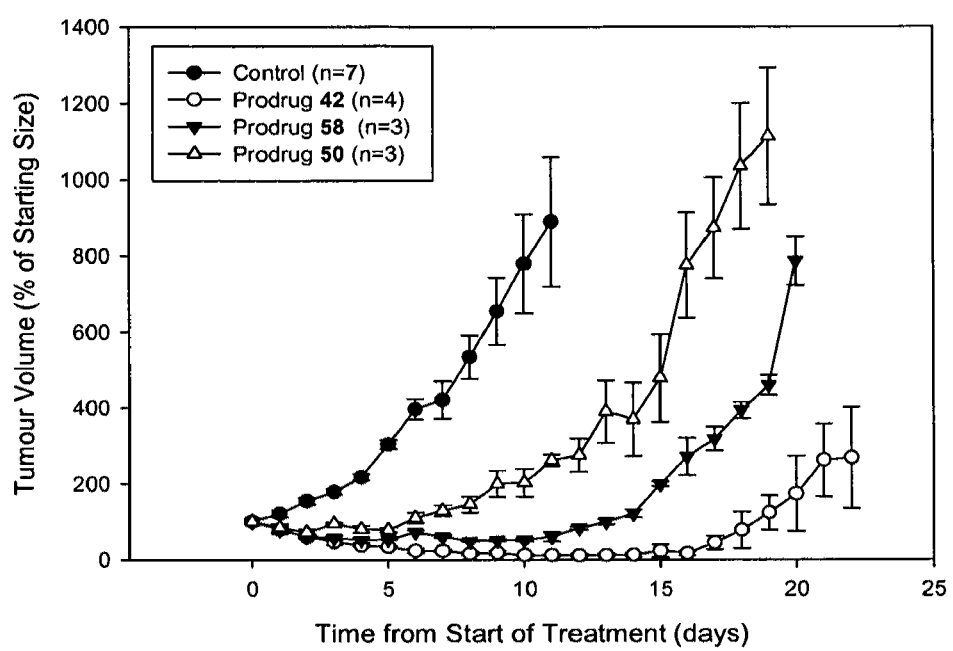
FIG. 20 shows efficacy of compounds 42, 50 and 58 of the invention against H1975 xenografts, when tested at their respective MTDs on a q3dx4 schedule.

Prodrugs 42, 50 and 58 were compared for efficacy in H1975 xenografts at their respective maximum tolerated doses (MTD) on a q3dx4 schedule, following IP dosing in lactate buffer (FIG. 20).

FIG. 20 shows efficacy of compounds 42, 50 and 58 against H1975 xenografts, when tested at their respective MTDs on a q3dx4 schedule.

Prodrug 42 (q3dx4 MTD=133 μmol/kg/dose) demonstrated considerable efficacy in H1975 xenografts (calculated Tumour Growth Inhibition, TGI=229%), while prodrug 50 (q3dx4 MTD=316 μmol/kg/dose) was weakly active (TGI=114%) and prodrug 58 (q3dx4 MTD=75 μmol/kg/dose) displayed intermediate activity (TGI=171%). Each prodrug is based on the same reductive trigger (105), differing only in the nature of the effector employed. The rank order of activity for the prodrugs (42>58>50) is consistent with the observed dose tolerance of the prodrugs in concert with the observed potency of the respective effectors in vitro in H1975 cells.

Figure 21:
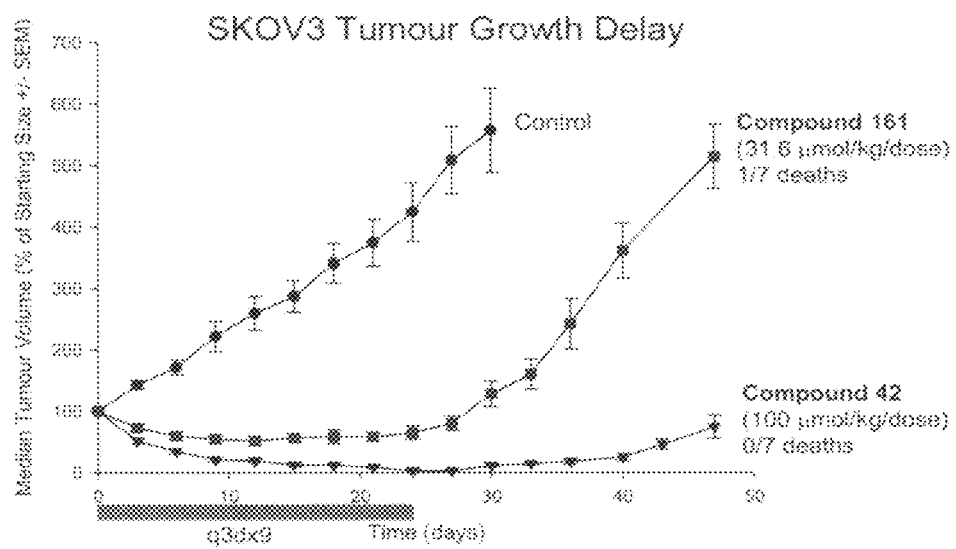
FIG. 21 shows efficacy of compounds 161 and 42 of the invention against SKOV3 xenografts.

B.2.13 In Vivo Efficacy of Compounds 42 and 161 Against SKOV3 and H1975 Xenografts FIG. 21 shows the efficacy of compounds 42 and 161 against SKOV3 xenografts. Prodrug 42 was compared directly to compound 161 for efficacy in SKOV3 xenografts at an equitoxic dose (100 and 31.6 μmol/kg/dose, respectively) on a q3dx9 schedule following IP dosing in lactate buffer. Prodrug 42 showed superior efficacy to compound 161 by growth delay, with 1/7 deaths observed for mice treated with compound 161 and 0/7 deaths observed for mice treated with prodrug 42.

Figure 22:
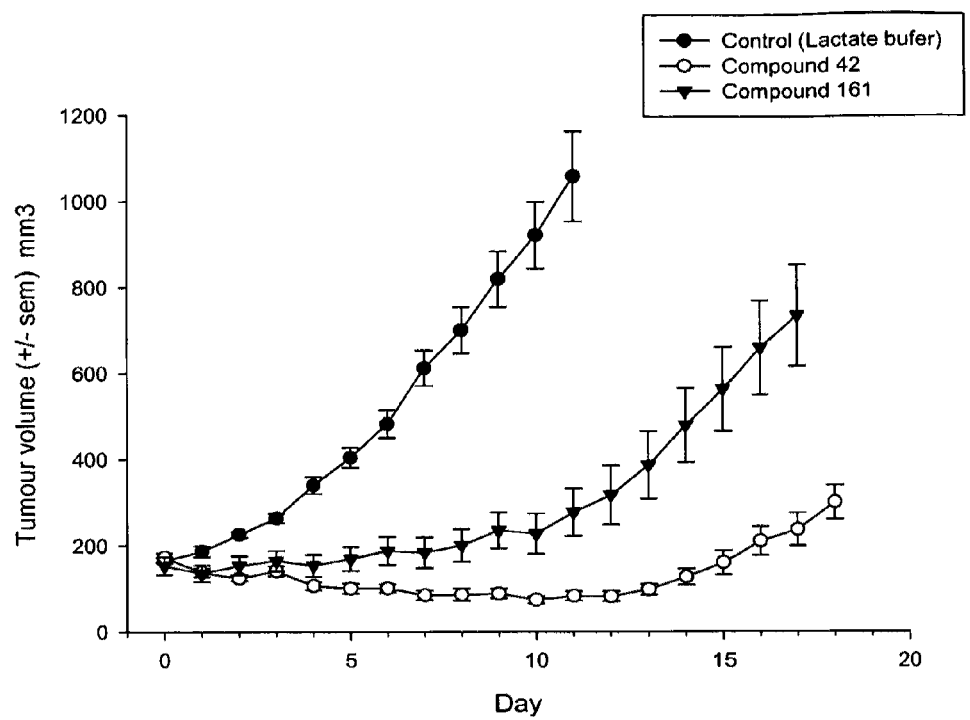
FIG. 22 shows the efficacy of compounds 42 and 161 against H1975 tumour xenografts grown in NIHIII nude mice.

FIG. 22 shows the efficacy of compounds 42 and 161 against H1975 tumour xenografts grown in NIHIII nude mice. Prodrug 42 was compared directly to compound 161 for efficacy in H1975 xenografts at an equitoxic dose (133 and 42.2 μmol/kg/dose, respectively) on a q3dx4 schedule following IP dosing in lactate buffer. Prodrug 42 showed superior efficacy to compound 161 by growth delay, with tumour growth inhibition (TGI) of 100% observed for mice treated with compound 161 and a TGI value of 188% for mice treated with prodrug 42.

B.2.14 In Vivo Efficacy of Prodrug 42 Against H1975 and A431 Xenografts

Figure 23:
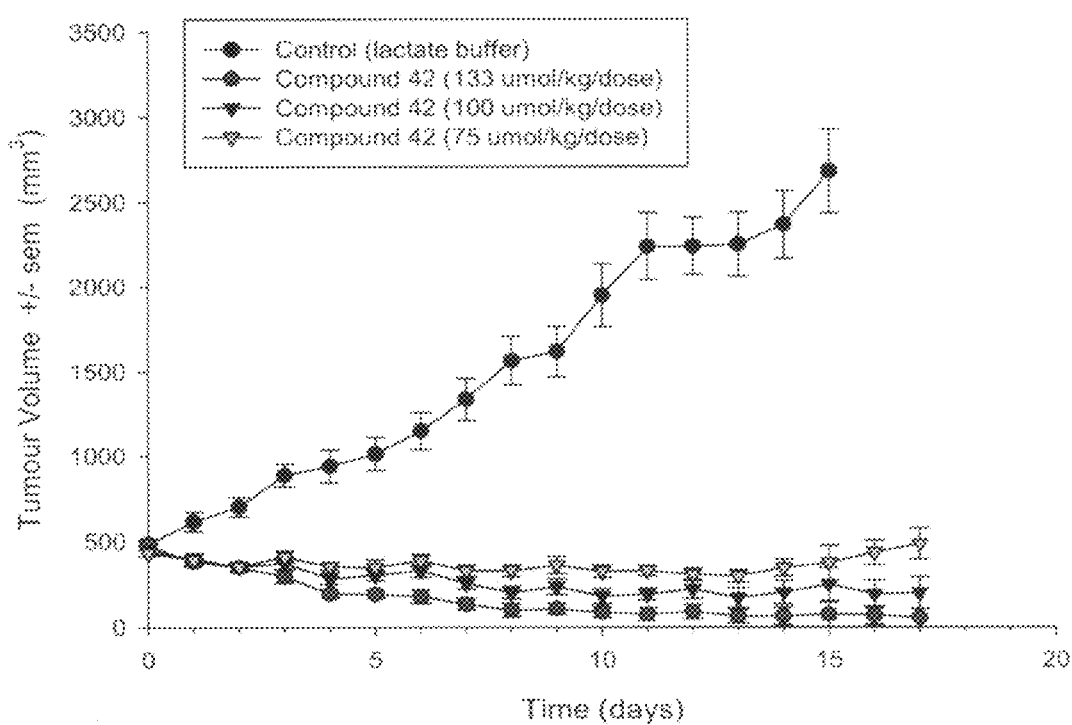
FIG. 23 shows the efficacy of prodrug 42 against large H1975 tumour xenografts grown in NIHIII nude mice.

FIG. 23 shows the efficacy of prodrug 42 against large H1975 tumour xenografts grown in NIHIII nude mice. Prodrug 42 was dosed at 133, 100 or 75 umol/kg/dose on a q3dx8 schedule following IP dosing in lactate buffer. All dose levels of prodrug 42 showed efficacy by H1975 growth delay, with tumour growth inhibition (TGI) of 275%, 213% and 154%, respectively, relative to lactate treated control (p<0.01). Thus prodrug 42 has excellent anti-tumour activity at doses below MTD establishing the presence of a therapeutic window.

Figure 24:
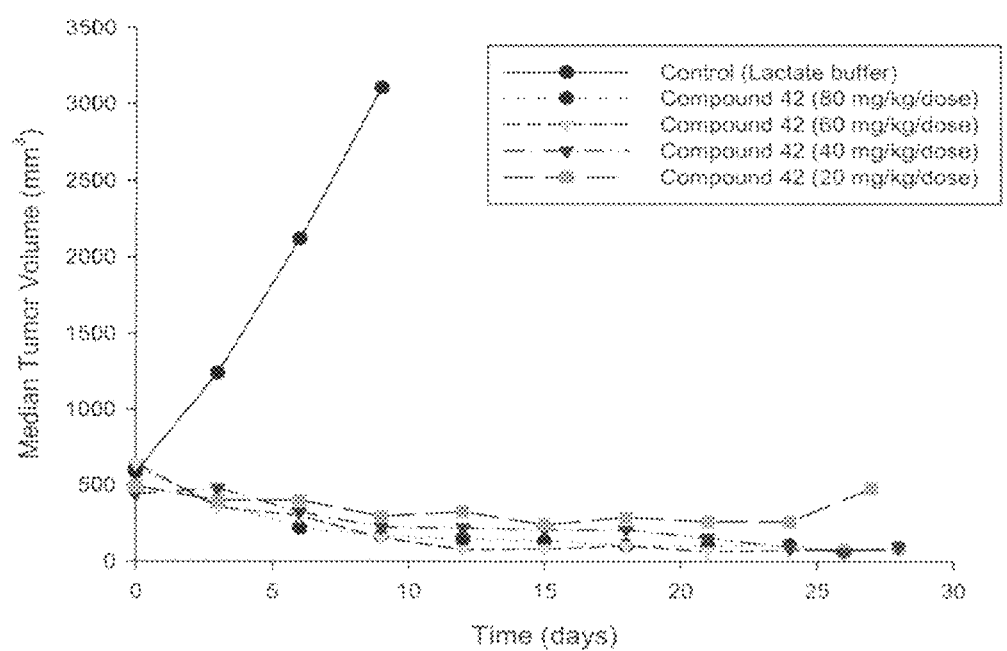
FIG. 24 shows the efficacy of prodrug 42 against large A431 tumour xenografts grown in NIHIII nude mice.

FIG. 24 shows the efficacy of prodrug 42 against large A431 tumour xenografts grown in NIHIII nude mice. Prodrug 42 was dosed at 80, 60, 40 or 20 mg/kg/dose on a q3dx8 schedule following IP dosing in lactate buffer. All dose levels of prodrug 42 showed efficacy by A431 growth delay, with tumour growth inhibition (TGI) of 843%, 786%, 800% and 400%, respectively, relative to lactate treated control (p<0.01). Thus prodrug 42 has excellent anti-tumour activity at doses below MTD establishing the presence of a therapeutic window.

B.2.15 Murine Toxicity and Pharmacokinetics of Prodrug 42

Table 10 describes the q3dx4 maximum tolerated dose (MTD) and the tissue and plasma pharmacokinetics of prodrug 42. Prodrug 42 demonstrated body weight loss with occasional loose stools, suggesting gastrointestinal toxicity may be dose limiting. Humane cull was performed if body weight loss was >15% of starting weight. MTD value was defined as less than 1 in 7 deaths by all drug related causes. Prodrug 42 was determined to be well tolerated on multi-dose schedules with body weight loss as the only observable toxicity.

The plasma and tissue pharmacokinetics of prodrug 42 and compound 161 (resulting from dosing with prodrug 42) were measured after a single intravenous dose (20 μmol/kg) in DMSO/5% dextrose (15:85). Prodrug 42 exhibited an area under the curve ($AUC_{0-24\,hr}$) in plasma, H1975 tumour, liver and skin of 24.7, 123, 256.2 and 197.7 μM.hr respectively. Compound 161 (from prodrug 42) exhibited an area under the curve ($AUC_{0-24\,hr}$) in plasma, H1975 tumour, liver and skin of 0.6, 7.6, 14.6 and 4.4 μM.hr respectively.

TABLE 11

In vivo toxicity and pharmacokinetics of prodrug 42

| | | Pharmacokinetics [b] | | | | | | | |
|---|---|---|---|---|---|---|---|---|---|
| Q3dx4 | | $AUC_{0-24\,hr}(\mu M \cdot hr)$ | | | | | | | |
| MTD [a] | Dose | Plasma | | H1975 Tumour | | Liver | | Skin | |
| (μmol/kg) | (μmol/kg) | 42 | 161 [c] | 42 | 161 [c] | 42 | 161 [c] | 42 | 161 [c] |
| 42 | 133 | 20 | 24.7 | 0.6 | 123 | 7.6 | 256.2 | 14.6 | 197.7 | 4.4 |

Footnotes for Table 11
[a] The test compound was dosed as a solution in lactate buffer at pH 4.0 via intraperitoneal injection on the schedule indicated. Performed in female H1975-tumour bearing NIH-III nude mice; 0 of 16 deaths across 3 independent studies.
[b] The test compound was dosed as a solution in DMSO/5% dextrose (15:85) via intravenous injection. Performed in female H1975-tumour bearing NIH-III nude mice; n = 3 mice per cohort. The plasma and tissue concentrations of the test compound were determined by LC-MS-MS at 2, 6 and 24 hr. $AUC_{0-24\,hr}$ were calculated from the concentration/time curves.
[c] $AUC_{0-24\,hr}$ values for compound 161 coming from dosing prodrug 42.

Figure 25:
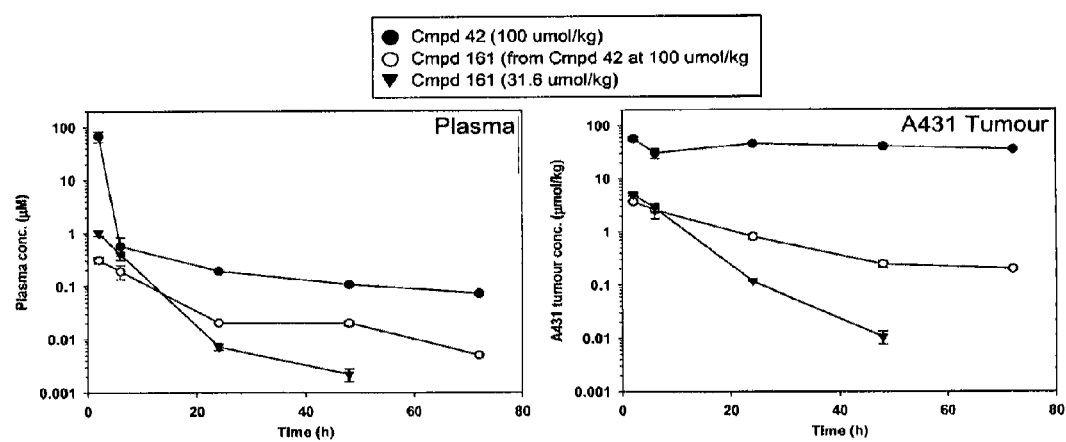
FIG. 25 shows the concentration of compound 42 and compound 161 (coming from dosing compound 42 and when dosed directly) as a function of time, in plasma and A431 tumour, when female A431-tumour bearing NIHIII mice are administered a single dose (ip) of each test compound at ~75% of q3dx4 MTD (100 and 31.6 umol/kg, respectively).

FIG. 25 shows the concentration of compound 42 and compound 161 (coming from dosing compound 42 and when dosed directly) as a function of time, in plasma and A431 tumour, when female A431-tumour bearing NIHIII mice are administered a single dose (ip) of each test compound at ~75% of q3dx4 MTD (100 and 31.6 umol/kg, respectively). Prodrug 42 gave a plasma $AUC_{0-72h}$ of 215 umol-h/L, some ~27-fold greater than achieved for administration of inhibitor 161 (8 umol-h/L). The latter gave a tumour $AUC_{0-inf}$ of 49 umol-h/kg. In contrast the prodrug 42 gave a tumour $AUC_{0-72h}$ of 2821 umol-h/kg with a stable tumour tissue concentration of ~30 umol/kg out to 72 h, such that a t½ could not be determined. Consistent with this long prodrug residency, inhibitor 161 released from prodrug 20 also displayed a prolonged t½ in tumour tissue, providing an $AUC_{0-inf}$ of 72 umol-h/kg. Thus the AUC of inhibitor 161 in A431 tumours was at least 1.5-fold higher after administration of prodrug 42 than following administration of inhibitor 161 itself at equivalent toxicity.

B.2.16 Summary

The collected data indicates quaternary ammonium salt prodrugs of irreversible erbB1, 2, 4 inhibitors, bearing a tertiary amine adjacent to a Michael acceptor, are less active in cell-based target modulation and anti-proliferative assays performed under oxic conditions. Prodrugs employing a fragmenting reductive trigger appropriately selected to fragment with a desirable rate constant upon one-electron reduction to release the tertiary amine-bearing irreversible erbB1, 2, 4 inhibitor are selectively more potent in cell-based anti-proliferative assays performed under anoxic conditions, can be delivered to mice at well tolerated doses and possess significant anti-tumour activity in A431, SKOV3 and H1975 tumour xenograft experiments.

INDUSTRIAL APPLICATION

The invention provides a series of prodrugs featuring a trigger that fragments when reduced, to release a kinase inhibitor. The prodrugs of the invention have a permanent positive charge. This feature is important in that the positive charge renders them less permeable to cells than the parent kinase inhibitor they are derived from.

Without wishing to be bound to any particular theory, it is believed that this lessening of permeability attenuates the cellular kinase inhibitory potency of the prodrugs relative to the parent kinase inhibitor, by compartmentalising the prodrug away from the intracellular kinase targets. The benefit of this attenuation of activity is to allow the prodrug to be administered to animals at higher exposure levels than the parent kinase inhibitor when the dose limiting toxicity of the kinase inhibitor derives from inhibition of the relevant kinases in healthy tissues. Efficient reductive fragmentation of the prodrug in the tumour, to release the kinase inhibitor therefore delivers higher kinase inhibitor concentrations in the tumour than can be achieved through systemic administration of the parent kinase inhibitor. In turn, superior efficacy is also achieved relative to the parent kinase inhibitor.

It is also believed that the positive charge of the prodrugs of the invention leads to sustained tumour residence over time. Results to date show that a substantially stable tumour tissue concentration over time (at least over 24 hours, and up to 72 hours) is achievable. This means that prodrug is available to be released and activated by one-electron reductases whenever and wherever within the tumour hypoxia may occur. This is a particular advantage given the transient and shifting nature of hypoxia within many tumours.

Selection of a trigger/kinase inhibitor combination with an appropriate E(1) and fragmentation rate constant (kfrag) is also believed to contribute to efficacy by assisting with hypoxic selectivity and by slowly releasing active kinase inhibitor from the prodrug, so that sufficient prodrug is retained within the tumour to target regions of hypoxia which appear in different parts of the tumour cell over time.

The compounds of the invention have application in any therapeutic approach in which inhibition of the activity of a kinase is desirable. In one specific aspect, this invention provides a method of treatment of abnormal cell growth in a mammal, including a human, comprising administering to said mammal an amount of a compound of the invention (preferably a compound of Formula I or Formula II) that is effective in treating abnormal cell growth. In one embodiment of this method, the abnormal cell growth is cancer, including, but not limited to, bone cancer, lung cancer, breast cancer, cancer of the head and neck, prostate cancer, pancreatic cancer, skin cancer, uterine cancer, ovarian cancer, chronic or acute leukaemia, carcinoma of the cervix, carcinoma of the vulva, carcinoma of the vagina, Hodgkin's Disease, cancer of the urethra, cancer of the adrenal gland, cancer of the small intestine, cancer of the kidney, cancer of the bladder, brain stem glioma and testicular cancer.

The compounds of the invention can be used alone or in combination with other therapeutic agents or treatment regimens, particularly for treating tumours. This allows for methods of treatment of abnormal cell growth in a mammal, including a human, comprising administering to said mammal an amount of a compound of the invention (preferably a compound of formula I or Formula II) that is effective in treating abnormal cell growth in combination with an anti-tumour agent selected from the group consisting of alkylating agents, anti-metabolites, mitotic inhibitors, intercalating agents, growth factor inhibitors, topoisomerase inhibitors, cell cycle inhibitors, biological response modifiers, antibodies, cytotoxics, anti-hormones and anti-androgens.

Similarly, the invention also provides a method of treatment of abnormal cell growth in a mammal, including a human, comprising administering to said mammal an amount of a compound of the invention (preferably a compound of Formula I or Formula II) that is effective in treating abnormal cell growth in combination with targeted radiotherapy.

When intended for use in any of the methods above, the compounds herein can be administered to humans and animals either orally, rectally, parenterally (intravenously, intramuscularly or subcutaneously), intracisternally, intravaginally, intraperitoneally, intravesically, locally or as a buccal or nasal spray.

Compositions suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, propyleneglycol, polyethyleneglycol, glycerol, vegetable oils and ethyl oleate.

Solid dosage forms for oral administration include capsules, tablets, pills, powders and granules. In such forms the active form may be admixed with at least one inert customary carrier such as sodium citrate, dicalcium phosphate or fillers, binders, humectants, disintegrating agents, solution retarders, adsorption accelerators, adsorbents and lubricants as is known to one skilled in the art.

Liquid dosage forms for oral administration include pharmaceutically acceptable emulsions, solutions, suspensions, syrups and elixirs.

The compounds of the present invention can be administered to a patient at pharmaceutically or therapeutically effective dosage levels in the range of about 0.1 to about 3,000 mg per day. The dosages employed will ultimately be dependent upon the condition or disorder being treated, and upon the treatment approach followed. Dosages will also alter dependent upon whether the compounds of the invention are administered alone as a monotherapy or together in combination therapy with one or more other active agents or treatment regimens (eg radiation).

Throughout this specification, unless the context requires otherwise, the words "comprise", "comprising" and the like, are construed in an inclusive sense as opposed to an exclusive sense, that is to say, in the sense of "including, but not limited to".

All publications referenced above are incorporated herein in their entirety.

The reference to any prior art in this specification is not, and should not be taken as an acknowledgement or any form of suggestion that that prior art forms part of the common general knowledge.

The foregoing describes the invention including preferred forms thereof. Alterations or modifications that would be apparent to the skilled person are intended to be included.

The invention claimed is:
1. A compound Formula II:

Formula II

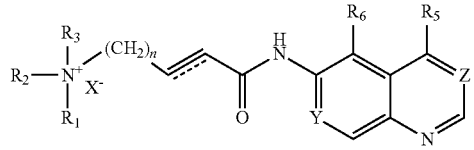

where:
X⁻ is a negatively charged counterion;
Y is N or C—$R_7$, where $R_7$ is selected from the group consisting of H, $C_1$-$C_6$ alkyl, $C_1$-$C_6$ alkoxy and a group of Formula VIa, VIb, and VIc Formula VI

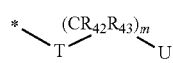
a

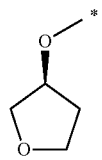
b

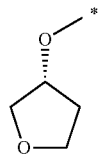
c where * is the point of attachment to C, and where
T is selected from the group consisting of O, NH, N($C_1$-$C_6$ alkyl) and a direct link;
m is an integer from 0 to 6;
U is selected from the group consisting of $OR_{44}$, $CF_3$, $OCF_3$, CN, $NR_{45}R_{46}$, pyrrolidinyl, piperidinyl, piperazinyl, N1-methylpiperazinyl, morpholinyl, $CON(R_{47})(R_{48})$, $SO_2N(R_{49})(R_{50})$, $N(R_{51})COR_{52}$, $N(R_{53})SO_2R_{54}$, $COR_{55}$, $SOR_{56}$, $SO_2R_{57}$ and $COOR_{58}$; and
$R_{42}$, $R_{43}$, $R_{44}$, $R_{45}$, $R_{46}$, $R_{47}$, $R_{48}$ $R_{49}$, $R_{50}$, $R_{51}$, $R_{52}$, $R_{53}$, $R_{54}$, $R_{55}$, $R_{56}$, $R_{57}$, $R_{58}$ are independently selected from the group consisting of H and $C_1$-$C_6$ alkyl;
Z is N or C—CN;
n is an integer from 0 to 6;

$R_1$ is selected from a group of Formula IIIa, IIIb, IIIc, IIId, IIIe, IIIf, IIIg, IIIh, IIIi, IIIj, IIIk, IIIl, IIIm, IIIn, IIIo, IIIp, or IIIq:

Formula III

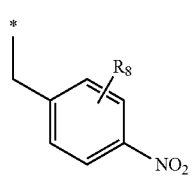
a

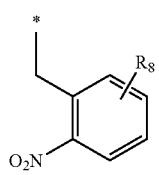
b

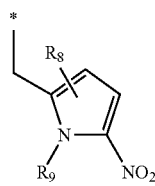
c

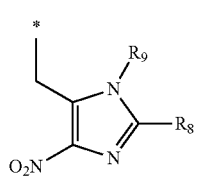
d

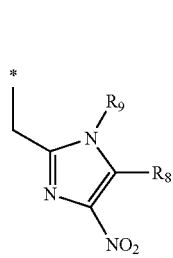
e

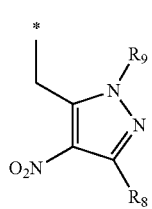
f

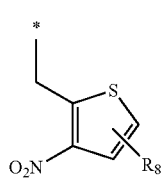
g

-continued

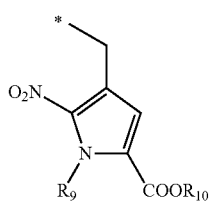

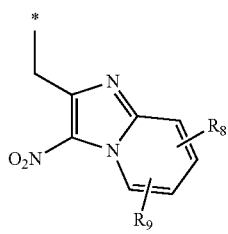

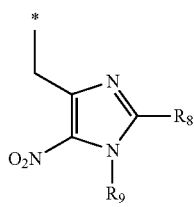

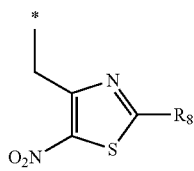

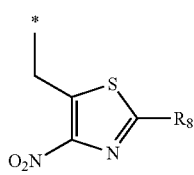

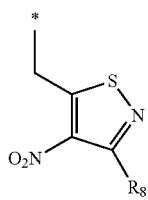

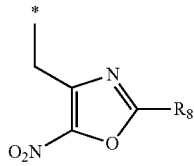

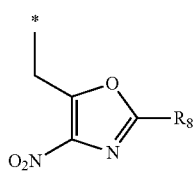

-continued

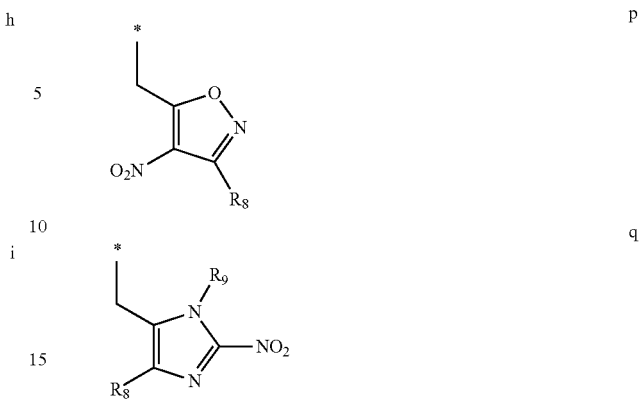

where:
* is the point of attachment to the quaternary nitrogen of the compound of Formula II;

$R_8$ is selected from the group consisting of H, $C_1$-$C_6$ alkyl, $C_1$-$C_6$ alkoxy, $C_2$-$C_6$ alkenyl, $C_2$-$C_6$ alkynyl, $CF_3$, $OCF_3$, F, Cl, Br, I, $NO_2$, CN, COOH, COO($C_1$-$C_6$ alkyl), $CONH_2$, CONH($C_1$-$C_6$ alkyl), CON($C_1$-$C_6$ alkyl)$_2$, CO($C_1$-$C_6$ alkyl), $SO_2NH_2$, $SO_2NH$($C_1$-$C_6$ alkyl), $SO_2N$($C_1$-$C_6$ alkyl)$_2$, $SO_2$($C_1$-$C_6$ alkyl) and a group of Formula VIa as defined above; where * is the point of attachment to a group of Formula IIIa-g or i-q;

$R_9$ is selected from the group consisting of H, $C_1$-$C_6$ alkyl and groups of Formula VIa as defined above; where * is the point of attachment to a group of Formula IIIc-f; h-j; or q; and $R_{10}$ is selected from the group consisting of H and $C_1$-$C_6$ alkyl;

$R_2$ and $R_3$ are independently selected from the group consisting of $C_1$-$C_6$ alkyl, cyclopropyl, cyclobutyl, cyclopentyl, cyclohexyl, $CH_2CH_2OH$, and $CH_2CH_2O$($C_1$-$C_6$ alkyl), or $R_2$ and $R_3$ may together with the nitrogen to which they are attached form a non-aromatic heterocyclic ring;

$R_5$ is selected from the group consisting of an aniline, an indole, an indoline, an amine, an aminoindole and an aminoindazole, each of which may be optionally substituted with one or more substituents selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, NH($C_1$-$C_6$ alkyl), N($C_1$-$C_6$ alkyl)$_2$, $CONH_2$, CO($C_1$-$C_6$ alkyl), $SO_2NH_2$ and $SO_2$($C_1$-$C_6$ alkyl); and $R_6$ is selected from the group consisting of H, $C_1$-$C_6$ alkyl, $C_1$-$C_6$ alkoxy, NH($C_1$-$C_6$ alkyl), N($C_1$-$C_6$ alkyl)$_2$ and a group of Formula Va or b Formula V

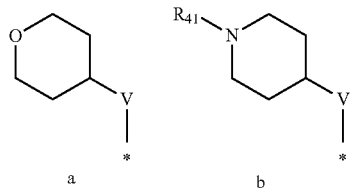

a  b where
* is the point of attachment;
V is selected from the group consisting of $(CH_2)_k$ O, NH and $N(C_1-C_6$ alkyl); k is an integer from 0 to 6; and
$R_{41}$ is selected from the group consisting of H and $C_1-C_6$ alkyl.

2. The compound according to claim 1, wherein $X^-$ is selected from the group consisting of halide, methanesulfonate, trifluoromethanesulfonate, acetate, trifluoroacetate, tosylate, lactate, citrate and formate.

3. The compound according to claim 1, wherein $X^-$ is halide.

4. The compound according to claim 1, wherein $X^-$ is formate or trifluoroacetate.

5. The compound according to claim 1, wherein $R_1$ is a group of Formula IIIc, where $R_8$ is H and $R_9$ is $CH_3$.

6. The compound according to claim 1, wherein $R_1$ is a group of Formula IIId, where $R_8$ is selected from a group consisting of H, $C_1-C_6$ alkyl, $C_1-C_6$ alkoxy, $C_2-C_6$ alkynyl, $CONH_2$, CONHMe, $CF_3$, $OCF_3$, Br, $NO_2$ and CN, and $R_9$ is selected from a group consisting of $CH_3$, $CH_2CH_2CONH_2$ and $CH_2CH_2CN$.

7. The compound according to claim 1, wherein $R_1$ is a group of Formula IIId, where $R_8$ is selected from the group consisting of H and $C_1-C_3$ alkyl and $R_9$ is selected from the group consisting of H and $C_1-C_6$ alkyl.

8. The compound according to claim 7 wherein $R_8$ is H.

9. The compound according to claim 7, wherein $R_9$ is H or $C_1-C_3$ alkyl.

10. The compound according to claim 7 wherein $R_9$ is methyl.

11. The compound according to claim 7 wherein $R_9$ is methyl and $R_8$ is H.

12. The compound according to claim 1, wherein $R_1$ is a group of Formula IIId, where $R_8$ is 1-propynyl and $R_9$ is $CH_3$.

13. The compound according to claim 1, wherein $R_1$ is a group of Formula IIId.

14. The compound according to claim 1, wherein $R_1$ is a group of Formula IIIq, where $R_8$ is selected from the group consisting of H, $C_1-C_6$ alkyl and $C_1-C_6$ alkoxy, and $R_9$ is $CH_3$.

15. The compound according to claim 1, wherein $R_1$ is selected from the group of Formula IIIc-1, IIId-1-10, IIIf-1 and IIIq-1-2:

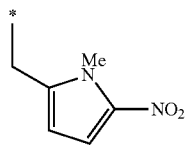
IIIc-1

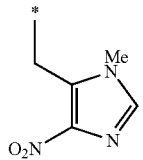
IIId-1

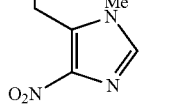

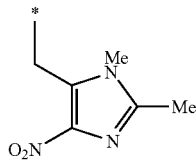
IIId-2

-continued

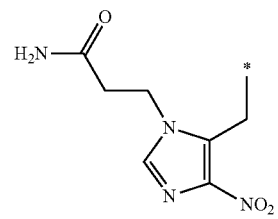
IIId-3

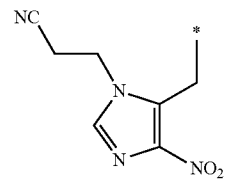
IIId-4

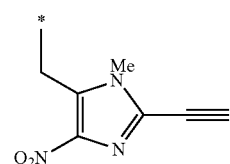
IIId-5

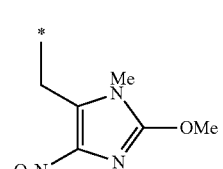
IIId-6

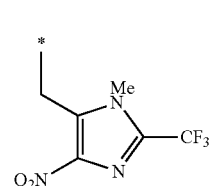
IIId-7

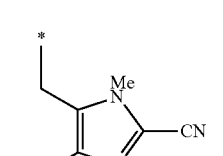
IIId-8

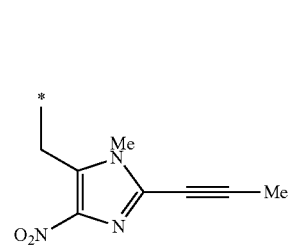
IIId-9

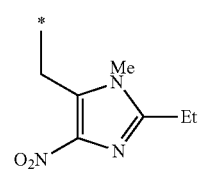
IIId-10

-continued

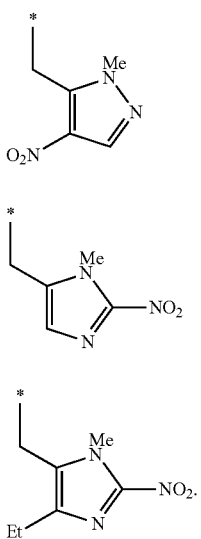

IIIf-1

IIIq-1

IIIq-2

16. The compound according to claim 1, wherein $R_5$ is selected from a group of Formula IVa-g:

Formula IV

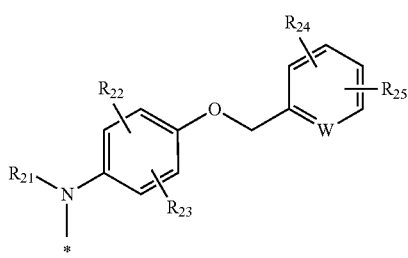

a b c d

-continued

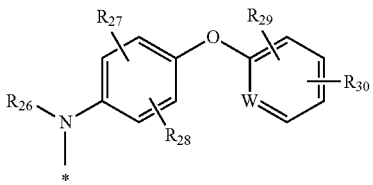

e

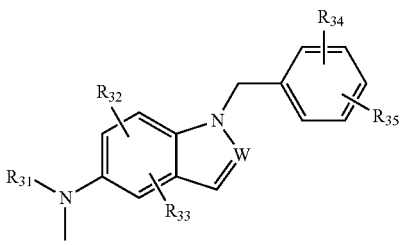

f

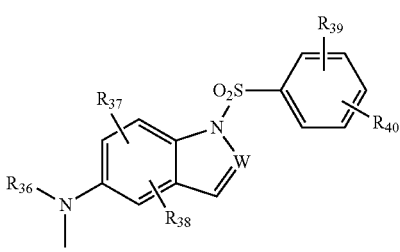

g where

* is the point of attachment;

$R_{11}$, $R_{18}$, $R_{19}$, $R_{21}$, $R_{26}$, $R_{31}$ and $R_{36}$, are independently selected from the group consisting of H and $C_1$-$C_6$ alkyl;

$R_{12}$, $R_{13}$, $R_{14}$, $R_{15}$, $R_{16}$, $R_{17}$, $R_{20}$, $R_{22}$, $R_{23}$, $R_{24}$, $R_{25}$, $R_{27}$, $R_{28}$, $R_{29}$, $R_{30}$, $R_{32}$, $R_{33}$, $R_{34}$, $R_{35}$, $R_{37}$, $R_{38}$, $R_{39}$ and $R_{40}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, NH($C_1$-$C_6$ alkyl), N($C_1$-$C_6$ alkyl)$_2$, $CONH_2$, CO($C_1$-$C_6$ alkyl), $SO_2NH_2$ and $SO_2$($C_1$-$C_6$ alkyl); and W is N or C—H.

17. The compound according to claim 1, wherein

Y is N,

Z is N or C—CN, $R_1$ is:

(a) a group of Formula IIIc, where $R_8$ is H; and $R_9$ is $CH_3$;

(b) a group of Formula IIId, where (i) $R_8$ is selected from the group consisting of H, $C_1$-$C_6$ alkyl, $C_1$-$C_6$ alkoxy, $C_2$-$C_6$ alkynyl, $CF_3$, $OCF_3$, Br, $NO_2$ and CN; and $R_9$ is selected from the group consisting of $CH_3$, $CH_2CH_2CONH_2$ and $CH_2CH_2CN$; or (ii) $R_8$ is 1-propynyl and $R_9$ is $CH_3$;

(c) a group of Formula IIIf, where $R_8$ is H and $R_9$ is $CH_3$; or (d) a group of Formula IIIq, where $R_8$ is selected from the group consisting of H, $C_1$-$C_6$ alkyl and $C_1$-$C_6$, and $R_9$ is $CH_3$;

$R_2$ and $R_3$ are $C_1$-$C_6$ alkyl, or together with the nitrogen to which they are attached form a ring selected from the group consisting of pyrrolidinium, piperidinium, piperazinium, N1-methylpiperazinium and morpholinium;

$R_5$ is:
(a) a group of Formula IVa, where
* is the point of attachment;
$R_{11}$ is H; and
$R_{12}$, $R_{13}$, $R_{14}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$;
(b) a group of Formula IVd, where
* is the point of attachment;
$R_{21}$ is H; and
$R_{22}$ and $R_{23}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$;
$R_{24}$ and $R_{25}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$; and
W is N or C—H; or
(c) a group of Formula IVf, where
* is the point of attachment;
$R_{31}$ is H;
$R_{32}$ and $R_{33}$ are independently selected from H or F;
$R_{34}$ and $R_{35}$ are independently selected from the group consisting of H, $C_1$-$C_6$ alkyl, F, Cl, Br, I, $CH_2F$, $CHF_2$, and $CF_3$; and
W is N or C—H;
$R_6$ is H;
$X^-$ is a negatively charged counterion; and
n is 1 or 2.

18. The compound according to claim 1, wherein
Y is C—H or C—($C_1$-$C_6$ alkoxy),
Z is N or C—CN;
$R_1$ is:
(a) a group of Formula IIIc, where $R_8$ is H and $R_9$ is $CH_3$;
(b) a group of Formula IIId, where
$R_8$ is selected from the group consisting of H, $C_1$-$C_6$ alkyl, $C_1$-$C_6$alkoxy, $C_2$-$C_6$ alkynyl, $CF_3$, $OCF_3$, Br, $NO_2$ and CN, and $R_9$ is selected from the group consisting of $CH_3$, $CH_2CH_2CONH_2$ and $CH_2CH_2CN$; or
$R_8$ is 1-propynyl and $R_9$ is $CH_3$;
(c) a group of Formula IIIf, where $R_8$ is H and $R_9$ is $CH_3$; or
(d) a group of Formula IIIq, where
$R_8$ is selected from the group consisting of H, $C_1$-$C_6$ alkyl and $C_1$-$C_6$ alkoxy, and $R_9$ is $CH_3$;
$R_2$ and $R_3$ are independently $C_1$-$C_6$ alkyl, or together with the nitrogen to which they are attached form a ring selected from the group consisting of pyrrolidinium, piperidinium, piperazinium, N1-methylpiperazinium and morpholinium;
$R_5$ is:
(a) a group of Formula IVa, where
* is the point of attachment;
$R_{11}$ is H; and
$R_{12}$, $R_{13}$, $R_{14}$ are independently selected from the group consisting of H, $C_1$-$C_6$ alkyl, $C_2$-$C_6$ alkenyl, $C_2$-$C_6$ alkynyl, alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$;
(b) a group of Formula IVd, where
* is the point of attachment;
$R_{21}$ is H; and
$R_{22}$ and $R_{23}$ are independently selected from the group consisting of H, $C_1$-$C_6$ alkyl, $C_2$-$C_6$ alkenyl, $C_2$-$C_6$ alkynyl, alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$;
$R_{24}$ and $R_{25}$ are independently selected from the group consisting of H, $C_1$-C6 alkyl, $C_2$-$C_6$ alkenyl, $C_2$-$C_6$ alkynyl, alkoxy, F, Cl, Br, I, CN, $CH_2F$, $CHF_2$, $CF_3$, OH, $NH_2$, $NO_2$, $NH(C_1$-$C_6$ alkyl), and $N(C_1$-$C_6$ alkyl)$_2$; and
W is N or C—H; or
(c) a group of Formula IVf, where
* is the point of attachment;
$R_{31}$ is H; and $R_{32}$ and $R_{33}$ are independently H or F;
$R_{34}$ and $R_{35}$ are independently selected from the group consisting of H, $C_1$-$C_6$ alkyl, F, Cl, Br, I, $CH_2F$, $CHF_2$, and $CF_3$, and W is N or C—H;
$R_6$ is H;
$X^-$ is a negatively charged counterion; and
n is 1 or 2.

19. The compound according to claim 1, where:
Y is C—$R_7$, where $R_7$ is a group of Formula VIb;
Z is N or C—CN;
$R_1$ is:
(a) a group of Formula IIIc, where $R_8$ is H and $R_9$ is $CH_3$;
(b) a group of Formula IIId, where
$R_8$ is selected from the group consisting of H, $C_1$-$C_6$ alkyl, $C_1$-$C_6$ alkoxy, $C_2$-$C_6$ alkynyl, $CF_3$, $OCF_3$, Br, $NO_2$ and CN, and $R_9$ is selected from the group consisting of $CH_3$, $CH_2CH_2CONH_2$ and $CH_2CH_2CN$;
or $R_8$ is 1-propynyl, and $R_9$ is $CH_3$;
(c) a group of Formula IIIf, where
$R_8$ is H and $R_9$ is $CH_3$; or
(d) a group of Formula IIIq, where
$R_8$ is selected from the group consisting of H, $C_1$-$C_6$ alkyl and $C_1$-$C_6$ alkoxy, and $R_9$ is $CH_3$;
$R_2$ and $R_3$ are independently $C_1$-$C_6$ alkyl, or together with the nitrogen to which they are attached form a ring selected from pyrrolidinium, piperidinium, piperazinium, N1-methylpiperazinium and morpholinium;
$R_5$ is:
(a) a group of Formula IVa, where
* is the point of attachment;
$R_{11}$ is H; and
$R_{12}$, $R_{13}$, $R_{14}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), $N(C_1$-$C_6$ alkyl)$_2$;
(b) a group of Formula IVd, where
* is the point of attachment;
$R_{21}$ is H; and
$R_{22}$ and $R_{23}$ are independently selected from the group consisting of H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), $N(C_1$-$C_6$ alkyl)$_2$;
$R_{24}$ and $R_{25}$ are independently selected from H, $C_1$-$C_6$ alkyl, $C_2$-$C_6$ alkenyl, $C_2$-$C_6$ alkynyl, $C_1$-$C_6$ alkoxy, F, Cl, Br, I, CN, $CH_2F$, $CHF_2$, $CF_3$, OH, $NH_2$, $NO_2$, $NH(C_1$-$C_6$ alkyl), $N(C_1$-$C_6$ alkyl)$_2$; and
W is N or C—H; or
(c) a group of Formula IVf, where
* is the point of attachment;
$R_{31}$ is H, and
$R_{32}$ and $R_{33}$ are independently H or F;
$R_{34}$ and $R_{35}$ are independently selected from the group consisting of H, $C_1$-$C_6$ alkyl, F, Cl, Br, I, $CH_2F$, $CHF_2$, and $CF_3$; and W is N or C—H;
$R_6$ is H;
$X^-$ is a negatively charged counterion; and
n is =1 or 2.

20. The compound according to claim 1, selected from the group consisting of:

- (2E)-4-{[4-(3-bromoanilino)-6-quinazolinyl]amino}-N,N-dimethyl-N-(4-nitrobenzyl)-4-oxo-2-buten-1-ammonium bromide;
- (2E)-4-{[4-(3-bromoanilino)-6-quinazolinyl]amino}-N,N-dimethyl-N-(2-nitrobenzyl)-4-oxo-2-buten-1-ammonium bromide;
- (2E)-4-{[4-(3-bromoanilino)-6-quinazolinyl]amino}-N,N-dimethyl-N-[(1-methyl-5-nitro-1H-pyrrol-2-yl)methyl]-4-oxo-2-buten-1-ammonium bromide;
- (2E)-4-{[4-(3-bromoanilino)-6-quinazolinyl]amino}-N,N-dimethyl-N-[(1-methyl-4-nitro-1H-imidazol-5-yl)methyl]-4-oxo-2-buten-1-ammonium bromide;
- (2E)-4-{[4-(3-bromoanilino)-6-quinazolinyl]amino}-N,N-dimethyl-N-[(1-methyl-4-nitro-1H-imidazol-2-yl)methyl]-4-oxo-2-buten-1-ammonium bromide;
- (2E)-4-{[4-(3-bromoanilino)-6-quinazolinyl]amino}-N,N-dimethyl-N-[(1-methyl-4-nitro-1H-pyrazol-5-yl)methyl]-4-oxo-2-buten-1-ammonium bromide;
- (2E)-4-{[4-(3-bromoanilino)-6-quinazolinyl]amino}-N,N-dimethyl-N-[(3-nitroimidazo[1,2-a]pyridin-2-yl)methyl]-4-oxo-2-buten-1-ammonium bromide;
- 1-((2E)-4-{[4-(3-bromoanilino)-6-quinazolinyl]amino}-4-oxo-2-butenyl)-1-[(1-methyl-4-nitro-1H-imidazol-5-yl)methyl]piperidinium bromide;
- 4-((2E)-4-{[4-(3-bromoanilino)-6-quinazolinyl]amino}-4-oxo-2-butenyl)-4-[(1-methyl-4-nitro-1H-imidazol-5-yl)methyl]morpholin-4-ium formate;
- (2E)-4-{[4-(3-chloro-4-fluoroanilino)-7-methoxy-6-quinazolinyl]amino}-N,N-dimethyl-N-[(1-methyl-4-nitro-1H-imidazol-5-yl)methyl]-4-oxo-2-buten-1-ammonium bromide;
- (2E)-4-{[4-(3-bromo-4-fluoroanilino)-6-quinazolinyl]amino}-N,N-dimethyl-N-[(1-methyl-4-nitro-1H-imidazol-5-yl)methyl]-4-oxo-2-buten-1-ammonium bromide;
- (2E)-4-{[4-(4-fluoro-3-methoxyanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide;
- (2E)-4-{[4-(3-bromo-4-fluoroanilino)pyrido[3,4-d]pyrimidin-6-yl]amino}-N,N-dimethyl-N-[(1-methyl-4-nitro-1H-imidazol-5-yl)methyl]-4-oxo-2-buten-1-ammonium bromide;
- (2E)-4-{[4-(3-bromo-4-fluoroanilino)pyrido[3,4-d]pyrimidin-6-yl]amino}-N-[(1,2-dimethyl-4-nitro-1H-imidazol-5-yl)methyl]-N,N-dimethyl-4-oxo-2-buten-1-ammonium bromide;
- (2E)-4-{[4-(3-bromo-4-fluoroanilino)pyrido[3,4-d]pyrimidin-6-yl]amino}-N-[(2-methoxy-1-methyl-4-nitro-1H-imidazol-5-yl)methyl]-N,N-dimethyl-4-oxo-2-buten-1-ammonium bromide;
- (2E)-4-{[4-(3-bromo-4-fluoroanilino)pyrido[3,4-d]pyrimidin-6-yl]amino}-N-[(2-ethynyl-1-methyl-4-nitro-1H-imidazol-5-yl)methyl]-N,N-dimethyl-4-oxo-2-buten-1-ammonium bromide;
- (2E)-4-{[4-(3-bromo-4-fluoroanilino)pyrido[3,4-c]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide;
- (2E)-N-{[1-(3-amino-3-oxopropyl)-4-nitro-1H-imidazol-5-yl]methyl}-4-{[4-(3-bromo-4-fluoroanilino)pyrido[3,4-c]pyrimidin-6-yl]amino}-N,N-dimethyl-4-oxo-2-buten-1-ammonium bromide;
- (2E)-4-{[4-(3-bromo-4-fluoroanilino)pyrido[3,4-c]pyrimidin-6-yl]amino}-N-[(2-cyano-1-methyl-4-nitro-1H-imidazol-5-yl)methyl]-N,N-dimethyl-4-oxo-2-buten-1-ammonium bromide;
- (2E)-4-{[4-(3-bromo-4-fluoroanilino)pyrido[3,4-c]pyrimidin-6-yl]amino}-N-[(2-cyano-1-methyl-4-nitro-1H-imidazol-5-yl)methyl]-N,N-dimethyl-4-oxo-2-buten-1-ammonium trifluoroacetate;
- (2E)-4-{[4-(3-bromo-4-fluoroanilino)pyrido[3,4-c]pyrimidin-6-yl]amino}-N-{[1-(2-cyanoethyl)-4-nitro-1H-imidazol-5-yl]methyl}-N,N-dimethyl-4-oxo-2-buten-1-ammonium bromide;
- (2E)-4-({4-[4-fluoro-3-(trifluoromethyl)anilino]pyrido[3,4-c]pyrimidin-6-yl}amino)-N,N-dimethyl-N-[(1-methyl-4-nitro-1H-imidazol-5-yl)methyl]-4-oxo-2-buten-1-ammonium bromide;
- (2E)-N-[(1,2-dimethyl-4-nitro-1H-imidazol-5-yl)methyl]-4-({4-[4-fluoro-3-(trifluoromethyl)anilino]pyrido[3,4-c]pyrimidin-6-yl}amino)-N,N-dimethyl-4-oxo-2-buten-1-ammonium bromide;
- (2E)-4-({4-[4-fluoro-3-(trifluoromethyl)anilino]pyrido[3,4-c]pyrimidin-6-yl}amino)-N-[(2-methoxy-1-methyl-4-nitro-1H-imidazol-5-yl)methyl]-N,N-dimethyl-4-oxo-2-buten-1-ammonium bromide;
- (2E)-N-[(2-ethynyl-1-methyl-4-nitro-1H-imidazol-5-yl)methyl]-4-({4-[4-fluoro-3-(trifluoromethyl)anilino]pyrido[3,4-c]pyrimidin-6-yl}amino)-N,N-dimethyl-4-oxo-2-buten-1-ammonium bromide;
- (2E)-4-({4-[4-fluoro-3-(trifluoromethyl)anilino]pyrido[3,4-c]pyrimidin-6-yl}amino)-N,N-dimethyl-N-{[1-methyl-4-nitro-2-(trifluoromethyl)-1H-imidazol-5-yl]methyl}-4-oxo-2-buten-1-ammonium bromide;
- (2E)-N-{[1-(3-amino-3-oxopropyl)-4-nitro-1H-imidazol-5-yl]methyl}-4-({4-[4-fluoro-3-(trifluoromethyl)anilino]pyrido[3,4-c]pyrimidin-6-yl}amino)-N,N-dimethyl-4-oxo-2-buten-1-ammonium bromide;
- (2E)-N-[(2-cyano-1-methyl-4-nitro-1H-imidazol-5-yl)methyl]-4-({4-[4-fluoro-3-(trifluoromethyl)anilino]pyrido[3,4-c]pyrimidin-6-yl}amino)-N,N-dimethyl-4-oxo-2-buten-1-ammonium bromide;
- (2E)-N-{[1-(2-cyanoethyl)-4-nitro-1H-imidazol-5-yl]methyl}-4-({4-[4-fluoro-3-(trifluoromethyl)anilino]pyrido[3,4-c]pyrimidin-6-yl}amino)-N,N-dimethyl-4-oxo-2-buten-1-ammonium bromide;
- (2E)-4-{[4-(3-ethynylanilino)pyrido[3,4-c]pyrimidin-6-yl]amino}-N,N-dimethyl-N-[(1-methyl-4-nitro-1H-imidazol-5-yl)methyl]-4-oxo-2-buten-1-ammonium bromide;
- (2E)-N-[(1,2-dimethyl-4-nitro-1H-imidazol-5-yl)methyl]-4-{[4-(3-ethynylanilino)pyrido[3,4-c]pyrimidin-6-yl]amino}-N,N-dimethyl-4-oxo-2-buten-1-ammonium bromide;
- (2E)-4-{[4-(3-ethynylanilino)pyrido[3,4-c]pyrimidin-6-yl]amino}-N-[(2-methoxy-1-methyl-4-nitro-1H-imidazol-5-yl)methyl]-N,N-dimethyl-4-oxo-2-buten-1-ammonium bromide;
- (2E)-4-{[4-(3-ethynylanilino)pyrido[3,4-c]pyrimidin-6-yl]amino}-N-[(2-ethynyl-1-methyl-4-nitro-1H-imidazol-5-yl)methyl]-N,N-dimethyl-4-oxo-2-buten-1-ammonium bromide;
- (2E)-4-{[4-(3-ethynylanilino)pyrido[3,4-c]pyrimidin-6-yl]amino}-N,N-dimethyl-N-{[1-methyl-4-nitro-2-(trifluoromethyl)-1H-imidazol-5-yl]methyl}-4-oxo-2-buten-1-ammonium bromide;

(2E)-N-{[1-(3-amino-3-oxopropyl)-4-nitro-1H-imidazol-5-yl]methyl}-4-{[4-(3-ethynylanilino)pyrido[3,4-c]pyrimidin-6-yl]amino}-N,N-dimethyl-4-oxo-2-buten-1-ammonium bromide;

(2E)-N-[(2-cyano-1-methyl-4-nitro-1H-imidazol-5-yl)methyl]-4-{[4-(3-ethynylanilino)pyrido[3,4-c]pyrimidin-6-yl]amino}-N,N-dimethyl-4-oxo-2-buten-1-ammonium bromide;

(2E)-N-{[1-(2-cyanoethyl)-4-nitro-1H-imidazol-5-yl]methyl}-4-{[4-(3-ethynylanilino)pyrido[3,4-c]pyrimidin-6-yl]amino}-N,N-dimethyl-4-oxo-2-buten-1-ammonium bromide;

(2E)-4-({4-(3-chloro-4-fluoroanilino)-7-[(3S)-tetrahydro-3-furanyloxy]-6-quinazolinyl}amino)-N,N-dimethyl-N-[(1-methyl-4-nitro-1H-imidazol-5-yl)methyl]-4-oxo-2-buten-1-ammonium trifluoroacetate;

(2E)-4-({4-[3-chloro-4-(2-pyridinylmethoxy)anilino]-3-cyano-7-ethoxy-6-quinolinyl}amino)-N,N-dimethyl-N-[(1-methyl-4-nitro-1H-imidazol-5-yl)methyl]-4-oxo-2-buten-1-ammonium trifluoroacetate;

(2E)-4-{[4-(3-chloro-4-fluoroanilino)-3-cyano-7-ethoxy-6-quinolinyl]amino}-N,N-dimethyl-N-[(1-methyl-4-nitro-1H-imidazol-5-yl)methyl]-4-oxo-2-buten-1-ammonium bromide;

2-(4-{[6-(2,6-dichlorophenyl)-8-methyl-7-oxo-7,8-dihydropyrido[2,3-c]pyrimidin-2-yl]amino}phenoxy)-N,N-diethyl-N-[(1-methyl-4-nitro-1H-imidazol-5-yl)methyl]ethanammonium bromide;

2-(4-{[6-(2,6-dichlorophenyl)-8-methyl-7-oxo-7,8-dihydropyrido[2,3-c]pyrimidin-2-yl]amino}phenoxy)-N-[(1,2-dimethyl-4-nitro-1H-imidazol-5-yl)methyl]-N,N-diethylethanammonium bromide;

4-{[6-(2,6-dichlorophenyl)-8-methyl-7-oxo-7,8-dihydropyrido[2,3-c]pyrimidin-2-yl]amino}-1-[(1-methyl-4-nitro-1H-imidazol-5-yl)methyl]pyridinium bromide;

1-[2-(4-{[6-(2,6-dichlorophenyl)-8-methyl-7-oxo-7,8-dihydropyrido[2,3-c]pyrimidin-2-yl]amino}phenoxy)ethyl]-1-[(1-methyl-4-nitro-1H-imidazol-5-yl)methyl]piperidinium bromide;

N,N-diethyl-2-[({5-[(Z)-(5-fluoro-2-oxo-1,2-dihydro-3H-indol-3-ylidene)methyl]-2,4-dimethyl-1H-pyrrol-3-yl}carbonyl)amino]-N-[(1-methyl-4-nitro-1H-imidazol-5-yl)methyl]ethanammonium trifluoroacetate;

N-[(1,2-dimethyl-4-nitro-1H-imidazol-5-yl)methyl]-N,N-diethyl-2-[({5-[(Z)-(5-fluoro-2-oxo-1,2-dihydro-3H-indol-3-ylidene)methyl]-2,4-dimethyl-1H-pyrrol-3-yl}carbonyl)amino]ethanammonium bromide;

4-({[4-(4-bromo-2-fluoroanilino)-6-methoxy-7-quinazolinyl]oxy}methyl)-1-methyl-1-[(1-methyl-4-nitro-1H-imidazol-5-yl)methyl]piperidinium trifluoroacetate;

(2E)-4-{[4-(3-bromo-4-fluoroanilino)pyrido[3,4-d]pyrimidin-6-yl]amino}-N-[(2-ethyl-1-methyl-4-nitro-1H-imidazol-5-yl)methyl]-N,N-dimethyl-4-oxo-2-buten-1-ammonium bromide;

(2E)-4-{[4-(3-bromo-4-fluoroanilino)pyrido[3,4-d]pyrimidin-6-yl]amino}-N,N-dimethyl-N-{[1-methyl-4-nitro-2-(1-propynyl)-1H-imidazol-5-yl]methyl}-4-oxo-2-buten-1-ammonium bromide;

(2E)-4-{[4-(3-bromo-4-fluoroanilino)pyrido[3,4-d]pyrimidin-6-yl]amino}-N,N-dimethyl-N-[(1-methyl-2-nitro-1H-imidazol-5-yl)methyl]-4-oxo-2-buten-1-ammonium bromide;

(2E)-4-{[4-(3-bromo-4-fluoroanilino)pyrido[3,4-d]pyrimidin-6-yl]amino}-N-[(4-ethyl-1-methyl-2-nitro-1H-imidazol-5-yl)methyl]-N,N-dimethyl-4-oxo-2-buten-1-ammonium bromide; and (2E)-N-[(2-ethyl-1-methyl-4-nitro-1H-imidazol-5-yl)methyl]-4-{[4-(3-ethynylanilino)pyrido[3,4-c]pyrimidin-6-yl]amino}-N,N-dimethyl-4-oxo-2-buten-1-ammonium bromide.

21. A pharmaceutical composition comprising a compound according to claim 1 in combination with one or more pharmaceutically acceptable excipients or diluents.

22. A pharmaceutical composition comprising a compound according to claim 1 in combination with one or more pharmaceutically acceptable excipients or diluents, for use in treating a proliferative disease in a mammal.

23. A kinase inhibitor suitable for use in the preparation of a compound according to claim 1,
which is
2E)-4-(dimethylamino)-N-{4-[4-fluoro-3-(trifluoromethyl)anilino]pyrido[3,4-c]pyrimidin-6-yl}-2-butenamide.

24. The compound according to claim 3, wherein $X^-$ is bromide or chloride.

25. The compound according to claim 18, wherein $R_8$ is selected from the group consisting of methyl, ethyl and $OCH_3$.

26. The compound according to claim 19, wherein $R_8$ is selected from the group consisting of methyl, ethyl and $OCH_3$.

27. The pharmaceutical composition according to claim 22 wherein the proliferative disease is cancer.

28. The pharmaceutical composition according to claim 22 wherein the mammal is a human.

* * * * *